(12) United States Patent
Qabar et al.

(10) Patent No.: US 7,345,040 B2
(45) Date of Patent: Mar. 18, 2008

(54) REVERSE-TURN MIMETICS AND COMPOSITIONS AND METHODS RELATING THERETO

(75) Inventors: Maher N. Qabar, Sammamish, WA (US); Marcin Stasiak, Seattle, WA (US); Jessymol Mathew, Raleigh, NC (US); Thomas Little, Redmond, WA (US); Danwen Huang, Sammamish, WA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 66 days.

(21) Appl. No.: 11/108,267

(22) Filed: Apr. 18, 2005

(65) Prior Publication Data

US 2005/0250780 A1 Nov. 10, 2005

Related U.S. Application Data

(63) Continuation-in-part of application No. PCT/US2003/032411, filed on Oct. 14, 2003.
(60) Provisional application No. 60/419,657, filed on Oct. 17, 2002.

(51) Int. Cl.
  *A61K 31/5025* (2006.01)
  *C07D 471/04* (2006.01)
  *C07D 487/04* (2006.01)
(52) U.S. Cl. ...................... 514/249; 544/279
(58) Field of Classification Search ................ 544/279; 514/249
  See application file for complete search history.

(56) References Cited

U.S. PATENT DOCUMENTS 5,440,013 A 8/1995 Kahn (Continued)

FOREIGN PATENT DOCUMENTS

WO WO 1992/13878 8/1992
WO WO 1994/03494 2/1994
WO WO 1996/22304 7/1996

(Continued)

OTHER PUBLICATIONS

Abignente et al., "Research on heterocyclic compounds. XVI. 2-Methylimidazo[1,2-a]pyrazine-3-carboxylic acids", *Chemical Abstracts Database*, 1985, Accession No. 103:87841.

(Continued)

*Primary Examiner*—James O. Wilson
*Assistant Examiner*—Cecilia M Jaisle
(74) *Attorney, Agent, or Firm*—Herbert L. Ley, III; Jay Z. Zhang; Myriad IP Dept.

(57) ABSTRACT

Reverse-turn mimetics and methods relating to the same having the following structure are disclosed:

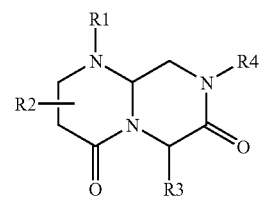

including pharmaceutically acceptable salts and stereoisomers thereof, wherein $R_1$, $R_2$, $R_3$ and $R_4$ are as defined herein. Such compounds have utility over a wide range of applications, including use as diagnostic and therapeutic agents. In particular, compounds of this invention, and pharmaceutical compositions containing such compounds, are neurokinin (tachykinin) antagonists. Libraries containing the reverse-turn mimetics of this invention are also disclosed.

65 Claims, 1 Drawing Sheet

U.S. PATENT DOCUMENTS

| | | | |
|---|---|---|---|
| 5,545,568 | A | 8/1996 | Ellman |
| 5,929,237 | A | 7/1999 | Kahn |
| 6,013,458 | A | 1/2000 | Kahn et al. |
| 6,184,223 | B1 | 2/2001 | Kahn et al. |
| 6,413,963 | B2 | 7/2002 | Kahn et al. |
| 6,548,500 | B2 | 4/2003 | Kahn et al. |

FOREIGN PATENT DOCUMENTS

| | | |
|---|---|---|
| WO | WO 1996/30396 | 10/1996 |
| WO | WO 1997/15557 | 5/1997 |
| WO | WO 1997/15577 | 5/1997 |
| WO | WO 1998/05333 | 2/1998 |
| WO | WO 1998/49168 | 11/1998 |
| WO | WO 2004/066947 | 8/2004 |

OTHER PUBLICATIONS

Antonov et al., "Activation of the Amide Grouping by Acylation", *Journal of General Chemistry of the USSR*, Oct. 1967, 37(10):2112-2120.

Barrow et al., "Spiroquinazoline, a novel substance P inhibitor with a new carbon skeleton, isolated from *Aspergillus flavipes*", *Chemical Abstracts Database*, 1994, Accession No. 121:129499.

Cutler et al., "Cinereain: a novel metabolite with plant growth regulating properties from *Botrytis cinerea*", *Chemical Abstracts Database*, 1988, Accession No. 109:165645.

Dennin et al., "Synthesis of derivatives of pyrazino[1,2-a]pyrimidin-4-ones", *Chemical Abstracts Database*, 1991, Accession No. 114:164135.

Faehnle et al., "Syntheses and reactions of peptide cyclols", *Chemical Abstracts Database*, 1985, Accession No. 102:7061.

Gatta et al., "New [f]-fused xanthines: synthesis of 1,3-dipropyl-1H-pyrazino, pyrido, pyrimido and pyrrolo [2,1-f]purine-2,4-diones", *Chemical Abstracts Database*, 1994, Accession No. 121:57444.

Jackson et al., "Potent α4β1 Peptide Antagonists as Potential Anti-Inflammatory Agents", *J. Med. Chem.*, Mar. 17, 1997, 40(21):3359-3368.

Kadam et al., "Fermentative manufacture of multiple drug resistance-attenuating ardeemins", *Chemical Abstracts Databse*, 1994, Accession No. 121:407435.

Kappe et al., "Cross-conjugated and pseudo-cross-conjugated mesomeric betaines. XVIII. Bicyclic mesoionic pyrimidines with cardiovascular activity", *Chemical Abstracts Database*, 1992, Accession No. 116:83634.

Ku et al., "Direct Design of a Potent Non-Peptide Fibrinogen Receptor Antagonist Based on the Structure and Conformation of a Highly Constrained Cyclic RGD Peptide", *J. Am. Chem. Soc.*, May 28, 1993, 115(19):8861-8862.

Lam et al., "A new type of synthetic peptide library for identifying ligand-binding activity", *Nature*, Nov. 7, 1991, 354:82-84.

Lucente et al., "Cyclization of Activated N-Benzyloxycarbonyl-tripeptides", *Tetrahedron Letters*, 1978, 11:1009-1012.

Lucente et al., "Synthesis and x-ray crystal structure of a tripeptidic cyclol", *Chemical Abstracts Database*, 1982, Accession No. 96:69410.

Numata et al., "Structures of cytotoxic substances and new quinazoline derivatives produced by a fungus from a saltwater fish", *Chemical Abstracts Database*, 1992, Accession No. 116:210833

Okawara et al., "Preparation and hydrogenolysis of fused piperazines by reaction of diamine and triamine derivatives with benzil. Application to the synthesis of terminal N-monoprotected triamines", *Chemical Abstracts Database*, 1992, Accession No. 117:191810.

Okawara et al., "Simple preparation of terminal N-monoprotected triamines using fused piperazines", *Chemical Abstracts Database*, 1991, Accession No. 114:101300.

Penn et al., "Biosynthesis of glyantrypine by *Aspergillus clavatus*," *Chemical Abstracts Database*, Accession No. 117:44249, 1992.

Penn et al., "Glyantrypine, a novel anthranilic acid-containing metabolite of *Aspergillus clavatus*", *Chemical Abstracts Database*, 1992, Accession No. 117:127875.

Pillay et al., "Molecular Mechanisms, Emerging Etiological Insights and Models to Test Potential Therapeutic Interventions in Alzheimer's Disease", *Current Alzheimer Research*, 2004, 1(4):295-306.

Pinnen et al., "Cyclization under mild conditions of anthraniloyl and N-methylanthraniloyl dipeptides", *Chemical Abstracts Database*, 1989, Accession No. 110:76029.

Pinnen et al., "Ten-membered cyclotripeptides: influence of the ring-flexibility on intramolecular reactions", *Chemical Abstracts Database*, 1985, Accession No. 102:132448.

Portegies et al., "AIDS Dementia Complex, Diagnosis and Drug Treatment Options", *CNS Drugs*, Jan. 1998, 9(1):31-40.

Rothe et al., "Cyclol formation during tripeptide cyclizations. Synthesis of a secondary cyclotripeptide, cyclo-(D-Phe-L-Pro-L-Pro)", *Chemical Abstracts Database*, 1982, Accession No. 97:56231.

Rothe et al., "Secondary all-L-cyclotripeptides", *Chemical Abstracts Database*, 1985, Accession No. 103:215766.

Sauter et al., "Novel basically substituted pyrimidines and benzothienopyrimidines", *Chemical Abstracts Database*, 1977, Accession No. 87:84931.

Souers et al., "Novel Inhibitors of α4β1 Integrin Receptor Interactions through Library Synthesis and Screening", *Bioorganic & Medicinal Chemistry Letters*, 1998, 8:2297-2302.

Tanaka et al., "Syntheses of pyrido[2,3-b]pyrazine derivaties", *Chemical Abstracts Database*, 1976, Accesson No. 84:31002.

The Merck Manual, Fifteenth Edition, 1987, pp. 1069-1083.

REVERSE-TURN MIMETICS AND COMPOSITIONS AND METHODS RELATING THERETO

RELATED APPLICATIONS

This application is a continuation-in-part of international patent application Ser. No. PCT/US2003/032411, filed Oct. 14, 2003, which is related to U.S. provisional application Ser. No. 60/419,657, filed Oct. 17, 2002, each of which are incorporated herein by reference in their entirety.

BACKGROUND OF THE INVENTION

1. Field of the Invention

The present invention relates generally to reverse-turn mimetics, as well as to compositions and methods related thereto.

2. Description of the Related Art

Reverse-turns comprise one of three classes of protein secondary structure and display three (gamma-turn), four (beta-turns), or more (loops) amino acid side chains in a fixed spatial relationship to each other. Reverse-turns have proven important in molecular recognition events (Rose et al., *Advances in Protein Chemistry* 37:1-109, 1985) and have engendered a burgeoning field of research into small molecule mimetics (e.g., Hanessian et al., *Tetrahedron* 53:12789-54, 1997). Many mimetics have either been external turn mimetics, which do not allow for the display of all the physiologically relevant side-chains (e.g., Freidinger et al., *Science* 210:656-58, 1980), or small, conformationally mobile cyclic peptide derivatives (e.g., Viles et al., *Eur. J. Biochem.* 242:352-62, 1996). However, non-peptide compounds have been developed, which closely mimic the secondary structure of reverse-turns found in biologically active proteins or peptides. For example, U.S. Pa. Nos. 5,475,085, 5,670,155 and 5,672,681 to Kahn all disclose conformationally constrained, non-peptidic compounds which mimic the three-dimensional structure of reverse-turns. More recently, U.S. Pat. No. 5,929,237 to Kahn, U.S. Pat. No. 6,013,458 to Kahn et al., U.S. Pat. No. 6,184,223 to Kahn et al., and U.S. Pat. No. 6,294,525 to Stasiak et al. disclosed additional, highly constrained bicyclic heterocycles as reverse-turn mimetics. Nevertheless, as no one template can mimic every type of turn, there remains a need in the art for reverse-turn templates.

Analgesia has historically been achieved in the central nervous system by opiates and analogs, which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (designated as neurokinin-1) are widely distributed throughout the mammalian nervous system (especially brain and spinal ganglia), the circulatory system and peripheral tissues (especially the duodenum and jejunum) and are involved in regulating a number of diverse biological processes. Such biological processes include sensory perception of olfaction, vision, audition and pain, movement control, gastric motility, vasodilation, salivation, and micturition (Pernow, *Pharmacol. Rev.* 35:85-141, 1983). Additionally, the neurokinin-1 and neurokinin-2 receptor subtypes are implicated in synaptic transmission (Laneuville et al., *Life Sci.* 42:1295-1305, 1988).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, the product of the oncogene ras, the yeast mating factor receptors, a Dictyostelium cAMP receptor, and receptors for other hormones and neurotransmitters (Hershey, *J. Biol. Chem.* 226:4366-73, 1991).

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to substance P, the known mammalian tachykinins include neurokinin A and neurokinin B. The current nomenclature designates the receptors for substance P, neurokinin A, and neurokinin B as neurokinin-1, neurokinin-2, and neurokinin-3 respectively.

More specifically, substance P is a neuropeptide that is produced in mammals and possesses a characteristic amino acid sequence (Chang et al., *Nature New Biol.* 232:86, 1971; Veber et al., U.S. Pat. No. 4,680,283). In mammals, substance P acts as a vasodilator, a depressant, stimulates salivation and produces increased capillary permeability. It is also capable of producing both analgesia and hyperalgesia, depending on dose and pain responsiveness of a mammal (Frederickson et al., *Science* 199:1359, 1978; Oehme et al., *Science* 208:305, 1980) and plays a role in sensory transmission and pain perception (Jessell et al., *Advan. Biochem. Psychopharmacol.* 28:189, 1981). For example, substance P is believed to be involved in the neurotransmission of pain sensations (Otsuka et al., "Role of Substance P as a Sensory Transmitter in Spinal Cord and Sympathetic Ganglia" in 1982 Substance P in the Nervous System, Ciba Foundation Symposium, 91, 13-34 (published by Pitman); Otsuka et al., *Trends Pharmacol. Sci.* 8:506-10, 1987), specifically in the transmission of pain in migraine (Sandberg et al., *J. Med. Chem.* 25:1009, 1982; Moskowitz et al., *Trends Pharmacol. Sci.* 13:307-11, 1992) and in arthritis (Levin et al., *Science* 226:547-49, 1984; Lotz et al., *Science* 235:893-95, 1987). Substance P may also play a role in demyelinating diseases such as multiple sclerosis and amyotrophic lateral sclerosis (Luber-Narod et al., poster C.I.N.P. XVIIIth Congress, $28^{th}$ Jun.-$2^{nd}$ Jul., 1992), and in disorders of bladder function such as bladder detrusor hyperreflexia (*Lancet,* $16^{th}$ May, 1239, 1992). Tachykinins have also been implicated in gastrointestinal (GI) disorders and diseases of the GI tract, such as inflammatory bowel disease (Mantyh et al., *Neuroscience* 25:817-37, 1988; Regoli in "Trends in Cluster Headache" Ed. F. Sicuteri et al., Elsevier Scientific Publisher, Amsterdam, pp. 85-95, 1987) and emesis (*Trends Pharmacol. Sci.* 9:334-41, 1988; Tatersall et al., *Eur. J. Pharmacol.* 250, R5—R6, 1993). It is also hypothesized that there is a neurogenic mechanism for arthritis in which substance P may play a role (Kidd et al., *Lancet, Nov.* 11, 1989; Gronblad et al., *J. Rheumatol.* 15:1807-10, 1988), and therefore, substance P is believed to be involved in the inflammatory response in diseases such as rheumatoid arthritis and osteoarthritis (O'Byrne et al., *Arthritis and Rheumatism* 33:1023-28, 1990).

Tachykinin receptor antagonists are believed to be useful for treatment of pain, headache (especially migraine), Alzheimer's disease, multiple sclerosis, attenuation of morphine withdrawal, cardiovascular changes, oedema, such as oedema caused by thermal injury, chronic inflammatory diseases, such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia (Maggi et al., *J. Auton. Pharmacol.* 13:23-93, 1993; Snider et al., *Chem. Ind.* 1:792-94, 1991). Other disease areas where tachykinin antagonists are useful include allergic conditions (Hamelet et al., *Can. J. Pharmacol. Physiol.* 66:1361-67, 1988), immunoregulation (Lotz et al., *Science* 241:1218-21, 1988; Kimball et al., *J. Immunol.* 141:3564-69, 1988; Perianin et al., *Biochem. Biophys. Res. Commun.* 161:520, 1989), postoperative pain and nausea (Bountra et al., *Eur. J. Pharmacol.* 249:R3—R4, 1993; Tattersall et al., *Neuropharmacology* 3:259-60, 1994), vasodilation, bronchospasm, reflex or neuronal control of the viscera (Mantyh et al., *Proc. Natl. Acad. Sci. USA* 85:3235-39, 1988) and, by arresting or slowing β-amyloid-mediated neurodegenerative changes (Yankner et al., *Science* 250:279-82, 1990) in senile dementia of the Alzheimer type, Alzheimer's disease and Downs Syndrome. Tachykinin antagonists may also be useful in the treatment of small cell carcinomas, in particular small cell lung cancer (SCLC) (Langdon et al., *Cancer Research* 52:4554-57, 1992). It is further-believed that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement of suppression such as systemic lupus erythmatosus (EP Pat. No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EP Pat. No. 0,394,989).

Substance P receptor antagonists may be useful in mediating neurogenic mucus secretion in mammalian airways and hence provide treatment and symptomatic relief in diseases characterized by mucus secretion, in particular, cystic fibrosis (Ramnarine et al., abstract presented at 1993 ALA/ATS Int'l Conference, 16-19 May 1993, published in *Am. Rev. of Respiratory Dis.*, May 1993). Neurokinin-1 receptor antagonists alone or in combination with bradykinin receptor antagonists are also believed to be useful in the prevention and treatment of inflammatory conditions in the lower urinary tract, especially cystitis (Giuliani et al., *J. Urology* 150:1014-17, 1993). Furthermore, antagonists selective for the neurokinin-1 and/or neurokinin-2 receptor may be useful in the treatment of asthmatic disease (Frossard et al., *Life Sci.* 49:1941-53, 1991; Advenier et al., *Biochem. Biophys. Res. Comm.* 184:1418-24, 1992; Barnes et al., *Trends Pharmacol. Sci.* 11:185-89, 1993).

The following documents relate to compounds that are reported to exhibit activity as neurokinin antagonists: U.S. Pat. No. 6,194,406; U.S. Pat. No. 6,191,135; U.S. Pat. No. 6,177,450; U.S. Pat. No. 6,147,083; U.S. Pat. No. 6,114,315; U.S. Pat. No. 6,110,919; U.S. Pat. No. 6,063,926; U.S. Pat. No. 6,048,859; EP Pat. No 1,099,446; EP Pat. No 1,110,958; Published PCT WO200125219; and Published PCT WO200144200.

While significant advances have been made in the synthesis and identification of conformationally constrained, reverse-turn mimetics, there is still a need in the art for small molecules that mimic the secondary structure of peptides. There is also a need in the art for libraries containing such members, particularly those small templates capable of supporting a high diversity of substituents. In addition, there is a need in the art for techniques for synthesizing these libraries and screening the library members against biological targets to identify bioactive library members. Further, there is a need in the art for small, orally available inhibitors of neurokinins, for use in treating inflammatory diseases, central nervous system disorders, certain respiratory diseases, as well as other disorders. In particular there is a need for inhibitors of neurokinin-1, neurokinin-2, and neurokinin-3, for use in the treatment or prevention of various mammalian disease states such as, for example, asthma, cough, chronic obstructive pulmonary disease (COPD), bronchospasm, emesis, neurodegenerative disease, ocular disease, inflammatory diseases such as arthritis, central nervous system conditions such as anxiety, migraine and epilepsy, nociception, psychosis, and/or various gastrointestinal disorders such as Crohn's disease.

The present invention fulfills these needs and provides further related advantages.

SUMMARY OF THE INVENTION

In brief, the present invention is directed to compounds that generally mimic the secondary structure of reverse-turn regions of biologically active peptides and proteins, as well as to compositions containing one or more of such compounds and to the use of such compounds and compositions for the prevention and treatment of central nervous system disorders, neurodegenerative disorders, respiratory diseases, inflammatory diseases, depression and various other conditions which are characterized by the presence of an excess substance P activity.

The compounds of the invention have the following Structure (I):

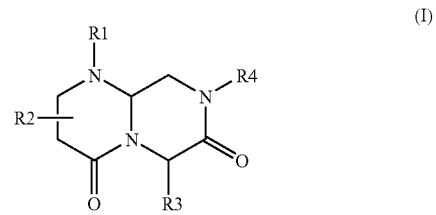

including pharmaceutically acceptable salts and stereoisomers thereof, wherein $R_1$, $R_2$, $R_3$ and $R_4$ are as defined below.

In another embodiment, libraries are disclosed containing compounds of Structure (I), as well as methods for synthesizing such libraries and methods for screening the same to identify biologically active compounds. Methods of use for treating cell-adhesion-mediated diseases with the compounds of this invention and compositions comprising them are also disclosed. Further, methods of use for treatment and prevention of inflammatory and central nervous system disorders, as well as several other disorders with the compounds of this invention and compositions comprising them are also disclosed.

These and other aspects of this invention will be evident upon reference to the following detailed description. To this end, various references are set forth herein which describe in more detail certain procedures, compounds and/or compositions, and are incorporated by reference in their entirety.

DETAILED DESCRIPTION OF THE INVENTION

Figure 1:
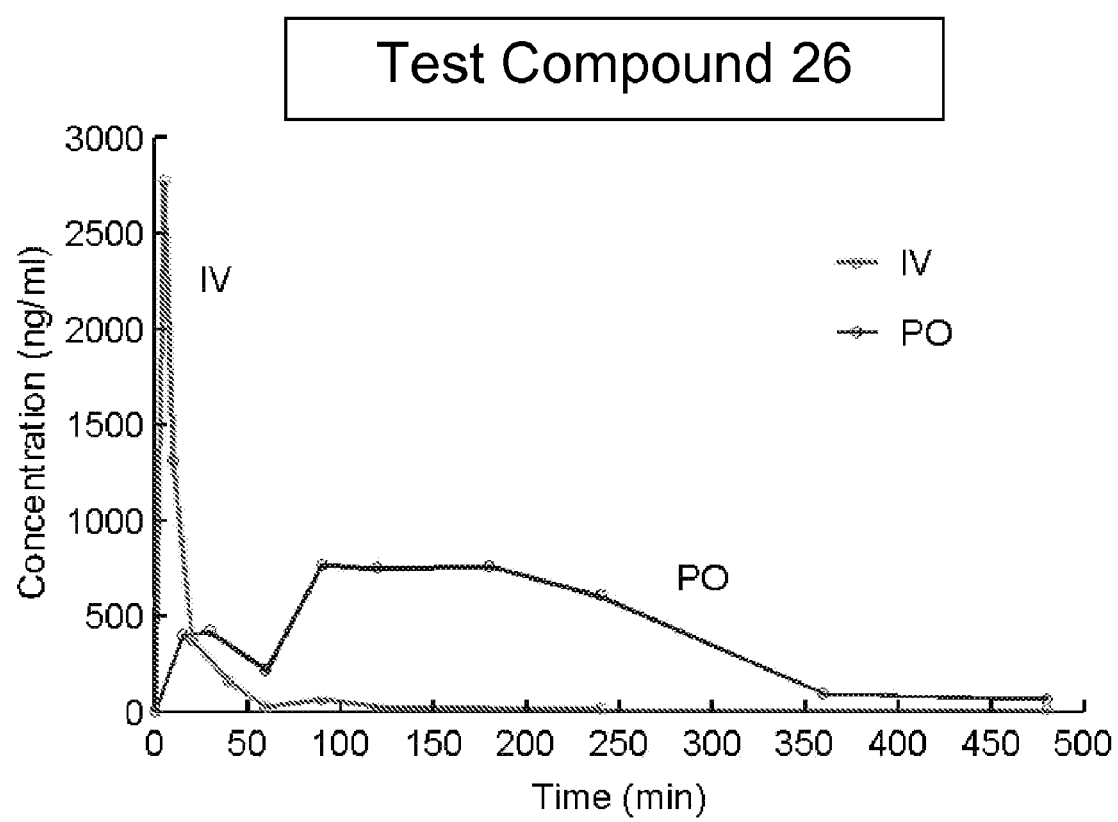
FIG. 1 illustrates bioavailability in monkeys of a representative reverse-turn mimetic of this invention.

As noted above, this invention is directed to compounds that generally mimic the secondary structure of reverse-turns, as well as to chemical libraries containing such compounds. Such compounds are useful as bioactive agents, including (but not limited to) use as diagnostic, prophylactic and/or therapeutic agents, especially as anti-inflammatory agents, for central nervous system disorders, and as well as several other disorders. The libraries of this invention are useful in the identification of such bioactive agents, and may contain from tens to hundreds to thousands (or greater) of individual compounds (also referred to herein as "members").

In one embodiment of the present invention, compounds are disclosed having the following Structure (I):

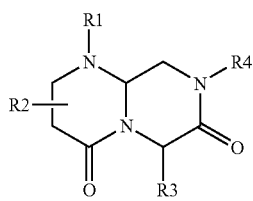

or a pharmaceutically acceptable salt or stereoisomer thereof,
wherein
$R_1$ is —X—$R_5$, where X is —C(=O)—, —C(=O)O—, —C(=O)NH— or —SO$_2$—, and $R_5$ is an amino acid side chain moiety or amino acid side chain derivative;

$R_2$ is hydrogen or —Y—$R_6$, where Y is a direct bond, —NH—, —NHC(=O)—, —NHC(=O)O—, —NHC(=O)NH— or —NHSO$_2$—, and $R_6$ is an amino acid side chain moiety or amino acid side chain derivative;

$R_3$ is —Z—$R_7$, where Z is a direct bond, —(CH$_2$)$_m$C(=O)NR$_8$—, —(CH$_2$)$_k$NHC(=O)— or —(CH$_2$)$_k$NHC(=O)NR$_8$—, $R_7$ and $R_8$ are independently amino acid side chain moieties or amino acid side chain derivatives, m is an integer from 1 to 4 and k is 1 or 2;

$R_4$ represents the remainder of the compound; and wherein any two adjacent CH groups (i.e., CH—CH) or adjacent NH and CH groups (i.e., NH—CH) of the fused bicyclic compound optionally form a double bond (i.e., C=C or N=C, respectively).

As used herein, an "amino acid side chain moiety" refers to any amino acid side chain moiety present in naturally occurring alpha-amino acids and other "non-protein" amino acids commonly utilized by those in the peptide chemistry arts when preparing synthetic analogues of naturally occurring peptides, including D and L forms. The "non-protein" amino acids refer to unnatural alpha-amino acids, beta-amino acids and gamma-amino acids commonly utilized by those in the peptide chemistry arts when preparing synthetic analogues of naturally occurring peptides, including D and L forms. Amino acid side chain moieties include, for example, the naturally occurring amino acid side chain moieties set forth in Table 1. Other naturally occurring amino acid side chain moieties include (but are not limited to) the side chain moieties of 3,5-dibromotyrosine, 3,5-diiodotyrosine, hydroxylysine, γ-carboxyglutamate, phosphotyrosine, phosphothreonine and phosphoserine. In addition, glycosylated amino acid side chains may also be used in the practice of this invention, including (but not limited to) glycosylated threonine, serine, glutamine and asparagine.

TABLE 1

Amino Acid Side Chain Moieties

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_2$ | Lysine |
| —(CH$_2$)$_3$NHC(NH$_2$)NH$_2$ | Arginine |
| —CH$_2$-(imidazole) | Histidine |
| —CH$_2$COOH | Aspartic acid |
| —CH$_2$CH$_2$COOH | Glutamic acid |
| —CH$_2$CONH$_2$ | Asparagine |
| —CH$_2$CH$_2$CONH$_2$ | Glutamine |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| —HN-(pyrrolidine) | Proline |
| —HN-(hydroxypyrrolidine)-OE | Hydroxyproline |

An "amino acid side chain derivative" represents modifications and/or variations to amino acid side chain moieties. For example, representative amino acid side chain derivatives include (but are not limited to) hydroxy, hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, propargyl-glycine, 1,2,4-triazolo- 3-alanine, 4,4,4-trifluoro-threonine, thyronine, 6-hydroxytryptophan, 5-hydro-xytryptophan, 3-hydroxykynurenine, 3-aminotyrosine, trifluoromethyl-alanine, 2-thienylalanine, (2-(4-pyridyl)ethyl)cysteine, 3,4-dimethoxy-phenylalanine, 3,5-bis-trifluoromethyl-phenylalanine, 3-(2-thiazolyl)-alanine, ibotenic acid, 1-amino-1-cyclopentane-carboxylic acid, 1-amino-1-cyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of lower alkyl, lower alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phosphotyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine, and the like. Any of these "amino acid side chain derivative" maybe substituted with a methyl group at the alpha, beta or gamma positions, a halogen at any aromatic residue on the amino side chain, or an appropriate protective group at the O, N, or S atoms of the side chain moieties. Appropriate protective groups are disclosed in "Protective Groups In Organic Synthesis," T. W. Greene and P. G. M. Wuts, J. Wiley & Sons, NY, N.Y., 1991.

In addition, the amino acid side chain moieties of alanine, valine, leucine, isoleucine and phenylalanine may generally be classified as alkyl, aryl, or arylalkyl moieties, optionally substituted with one or more substituents as defined below. Similarly, the amino acid side chain moieties of histidine, tryptophan, proline and hydroxyproline may generally be classified as heterocycle or heterocyclealkyl moieties, optionally substituted with one or more substituents as defined below. Accordingly, and as used herein, "amino acid side chain derivatives" also include substituted or unsubstituted alkyl, aryl, arylalkyl, heteroaryl, heteroarylalkyl, heterocycle and heterocyclealkyl moieties.

"Alkyl" means a straight chain or branched, cyclic or noncyclic, saturated or unsaturated alkyl containing from 1 to 12 carbon atoms. Similarly, a "lower alkyl" is as defined above, but contains from 1 to 4 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclohexyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like. Representative unsaturated cyclic alkyls include cyclopentenyl, cyclohexenyl, —CH$_2$cyclohexenyl, and the like.

"Aryl" means an aromatic carbocyclic moiety such as phenyl and naphthyl.

"Arylalkyl" means an alkyl having at least one alkyl hydrogen atom replaced with an aryl moiety, such —CH$_2$(aryl) (e.g., benzyl), —(CH$_2$)$_2$(aryl), —(CH$_2$)$_3$(aryl), —CH(aryl)$_2$, and the like.

"Heteroaryl" means an aromatic heterocycle ring of 5 to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, and the like.

"Heteroarylalkyl" means an alkyl having at least one alkyl hydrogen atom replaced with a heteroaryl moiety, such as —CH$_2$(heteroaryl), and the like.

"Heterocycle" means a 5 to 7 membered monocyclic, or 7 to 10 membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydrothienyl, tetrahydrothiopyranyl, tetrahydropyrimidinyl, and the like.

"Heterocyclealkyl" means an alkyl having at least one alkyl hydrogen atom replaced with a heterocycle moiety, such as —CH$_2$(heterocycle), —(CH$_2$)$_2$(heterocycle) and the like.

The term "substituted" as used herein means any of the above groups—that is, alkyl, aryl, arylalkyl, heteroaryl, heteroarylalkyl, heterocycle or heterocyclealkyl—wherein at least one hydrogen atom is replaced with a substituent. In the case of an oxo substituent ("=O"), two hydrogen atoms are replaced. A "substituent" in this regard is halogen (such as F, Cl, Br, and I), oxo, hydroxy, haloalkyl (such as trifluoromethyl, —CH$_2$F$_2$—CF$_2$CF$_3$, and the like), —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl (wherein the substituent is as defined above), or wherein any two R groups attached to the same nitrogen atom, taken together with the nitrogen atom to which they are attached, form a heterocycle or a substituted heterocycle (wherein the substituent is as defined above).

Unless specifically stated otherwise or indicated by a bond symbol (dash or double dash), the connecting point to a recited group will be on the right-most stated group. Thus, for example, a hydroxyalkyl group is connected to the main structure through the alkyl and the hydroxyl is a substituent on the alkyl.

"Haloalkyl" means an alkyl having at least one alkyl hydrogen atom replaced with halogen.

"Aminoalkyl" means an alkyl having at least one alkyl hydrogen atom replaced with an amino (—NH$_2$) group, such as —CH$_2$NH$_2$, or —NH(alkyl) such as —NH(methyl), and the like.

"Alkoxy" means —O-alkyl, such as methoxy, ethoxy, n-propoxy, n-butoxy, n-pentoxy, isopropoxy, sec-butoxy, and the like.

"Aryloxy" means —O-aryl, such as phenoxy, and the like

"Arylalkoxy" means —O-(arylalkyl), such as benzoxy, and the like.

A "peptide" means at least two naturally or unnaturally occurring alpha-amino acids joined via a peptide bond. Depending upon the number of amino acids joined via peptide bonds, the resulting peptide may also be referred to as a "polypeptide" or "protein." Similarly, a "peptide derivative" means a peptide which has been covalently modified and/or which contains amino acids other than alpha-amino acids. Representative peptide derivatives include peptides which are N-alkylated, N-acylated or N-sulfonylated at the amino termini, with, for example, methyl, benzyl, acetyl, benzoyl, methanesulfonyl, phenylsulfonyl, allyloxycarbonyl, t-butyloxycarbonyl, benzyloxycarbonyl, or fluorenyloxycarbonyl moieties; peptides in which the carboxy termini are esterified (methyl, ethyl, benzyl) or reduced to hydroxy or aldehyde; peptides which are N-alkylated at peptide bonds with, for example, methyl or 2-hydroxy-4-methoxybenzyl; and peptides which incorporate beta- or gamma-amino acids such as beta-alanine or gamma-aminobutyric acid.

A "linker" is any covalent bridging moiety that facilitates linkage of a compound of Structure (I), through the respective R$_1$, R$_2$, R$_3$ and/or R$_4$ moiety, to another moiety, agent, compound, solid support, molecule, amino acid, peptide or protein. For example, the compounds of this invention may be linked to one or more known compounds, such as biotin, for use in diagnostic or screening assays. Furthermore, one (or more) of R$_1$, R$_2$, R$_3$ or R$_4$ may be a linker joining the compound of Structure (I) to a solid support (such as a support used in solid phase peptide synthesis). Examples of such linkers include p-alkoxybenzyl alcohol, phenylacetamidomethyl, and 2-chlorotrityl chloride.

A "solid support" means any composition of matter to which another compound is attached directly or attached through a linker and which is insoluble in at least one solvent that the attached compound is soluble in. Alternatively, a "solid support" may be a composition of matter with similar solubility characteristics to the attached compound, but which may be readily precipitated from solution and filtered off as a solid. Representative examples include polystyrene, polyethylene glycol, polystyrene grafted with polyethylene glycol, polyacrylamide, polyamide-polyethylene glycol copolymer, controlled-pore glass, and silica.

The phrase "remainder of the compound" means any moiety, agent, compound, solid support, molecule, linker, amino acid, peptide or protein covalently attached to the reverse-turn mimetic at the R$_4$ position, including amino acid side chain moieties, amino acid side chain derivatives, and peptide derivatives as defined above. Accordingly, in an alternative depiction of Structure (I), the bond between the ring nitrogen atoms and the corresponding R$_4$ moiety may be left undefined, as represented by the following Structure (I'):

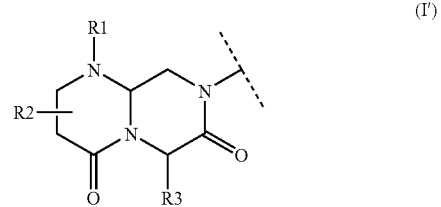

wherein "-----" represents the remainder of the compound joined to the corresponding ring nitrogen through a covalent bond, and R$_1$, R$_2$ and R$_3$ are as defined above.

The compounds of Structure (I) may have chiral centers and may occur as racemates, racemic mixtures and as individual enantiomers or diastereomers. Such compounds may also possess axial chirality which may result in atropisomers. All such isomeric forms are included within the term "stereoisomer", including any and all mixtures thereof. For example, a solid line designation for attachment of the various R groups to a carbon atom on the fused bicyclic ring indicates that these R groups may lie either above or below the plane of the page. If a compound is intended to mimic a reverse-turn of naturally occurring amino acids (i.e., "L-amino acids"), the R groups would generally lie below the plane of the page (i.e., "⋯⋯||R") in Structure (I). However, if the reverse-turn mimetic of this invention is intended to mimic a reverse-turn containing one or more D-amino acids, then the corresponding R group or groups would lie above the plane of the page (i.e., "◀▬▬R") in Structure (I).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof. Thus, the term "pharmaceutically acceptable salt" of Structure (I) is intended to encompass any and all acceptable salt forms.

Depending upon the choice of the R$_2$ group, in further embodiments of Structure (I), compounds of this invention have Structure (II) when R$_2$ is hydrogen, or have Structures (III) or (IV) when R$_2$ is not hydrogen:

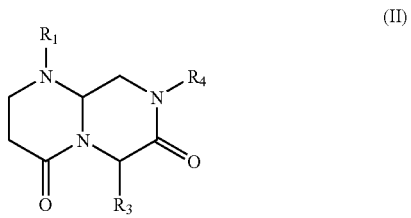

-continued

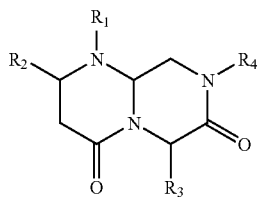
(III)

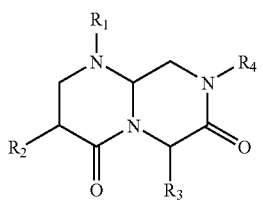
(IV)

In more specific embodiments of Structure (II), compounds of this invention have the following conformations (V), (VI) or (VII):

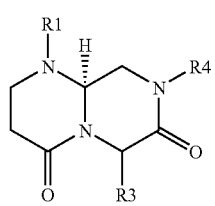
(V)

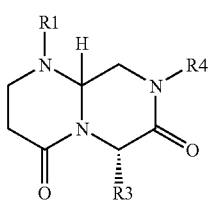
(VI)

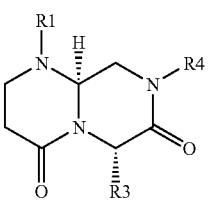
(VII)

Similarly, in more specific embodiments of Structure (III), compounds of this invention have the following conformations (VIII), (IX), (X), (XI), (XII), (XIII), (XIV) or (XV):

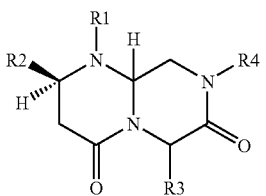
(VIII)

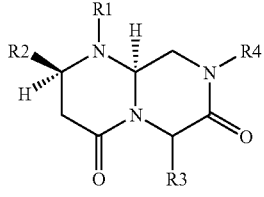
(IX)

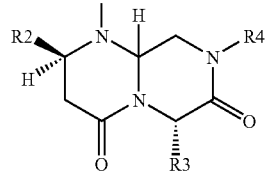
(X)

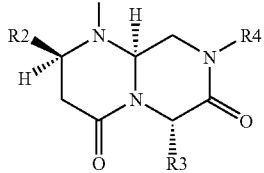
(XI)

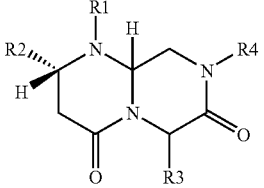
(XII)

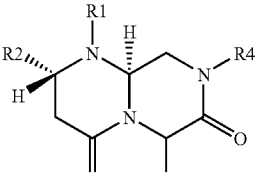
(XIII)

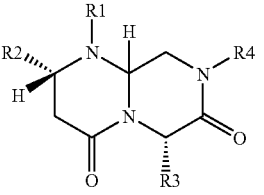
(XIV)

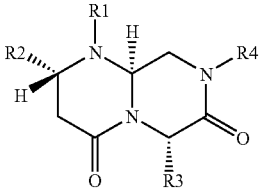
(XV)

Similarly in more specific embodiments of Structure (IV), compounds of this invention have the following conformations (XVI), (XVII), (XVIII), (XIX), (XX), (XXI), (XXII) or (XXIII):

(XVI) 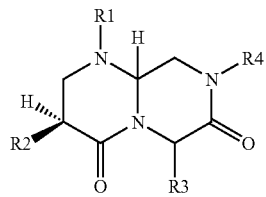

(XVII) 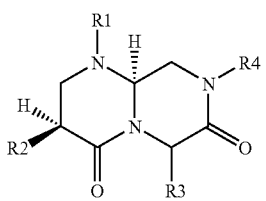

(XVIII) 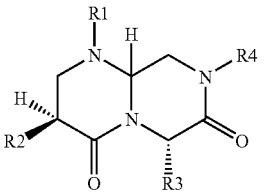

(XIX) 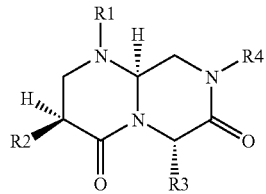

(XX) 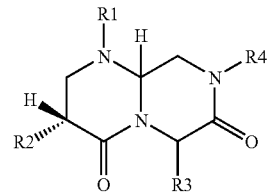

(XXI) 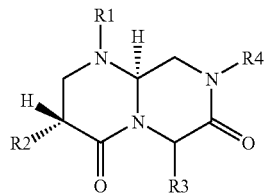

(XXII) 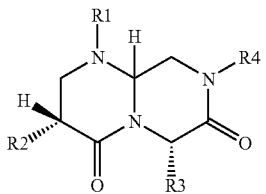

(XXIII) 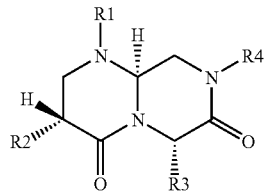

In still more specific embodiments of Structure (I), as well as the more specific embodiments of Structures (II), (III) and (IV):

$R_1$ is
(1) —C(=O)O—$R_5$,
(2) —C(=O)NH—$R_5$,
(3) —SO$_2$—$R_5$, or
(4) —C(=O)—$R_5$,
wherein
$R_5$ is $R_{1a}$, $R_{1b}$, $R_{1c}$, $R_{1d}$ or $R_{1e}$;
$R_{1a}$ is
(1) alkyl, or
(2) aminoalkyl,
wherein alkyl or aminoalkyl are optionally and independently substituted with one or more substituents independently selected from $R_s$ and $R_t$;
$R_{1b}$ is —(CH$_2$)$_1$—NR$_d$R$_e$;
$R_{1c}$ is
(1) aryl,
(2) arylalkyl, or
(3) Het,
wherein aryl, arylalkyl or Het are optionally and independently substituted with one or more substituents independently selected from $R_s$ and $R_t$;
$R_{1d}$ is
(1) phenyl, or
(2) benzyl,
wherein phenyl and benzyl are optionally and independently substituted with one or more substituents independently selected from $R_s$ and $R_t$;
$R_{1e}$ is 3,5-bistrifluoromethylbenzyl;
$R_2$ is
(1) hydrogen,
(2) —NHR$_6$,
(3) —NHC(=O)R$_6$,
(4) —NHC(=O)OR$_6$,
(5) —NHC(=O)NHR$_6$,
(6) —NHSO$_2$R$_6$, or
(7) —R$_6$,
wherein R$_6$ is R$_e$ and is optionally substituted with one or more substituents independently selected from $R_s$ and $R_t$;
$R_3$ is
(1) —(CH$_2$)$_m$C(=O)N(R$_7$R$_8$),
(2) —(CH$_2$)$_k$NHC(=O)R$_7$,
(3) —(CH$_2$)$_k$NHC(=O)N(R$_7$R$_8$), or
(4) —R$_7$,
wherein R$_7$ and R$_8$ are each independently selected from R$_e$ and are optionally and independently substituted with one or more substituents independently selected from $R_s$ and $R_t$;
R4 is
(1) alkyl,
(2) aminoalkyl,
(3) aryl, (4) arylalkyl,
(4) Het,
(5) —(CH$_2$)$_m$NH(C═O)-aryl, or
(6) —(CH$_2$)$_m$NR$_d$R$_e$,
  wherein alkyl, aminoalkyl, aryl, arylalkyl and Het are optionally and independently substituted with one or more substituents independently selected from R$_s$ and R$_t$;

R$_s$ is
(1) halogen,
(2) hydrogen,
(3) haloalkyl,
(4) —CN,
(5) —CF$_3$,
(6) —C(═O)OR$_d$,
(7) —C(═O)R$_d$,
(8) —C(═NR$_d$)(NR$_d$R$_e$),
(9) —NR$_d$R$_e$,
(10) —NR$_d$C(═O)R$_e$,
(11) —NR$_d$C(═O)OR$_e$,
(12) —NR$_d$C(═O)NR$_d$R$_e$,
(13) —NO$_2$,
(14) —OCF$_3$,
(15) —OR$_d$,
(16) —OC(═O)R$_d$,
(17) —OC(═O)NR$_d$R$_e$,
(18) —SR$_d$,
(19) —S(O)$_k$R$_d$,
(20) —S(O)$_2$OR$_d$,
(21) —S(O)$_k$NR$_d$R$_e$, or
(22) a group selected from R$_t$;

R$_t$ is
(1) alkyl,
(2) alkoxy,
(3) aryloxy,
(4) arylalkoxy, or
(5) a group selected from R$_s$,
  wherein alkyl, alkoxy, aryloxy, and arylalkoxy are optionally and independently substituted with one or more substituents selected from R$_s$;

R$_d$ and R$_e$ are independently selected from hydrogen, alkyl (including alkenyl and alkynyl), aminoalkyl, aryl, arylalkyl and Het;

R$_d$ and R$_e$ taken together with the atoms to which they are attached form a mono- or bi-cyclic heterocyclic ring of 3 to 7 members containing 0 to 3 additional heteroatoms independently selected from nitrogen, oxygen and sulfur;

k is an integer from 1 to 2;
l is an integer from 1 to 10;
m is an integer from 1 to 4; and
Het is heterocycle, heterocyclealkyl, heteroaryl or heteroarylalkyl.

In still more specific embodiments of the foregoing:

R$_{1a}$ is

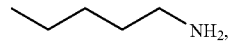
(1)

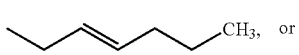
(2)

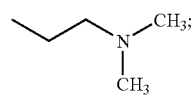
(3)

R$_{1c}$ is

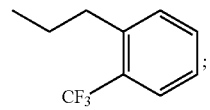

R$_{1d}$ is

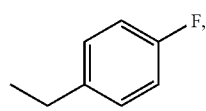
(1)

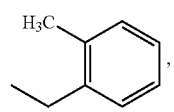
(2)

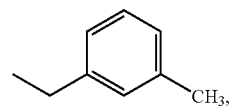
(3)

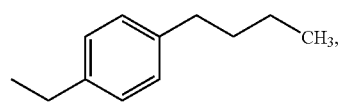
(4)

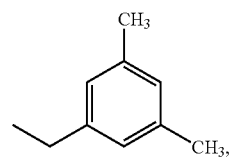
(5)

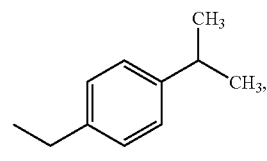
(6)

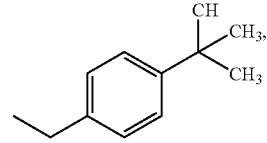
(7)

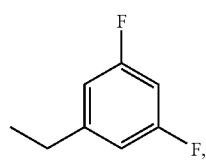
(8)

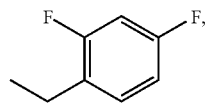
(9)

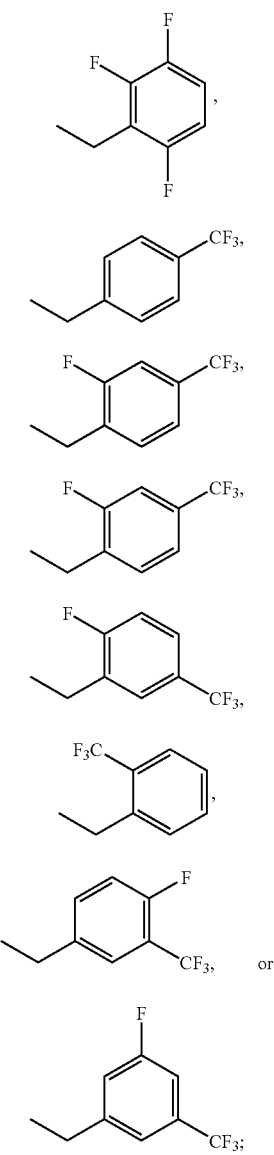
$R_{1e}$ is 3,5-bistrifluoromethylbenzyl;
$R_2$ is
(1) hydrogen,
(2) methyl,
(3) ethyl,
(4) propyl,
$R_3$ is
(1) hydrogen,
(2) methyl,
(3) ethyl,
(4) 1-propyl,
(5) 2-propyl,
(6) n-butyl,
(7) 2-butyl,

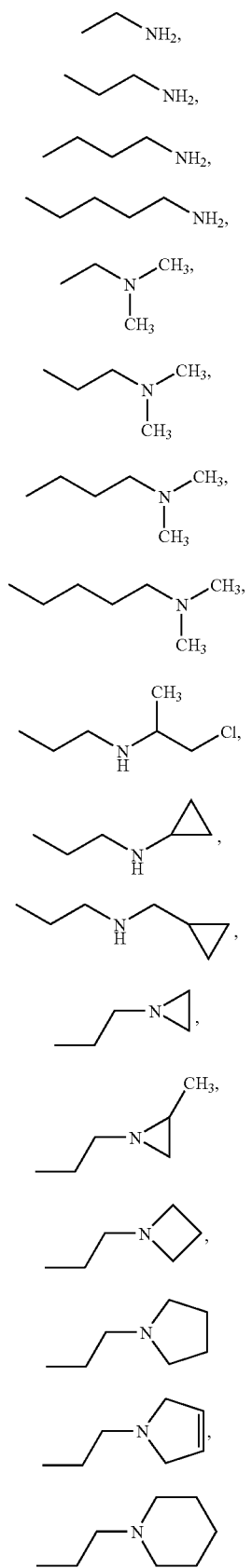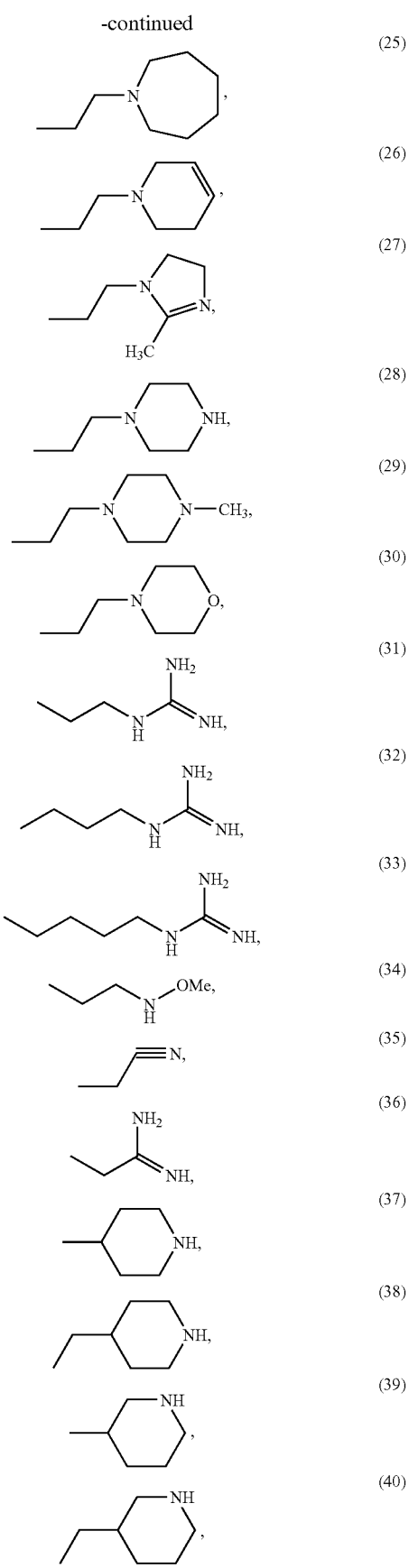

-continued
(41) 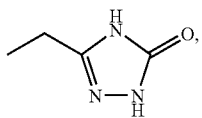
(42) 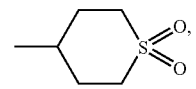
(43) 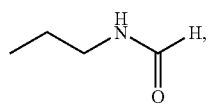
(44) 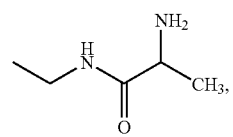
(45) 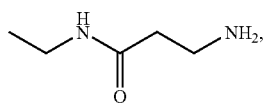
(46) 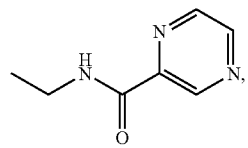
(47) 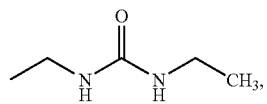
(48) 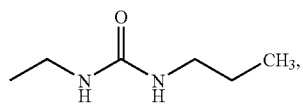
(49) 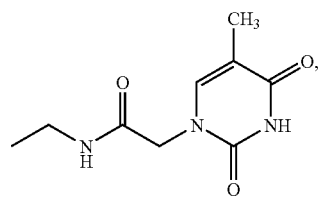
(50) 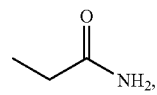
(51) 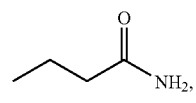
(52) 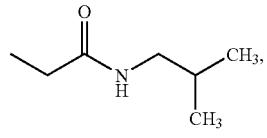
-continued
(53) 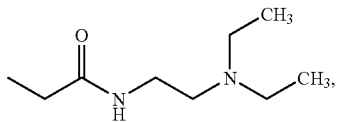
(54) 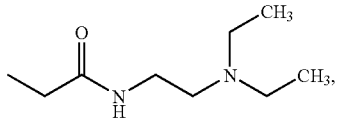
(55) 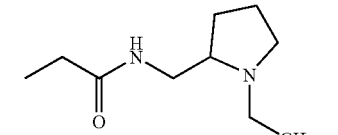
(56) 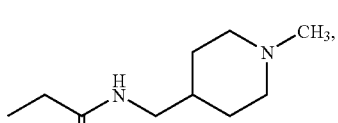
(57) 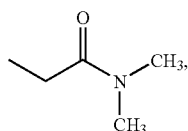
(58) 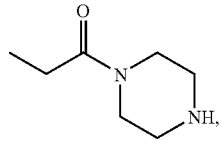
(59) 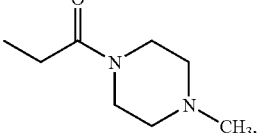
(60) 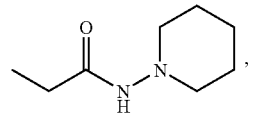
(61) 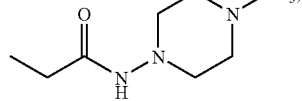
(62) 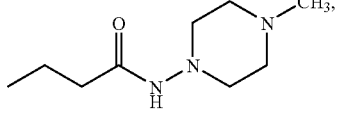
(63) 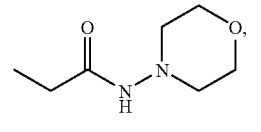

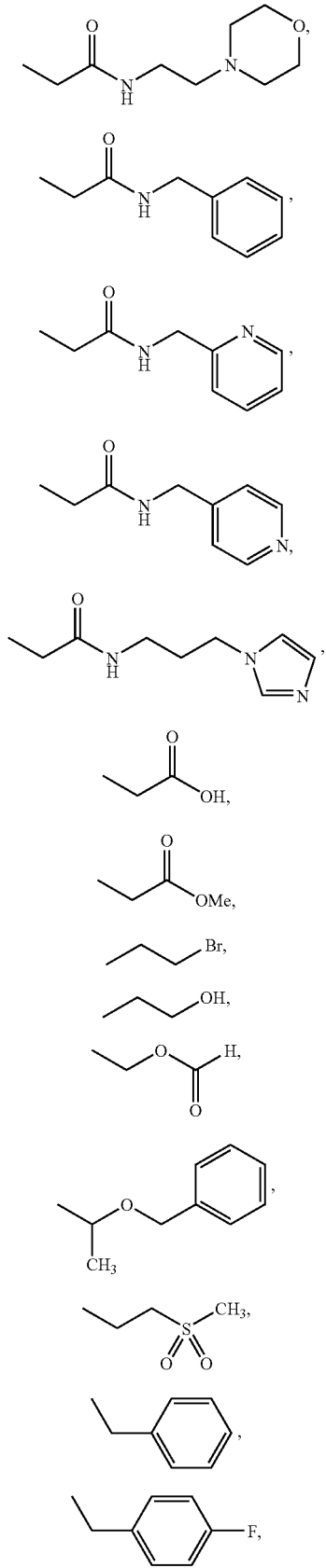
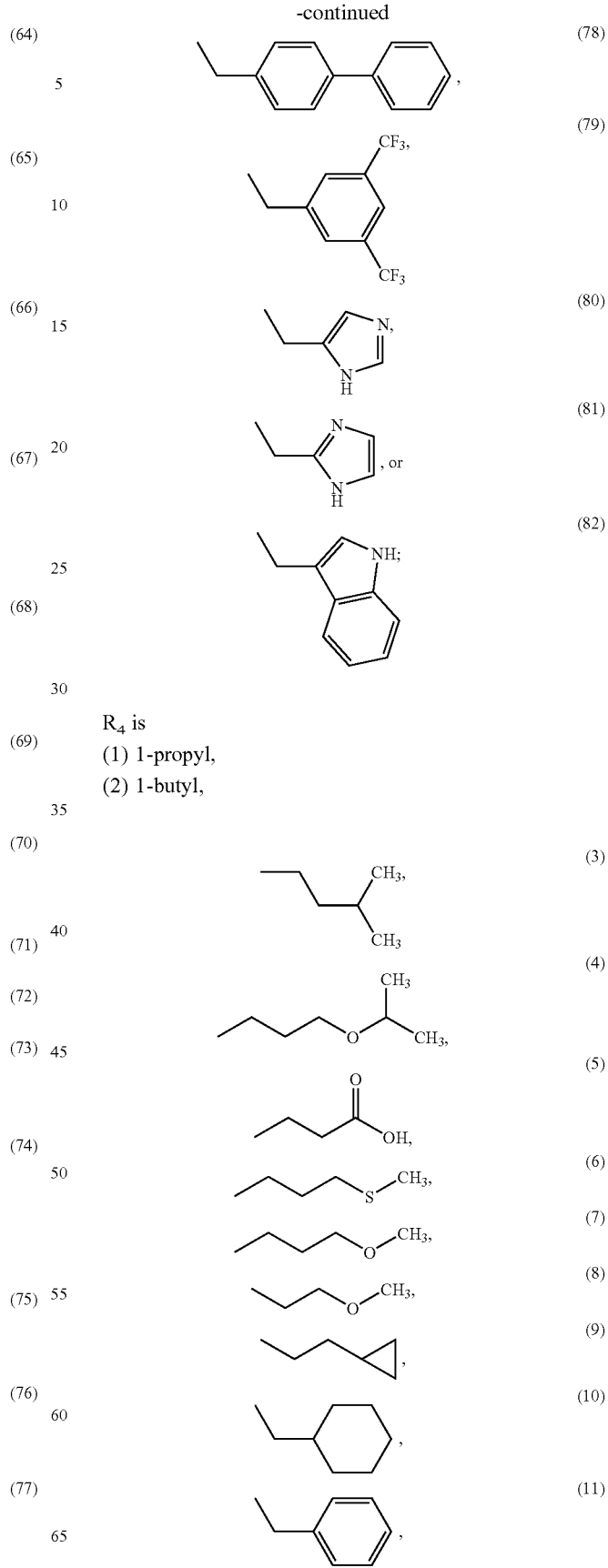
$R_4$ is
(1) 1-propyl,
(2) 1-butyl,

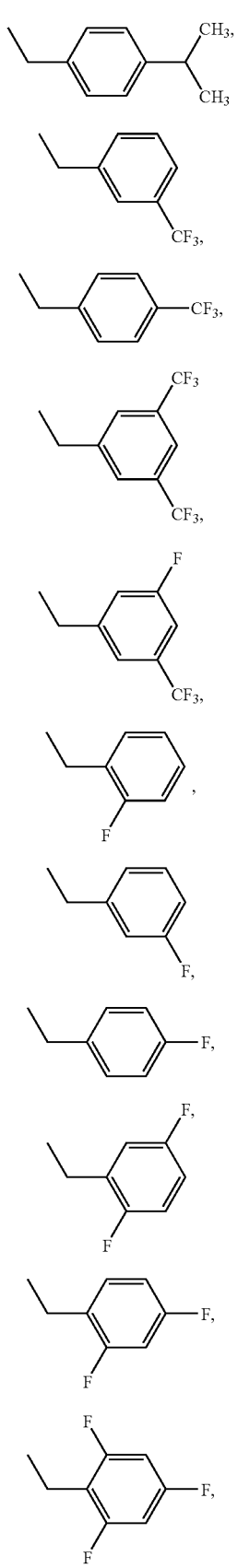
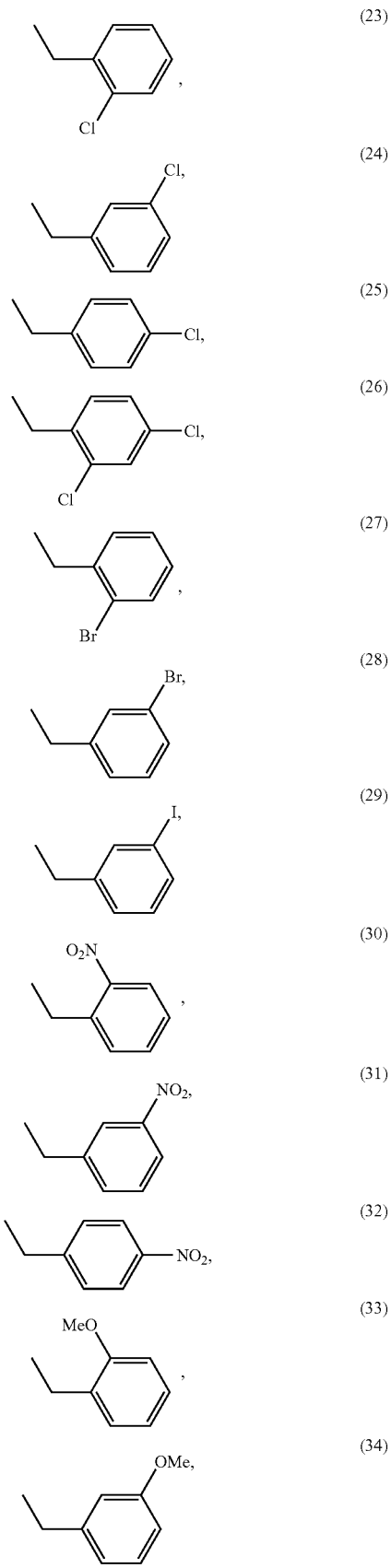

-continued
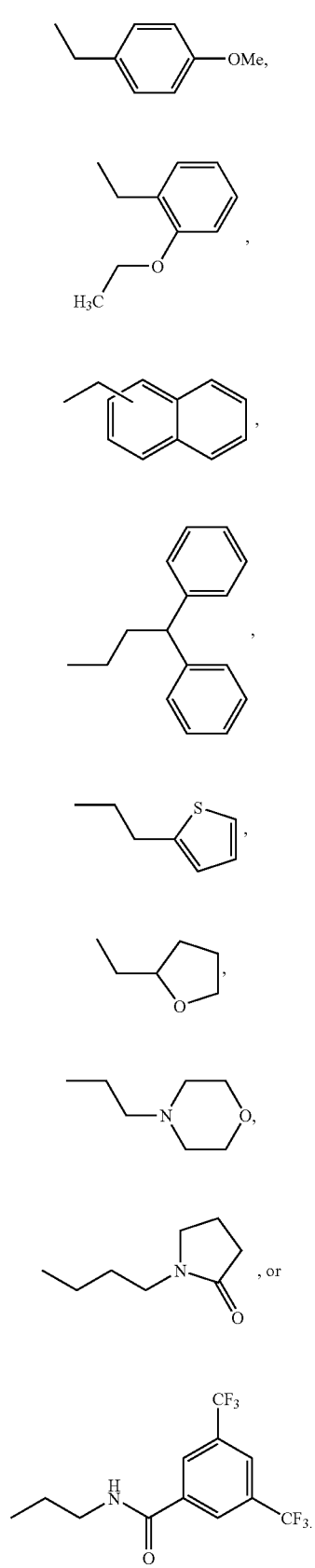
Representative compounds of this invention include (but are not limited to) the compounds set forth in Table 2.
TABLE 2
Representative Compounds
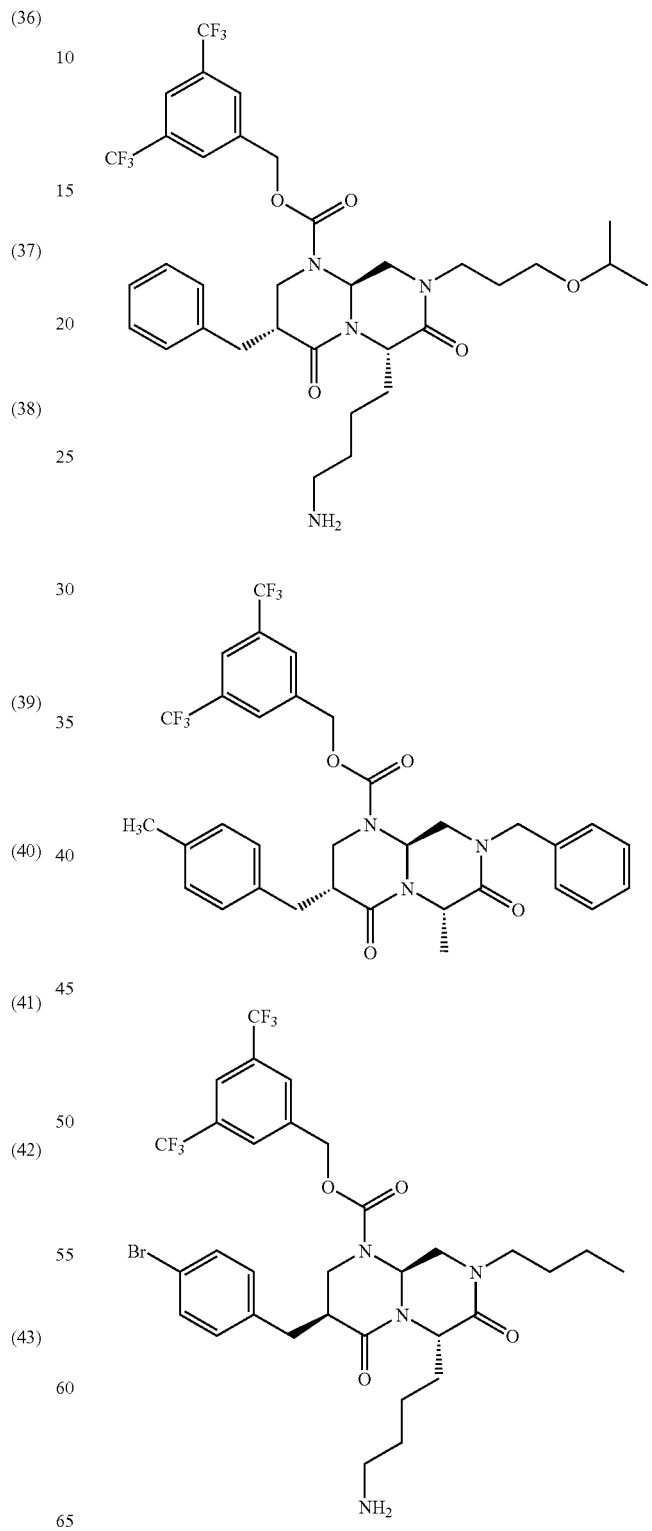

TABLE 2-continued
Representative Compounds
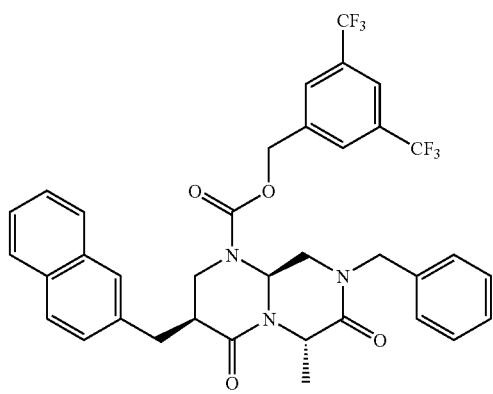
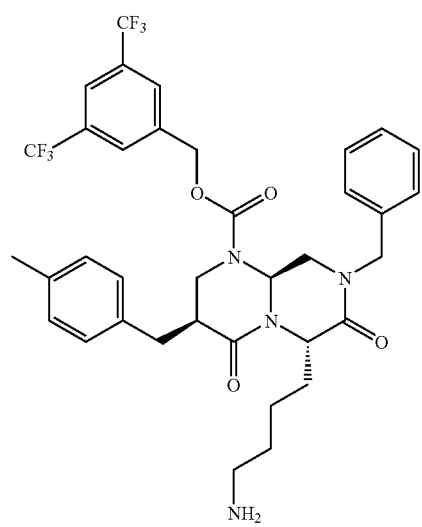
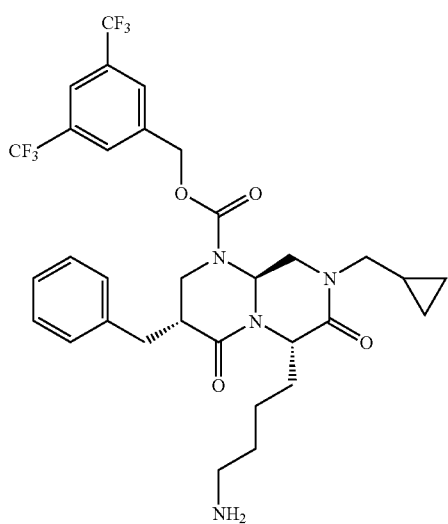
TABLE 2-continued
Representative Compounds
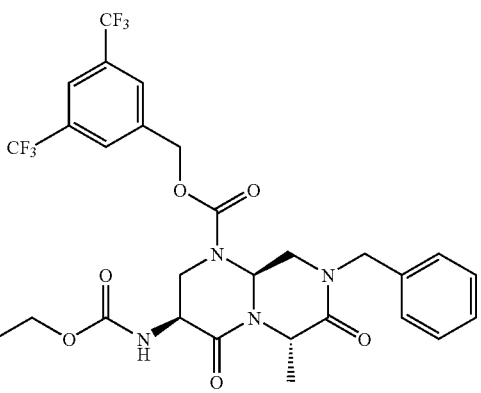
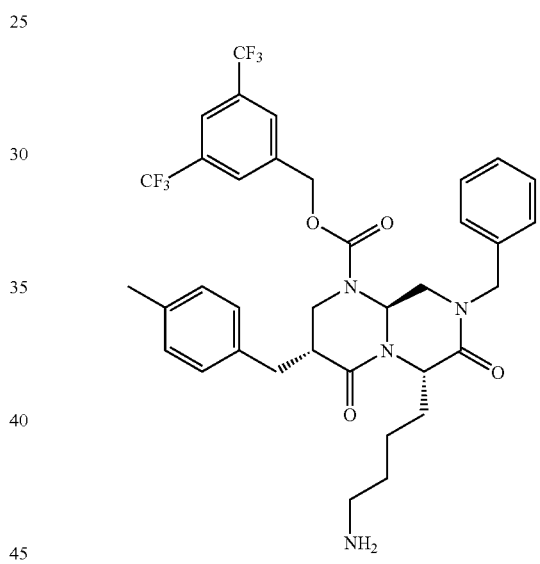
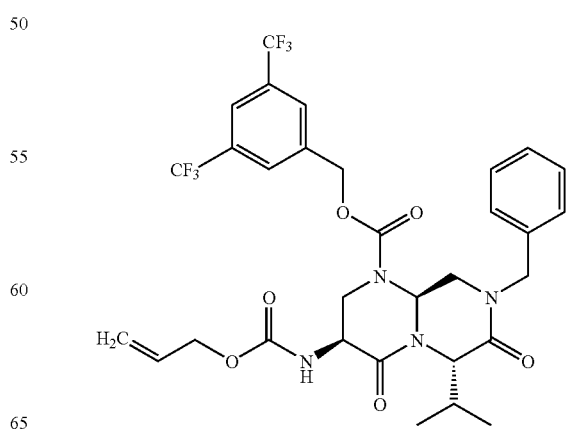

TABLE 2-continued
Representative Compounds
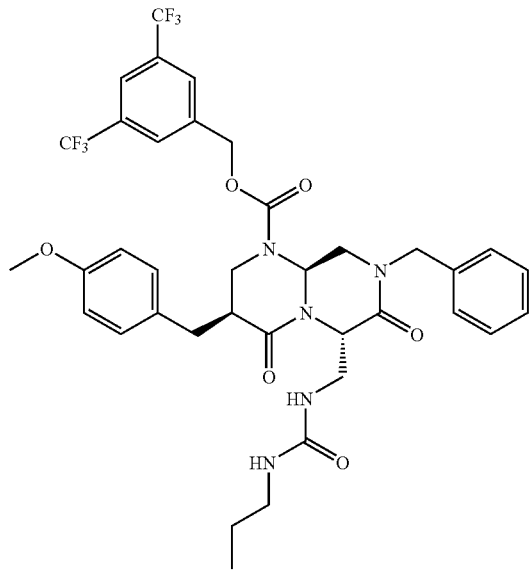
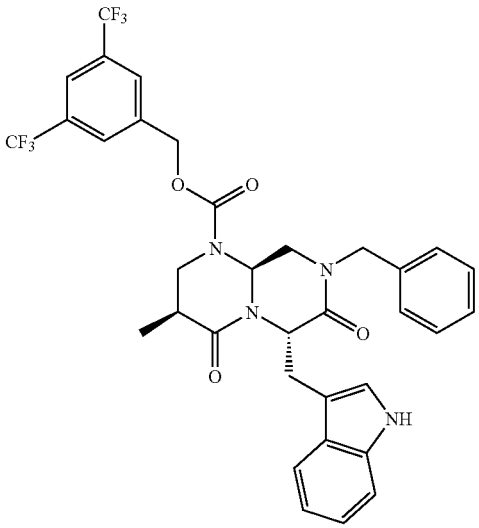

TABLE 2-continued
Representative Compounds
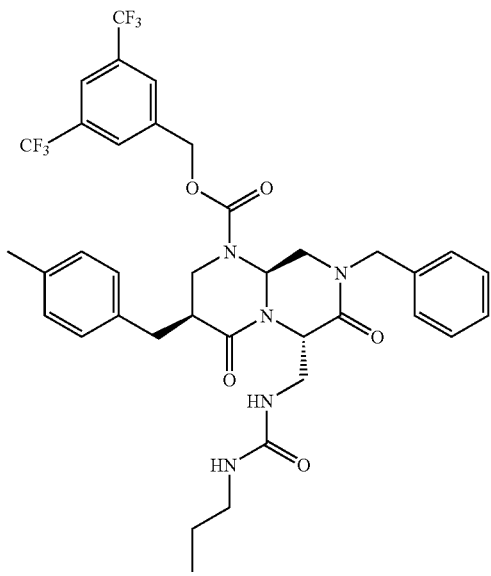
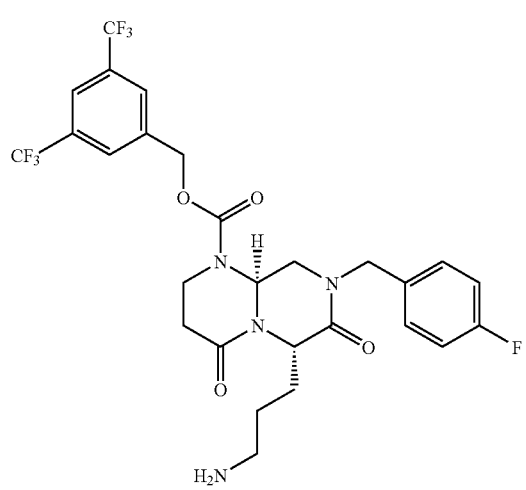
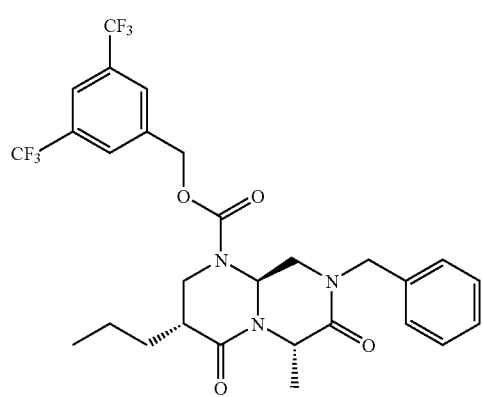
TABLE 2-continued
Representative Compounds
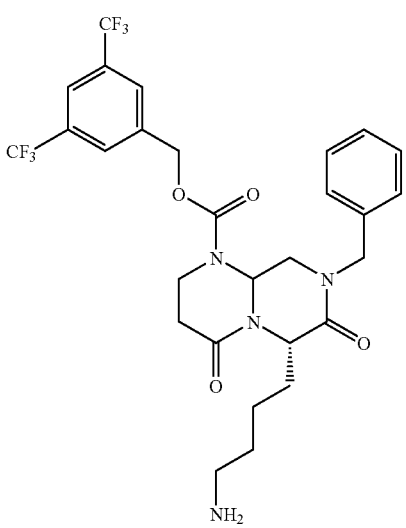
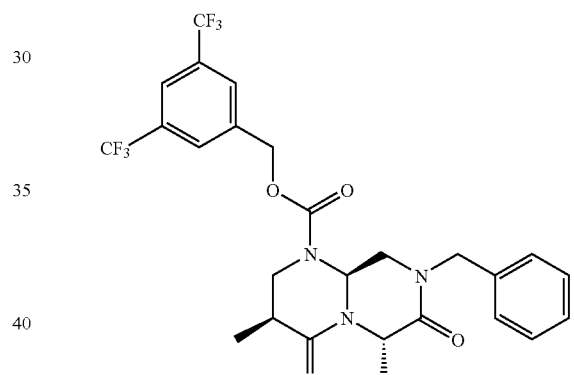
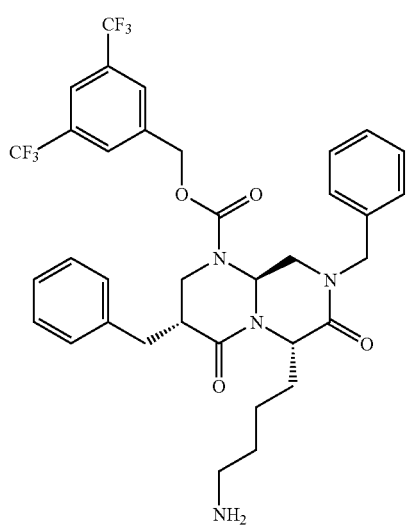

TABLE 2-continued
Representative Compounds
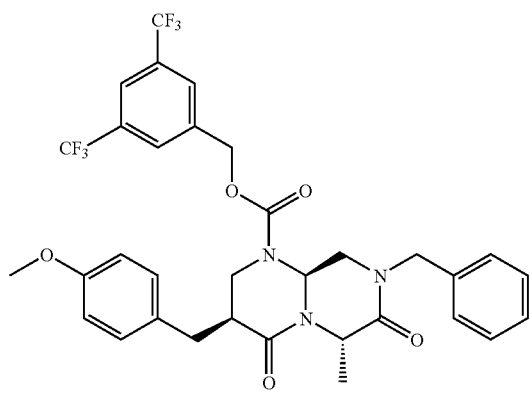
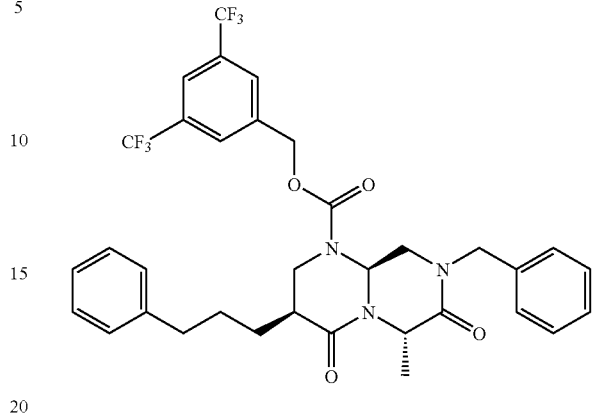
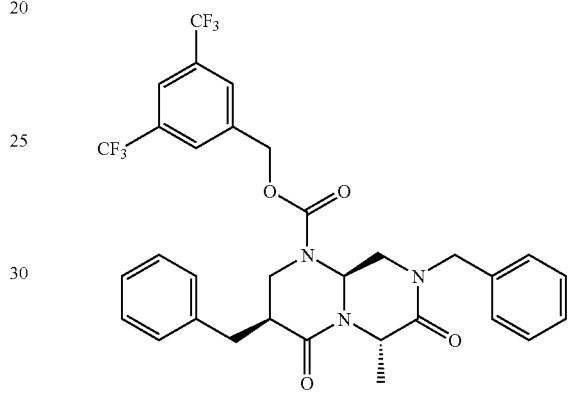
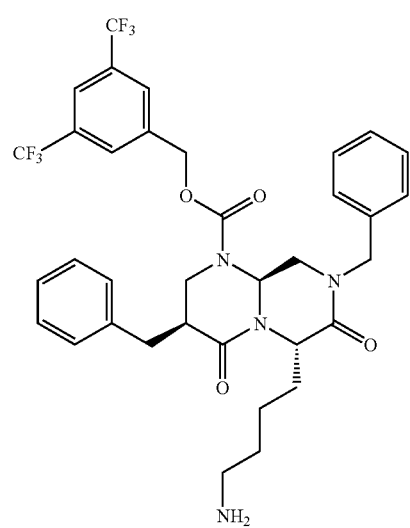
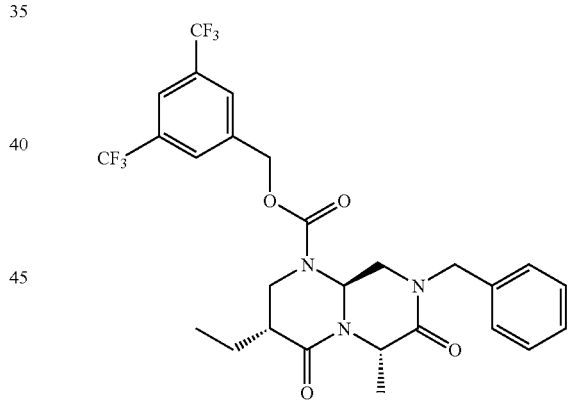
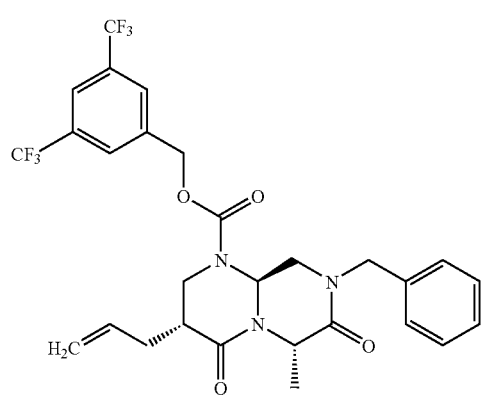
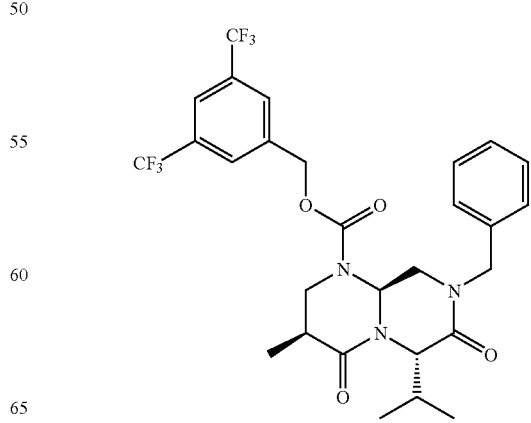

TABLE 2-continued
Representative Compounds
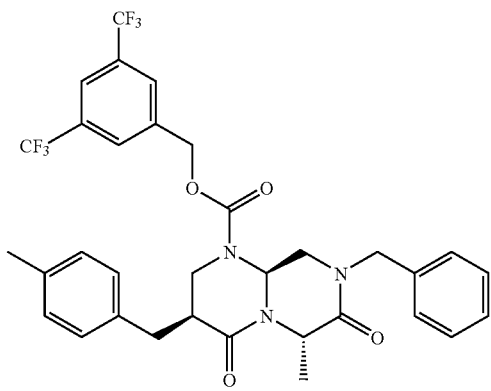
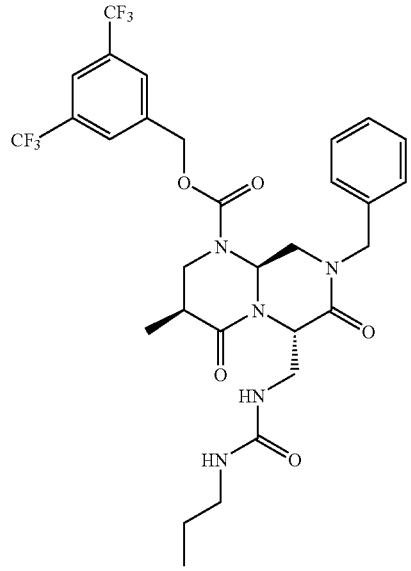
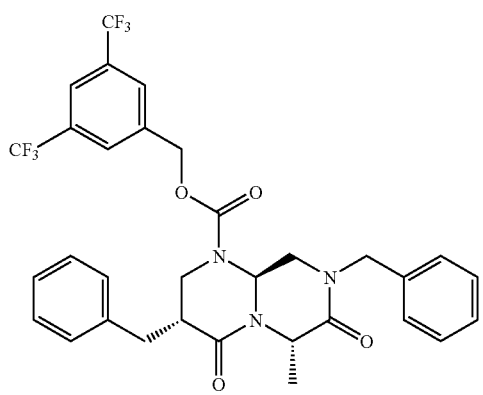
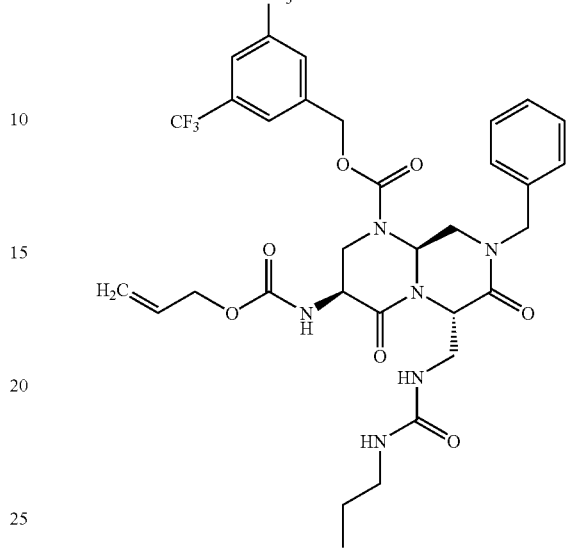
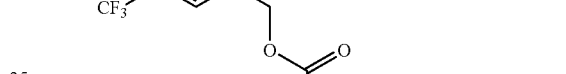
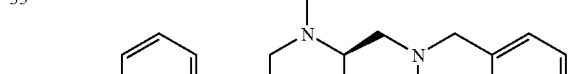
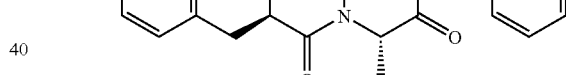

TABLE 2-continued
Representative Compounds
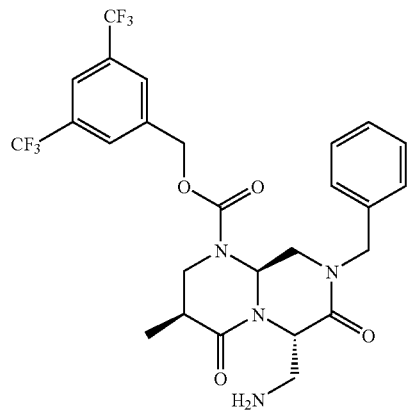
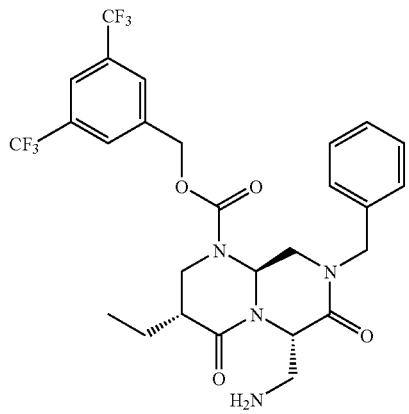
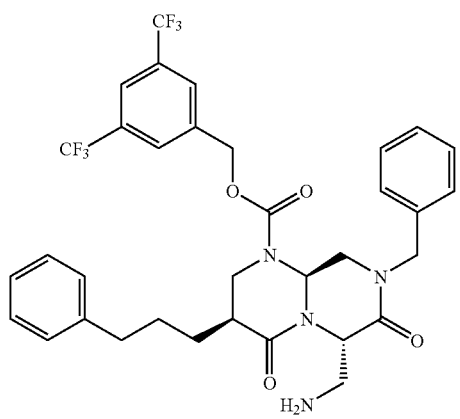
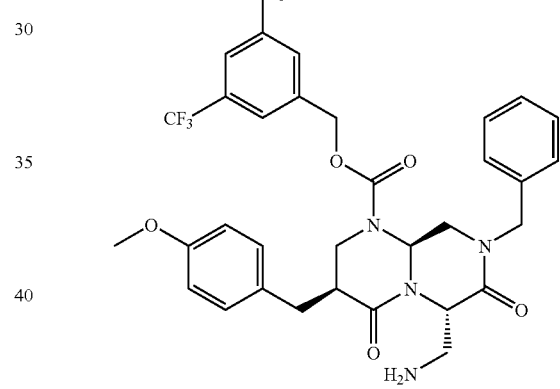
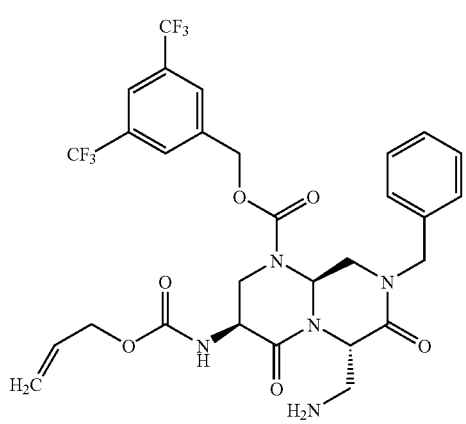
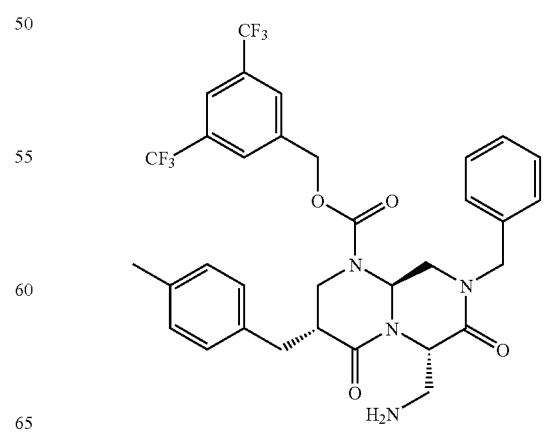

TABLE 2-continued
Representative Compounds
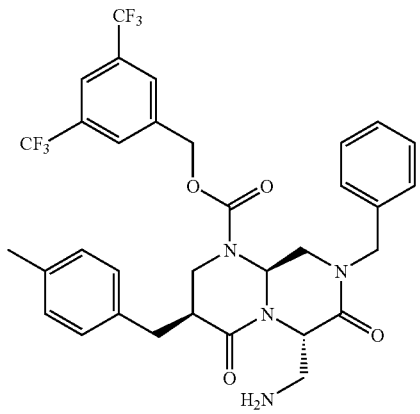
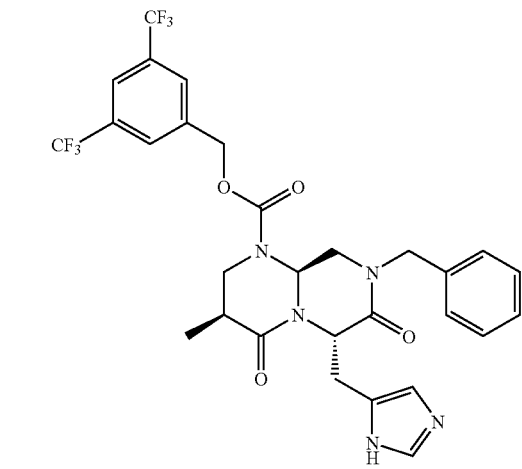
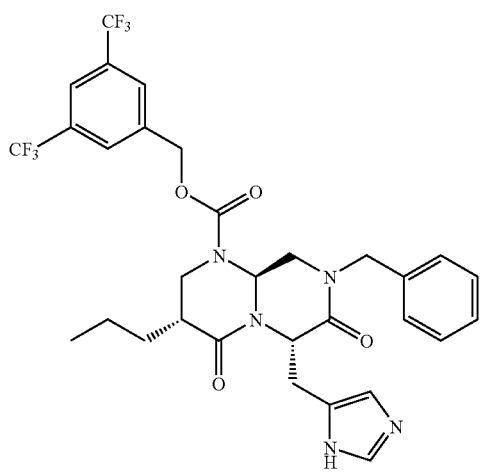
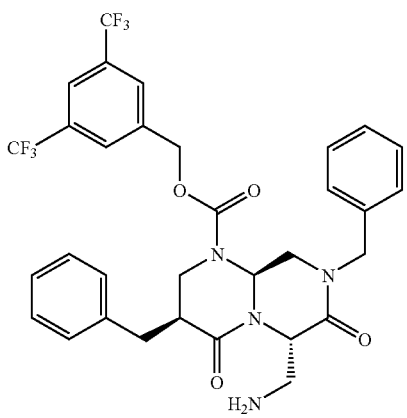
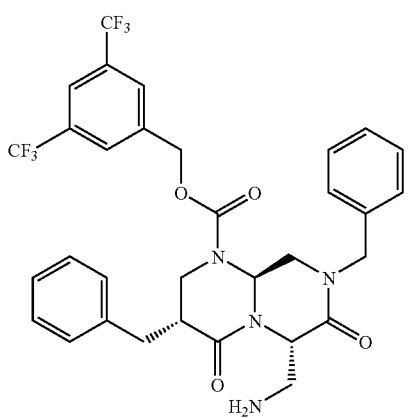
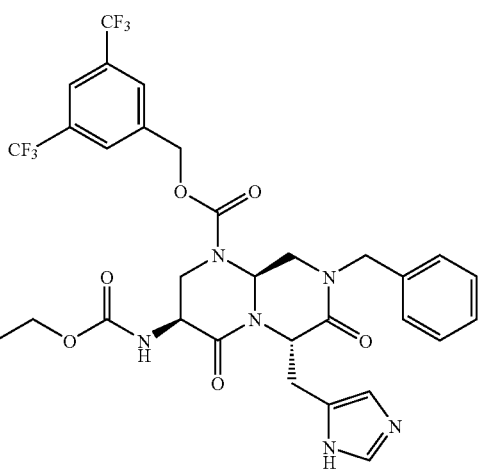

TABLE 2-continued
Representative Compounds
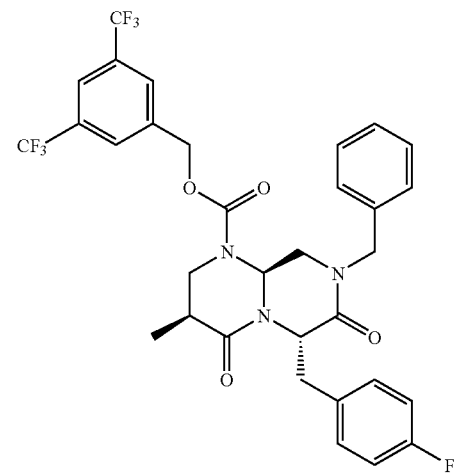
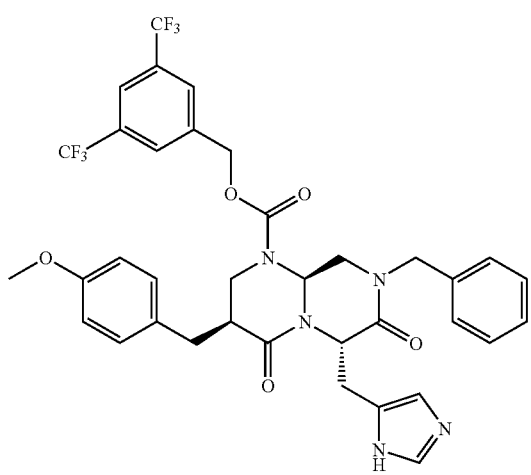
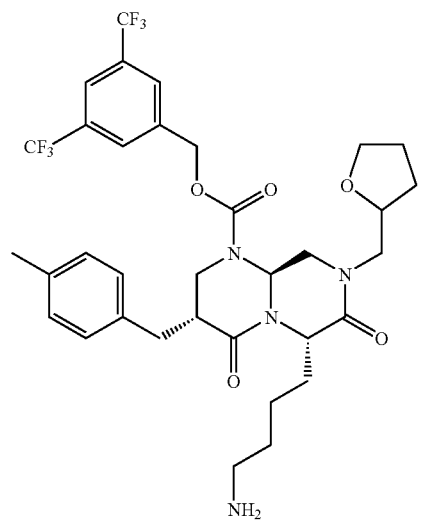
TABLE 2-continued
Representative Compounds
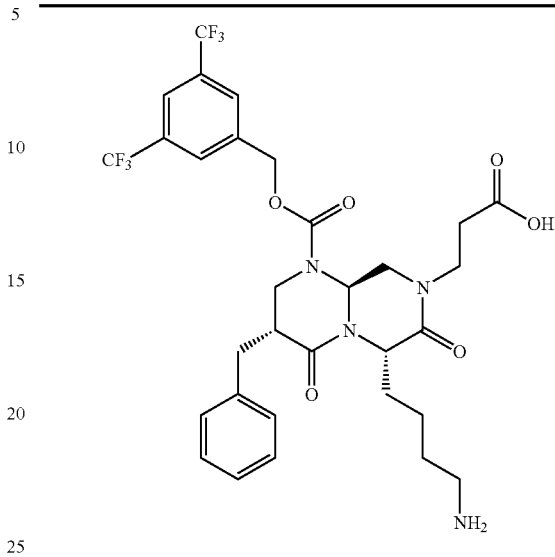
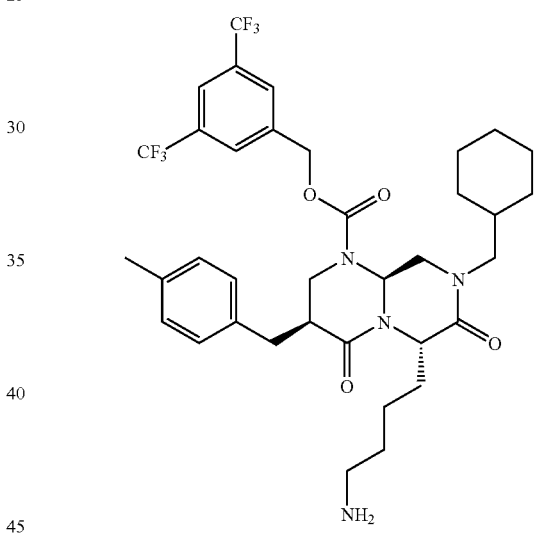
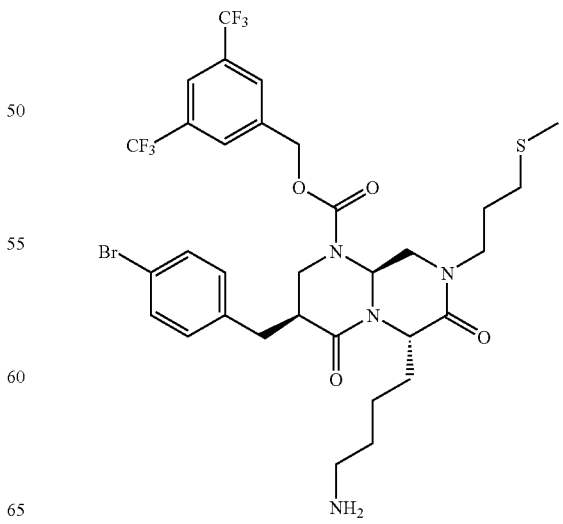

TABLE 2-continued
Representative Compounds
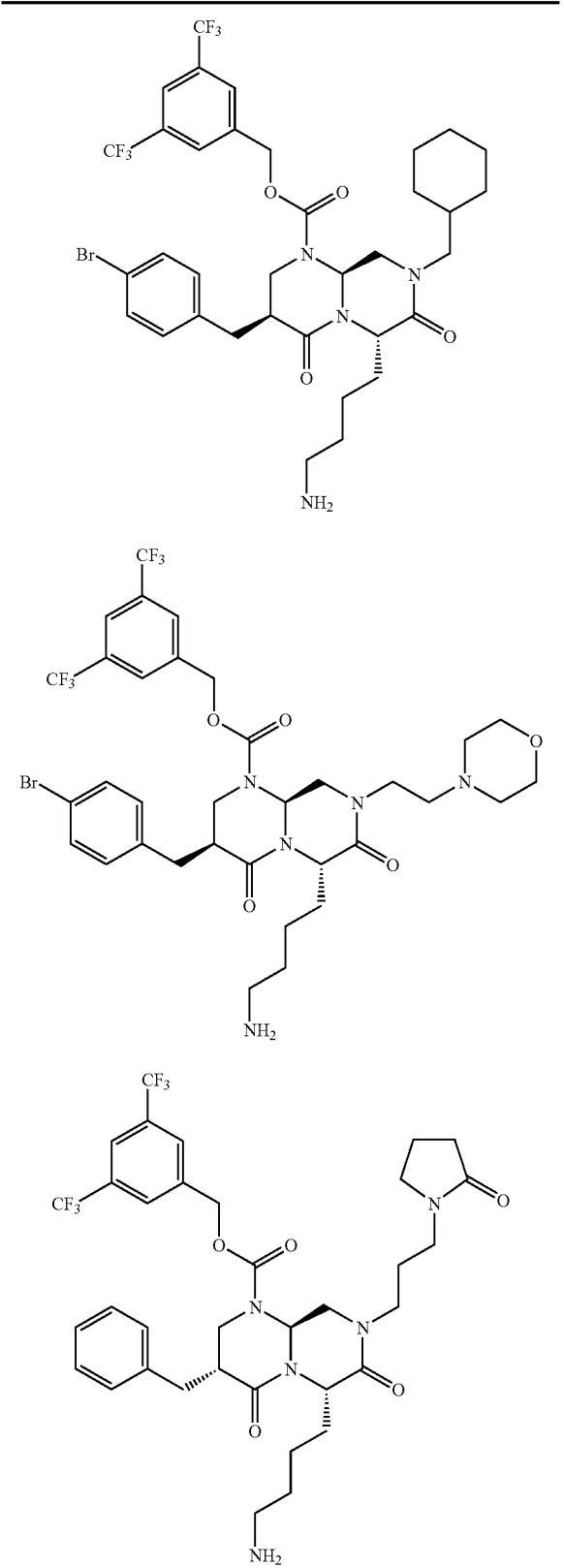
TABLE 2-continued
Representative Compounds
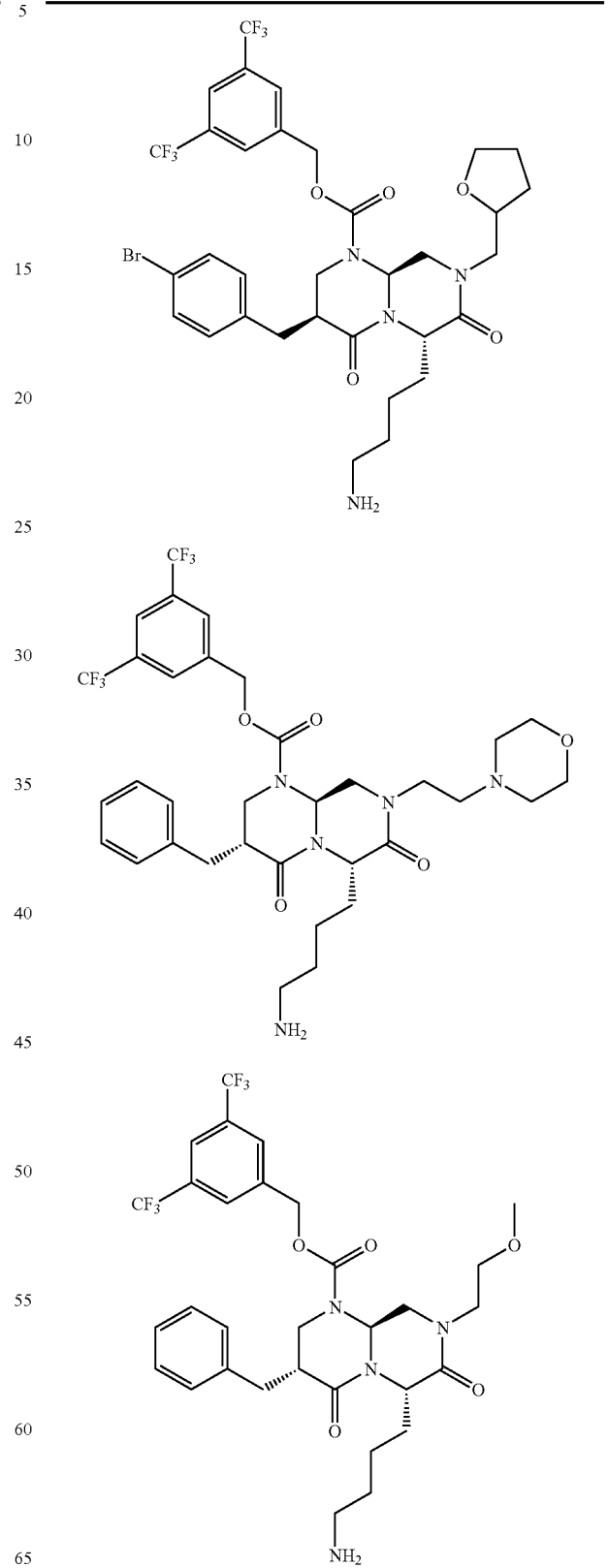

TABLE 2-continued
Representative Compounds
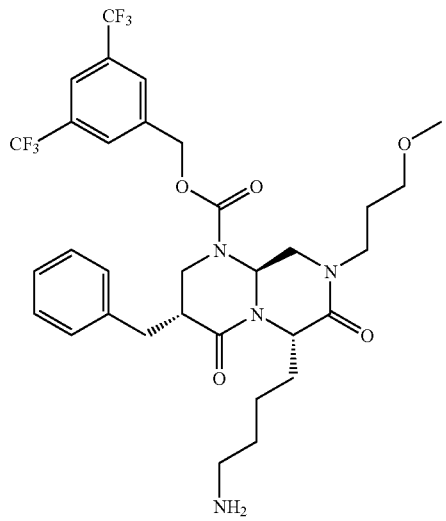
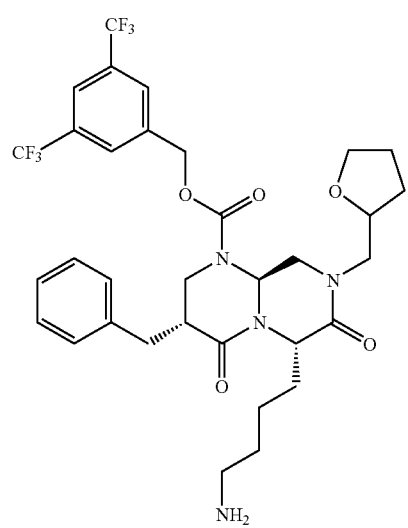
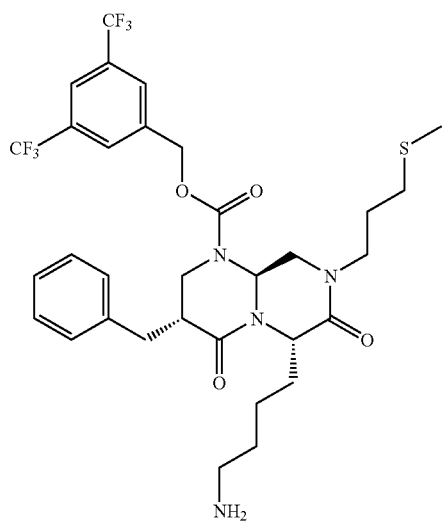
TABLE 2-continued
Representative Compounds
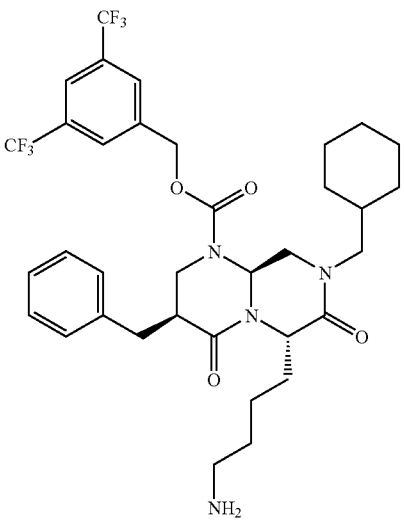
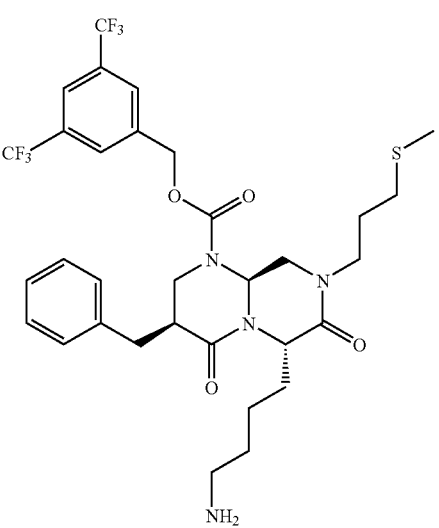
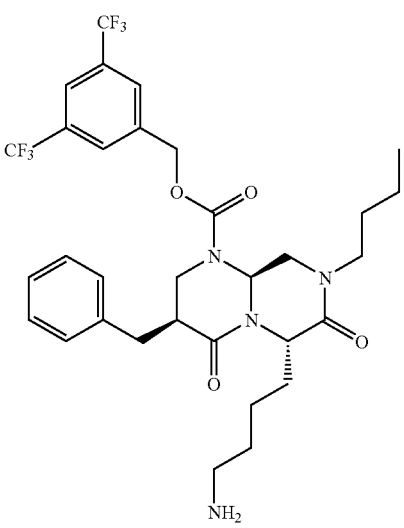

TABLE 2-continued
Representative Compounds
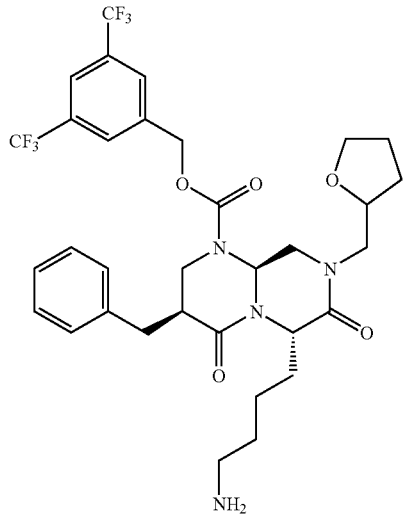
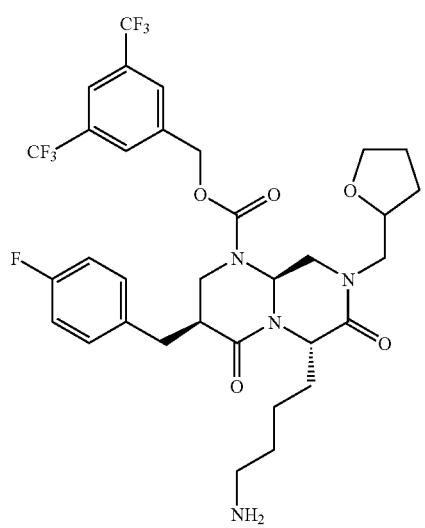
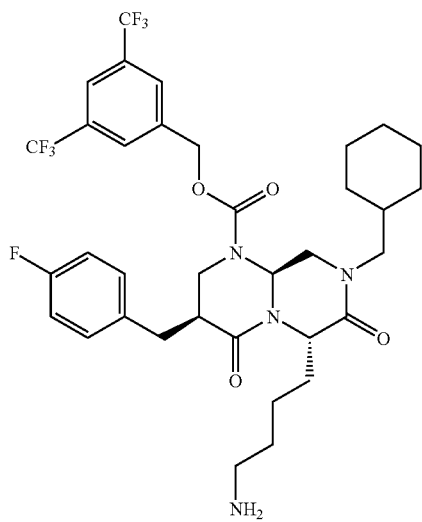

TABLE 2-continued
Representative Compounds
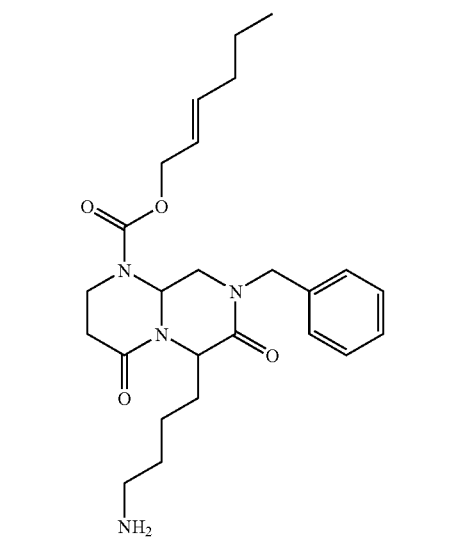
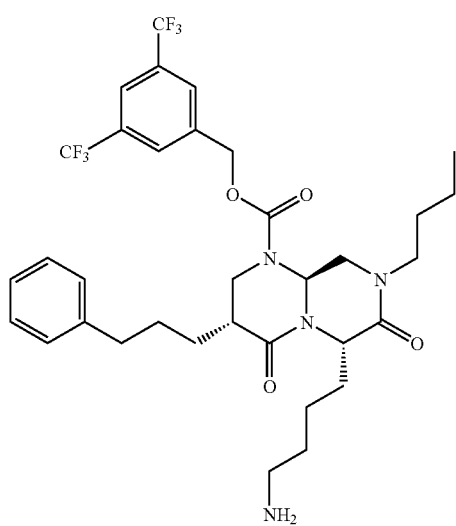
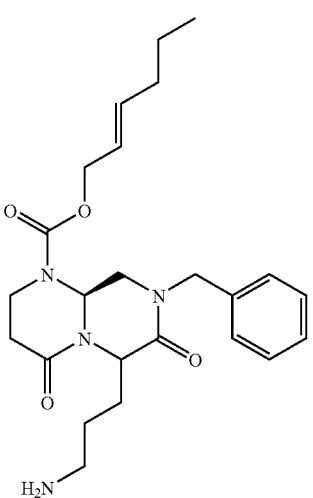
TABLE 2-continued
Representative Compounds
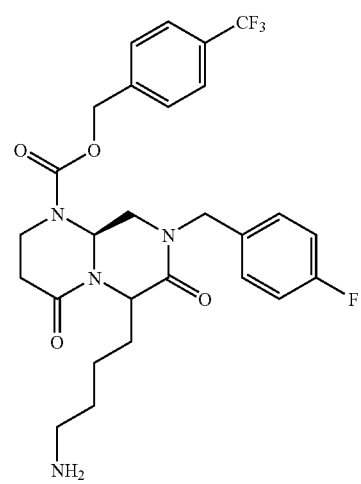
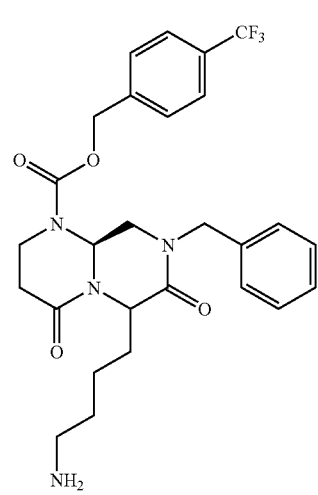
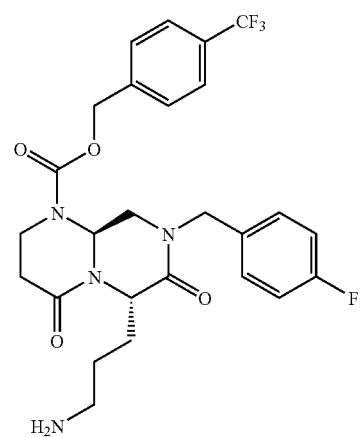

TABLE 2-continued
Representative Compounds
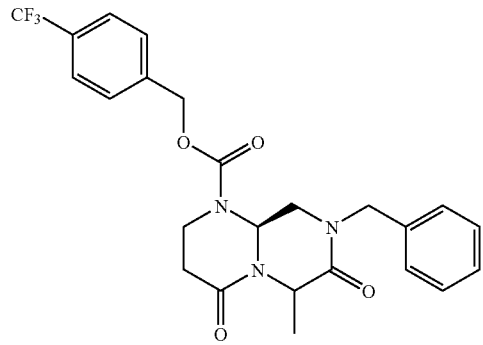
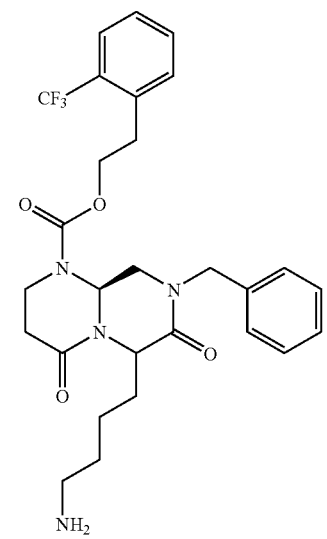
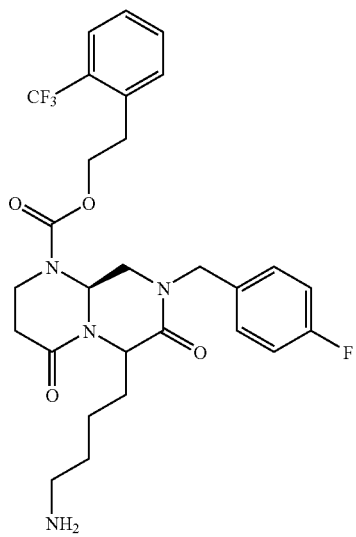
TABLE 2-continued
Representative Compounds
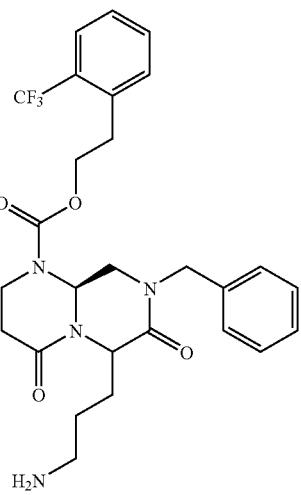
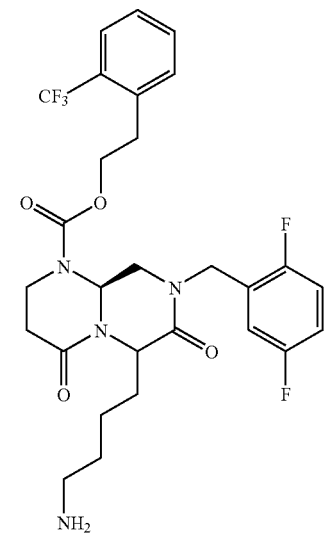

TABLE 2-continued
Representative Compounds
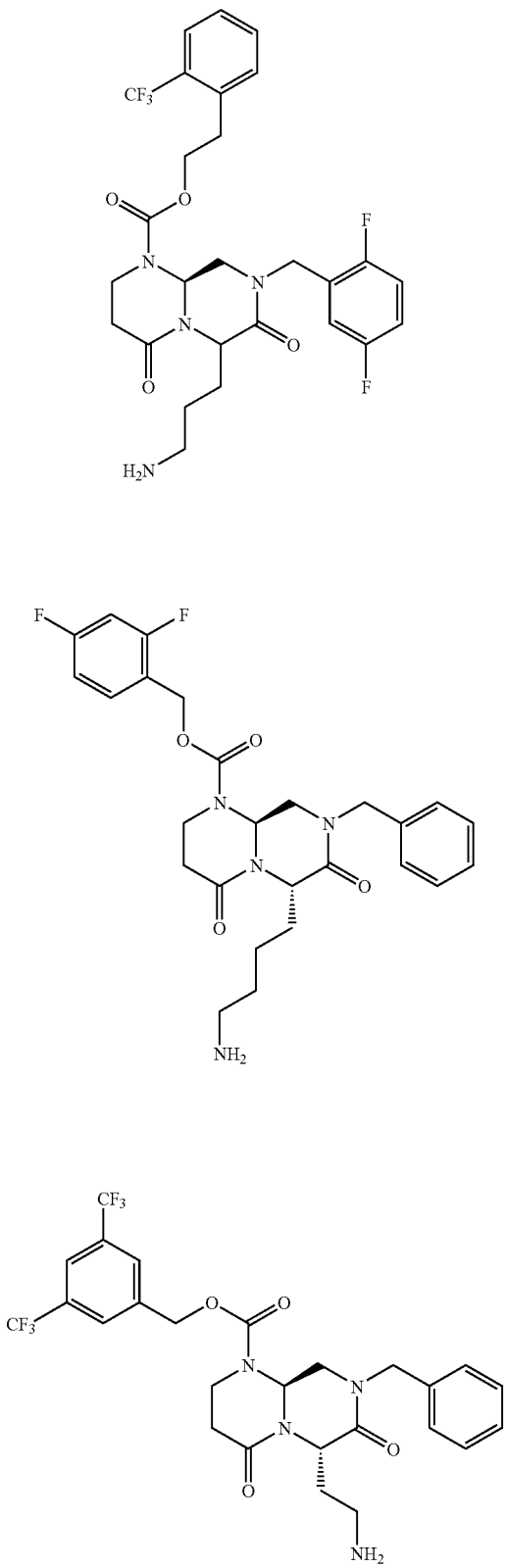
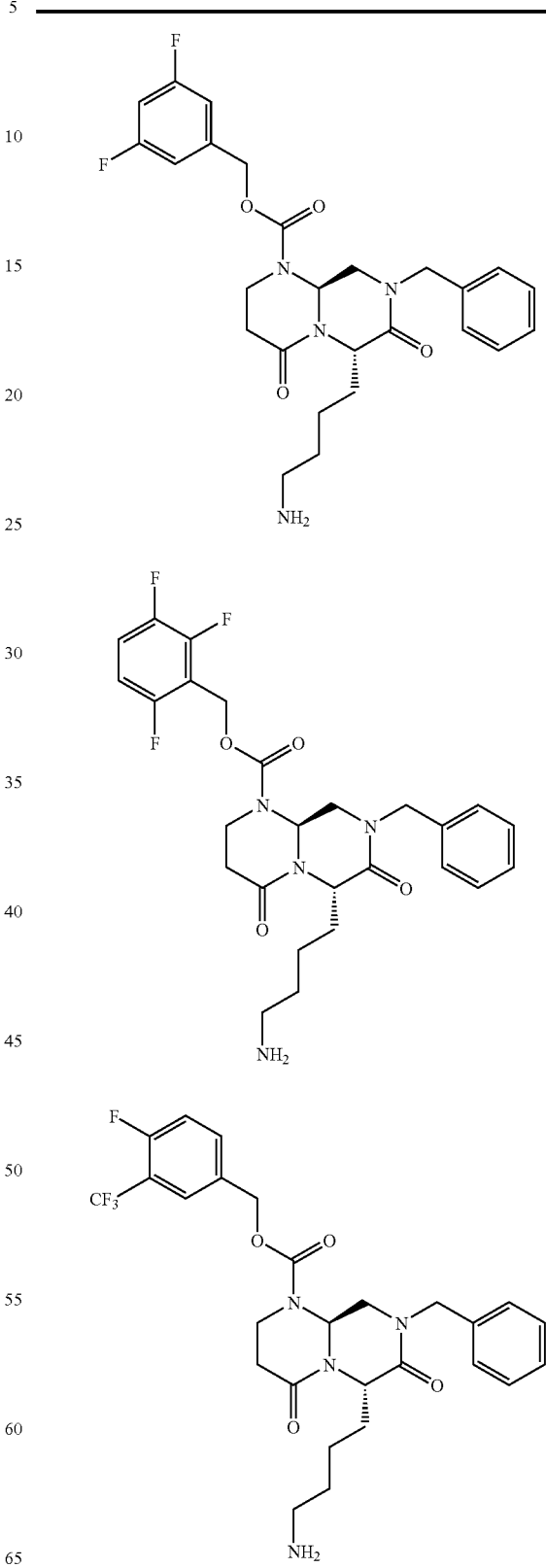

TABLE 2-continued
Representative Compounds
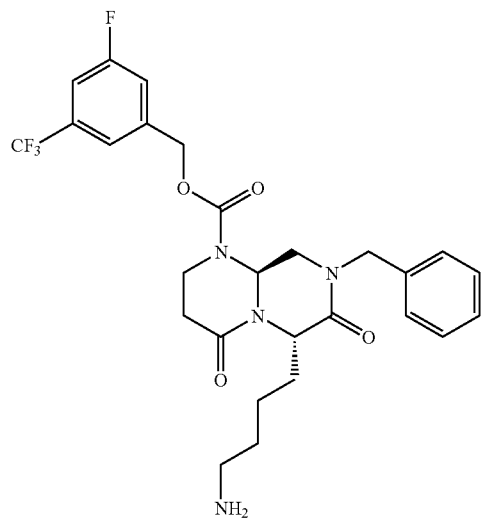
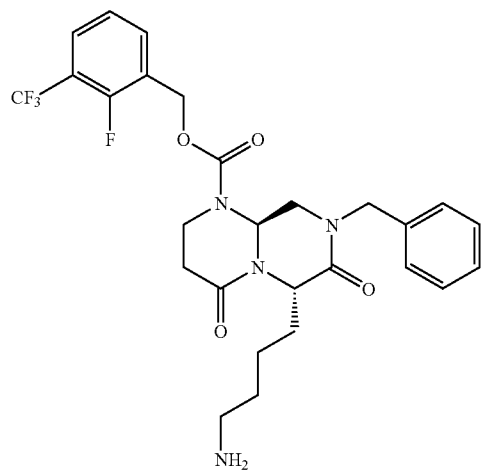
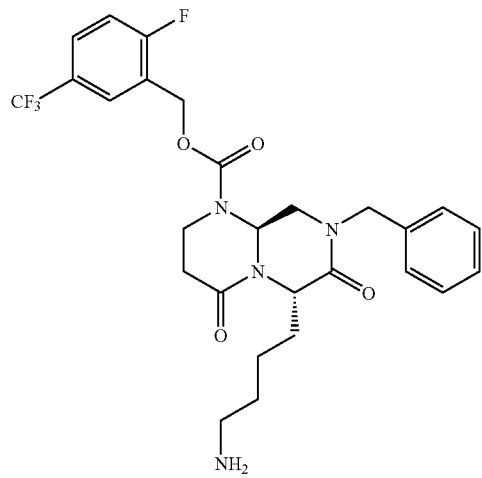
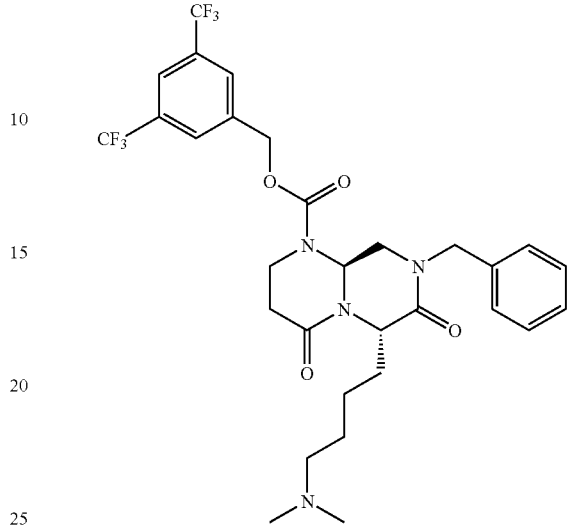
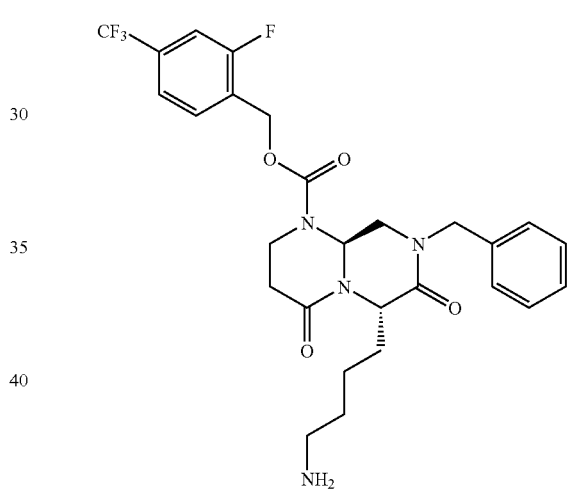
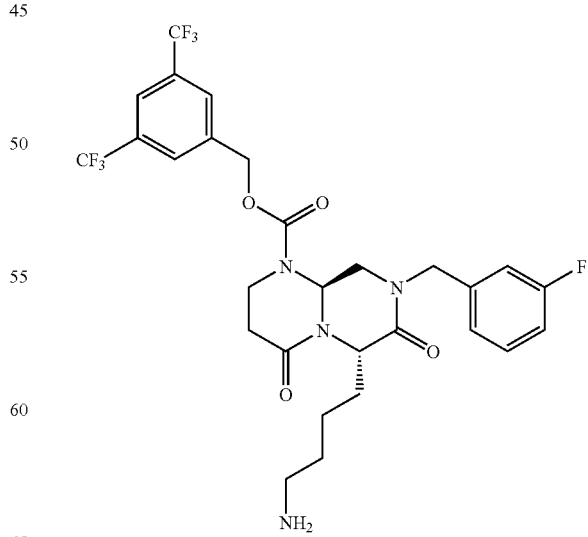

TABLE 2-continued
Representative Compounds
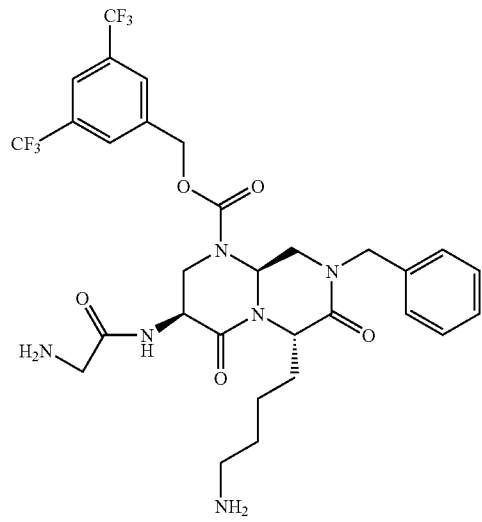
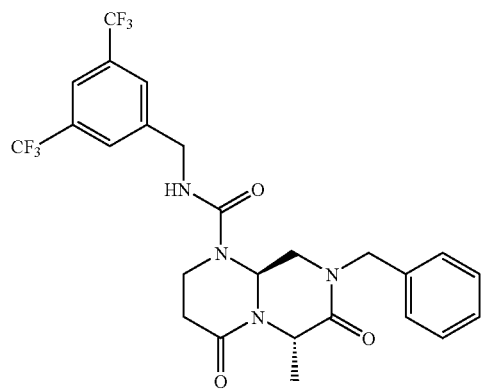
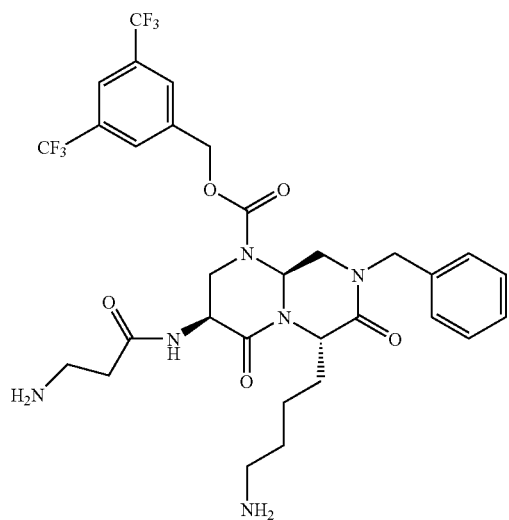
TABLE 2-continued
Representative Compounds
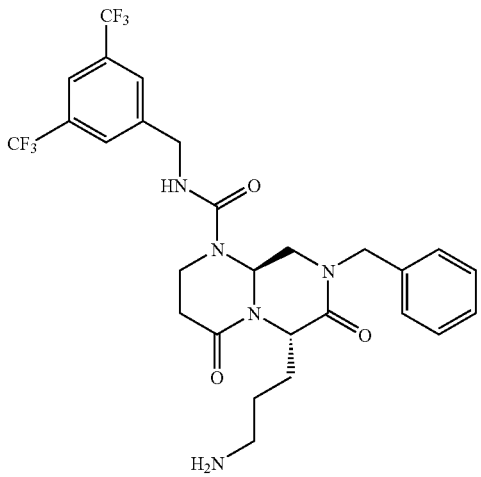
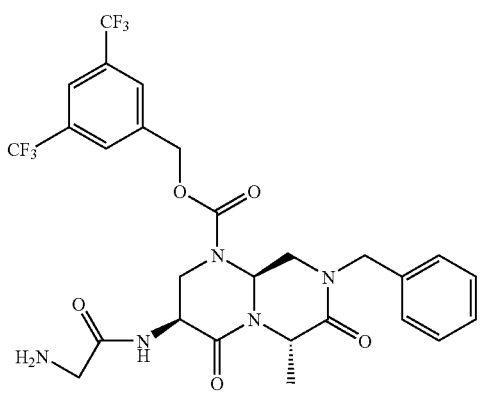
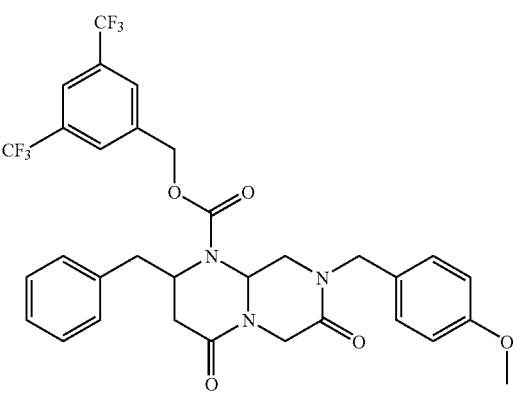

TABLE 2-continued
Representative Compounds
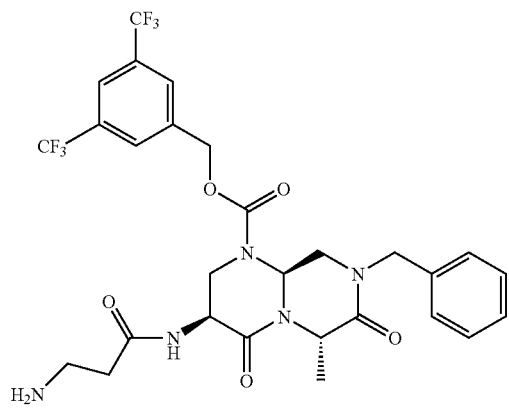
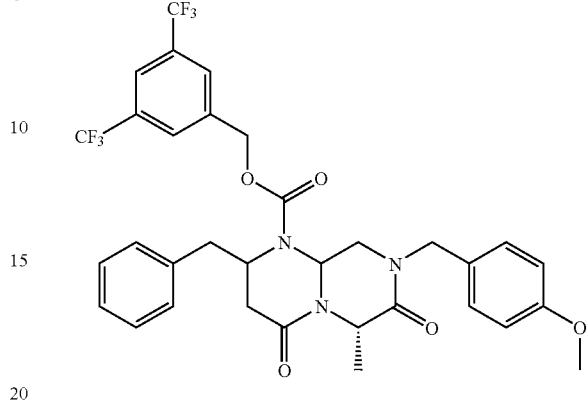
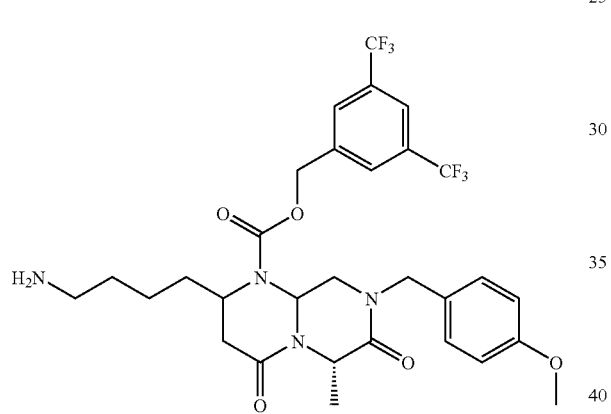
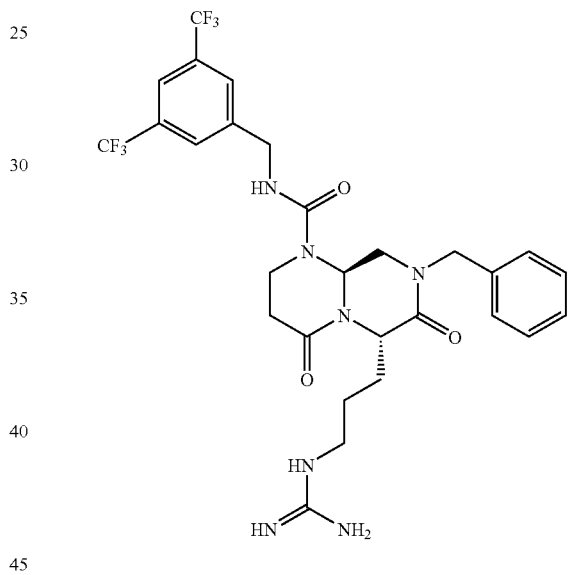
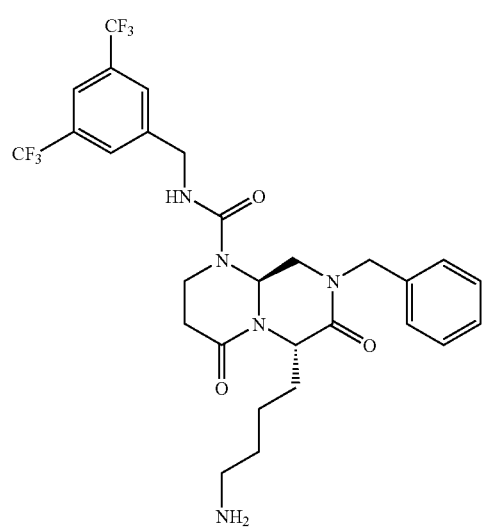
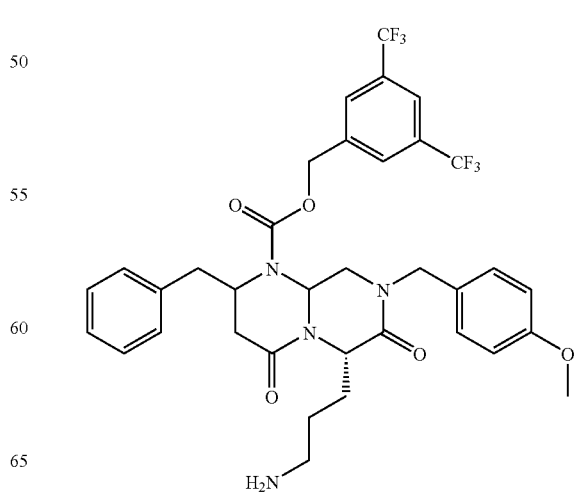

TABLE 2-continued
Representative Compounds
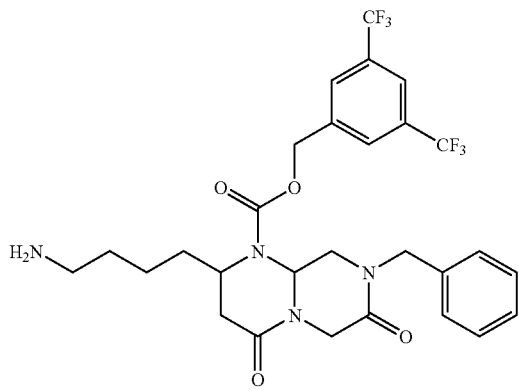
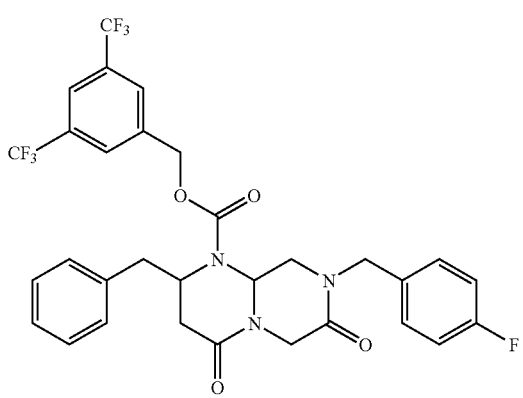
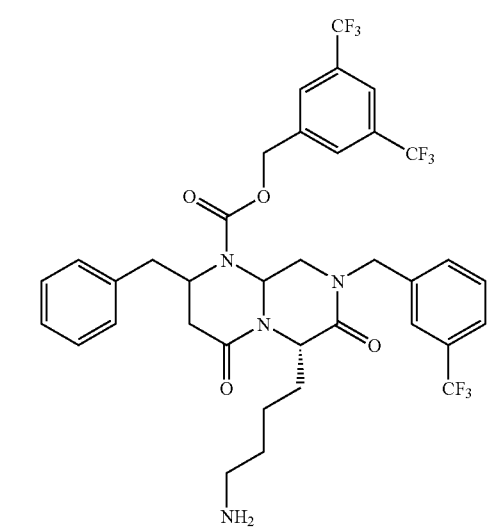
TABLE 2-continued
Representative Compounds
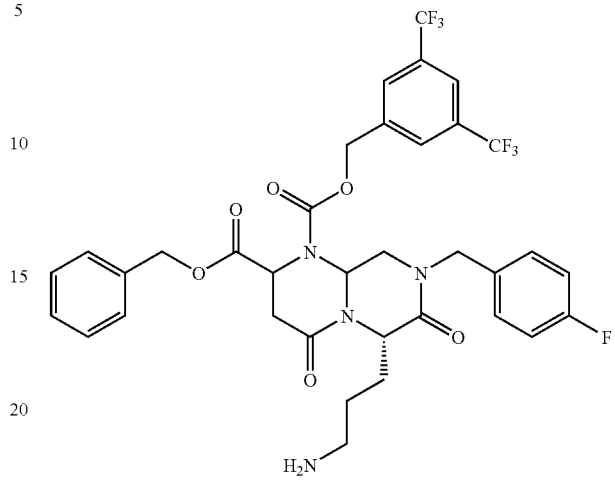
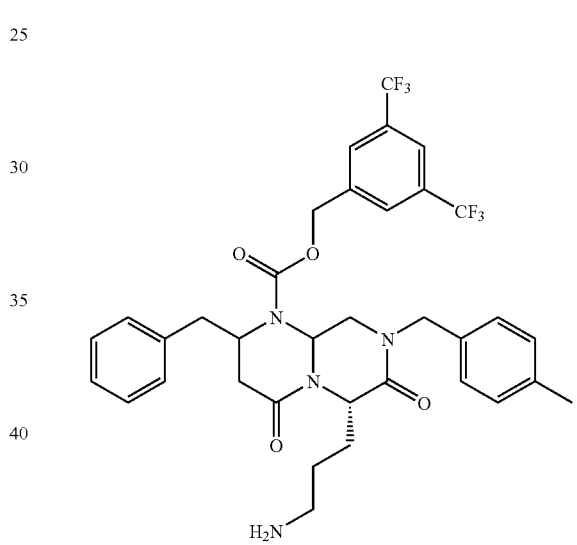
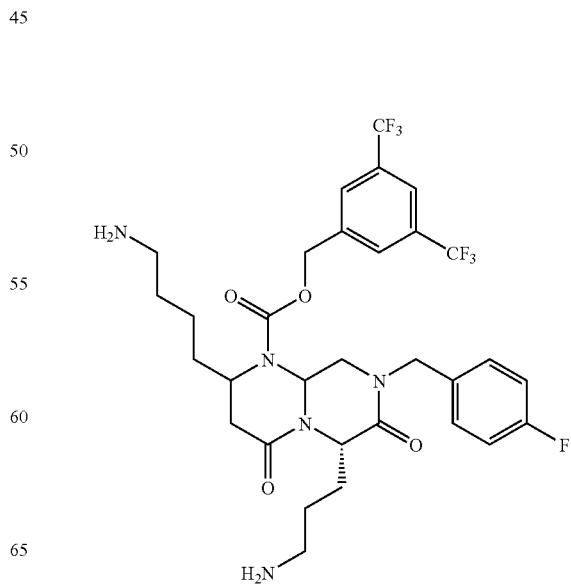

TABLE 2-continued
Representative Compounds
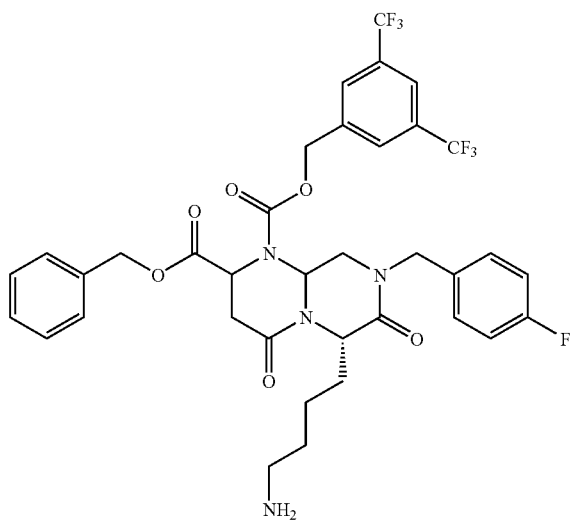
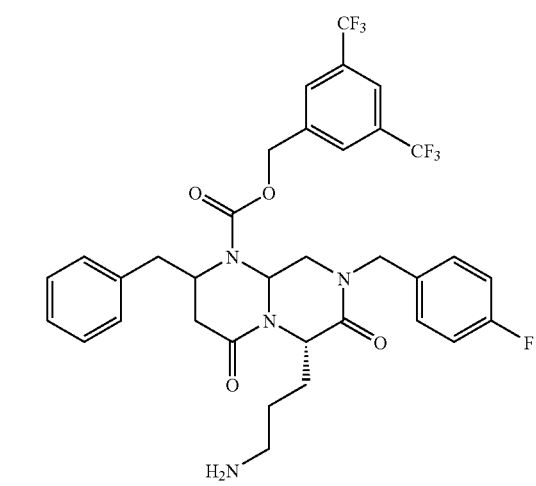
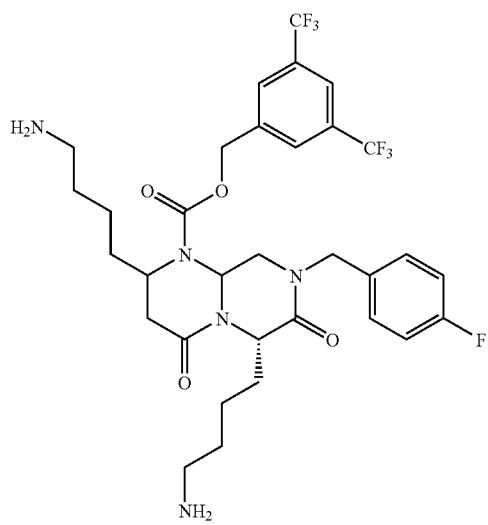
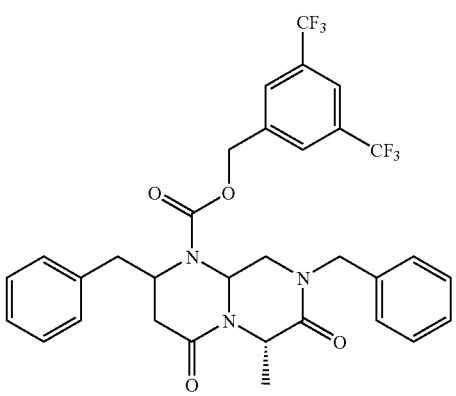
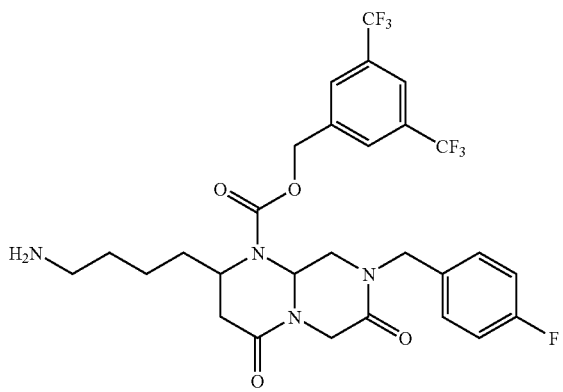
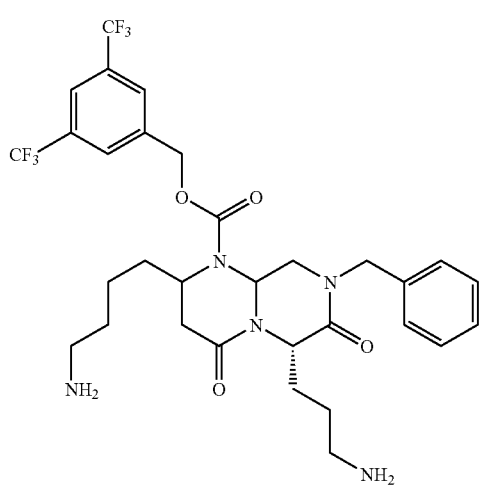

TABLE 2-continued
Representative Compounds
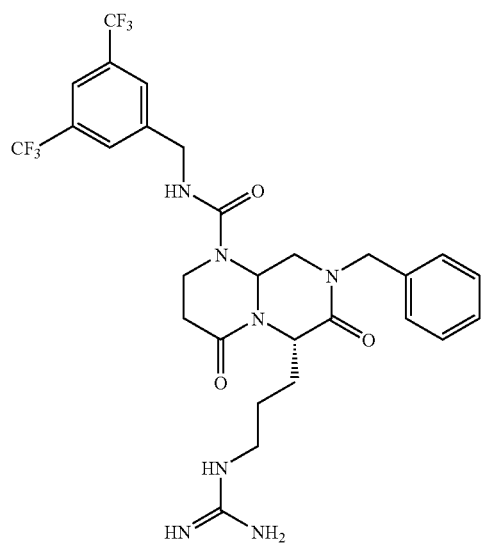
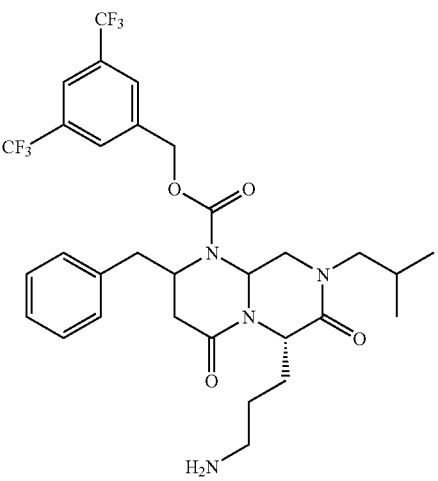
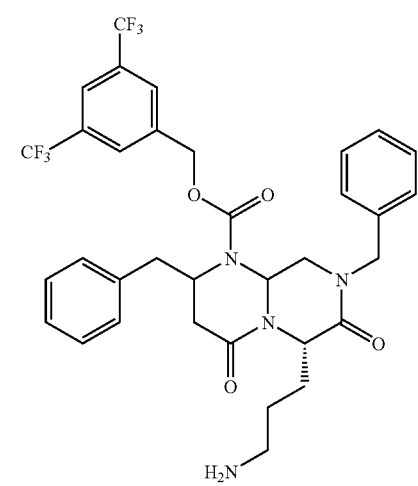
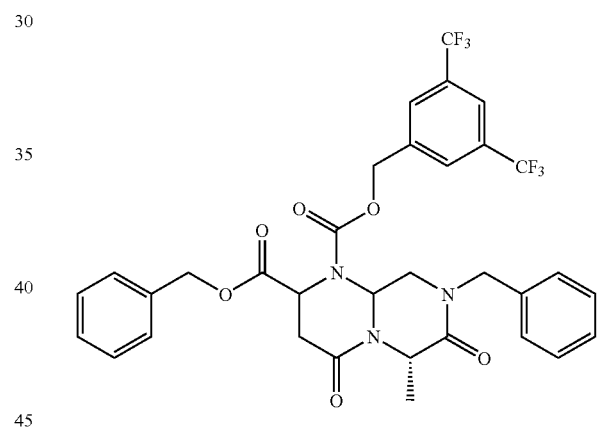
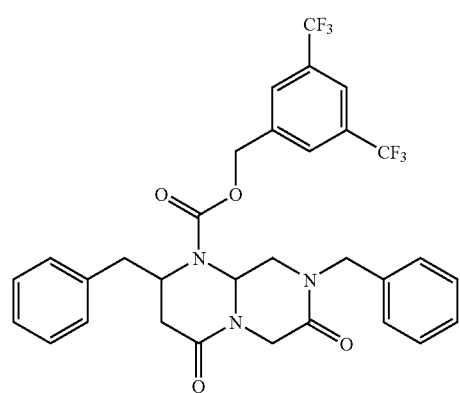
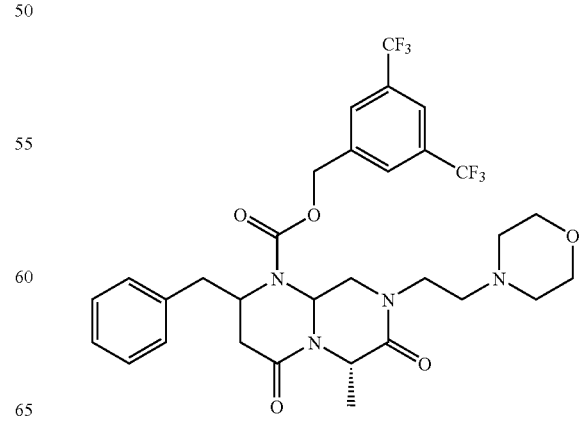

TABLE 2-continued
Representative Compounds
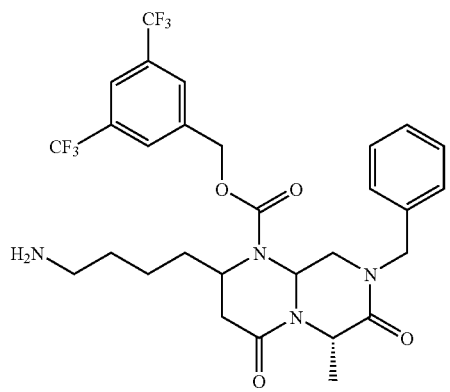
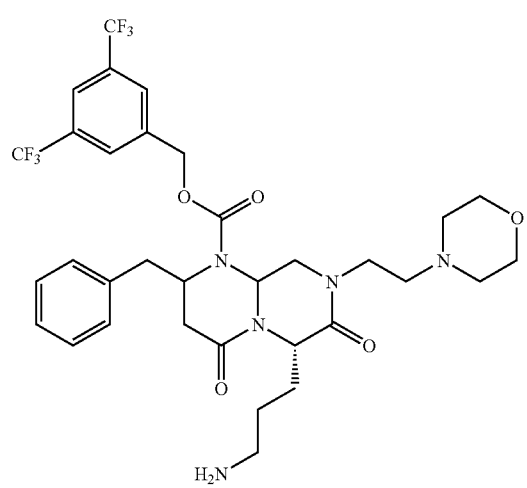
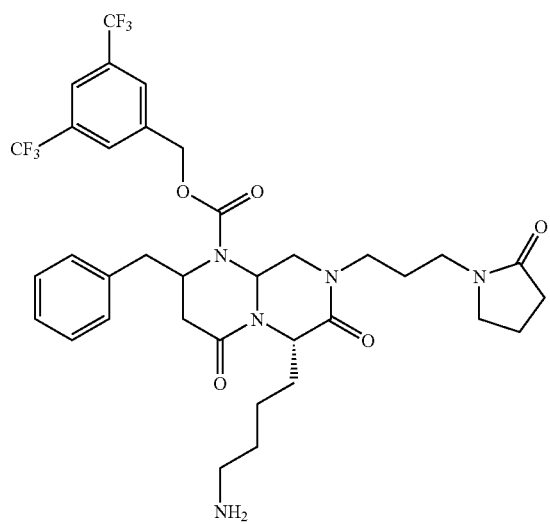
TABLE 2-continued
Representative Compounds
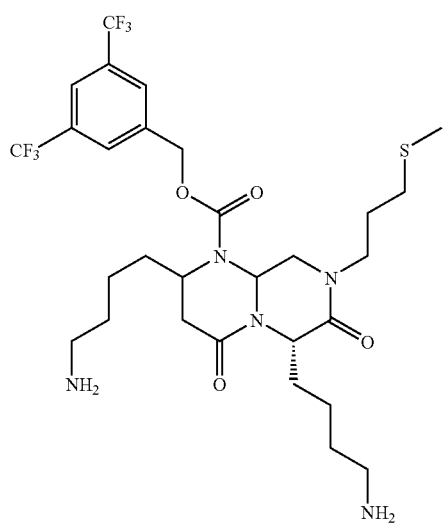
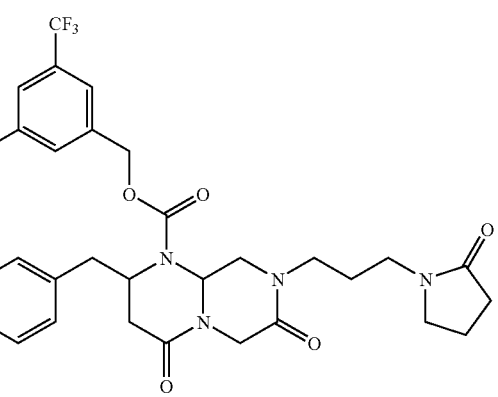
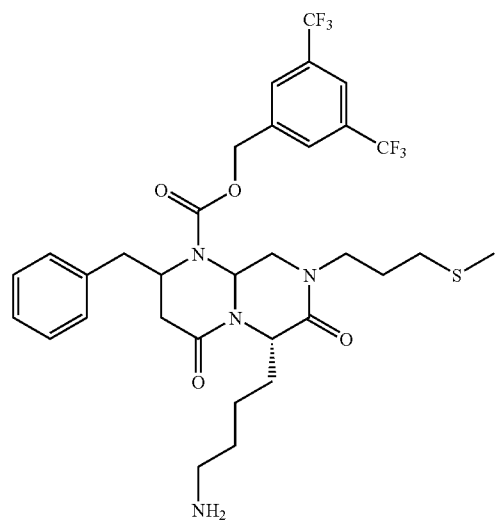

TABLE 2-continued
Representative Compounds
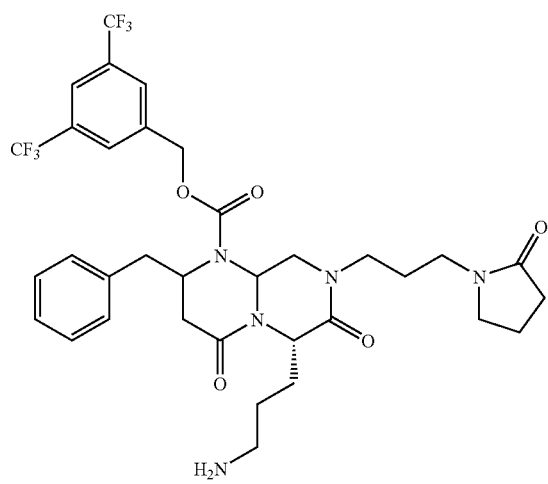
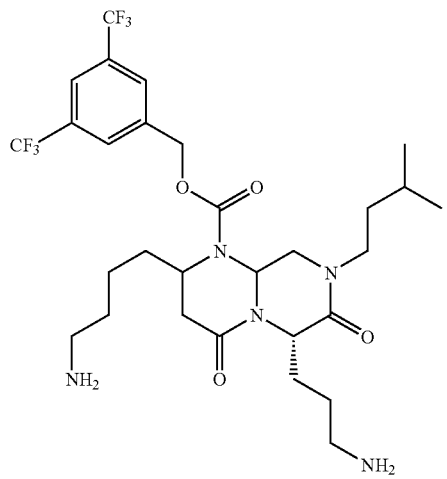
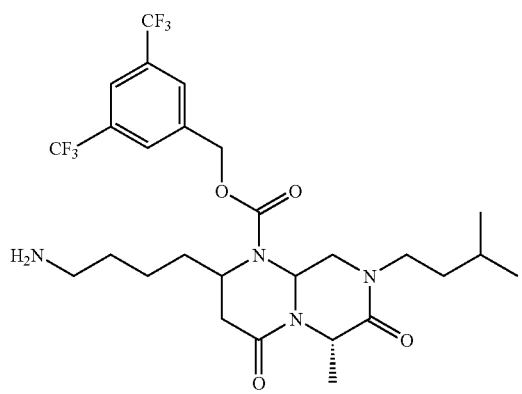
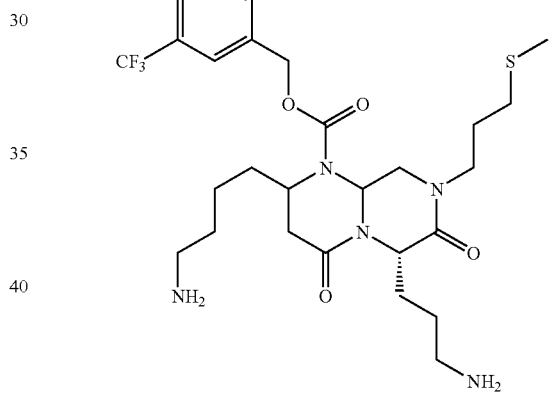
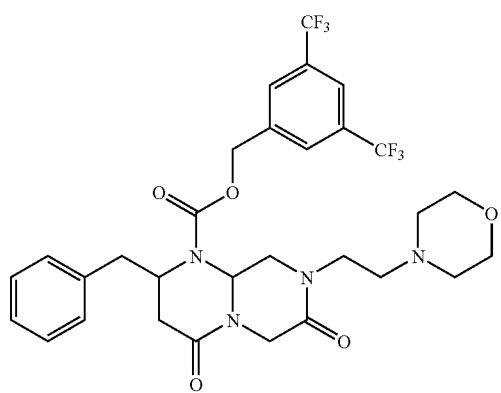
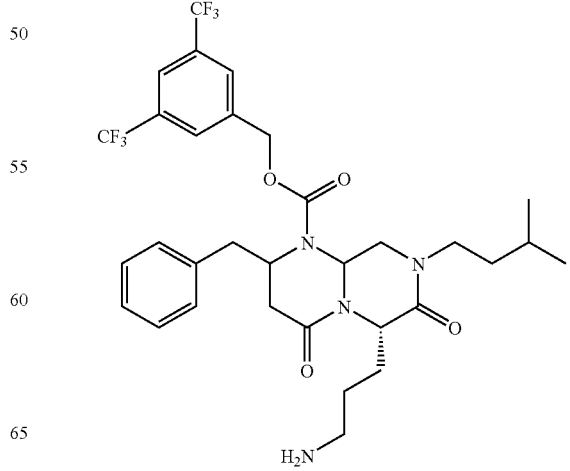

TABLE 2-continued
Representative Compounds
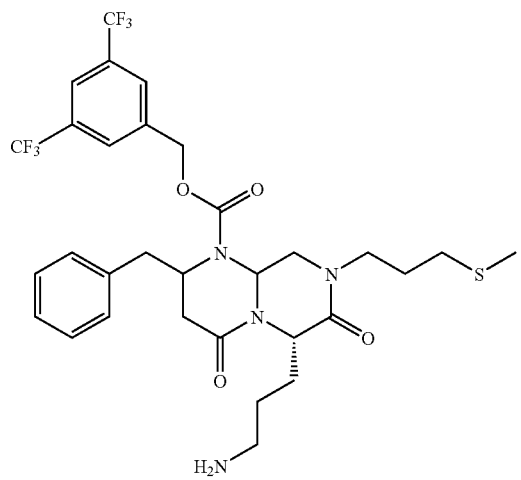
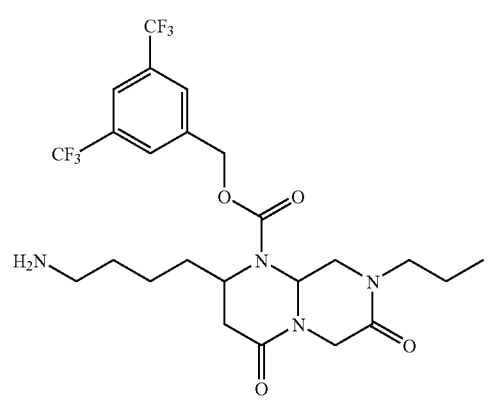
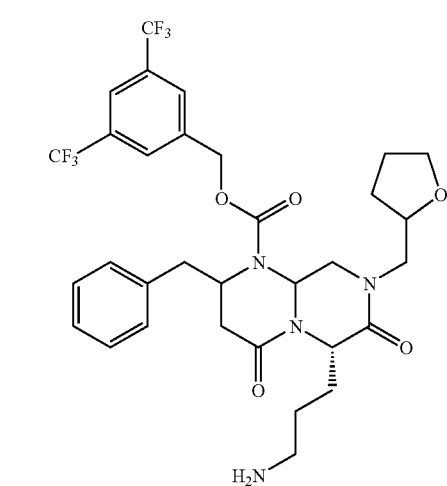
TABLE 2-continued
Representative Compounds
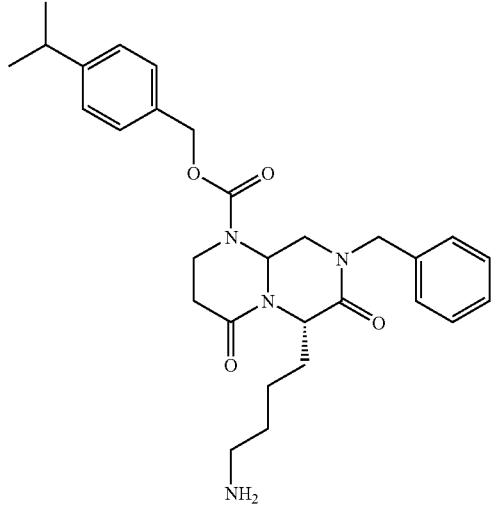
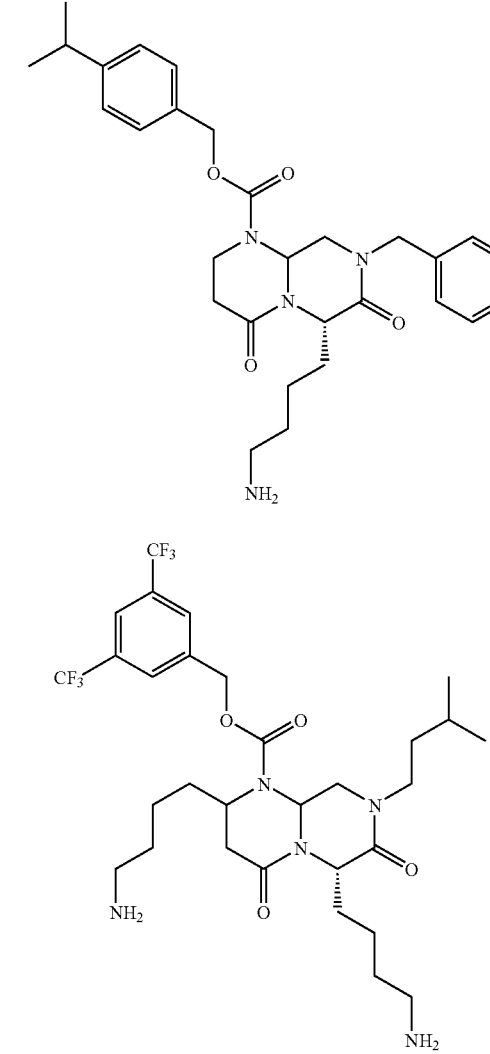

TABLE 2-continued
Representative Compounds
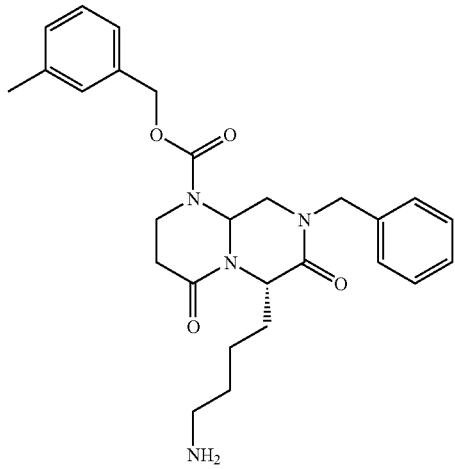
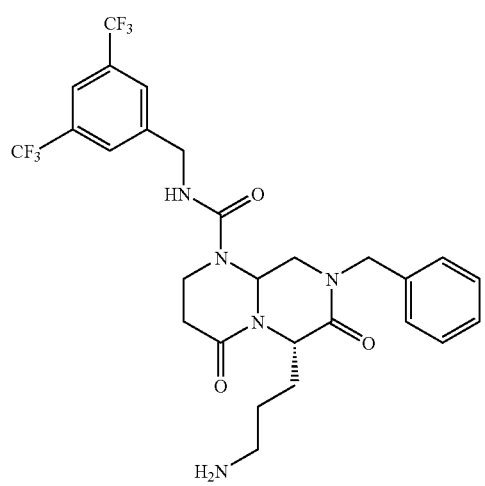
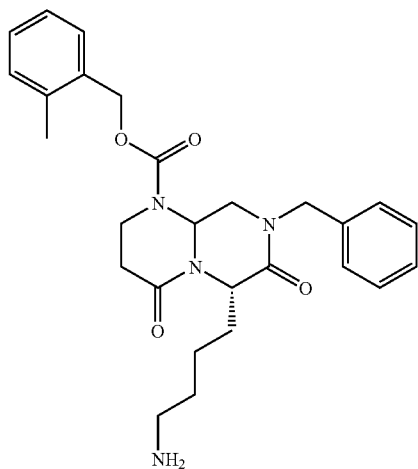
TABLE 2-continued
Representative Compounds
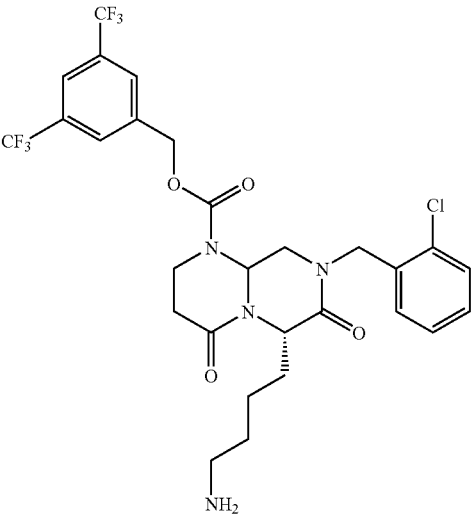
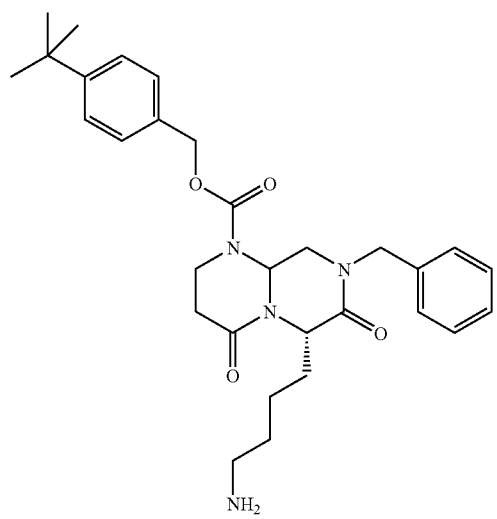
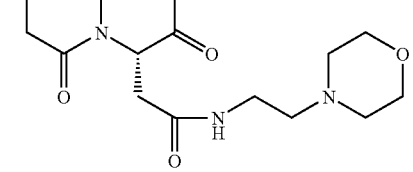

TABLE 2-continued
Representative Compounds
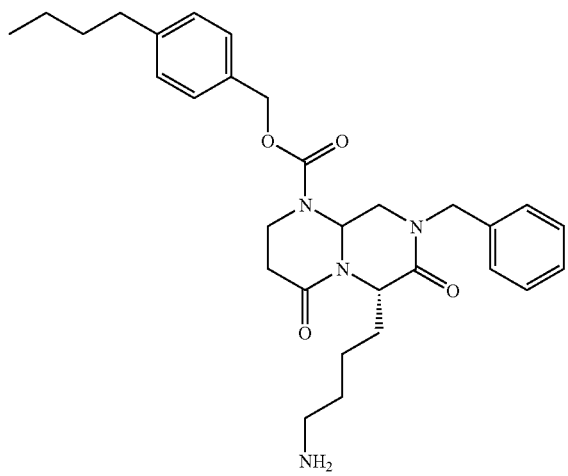
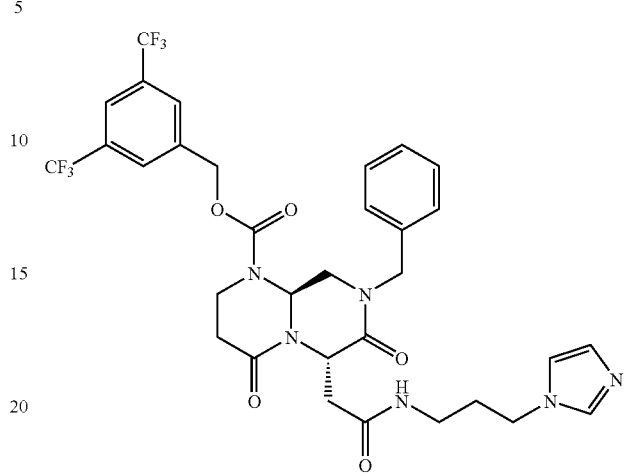
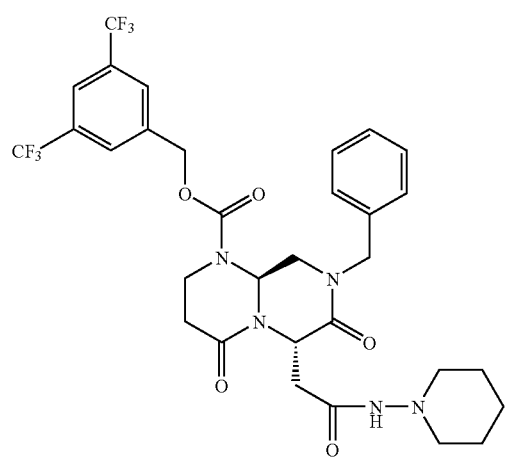
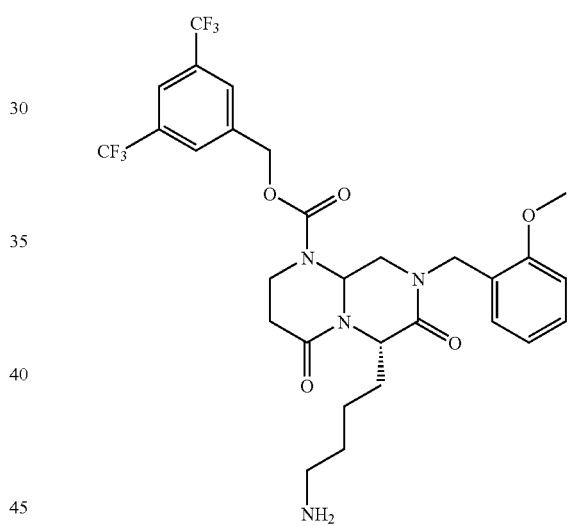
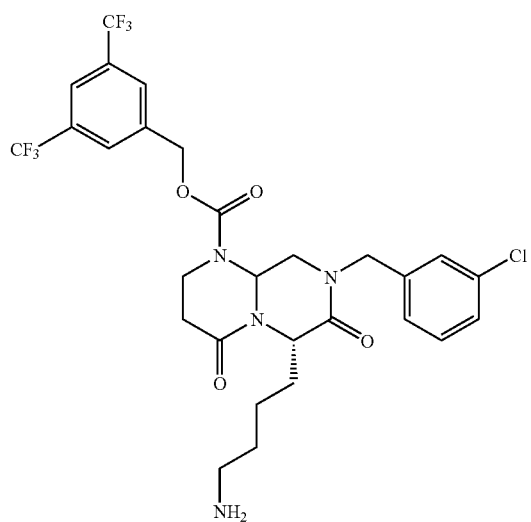
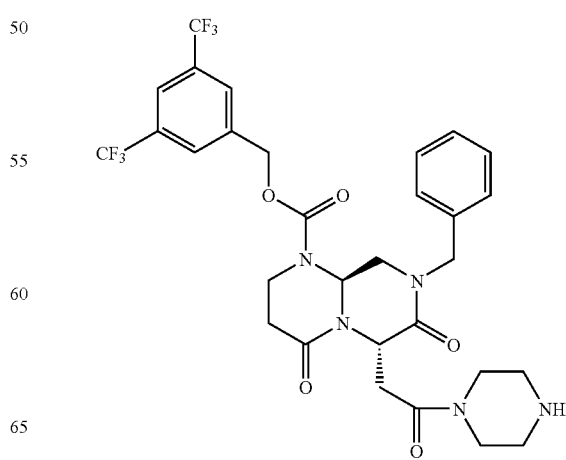

TABLE 2-continued
Representative Compounds
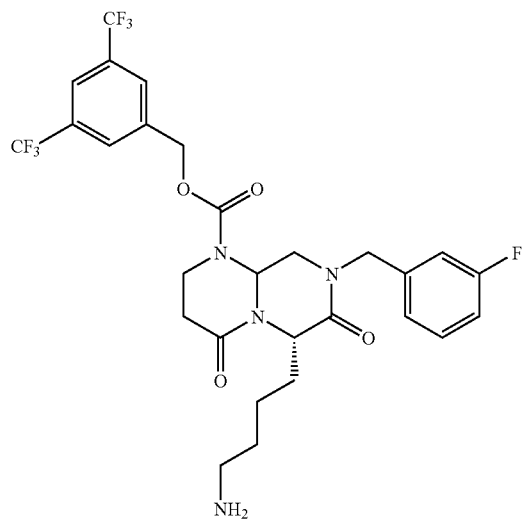
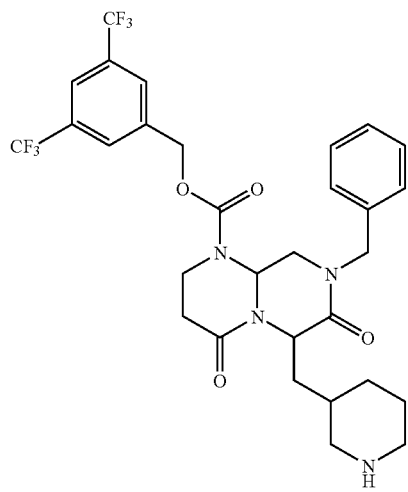
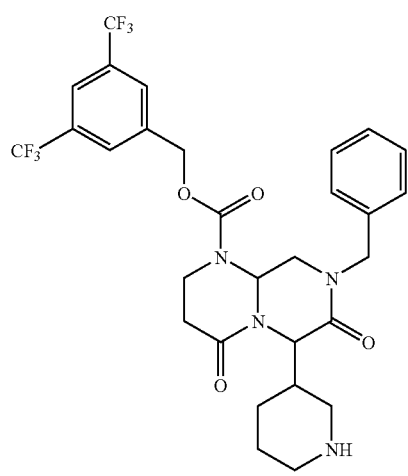
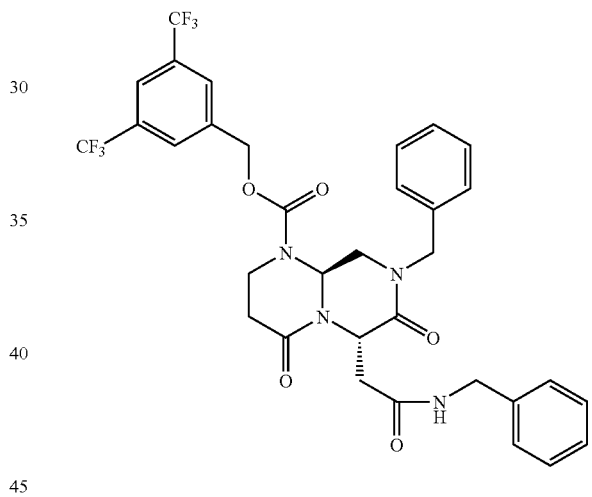
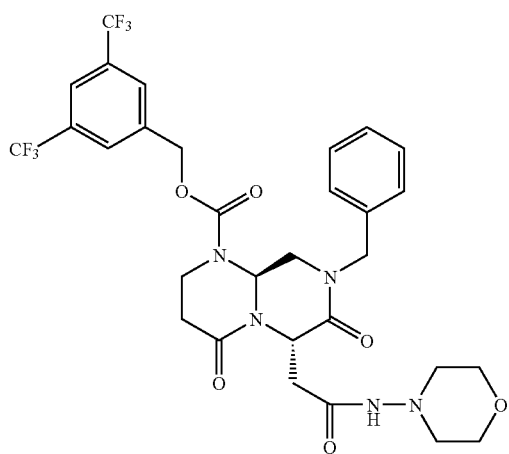
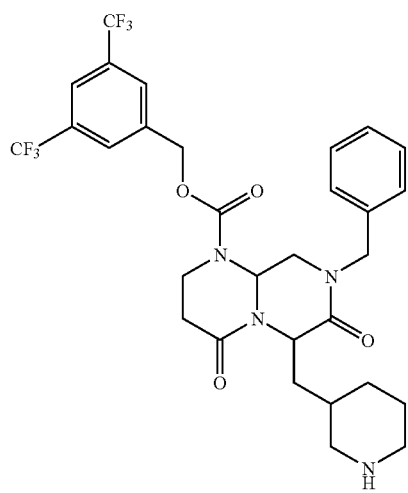

TABLE 2-continued
Representative Compounds
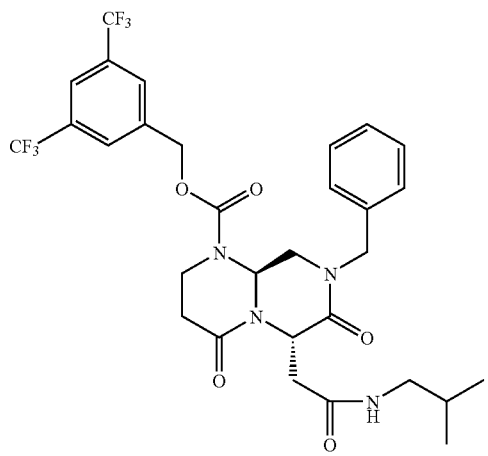
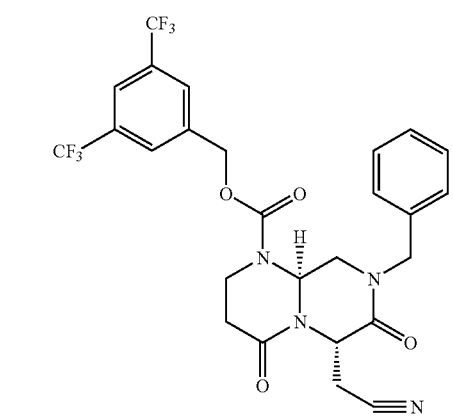
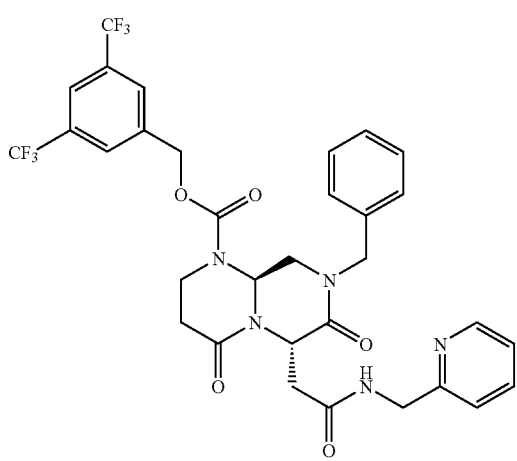
TABLE 2-continued
Representative Compounds
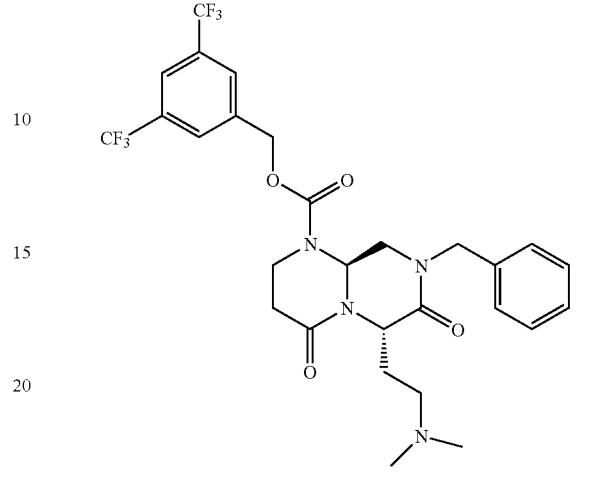
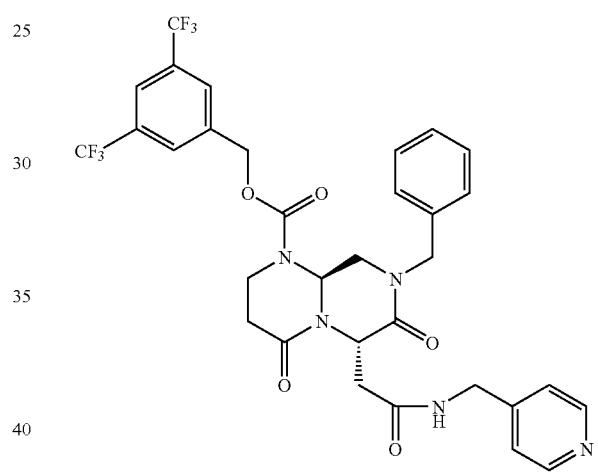
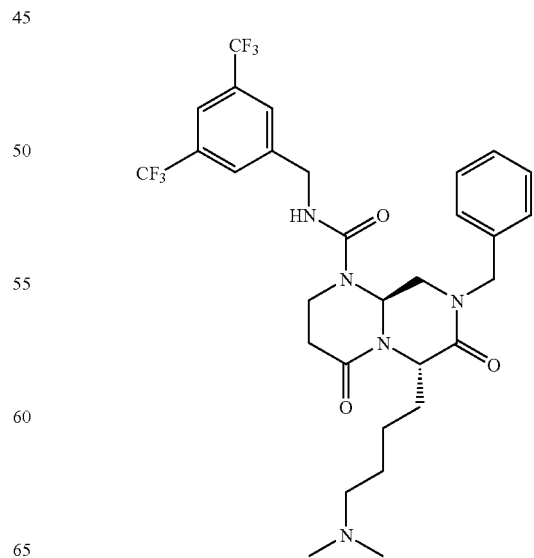

TABLE 2-continued
Representative Compounds
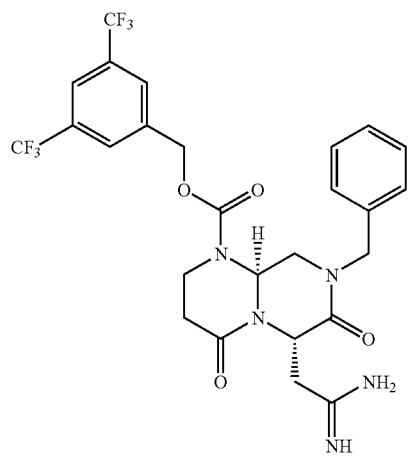
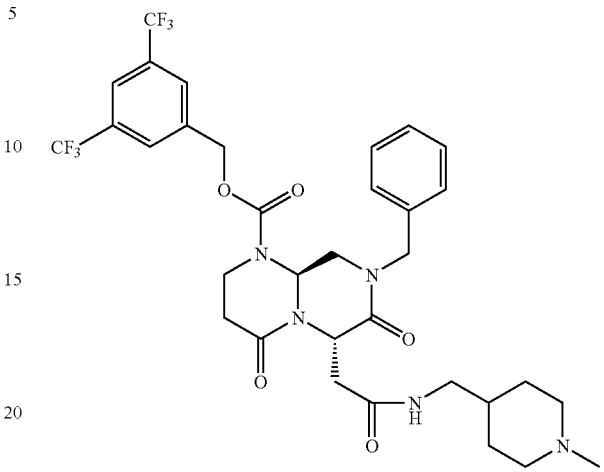
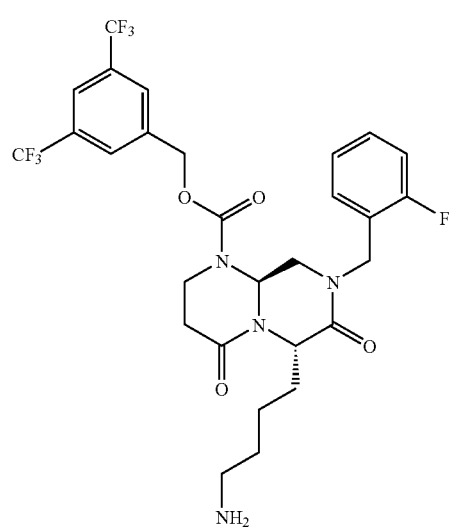
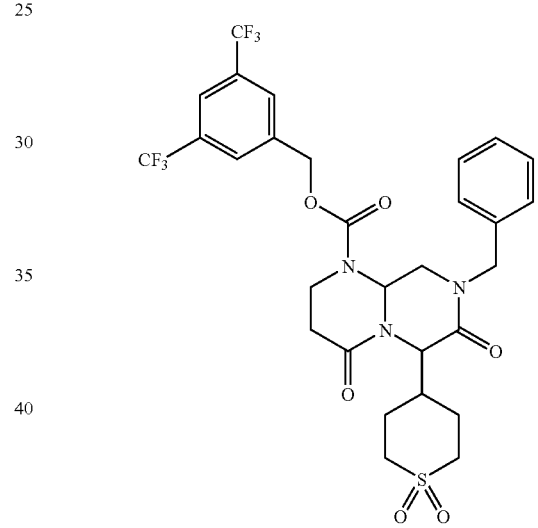
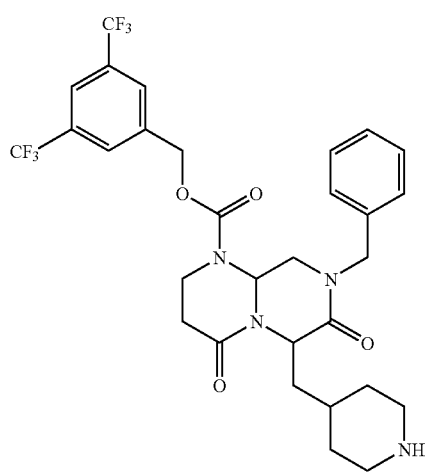
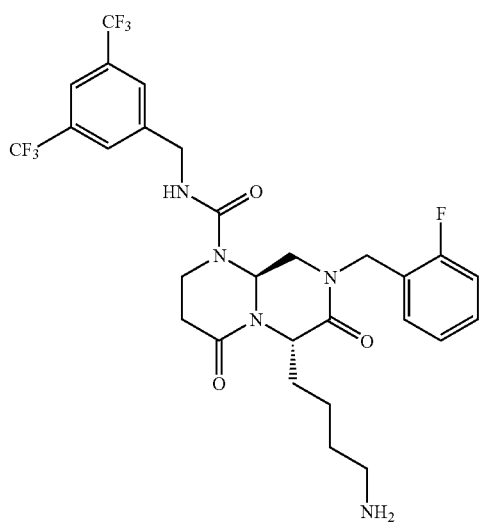

TABLE 2-continued
Representative Compounds
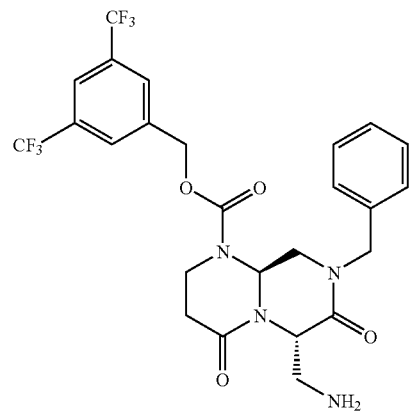
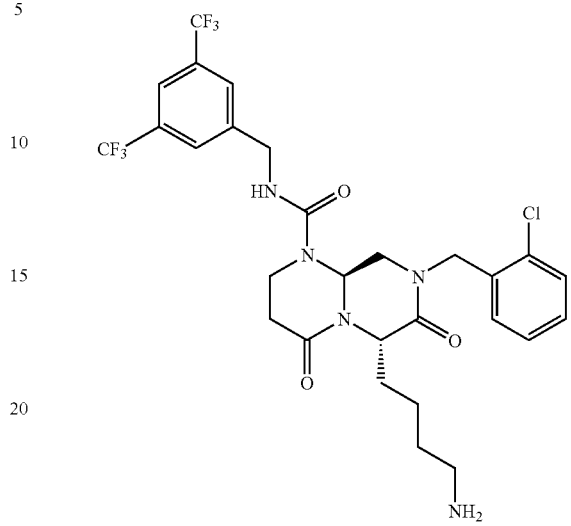
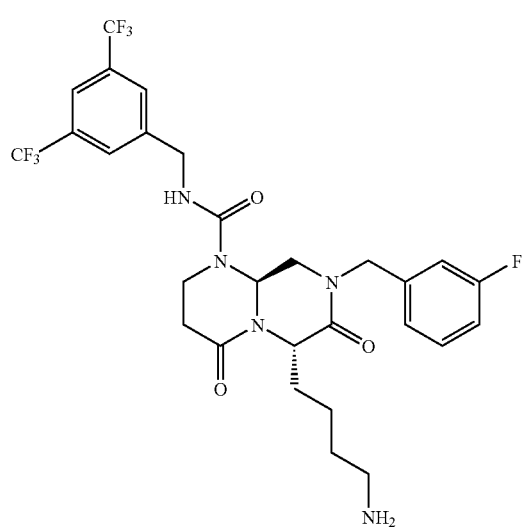
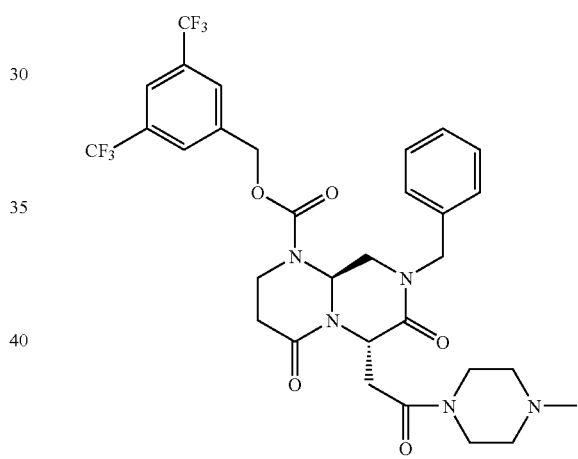
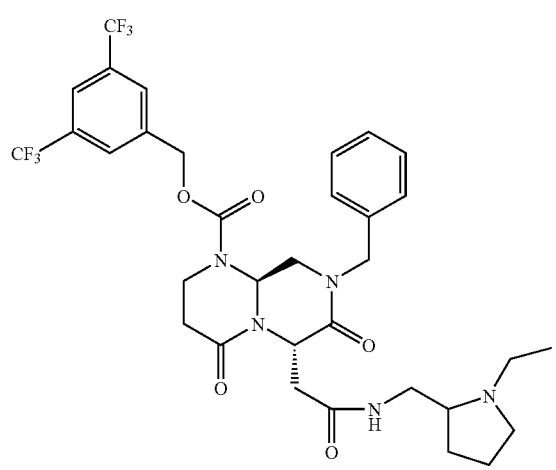
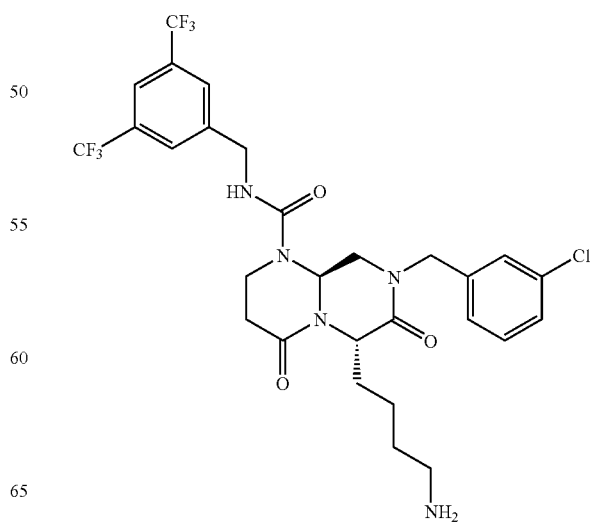

87
TABLE 2-continued
Representative Compounds
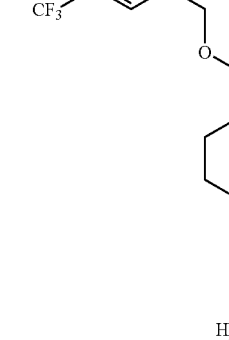
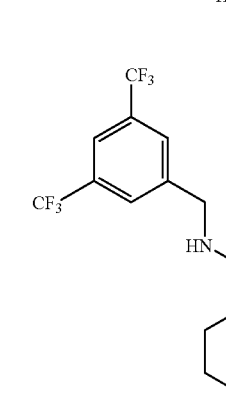
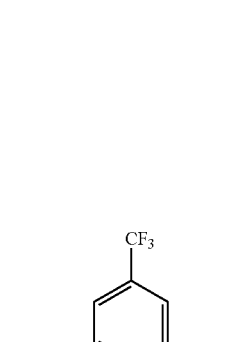
88
TABLE 2-continued
Representative Compounds
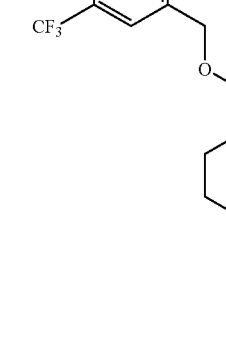

TABLE 2-continued
Representative Compounds
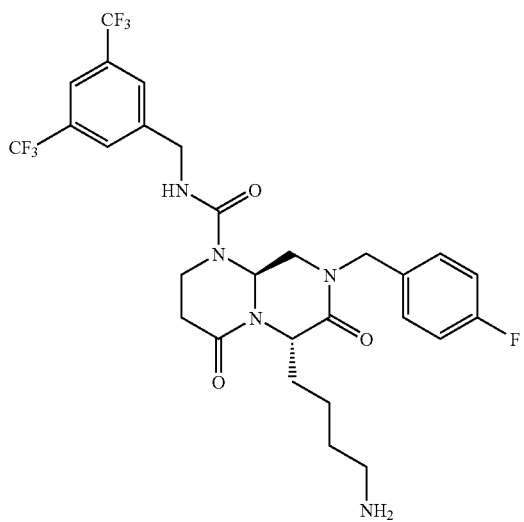
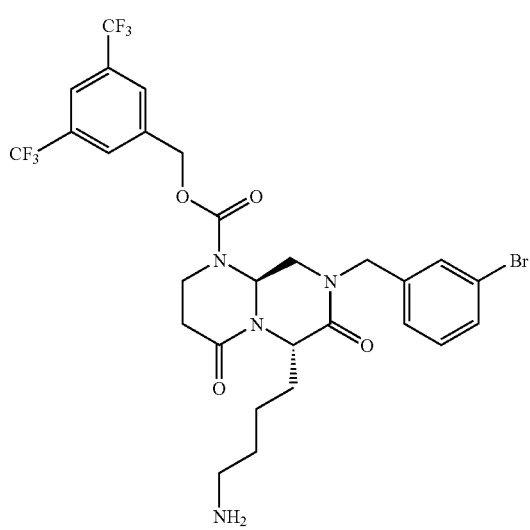
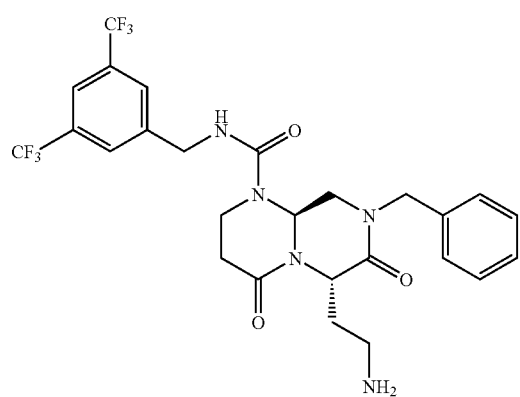
TABLE 2-continued
Representative Compounds
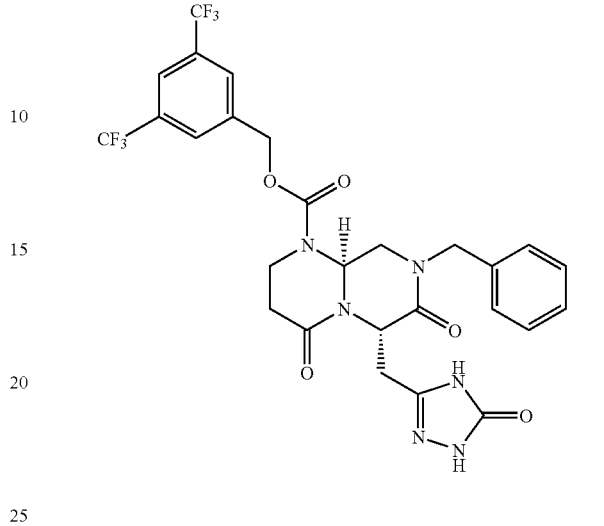
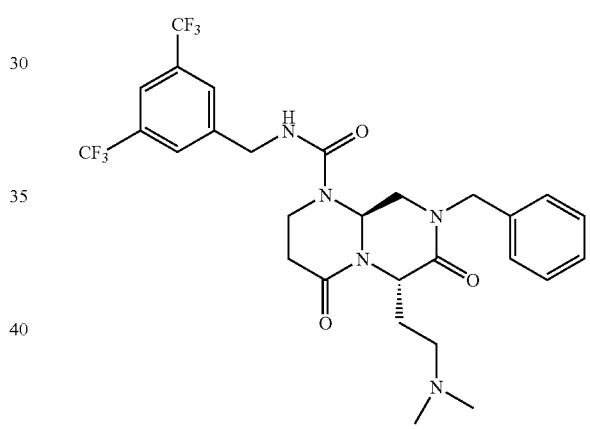
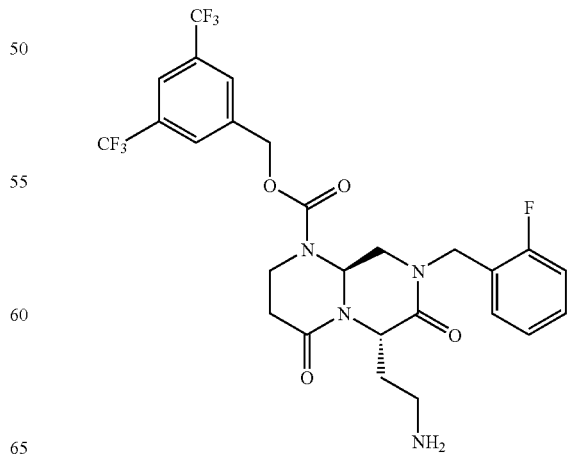

TABLE 2-continued
Representative Compounds
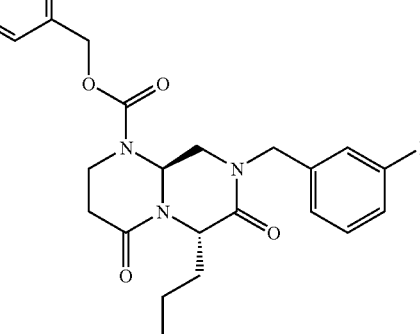
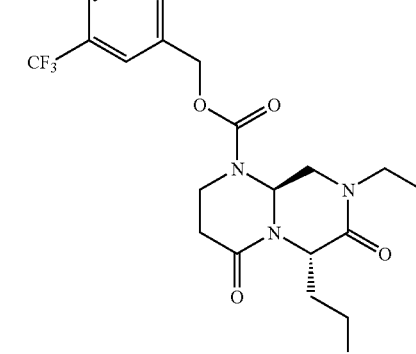
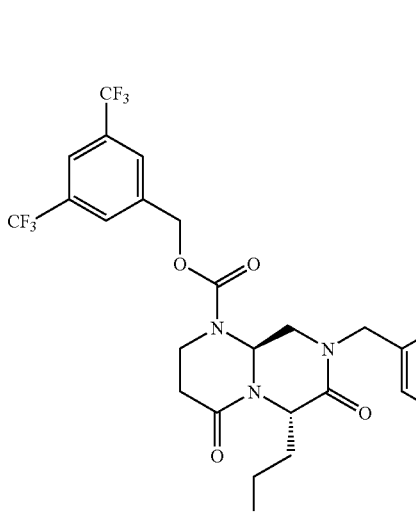

TABLE 2-continued
Representative Compounds
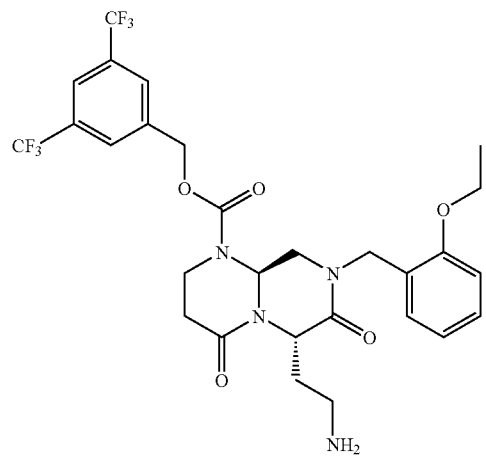
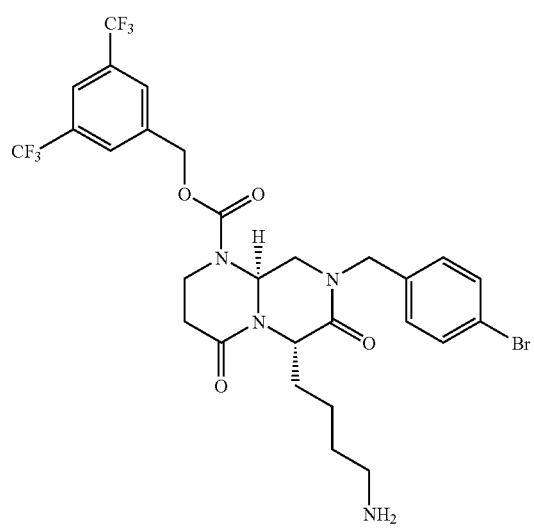
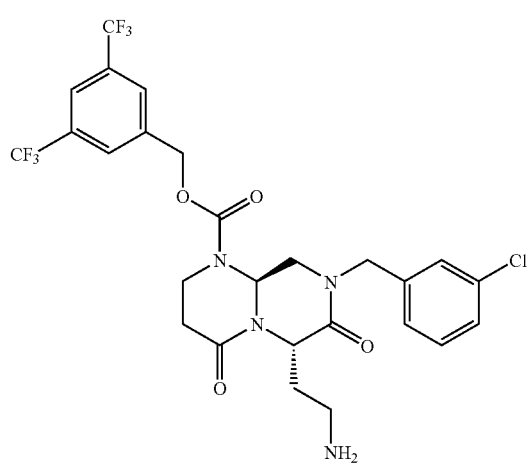
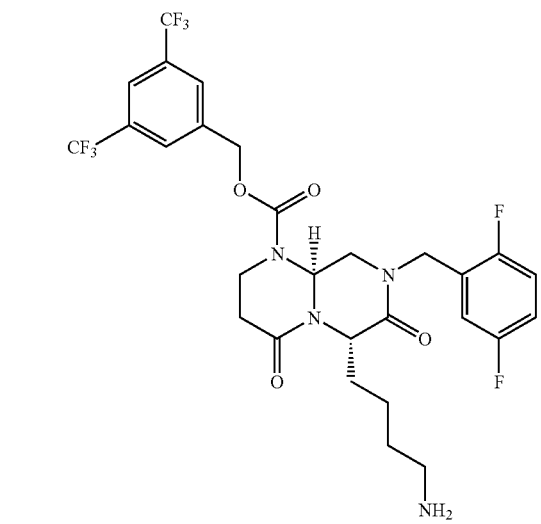
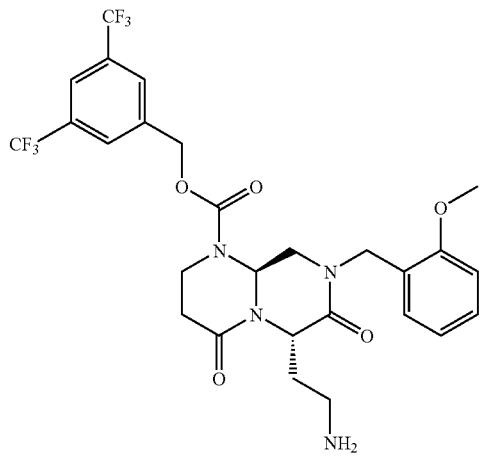
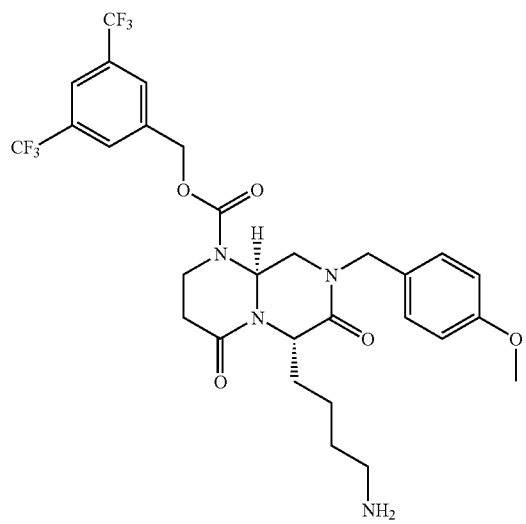

TABLE 2-continued
Representative Compounds
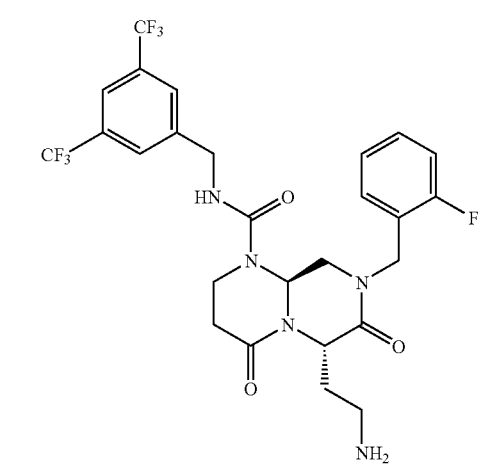
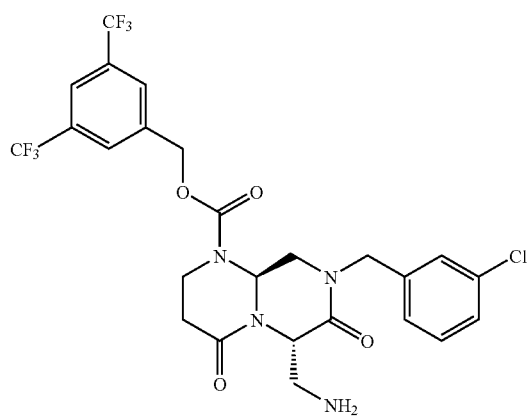
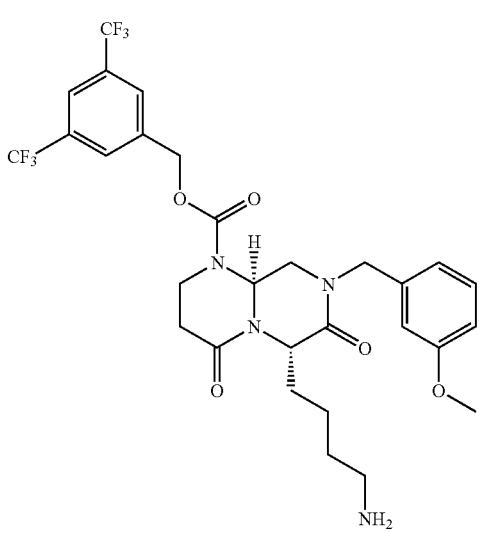
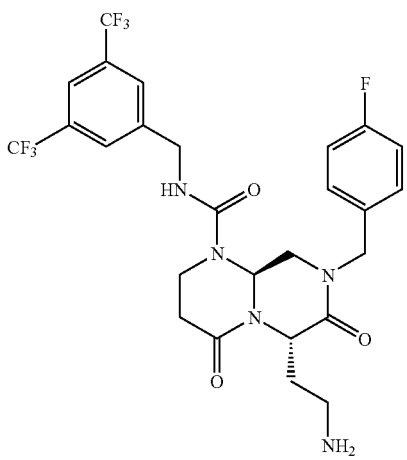

TABLE 2-continued
Representative Compounds
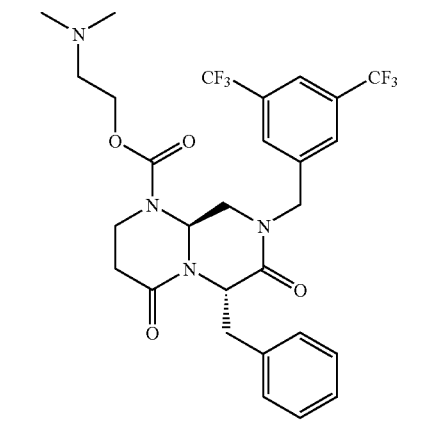
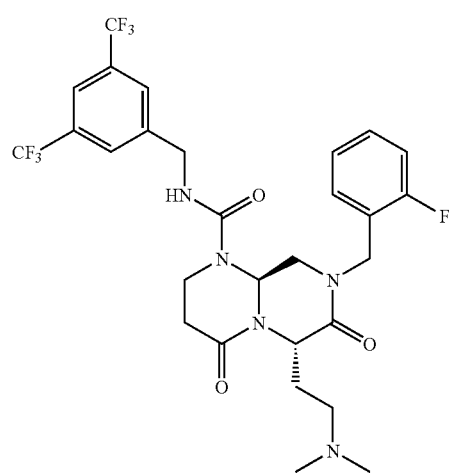
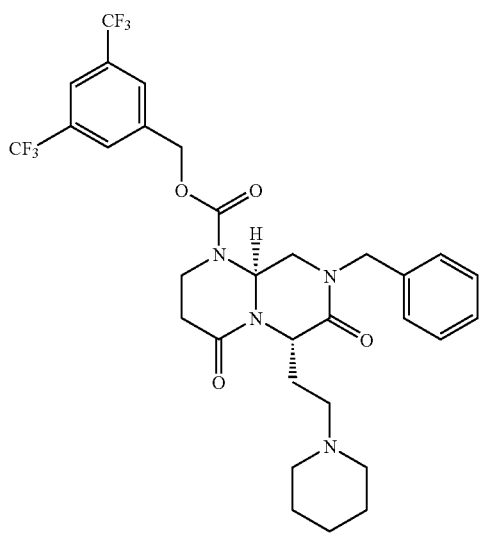
TABLE 2-continued
Representative Compounds
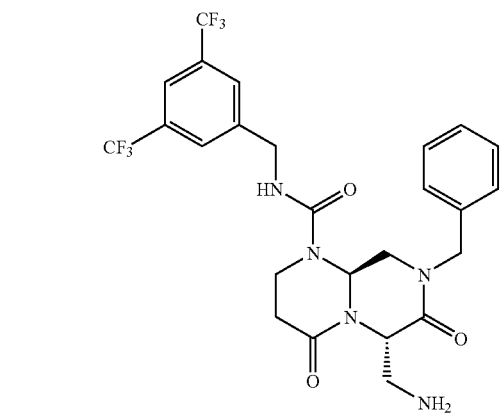
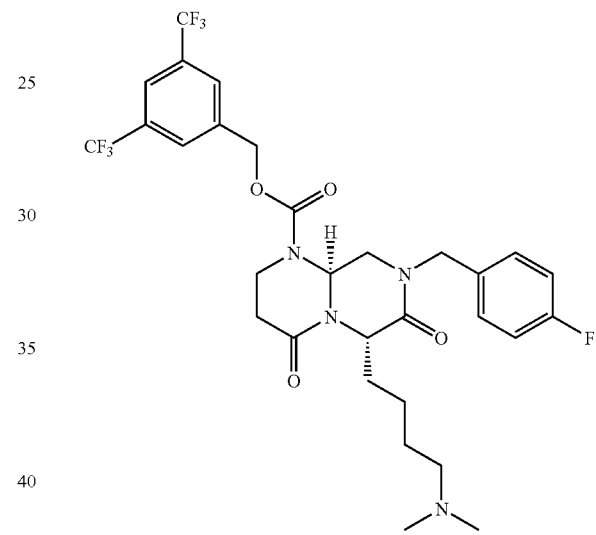
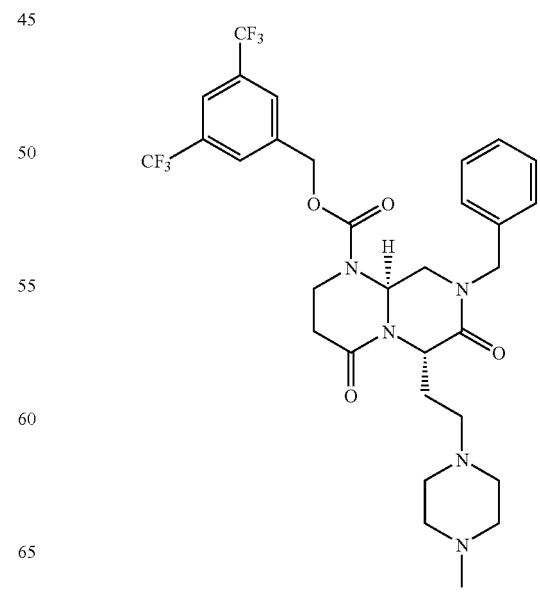

TABLE 2-continued
Representative Compounds
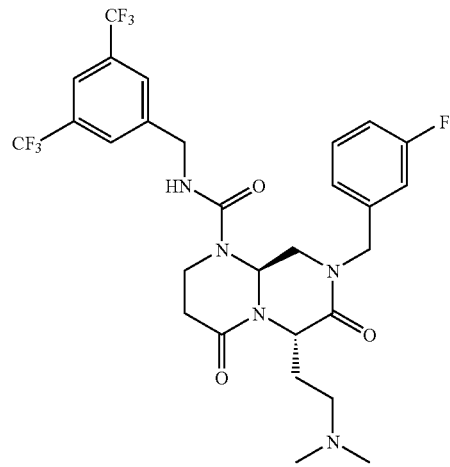
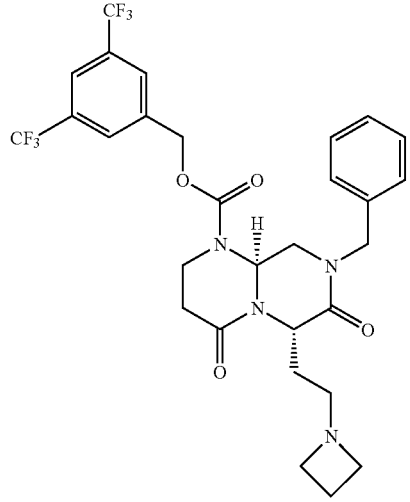
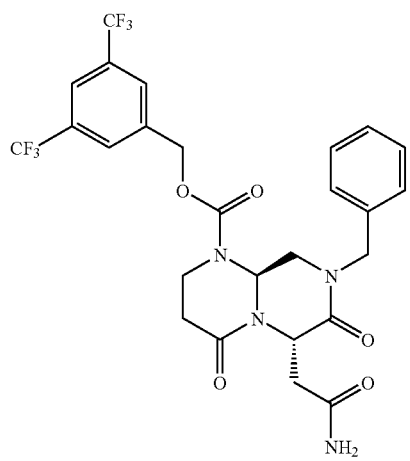
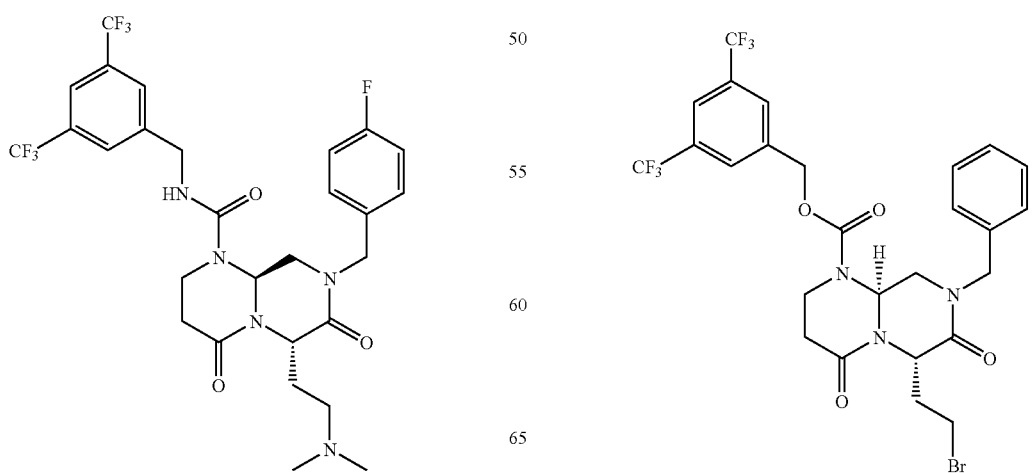

TABLE 2-continued
Representative Compounds
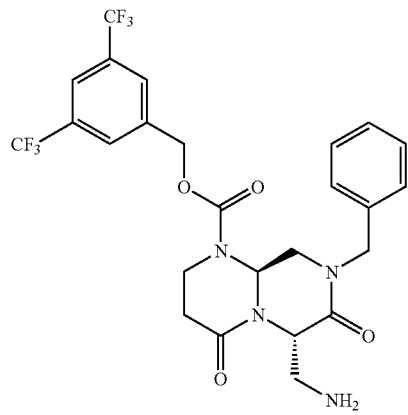
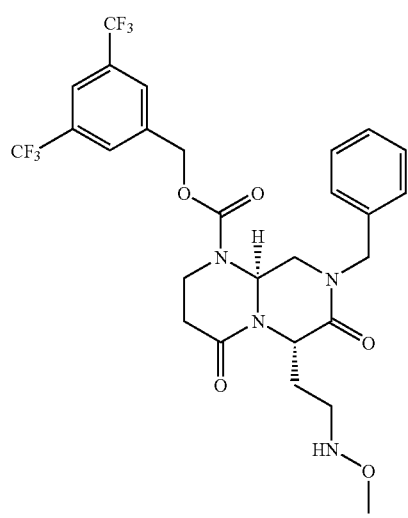
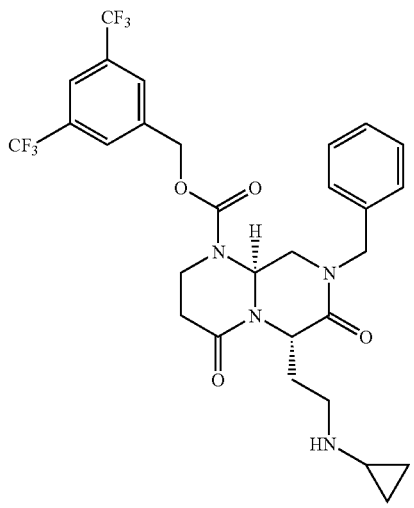
TABLE 2-continued
Representative Compounds
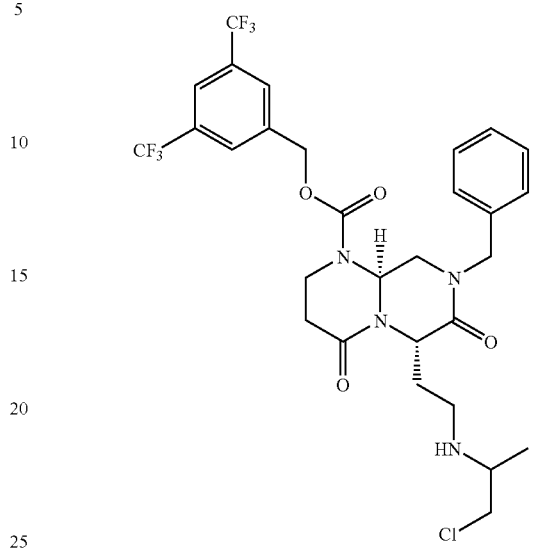
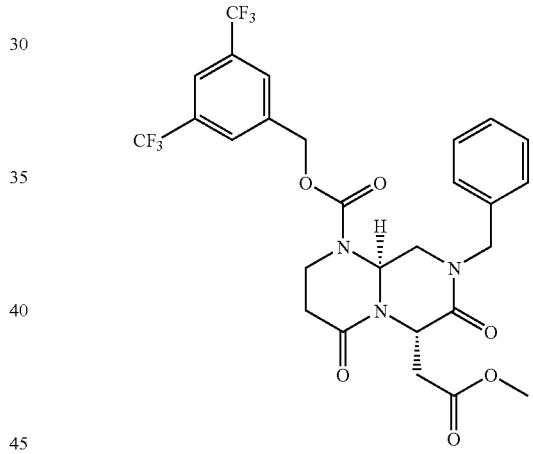
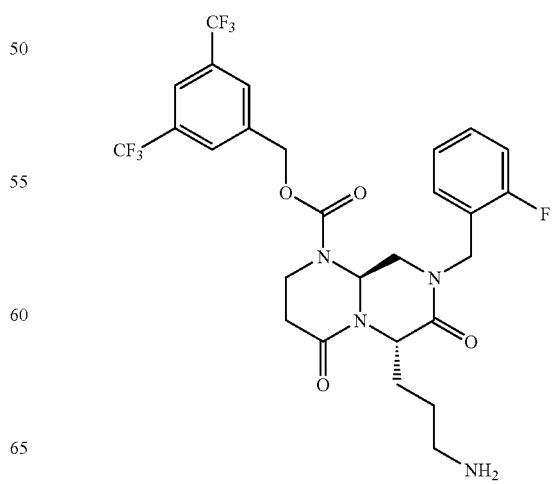

TABLE 2-continued
Representative Compounds
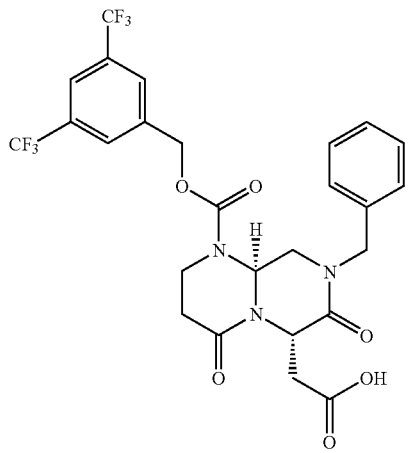
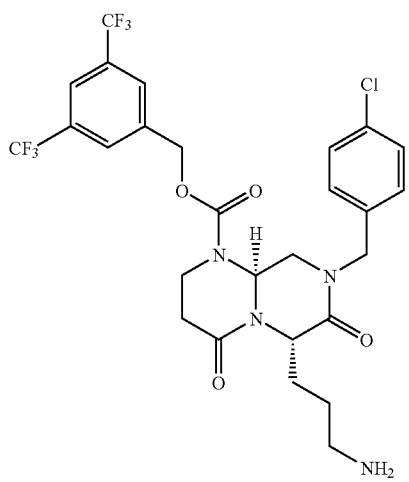
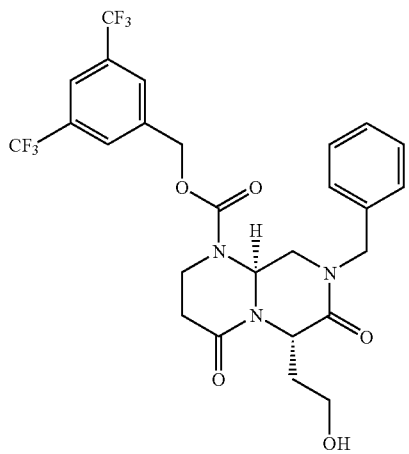
TABLE 2-continued
Representative Compounds
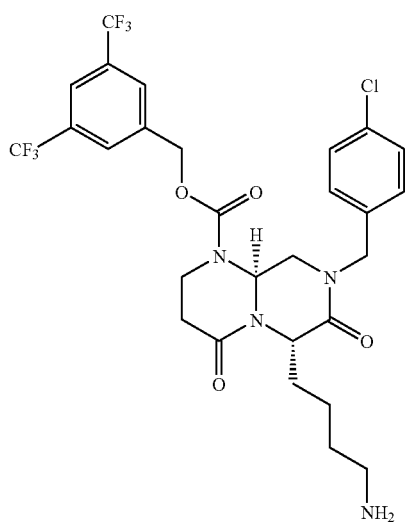
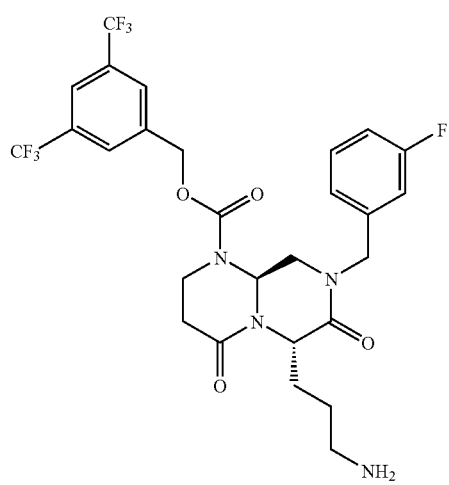
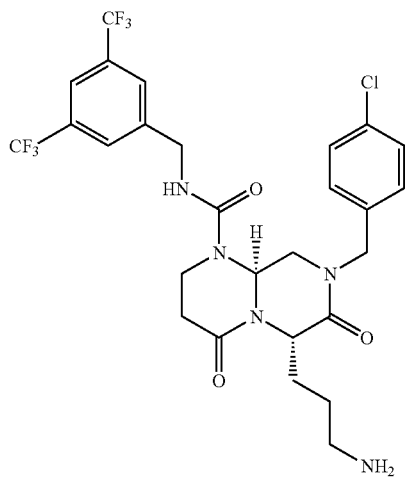

TABLE 2-continued
Representative Compounds
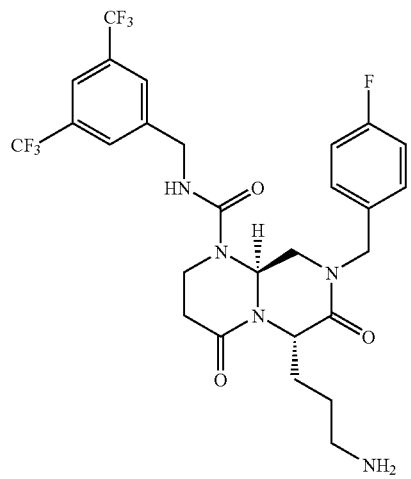
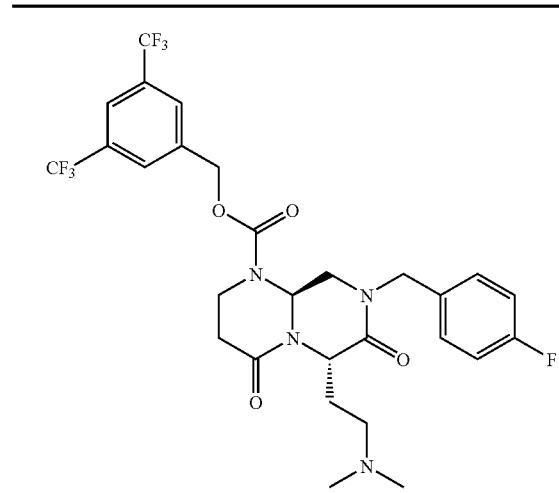
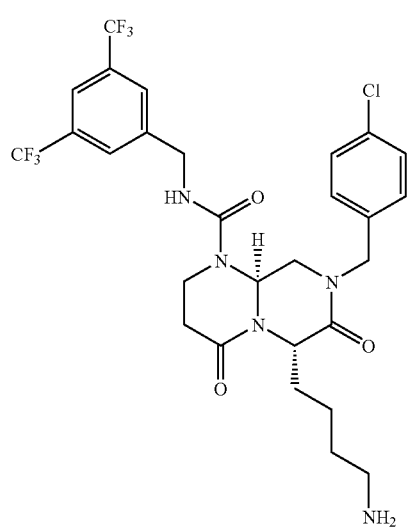
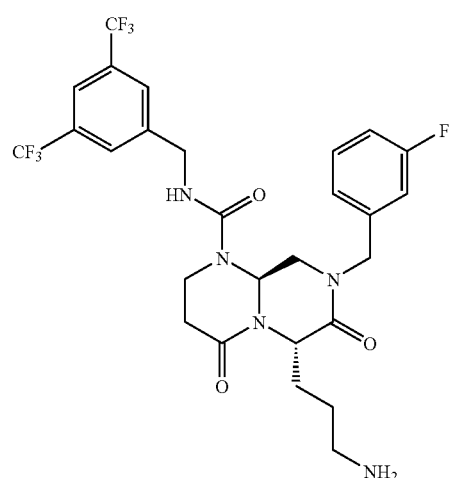
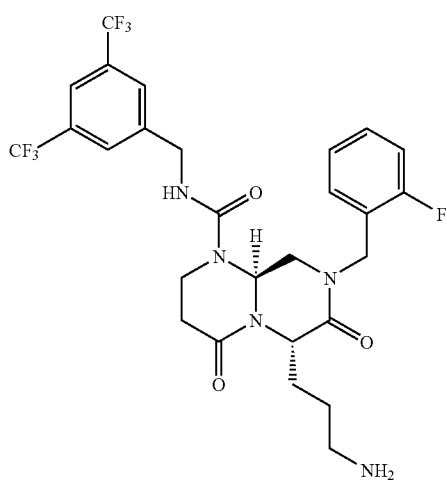
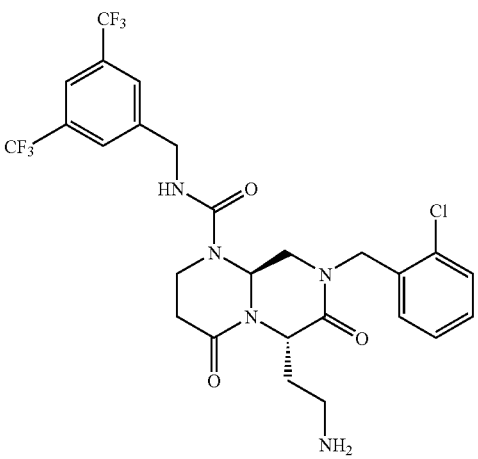

TABLE 2-continued
Representative Compounds
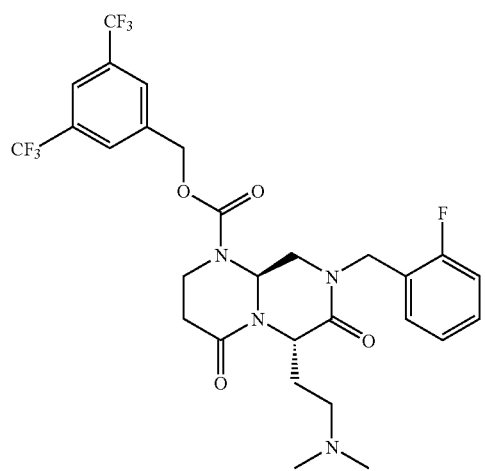
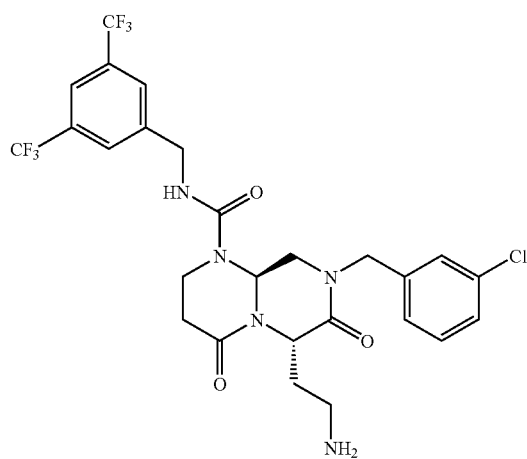
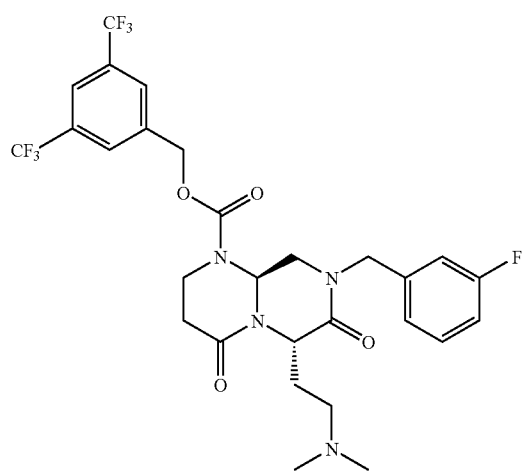
TABLE 2-continued
Representative Compounds
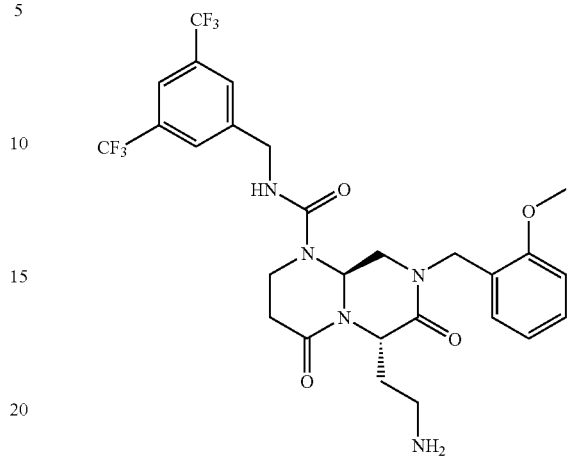
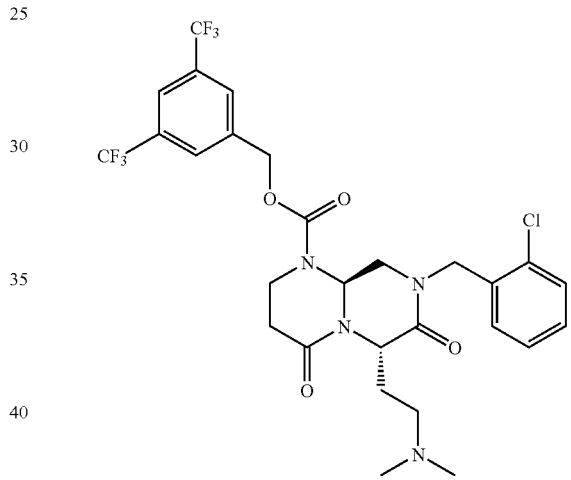
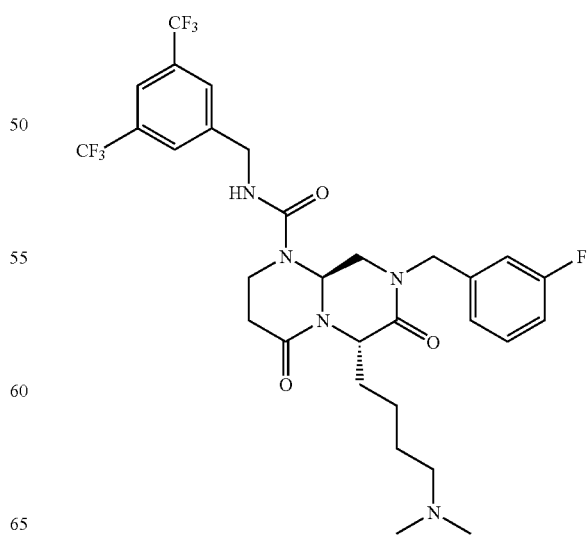

TABLE 2-continued
Representative Compounds
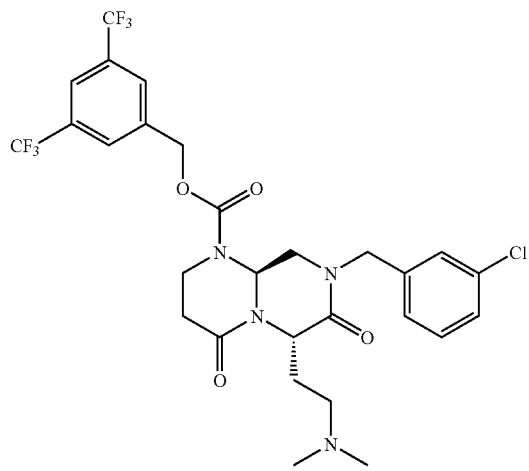
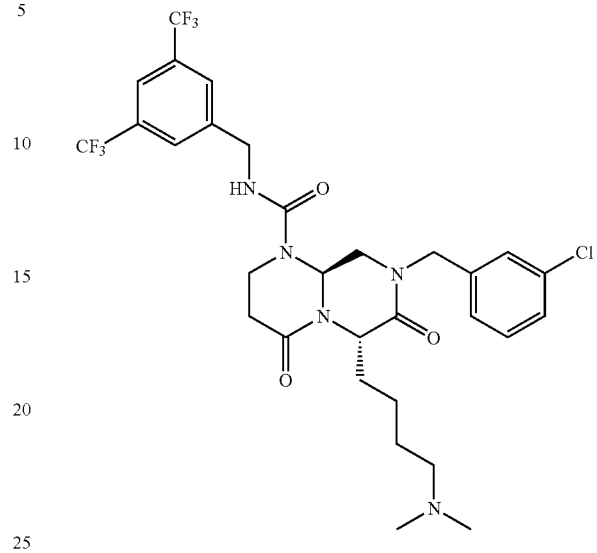
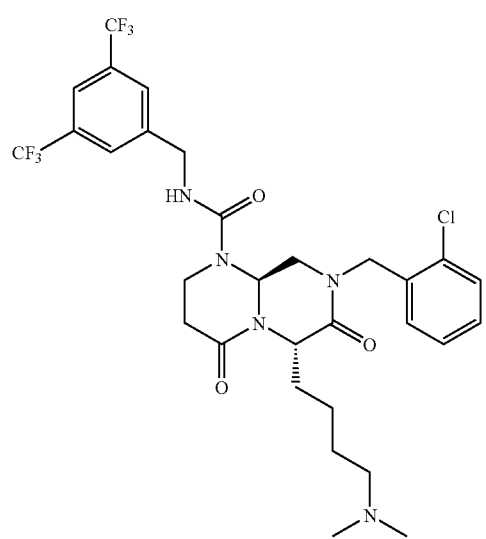
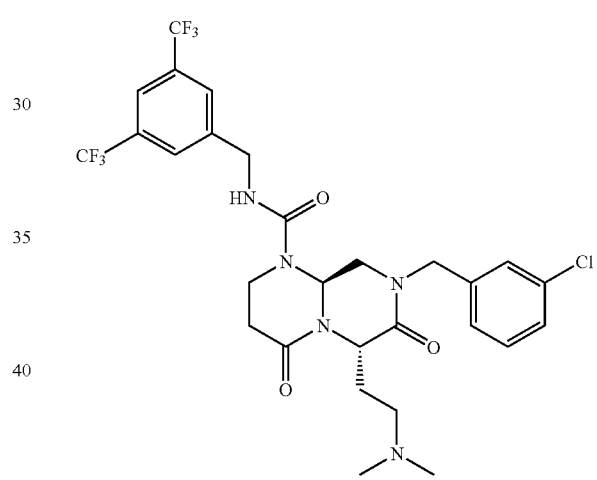
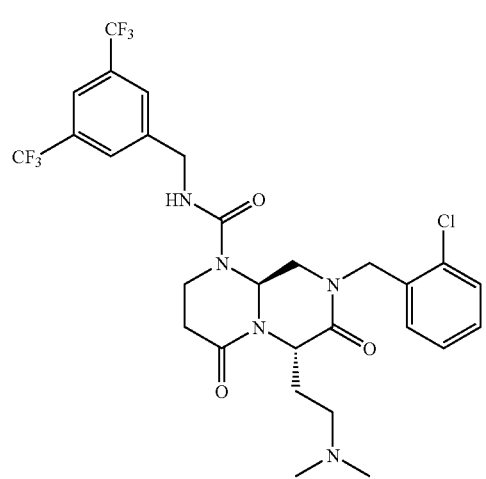
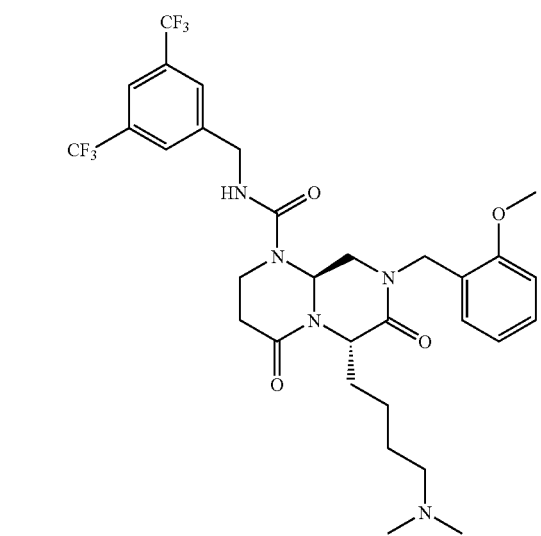

TABLE 2-continued
Representative Compounds
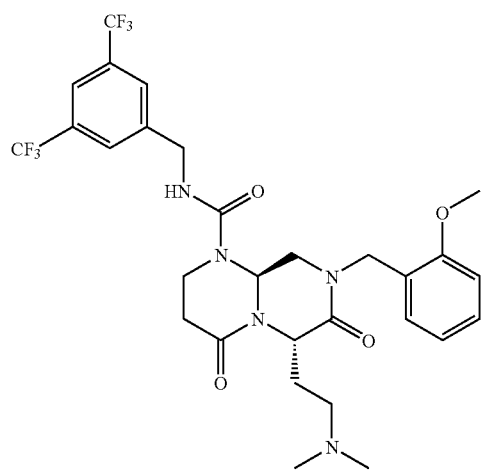
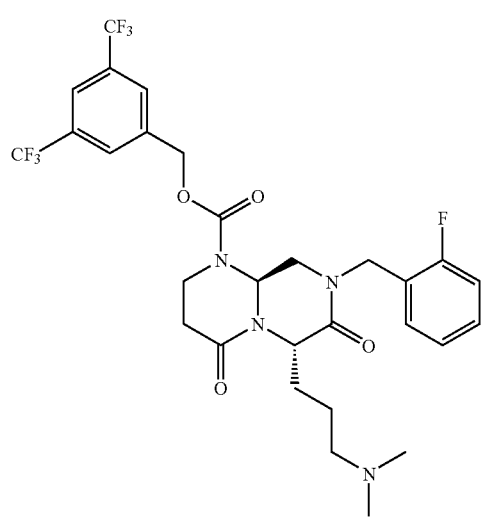
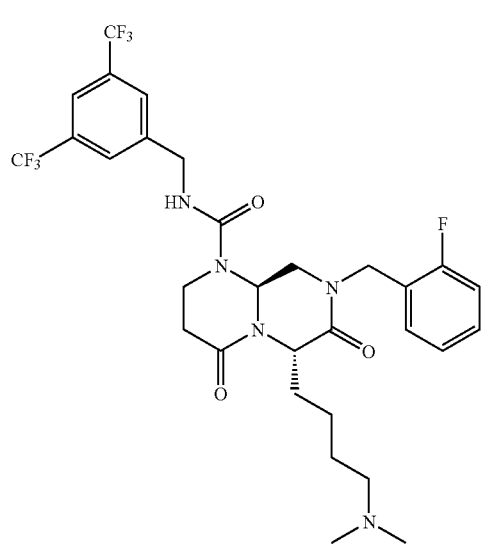
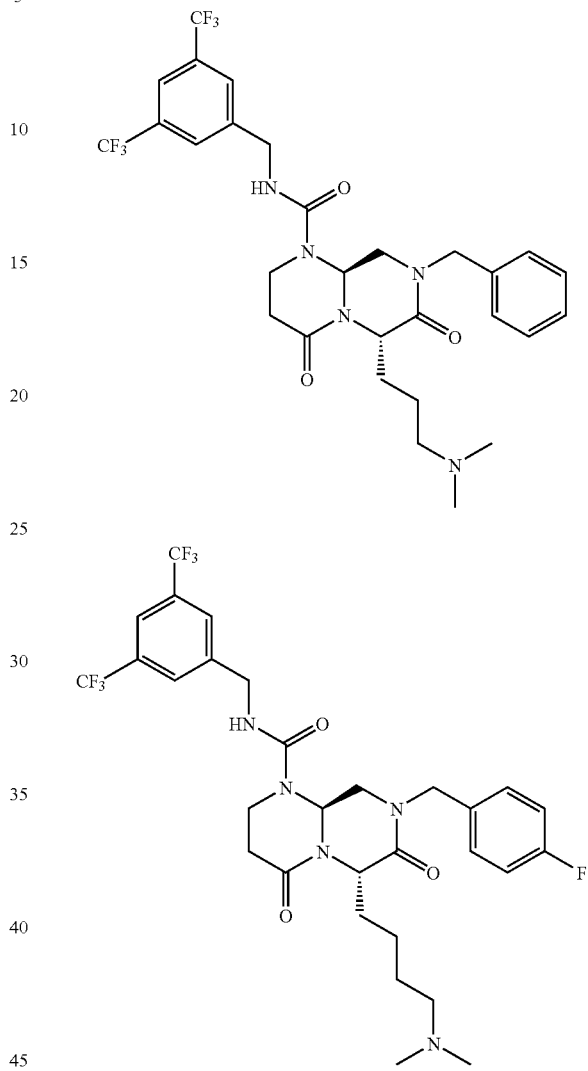
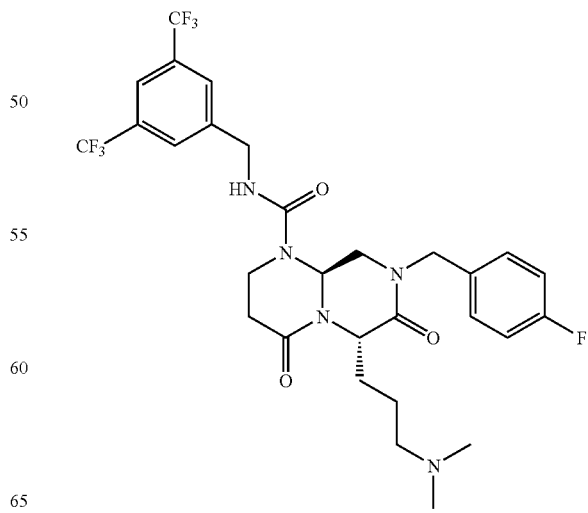

TABLE 2-continued

Representative Compounds

TABLE 2-continued
Representative Compounds
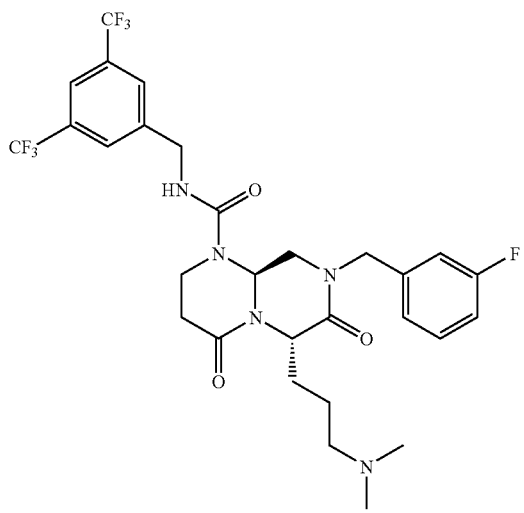
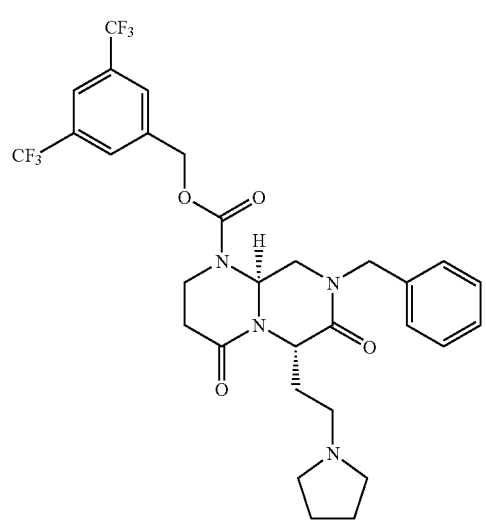
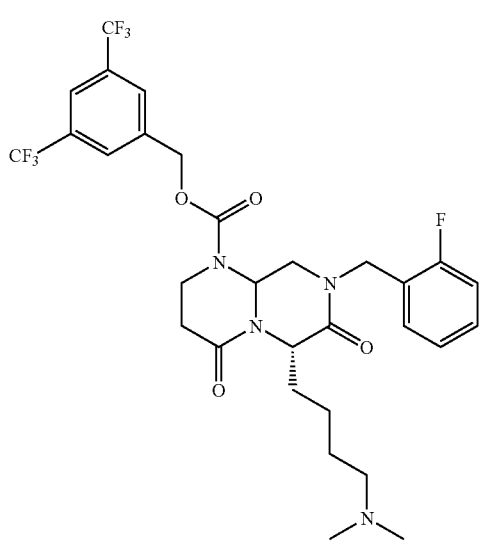
TABLE 2-continued
Representative Compounds
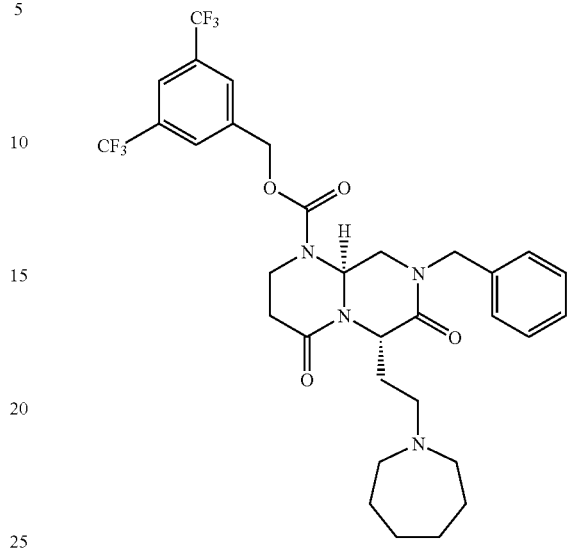
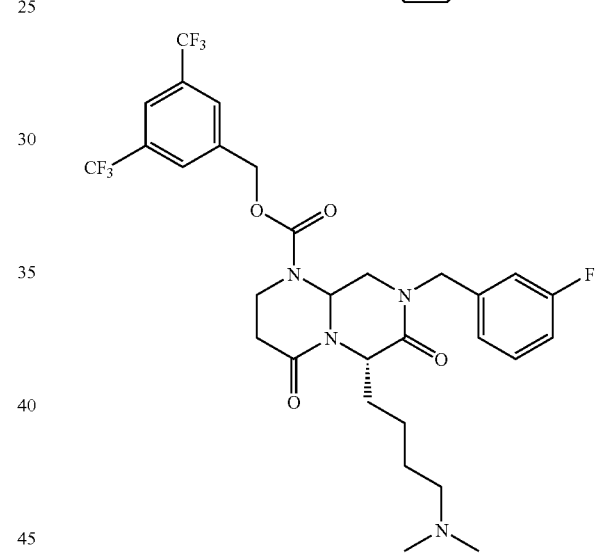
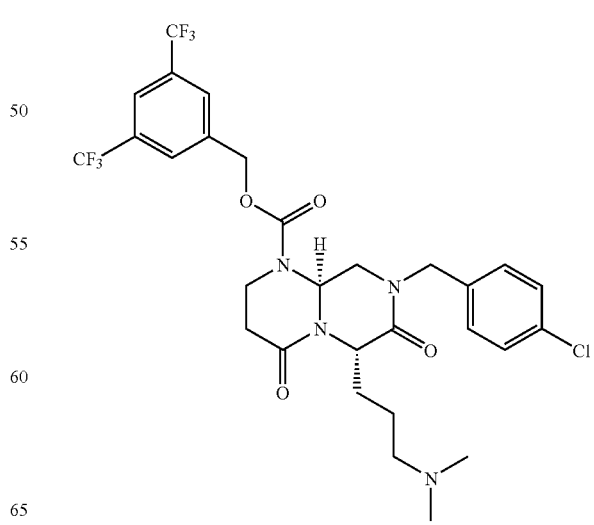

TABLE 2-continued
Representative Compounds
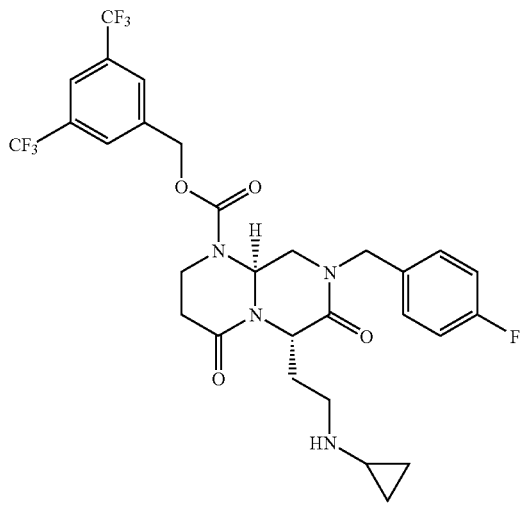
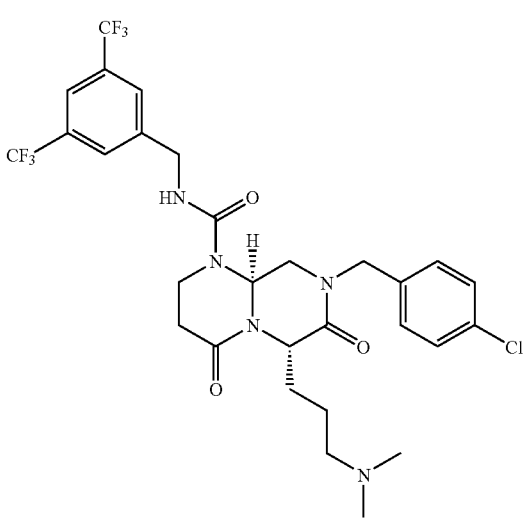
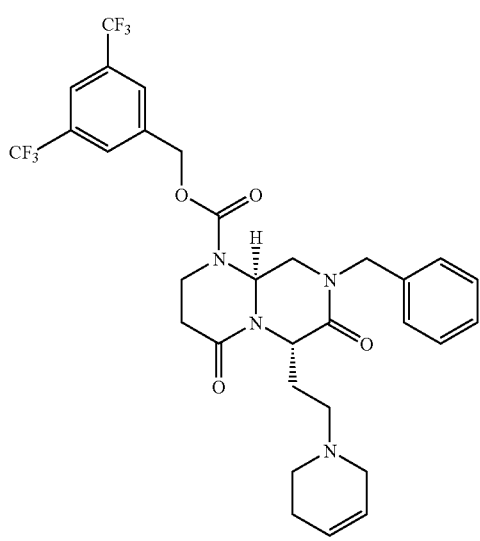
TABLE 2-continued
Representative Compounds
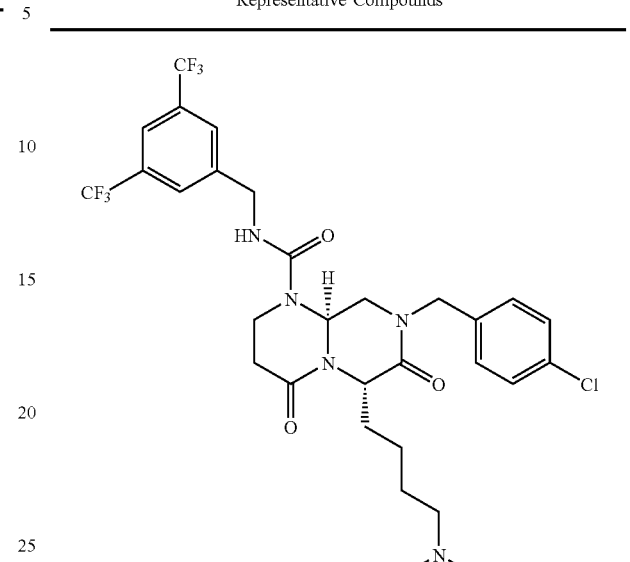
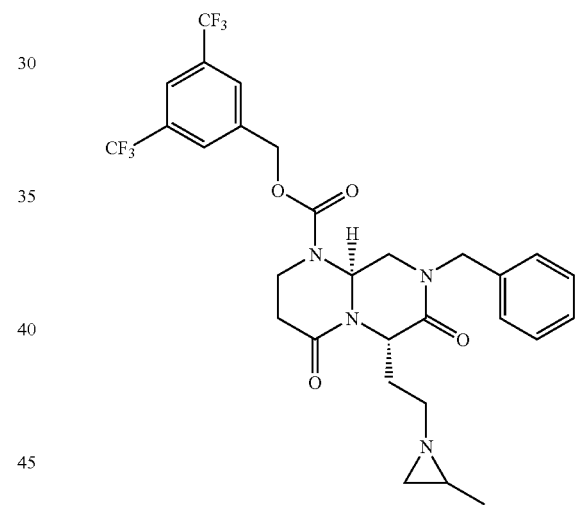
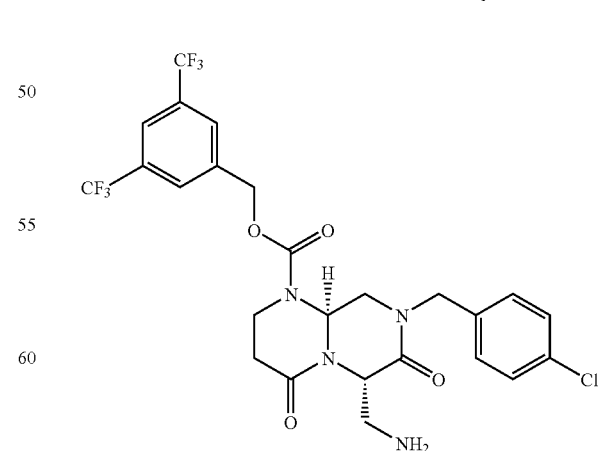

TABLE 2-continued
Representative Compounds
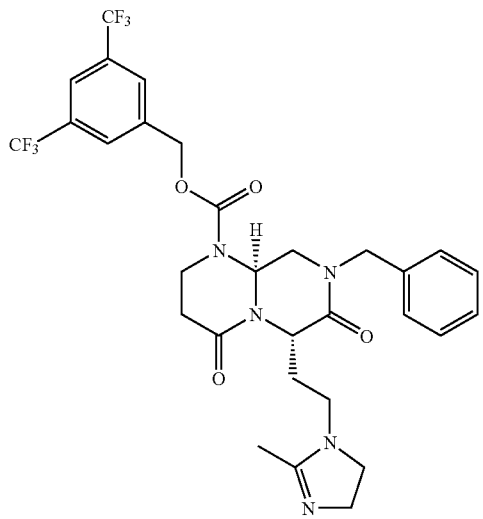
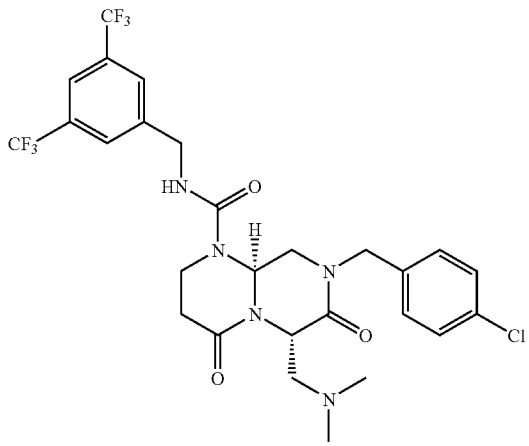
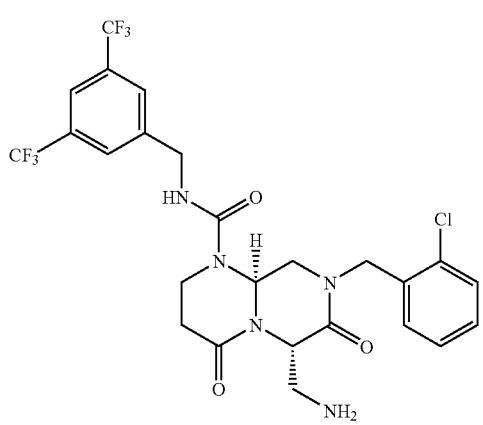
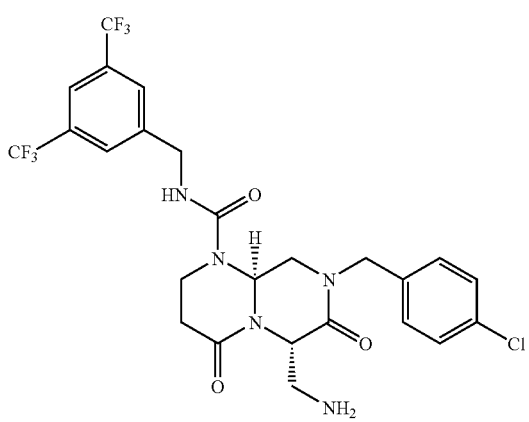
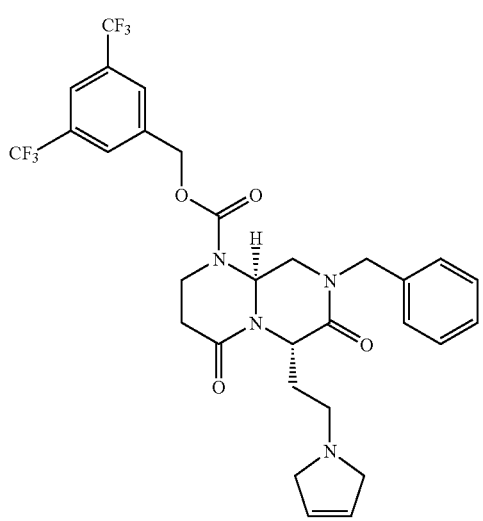
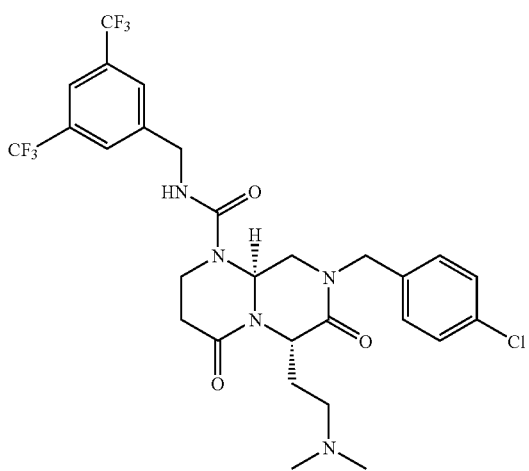

TABLE 2-continued
Representative Compounds
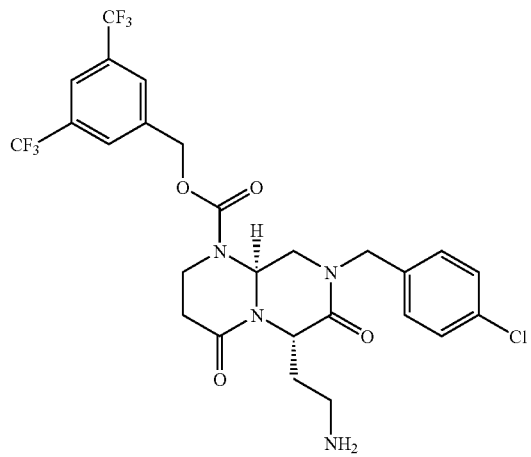
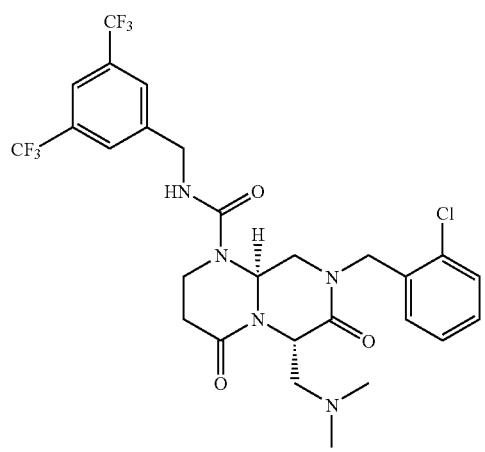
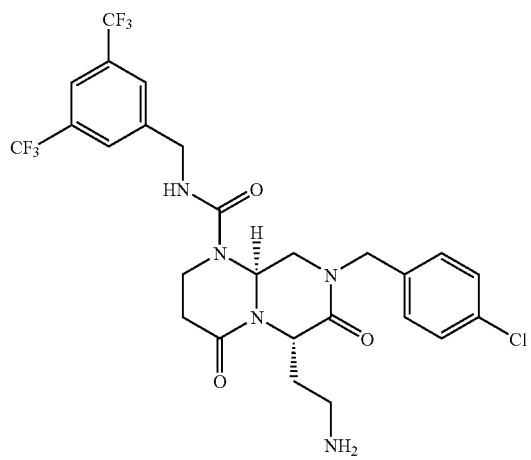
TABLE 2-continued
Representative Compounds
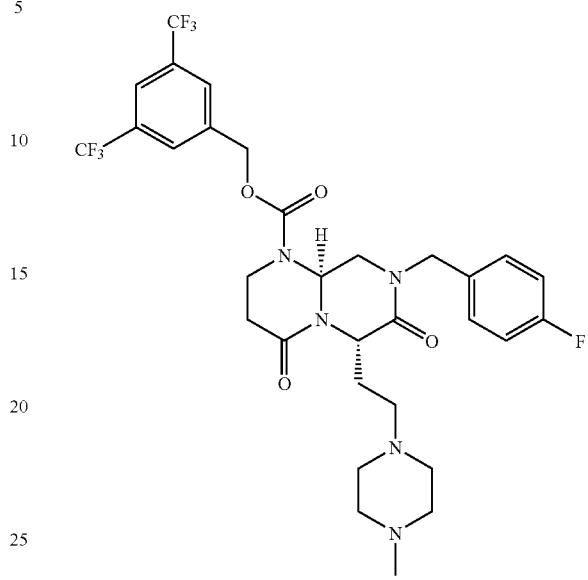
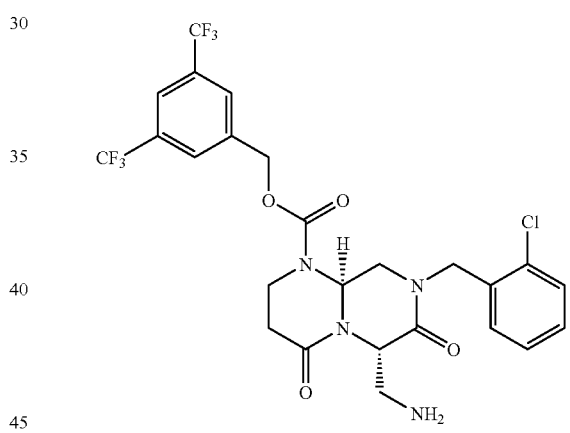
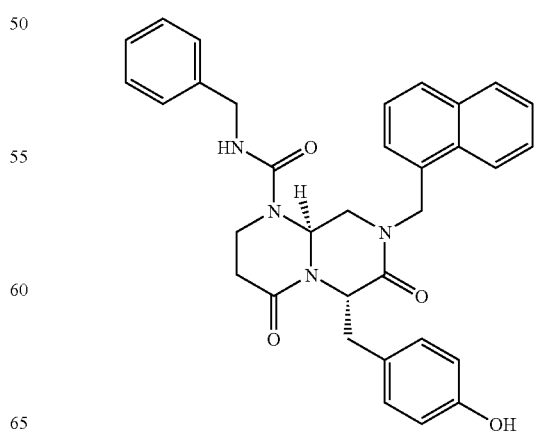

In specific embodiments the compounds of the present invention include those compounds of structure (I) wherein X is —C(C=O)O—, $R_2$ is H, $C_1$-$C_6$ alkyl, or $C_7$-$C_{11}$ arylalkyl; $R_3$ is —$(CH_2)_{1-6}$—N(R')(R''), wherein R' and R'' are independently H or —C(NH)($NH_2$); $R_4$ is $C_7$-$C_{11}$ arylalkyl; and $R_5$ is $C_7$-$C_{11}$ arylalkyl, and wherein $R_4$ and $R_5$ are optionally and independently substituted with 1-3 halogen, 1-3 $C_1$-$C_3$ haloalkyl, or 1-3 $C_1$-$C_3$ alkyl.

In other specific embodiments the compounds of the present invention include those compounds of structure (I) wherein X is —C(C=O)NH—, $R_2$ is H, $C_1$-$C_6$ alkyl, or $C_7$-$C_{11}$ arylalkyl; $R_3$ is

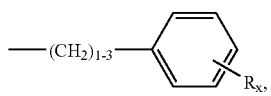

wherein $R_X$ is H, OH or halo; $R_4$ is $C_7$-$C_{11}$ arylalkyl; and $R_5$ is $C_7$-$C_{11}$ arylalkyl, and wherein $R_2$, $R_4$ and $R_5$ are optionally and independently substituted with 1-3 halogens, 1-3 $C_1$-$C_3$ haloalkyls, or 1-3 $C_1$-$C_3$ alkyl.

In still other specific embodiments the compounds of the present invention include those compounds of structure (I) wherein $R_1$ is —C(=O)(NH)—$R_5$ or —C(=O)O—$R_5$; $R_2$ is H, $C_1$-$C_6$ alkyl, or $C_7$-$C_{11}$ arylalkyl; $R_3$ is an amino acid side chain moiety; $R_4$ is $C_7$-$C_{11}$ arylalkyl; and $R_5$ is $C_6$-$C_{10}$ aryl or $C_7$-$C_{11}$ arylalkyl, and wherein $R_4$ and $R_5$ are optionally and independently substituted with 1-3 substituents selected from the group consisting of halogen, $C_1$-$C_3$ haloalkyl, $C_1$-$C_3$ alkyloxy, and $CH_3$(C=O)—.

The compounds of the present invention may generally be prepared by sequential coupling of the individual component pieces either stepwise in solution or by solid phase synthesis as commonly practiced in solid phase peptide synthesis. To this end, the compounds may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis*, 1984, Pierce Chemical Comp., Rockford, Ill.; Atherton, E., Shepard, R. C. *Solid Phase Peptide Synthesis: A Practical Approach*; IRL: Oxford, 1989) or on a silyl-linked resin by alcohol attachment (Randolph et al., *J. Am. Chem. Soc.* 117:5712-14, 1995). The utility and ease of synthesis of the present invention is further exemplified by the applicability of a wide variety of commercially available resins. To this end, a core of either polystyrene or ArgoGel (polyethyleneglycol grafted polystyrene; Argonaut, San Carlos, Calif.) utilizing aminomethyl polystyrene, benzhydrylamine (BHA) methylbenzhydrylamine (MBHA) (Matsueda et al., *Peptides* 2:45, 1981), phenoxybenzylalcohol (Wang resin) (Wang *J. Am. Chem. Soc.* 95:1328, 1973), 2-chlorotrityl (Barlos et al., *Tetrahedron Lett.* 30:3943, 1989, ibid 30:3947, 1989), and PAL (Albericio et al., *J. Org. Chem.* 55:3730, 1990) resins and other resins could be used in the synthesis of the present invention.

In addition, a combination of both solution and solid phase synthesis techniques may be utilized to synthesize the compounds of this invention. For example, a solid support may be utilized to synthesize the linear peptide sequence up to the point that the conformationally constrained reverse-turn is added to the sequence. A suitable conformationally constrained reverse-turn mimetic, which has been previously synthesized by solution synthesis techniques, may then be added as the next "amino acid" to the solid phase synthesis (i.e., the conformationally constrained reverse-turn mimetic, which has at least two reactive sites, may be utilized as the next residue to be added to the linear peptide). Upon incorporation of the conformationally constrained reverse-turn mimetic into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

In another aspect of this invention, methods for constructing the libraries are disclosed. Traditional combinatorial chemistry (e.g., *The Combinatorial Index* Bunin, Academic Press, New York, 1998; Gallop et al., *J. Med. Chem.* 37:1233-51, 1994) and parallel synthesis techniques permit a vast number of compounds to be rapidly prepared by the sequential combination of reagents to a basic molecular scaffold. For example, the above disclosed synthesis may be carried out using the directed sorting technique of Nicolaou and coworkers (Nicolaou et al., *Angew. Chem. Int'l. Ed.* 34:2289-91, 1995). Presently, equipment for this technique is commercially available from IRORI (La Jolla, Calif.). Alternatively, the above disclosed synthesis may be carried out by parallel synthesis using a 48- or 96-well plate format wherein each well contains a fritted outlet for draining solvents and reagents (*A Practical Guide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the calorimetric assay disclosed by Lam et al. (*Nature* 354:82-84, 1991) or Griminski et al. (*Biotechnology* 12:1008-11, 1994). In a preferred embodiment, the library members are in solution and the target is immobilized on a solid phase. Alternatively, the library may be immobilized on a solid phase and may be probed by contacting it with the target in solution.

In another aspect, the present invention encompasses pharmaceutical compositions prepared for storage or administration which comprise a therapeutically effective amount of a compound of the present invention in a pharmaceutically acceptable carrier or diluent. Therapy with inhibitors of cell adhesion is indicated for the treatment, delay of onset of symptoms, or prevention of a variety of inflammatory conditions, particularly rheumatoid arthritis, inflammatory bowel disease and asthma. Those experienced in this field are readily aware of the circumstances requiring anti-inflammatory therapy.

As used herein, the phrase "treating . . . with . . . (a compound)" or a paraphrase or equivalent thereof means (1) administering the compound to a patient, (2) administering to a patient the compound or another agent to cause the presence or formation of the compound inside the patient.

The "therapeutically effective amount" of a compound of the present invention will depend on the route of administration, the type of warm-blooded mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted, those skilled in the medical arts will recognize.

The "therapeutically effective amount" of the compound of the present invention can range broadly depending upon the desired effects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceutical Sciences*, Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compounds of the present invention are useful in the prevention and treatment of a wide variety of clinical conditions which are characterized by the presence of an excess tachykinin, in particular substance P, activity. These conditions may include: disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS), amyotrophic lateral sclerosis (ALS; Lou Gehrig's disease) and other neuropathological disorders such as peripheral neuropathy, AIDS related neuropathy, diabetic neuropathy, chemotherapy-induced neuropathy, and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharyngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such eczema and rhinitis; hyper sensitivity disorders such as poison ivy; ophthalmic diseases such a conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; postoperative neuroma, particularly of mastectomy; vulvar vestibulitis; amniogenesis; adverse immunological reactions such as rejection of transplanted tissues and disorders related to immune enhancement of suppression, such as systemic lupus erythmatosus; gastrointestinal (GI) disorders, including inflammatory disorders, and disease of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain of nociception, for example, chronic pain of that attributable to, or associated with, any of the foregoing conditions, especially the transmission of pain in migraine such as headache, toothache, cancerous pain, back pain, and superficial pain on congelation, burn, herpes zoster of diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by, for example, chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. The compounds of the present invention are especially useful in the treatment of emesis induced by antineoplastic (cytotoxic) agents including those routinely used in cancer chemotherapy.

Examples of such chemotherapeutic agents include: alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described in, for example, DJ Stewart in "Nausea and Vomiting: Recent Research and Clinical Advances", Eds. J. Kucharczyk et al., *CRC Press Inc., Boca*

Raton, Fla., USA (1991), pages 177-203. Commonly used chemotherapeutic agents include cisplatin, dacarbazine, mechlorethamine, streptozocin, cyclophosphamide, carmustine, lomustine, doxorubicin, daunorubicin, procarbazine, mitomycin, cytarabine, etoposide, methotrexate, 5-fluorouracil, vinblastine, vincristine, bleomycin, and chlorambucil (Gralla et al., *Cancer Treatment Reports* 68, 163-72, 1984).

The compounds of the present invention are also of use in the treatment of emesis induced by radiation including radiation therapy such as in the treatment of cancer, or radiation sickness, and in the treatment of post-operative nausea and vomiting.

Further, the compounds of the present invention can act as calcium channel blocking agents. As such, the compounds of the present invention are useful in the prevention or treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrug resistance in tumor cells by enhancing the efficacy of chemotherapeutic agents. In addition, the compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; asthma; osteoarthritis; rheumatoid arthritis; and especially migraine. The compounds of the present invention are also particularly useful in the treatment of diseases characterized by neurogenic mucus secretion, especially cystic fibrosis.

The compounds of the present invention may be used singularly, as a combination of two or more compounds, in combination with other known inhibitors of central nervous disorders, or in combination with known inhibitors of other disorders. For example the compounds of this invention may be used therapeutically with corticosteroids, non-steroidal anti-inflammatory agents, COX-2 inhibitors, matrix metalloprotease inhibitors or lipoxygenase inhibitors. The compounds of the invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, intranasal, intrarectal or intramuscular form, all using forms well known to those of ordinary skill in the pharmaceutical arts. The compounds may be administered intraocularly or topically as well as orally or parenterally.

The compounds of this invention may be administered by inhalation, and thus may be delivered in the form of an aerosol spray from pressurized packs or nebulizers. The compounds may also be delivered as powders, which may be formulated, and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compounds are coupled. The neurokinin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the neurokinin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of this invention may be used in the form of a pharmaceutical preparation, for example in solid, semisolid or liquid form, which contains one or more of the compounds of the present invention, as an active ingredient, in a mixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparation in solid, semisolid, or liquid form, and in addition, auxiliary, stabilizing, thickening and coloring agents and perfumes may be used. The active object compounds are included in the pharmaceutical composition in an amount sufficient to produce the desired effect upon the process or condition of the disease.

For preparing solid compositions such as tablets, the principal active ingredient is mixed with a pharmaceutical carrier; conventional tableting ingredients such as corn starch, lactose, sucrose, sorbitol, talc, stearic acid, magnesium stearate, dicalcium phosphate or gums, and other pharmaceutical diluents; water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers coatings, such materials including a number of polymeric acids and mixtures of polymeric acids with such materials as shellac, acetyl alcohol and cellulose acetate.

Liquid forms in which the compositions of the present invention may be incorporated for administration orally or by injection include aqueous solution, suitably flavored syrups, aqueous or oil suspensions, and emulsions with acceptable oils such as cottonseed oil, sesame oil, coconut oil or peanut oil, or with solubilizing or emulsifying agents suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, or gelatin.

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as set forth above. Preferably the compositions are administered by the oral or nasal respiratory route for local or systemic effect. Compositions in preferably sterile pharmaceutically acceptable solvents may be nebulized by use of inert gases. Nebulized solutions may be breathed directly form the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent. For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

Similarly, for the treatment of respiratory diseases, such as asthma, a compound of the present invention may be used in conjunction with a bronchodilator, such as a 2-adrenergic receptor agonist of a tachykinin antagonist, which acts at neurokinin-2 receptors. Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, a compound of the present invention may be used in conjunction with a tachykinin antagonist which acts at neurokinin-2 receptors, or with a tachykinin receptor antagonist which acts at neurokinin-1, neurokinin-2, and neurokinin-3 receptors. Similarly, for the prevention or treatment of emesis, a compound of the present invention may be used in conjunction with other anti-emetic agents, especially $5HT_3$ receptor antagonists, such as ondansetron, granisetron, tropisetron, decadron, zatisetron, as well as other commercially and naturally available pharmacologically active agents. Likewise, for the prevention or treatment of migraine, a compound of the present invention may be used in conjunction with other anti-migraine agents, such as ergotamines or $5HT_3$ agonists, especially sumatriptan. Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agents may be administered to a patient simultaneously, sequentially, or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication of special diets then being followed by patient, and other factors which those skilled in the art will recognize, with the appropriate dosage ultimately at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day, A compound may be administered on a regiment of 1 to 4 times per day, preferably once or twice per day.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

The following examples are provided for purposes of illustration, not limitation. These examples illustrate the syntheses of reverse-turn mimetics of this invention. Specifically, the preparation of reverse-turn mimetics was carried out on solid phase. The solid phase syntheses of these reverse-turn mimetics demonstrate that libraries containing such members may be readily prepared.

| Abbreviations used in Examples | |
|---|---|
| Reagents: | |
| AcOH | acetic acid |
| Ac₂OH | acetic anhydride |
| BOP | benzotriazol-1-yloxy-tris(dimethylamino)-phosphonium hexafluorophosphate |
| DIAD | diisoproppyl azodicarboxylate |
| DIC | diisopropyl carbonyl diimide |
| DIEA | N,N-diisopropylethylamine |
| HATU | O-(7-azabenzotriazol-1-yl)-1,1,3,3-tetramethyluronium hexafluorophosphate |
| HOAt | 1-hydroxy-7-azabenzotriazole |
| HOBt | 1-hydroxybenzotriazole hydrate |
| MCPBA | meta-chloroperoxybenzoic acid |
| PyBOP | benzotriazol-1-yloxy-tris(pyrrolidino)-phosphonium hexafluorophosphate |
| TFA | trifluoroacetic acid |
| TPP | triphenylphosphine |
| Solvents: | |
| ACN | acetonitrile |
| DCM | dichloromethane |
| DMF | dimethylformamide |
| DMSO | dimethylsulfoxide |
| Et₂O | diethyl ether |
| MeOH | methanol |
| THF | tetrahydrofuran |
| Protecting Groups: | |
| All | allyl |
| Alloc | allyloxy carbonyl |
| Fmoc | 9-fluorenylmethoxy carbonyl |
| tButyl | tertiary-Butyl |
| Trt | triphenylmethyl |
| Others: | |
| rt | room temperature |
| eq | equivalent |
| g | gram |
| h | hour |
| min | minute |

EXAMPLES

The following examples are provided for purposes of illustration, not limitations. These examples illustrate the syntheses of substance P reverse-turn mimetics of this invention.

LCMS analysis was performed on reverse-phase C₁₈ Zorbax columns using the following solvent system: A, water with 0.1% formic acid; B, acetonitrile with 0.1% formic acid. The following conditions were applied: column 2.1×30 mm, 5-95% B in 4 min, flow 0.3 ml/min. Mass spectra for separated peaks were obtained by electrospray (ES) using a MicroMass LCZ mass spectrometer.

Example 1

Solution Phase Synthesis of Representative Compounds

These examples illustrate the preparation of certain representative [4.4.0] bicyclic compounds in solution.

Method A

Synthesis of Structure (1):

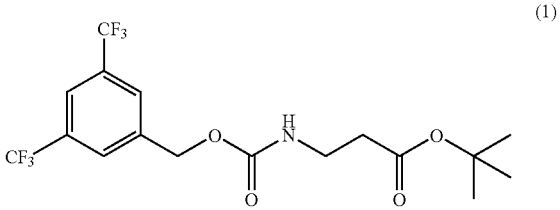

(1)

A solution of 3,5-bistrifluoromethylbenzyl alcohol (15.0 g, 61.4 mmole) and pyridine (4.86 g, 61.4 mmole) in 100 ml of dry CH₂Cl₂ was added over a 15 minute period to a stirred solution of 4-nitrophenyl chloroformate (12.38 g, 61.4 mmole) in 150 ml dry CH₂Cl₂ under an atm. of argon in an ice water bath. The mixture was allowed to warm to rt over a period of 2 hrs at which time beta-alanine-t-butylester HCl (13.94 g, 76.7 mmole) was added followed by triethylamine (12.97 g, 128.2 mmole). The mixture was stirred to rt overnight at which time it was evaporated to near dryness. Then 500 ml of ethyl acetate was added and extracted with 2×200 ml 1N HCl, 3×200 ml 2N NaOH, dried over Na₂SO₄ and evaporated to dryness. This was redissolved in 200 ml hexanes with sonication and placed in the freezer for 1 hr. The product was collected by filtration and washed with 100 ml cold hexanes and dried as a white solid, 22.57 g (88%). ¹H-NMR (500 MHz, CDCl₃, rt, ppm): δ 1.45 (s, 9H), 2.42-2.48 (m, 2H), 3.40-3.46 (m, 2H), 5.20 (s, 2H), 5.42 (bs, 1H), 7.79 (s, 2H), 7.82 (s, 1H). MS (ES+): m/z 416.5 [M+H]⁺.

Synthesis of Structure (1'):

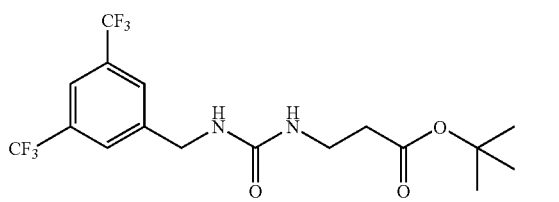

(1')

3,5-bistrifluoromethylbenzyl amine (15.0 g, 61.7 mmole) and pyridine (4.88 g, 61.7 mmole) was dissolved in 100 ml of dry CH₂Cl₂ and added over 5 min. to a stirred solution of 4-nitrophenyl chloroformate (12.44 g, 61.7 mmole) in 150 ml dry CH₂Cl₂ under argon in an ice water bath. The mixture was allowed to warm to room temperature over a period of 2 hrs at which time beta-alanine-t-butylester HCl (14.0 g, 77.1 mmole) was added followed by triethylamine (15.6 g, 154.2 mmole). The mixture was stirred and allowed to warm to rt overnight at which time it was evaporated to near dryness. To this residue, 500 ml of ethyl acetate was added and then extracted with 2×200 ml 1N HCl, 3×200 ml 2N NaOH, dried over Na$_2$SO$_4$ and evaporated to dryness. Column chromatography using ethyl acetate/hexanes yielded 16.9 g (66%) of product as a white solid. $^1$H-NMR (DMSO-d$_6$): δ 1.36 (s, 9H), 2.30 (t, 2H), 3.18 (q, 2H), 4.34 (d, 2H), 6.15 (t, 1H), 6.67 (t, 1H), 7.85-7.97 (m, 3H). MS (ES+): m/z 415.5 [M+H]$^+$.

Synthesis of Structure (2):

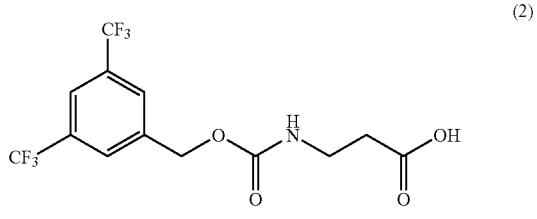

(2)

Compound (1) (22.5 g, 54.2 mmole) was stirred in 50 ml of TFA/H2O (9:1) for 2 hrs at rt. The mixture was evaporated to dryness and placed on a high vacuum overnight. The remaining solid was triturated with hexanes, collected by filtration and dried as a white solid, 17.2 g (88%). $^1$H-NMR (500 MHz, CDCl$_3$, rt, ppm): δ 2.63-2.69 (m, 2H), 3.48-3.55 (m, 2H), 5.20 (s, 2H), 5.38 (bs, 1H), 7.79 (s, 1H), 7.83 (s, 1H). MS (ES+): m/z 360.4 [M+H]$^+$.

Synthesis of Structure (2'):

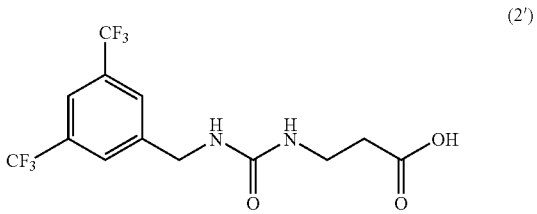

(2')

Compound (1') (16.9 g, 40.8 mmole) was stirred in 50 ml of TFA/H2O (9:1) for 2 hrs at room temp. The mixture was evaporated to dryness and placed on a high vacuum overnight. The remaining solid was triturated with hexanes, collected by filtration and dried. This resulted in 12.2 g (84%) of product as a white solid. $^1$H-NMR (DMSO-d$_6$): δ 2.30 (t, 2H), 3.19 (q, 2H), 4.34 (d, 2H), 6.19 (t, 1H), 6.66 (t, 1H), 7.82-7.98 (m, 3H). MS (ES+): m/z 359.4 [M+H]$^+$.

Synthesis of Structure (3):

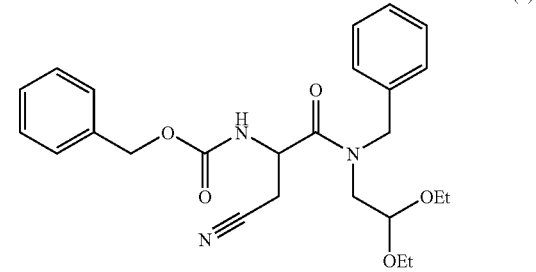

(3)

Z-beta-cyanoalanine (5.09 g, 20.5 mmole) was dissolved in 75 ml DMF with stirring. Diisopropylethyl-amine (2.92 g, 22.6 mmole) and HATU (8.60 g, 22.6 mmole) was added and this mixture was stirred at rt for 30 min. Then, N-diethyl acetal (5.03 g, 22.6 mmole) was added and this mixture was stirred for 16 hrs at rt. The mixture was then evaporated to dryness followed by column chromatography (40% ethyl acetate/hexanes) to yielded 7.25 g (78%) of product as the oil. $^1$H-NMR (500 MHz, DMSO-d$_6$, rt, ppm): δ 1.07 (m, 6H), 2.83 (m, 2H), 3.12 (dd, 1H), 3.19 (ddd, 1H), 3.41 (m, 1H), 3.58 (m, 2H), 3.72 (dd, 1H), 4.44-5.10 (m, 6H), 7.16-7.36, (m, 10H), 8.17 (m, 1H). MS (ES+): m/z 454.6 [M+H]$^+$.

Synthesis of Structure (4):

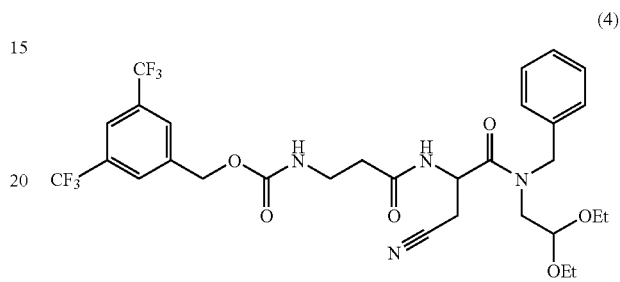

(4)

Compound (3) (7.2 g, 15.9 mmole) was dissolved in 100 ml of ethyl acetate and the solution was degassed with a stream of nitrogen gas. Then 5% Pd/C Degussa type E101 NO/W (1.5 g) was added and a vacuum was pulled with an aspirator. The solution was then stirred under an atmosphere of hydrogen for 16 hrs. The catalyst was removed by filtration over a bed of celite followed by evaporation resulting in 5.2 g (>100%) of deprotected crude product as an oil. Compound (2) (5.7 g, 15.9 mmole) was dissolved in 75 ml DMF with stirring. HOBT hydrate (2.43 g, 15.9 mmole) was added and after dissolution, DIC (2.01 g, 15.9 mmole) was added and the mixture was stirred for 30 min. at rt. The deprotected Compound (3) dissolved in 10 ml DMF was then added and the mixture was stirred at rt for 16 hrs. Evaporation to dryness followed by column chromatography (30% acetone/hexanes) yielded 6.5 g. of product as a white solid. $^1$H-NMR (500 MHz, DMSO-d$_6$, rt, ppm): δ 1.04-1.10 (m, 6H), 2.03-2.23 (m, 1H), 2.34 (t, 1H), 2.79 (m, 2H), 3.1 (m, 1H), 3.21 (m, 2H), 3.42 (m, 1H), 3.56 (m, 2H), 3.72 (dd, 1H), 4.48 (m, 2H), 4.56-4.73 (m, 2H), 5.17 (s, 2H), 5.25 (m, 1H), 7.15-7.40 (m, 7H), 8.03 (s, 2H), 8.72 (m, 1H). MS (ES+): m/z 661.7 [M+H]$^+$.

Synthesis of Structure (5):

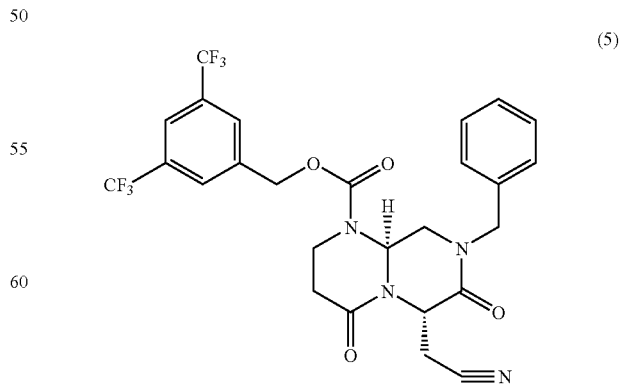

(5)

Compound (4) (6.0 g, 9.1 mmole) was stirred in 20 ml of formic acid for 16 hrs. Evaporation to dryness followed by column chromatography (50% CH$_2$Cl$_2$/EtOAc) yielded 4.2 g. (81%) of product as a white solid. $^1$H-NMR (500 MHz, DMSO-d$_6$, rt, ppm): δ 2.29 (m, 1H), 2.50 (m, 1H), 3.04 (m, 1H), 3.23 (m, 2H), 3.38 (m, 1H), 3.77 (m, 1H), 4.01 (dd, 1H), 4.58 (m, 2H), 5.09 (bs, 1H), 5.27 (bs, 2H), 5.93 (bs, 1H), 5.24 (m, 5H), 8.08 (m, 3H). MS (ES+): m/z 569 [M+H]$^+$.

Synthesis of Structure (6):

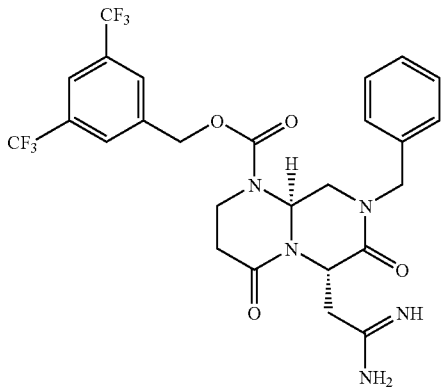

(6)

Compound (5) (300 mg, 0.53 mmole) was dissolved in 5 ml of absolute EtOH with stirring and cooled in an ice bath. The mixture was then saturated with a stream of HCl gas for 5 min. and then allowed to warm to rt over 16 hrs. The mixture was then evaporated to dryness. The residue was redissolved in 5 ml of absolute EtOH and cooled in an ice bath. The mixture was then saturated with a stream of ammonia gas for 5 min. and then allowed to warm to rt over 2 hrs. Evaporation to dryness followed by trituration with diethyl ether and filtration yielded 225 mg of a crude product. $^1$H NMR was carried out on HPLC purified product of this mimetic and spectra were assigned by combination of 1D and 2D DQF-COSY, TOCSY, and ROESY experiments. All spectra were consistent with the structure indicated above. $^1$H-NMR (500 MHz, CDCl$_3$/MeOD 10/1, rt, ppm): d 2.36 (m, 1H), 2.58 (m, 1H), 2.84 (m, 1H), 3.10-3.34 (m, 3H), 4.11-4.30 (m, 3H), 4.83 (m, 1H), 4.15 (m, 1H), 5.29 (m, 2H), 5.76 (m, 1H), 7.15-7.30 (m, 5H), 7.75 (s, 2H), 7.79 (s, 1H). MS (ES+): m/z 586 [M+H]$^+$. RP-HPLC(C-18 semi-preparative, 7.8×300 mm): A:0.1% TFA/H$_2$O, B: 0.1% TFA/CH$_3$CN, gradient 15-45% B/25 min, 4 ml/min, 215 nm, tR 21.6°.

Synthesis of Structure (7):

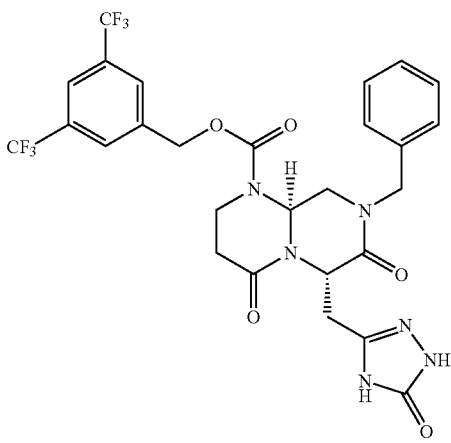

(7)

Compound (5) (1.0 g., 1.76 mmole) was dissolved in 50 ml of absolute EtOH with stirring and cooled in an ice bath. The mixture was then saturated with HCl gas for 5 min. and then allowed to warm to room temp. over 16 hrs. The mixture was then evaporated to dryness. The residue was then redissolved in 50 ml of absolute EtOH with stirring. Methyl hydrazino carboxylate (182 mg, 2.2 mmole) was added and the solution was stirred at room temp. for 4 hrs. Ammonium acetate (13.57 g, 176 mmole) and 50 ml of absolute EtOH was added and the mixture was refluxed for 8.0 hrs. The mixture was evaporated to dryness and 50 ml of H$_2$O was added and then extracted with 3×50 ml of CH$_2$Cl$_2$. The combined organic layers were dried over Na$_2$SO$_4$ and evaporated to dryness. Column chromatography (5% MeOH/CH$_2$Cl$_2$) yielded 350 mg (33%) as a white solid. $^1$H-NMR (500 MHz, DMSO-d$_6$, rt, ppm): δ 2.23 (m, 1H), 2.35 (m, 1H), 2.97 (m, 2H), 3.16 (m, 1H), 3.37 (m, 1H), 3.73 (m, 1H), 3.96 (dd, 1H), 4.41 (m, 1H), 4.64 (m, 1H), 5.24 (m, 3H), 5.85 (m, 1H), 5.26 (m, 5H), 8.06 (m, 3H), 11.19 (m, 2H). MS (ES+): m/z 602 [M+H]$^+$.

Synthesis of Structure (8):

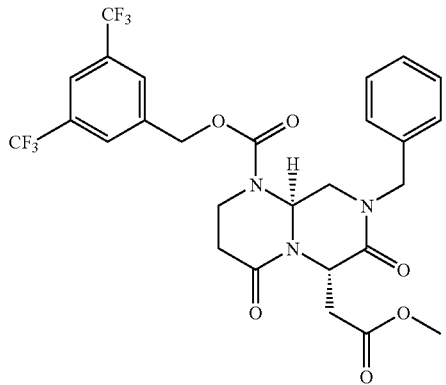

(8)

Compound (8) was synthesized according to the procedure for Compound (5) except Z-ASP(OME)-OH was used instead of Z-beta-cyanoalanine. $^1$H-NMR (500 MHz, DMSO-d$_6$, rt, ppm): δ 2.25 (d, 1H), 2.43 (bs, 1H), 2.48 (m, 1H), 2.83 (dd, 1H), 3.00 (bs, 1H), 3.18 (dd, 1H), 3.51 (bs, 3H), 3.77 (bs, 1H), 3.99 (dd, 1H), 4.44 (bt, 1H), 4.62 (d, 1H), 5.02 (bs, 1H), 5.27 (m, 2H), 6.02 (bd, 1H), 7.15-7.32 (m, 5H), 8.08 (bs, 3H). MS (ES+): m/z 602 [M+H]$^+$.

Synthesis of Structure (9):

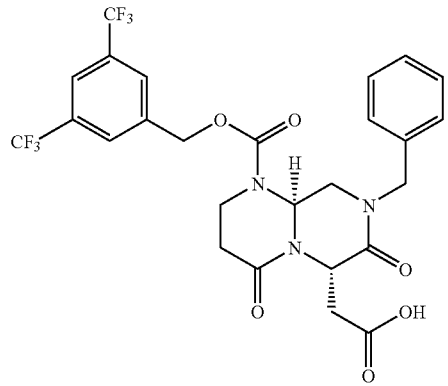

(9)

Compound (8) (4.42 g, 7.35 mmole) and LiOH monohydrate (0.3084 g, 7.35 mmole) was stirred in 30 ml of THF/H₂O (1:1) for 16 hrs. at room temp. The THF was removed by evaporation and 30 ml of H₂O was added with stirring. The pH was adjusted to ~2 with the dropwise addition of conc. HCl. The product was collected by filtration and washed with 2×50 ml of H₂O and dried leaving 4.16 g (96%) of product as a white solid (9). ¹H-NMR (500 MHz, DMSO-d₆, rt, ppm): δ 2.24 (d, 1H), 2.39 (bs 1H), 2.48 (m, 1H), 2.74 (d, 1H), 2.99 (d, 1H), 3.17 (bs, 1H), 3.75 (bs, 1H), 3.98 (dd, 1H), 4.41 (d, 1H), 4.65 (m, 1H), 5.26 (bs, 2H), 6.18 (bs, 1H), 7.30 (m, 5H), 8.06 (m, 3H). MS (ES+): m/z 588 [M+H]⁺.

Synthesis of Structure (10):

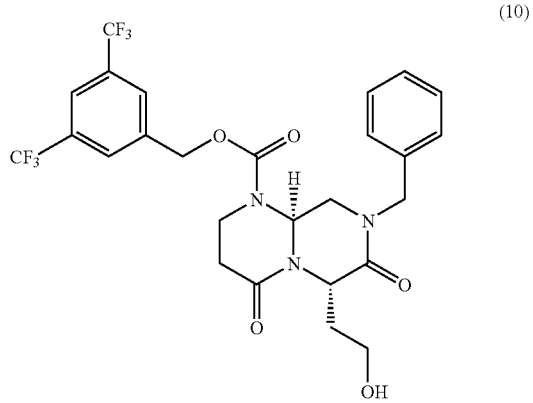

(10)

Compound (9) (4.1 g, 6.98 mmole) and CDI (1.584 g, 9.77 mmole) was stirred in 40 ml of anhydrous THF for 30 min at rt. After cooling to ~5° in an ice bath, NaBH₄ (0.449 g, 11.87 mmole) in 12 ml. of H₂O was gradually added over 2 min. and then allowed to warm to rt over 2 hrs. The pH was adjusted to ~2 with 2N HCl and extracted with 2×50 ml. of ethyl acetate. The combined organic layers was washed with 30 ml. of brine, dried over Na₂SO₄ and evaporated. Column chromatography of crude in 70% ethyl acetate/hexanes gave 2.24 g (56%) as a frothy white solid (10). ¹H-NMR (500 MHz, DMSO-d₆, rt, ppm): δ 1.97 (m, 1H), 2.04 (m, 1H), 2.28 (d, 1H), 2.49 (m, 1H), 3.18 (dd, 1H), 3.42 (m, 3H), 3.70 (t, 1H), 3.98 (m, 1H), 4.36 (d, 1H), 4.63 (bs, 1H), 5.08 (dd, 1H), 5.27 (m, 2H), 5.78 (bs, 1H), 7.22 (m, 5H), 8.07 (m, 3H). MS (ES+): m/z 574 [M+H]⁺.

Synthesis of Structure (11):

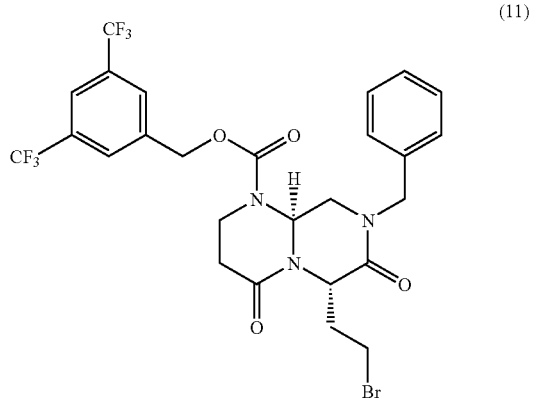

(11)

Compound (10) (2.2 g, 3.84 mmole) and CBr₄ (6.37 g, 19.2 mmole) was dissolved in 50 ml. anhyd. CH₂Cl₂ with stirring at rt. PPh₃ (1.51 g, 5.76 mmole) was added in portions over a 15 min. period and stirring was continued overnight. Evaporation to dryness followed by column chromatography in 30% ethyl acetate/hexanes gave 1.86 g (76%) as a frothy white solid (11). ¹H-NMR (500 MHz, DMSO-d₆, rt, ppm): δ 2.27 (d, 1H), 2.34 (m, 1H), 2.46 (m, 1H), 2.49 (m, 1H), 3.19 (dd, 1H), 3.51 (m, 2H), 3.70 (t, 1H), 3.98 (m, 1H), 4.42 (d, 1H), 4.55 (bs, 1H), 5.07 (bs, 1H), 5.28 (s, 2H), 5.70 (dd, 1H), 7.18-7.31 (m, 5H), 8.09 (m, 3H). MS (ES+): m/z 638 [M+H]⁺.

Synthesis of Structure (12):

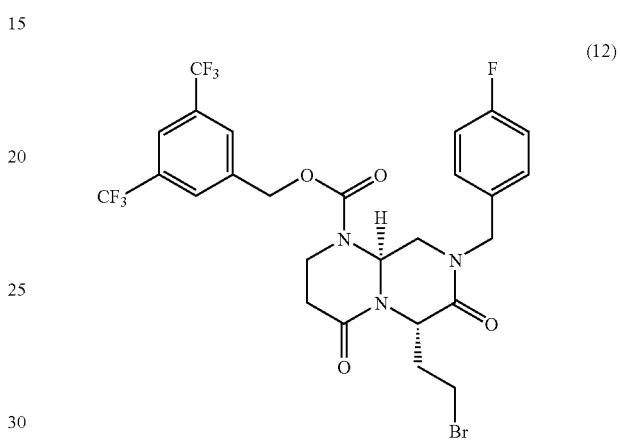

(12)

Compound (12) was synthesized according to the procedure for Compound (11) except N-4-fluorobenzylaminoacetaldehyde diethylacetal was used instead of N-benzylaminoacetaldehyde diethylacetal. ¹H-NMR (500 MHz, DMSO-d₆, rt, ppm): δ 2.26 (d, 1H), 2.33 (m, 1H), 2.44 (m, 1H), 2.48 (m, 1H), 3.20 (dd, 1H), 3.50 (m, 2H), 3.69 (t, 1H), 3.98 (m, 1H), 4.46 (m, 2H), 5.06 (bs, 1H), 5.28 (s, 2H), 5.70 (dd, 1H), 7.00-7.29 (m, 5H), 8.09 (m, 3H). MS (ES+): m/z 656 [M+H]⁺.

Synthesis of Structure (13):

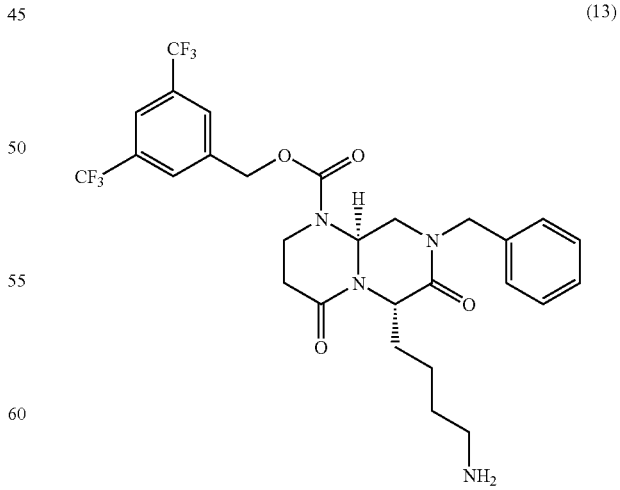

(13)

Compound (13) was synthesized following the procedure given under the general solid phase synthesis (Method F2) and general cleavage conditions. ¹H NMR was carried out on HPLC purified product. $^1$H NMR (500 MHz, DMSO-d$_6$, rt, ppm): δ 1.32-1.39 (m, 2H), 1.50-1.61 (m, 2H), 1.76-1.82 (m, 1H), 1.92-1.98 (m, 1H), 2.31 (d, 1H), 2.72-2.78 (m, 2H), 3.21-3.23 (m, 1H), 3.49 (bs, 1H), 3.71 (t, J=11 Hz, 1H), 3.98-4.02 (m, 1H), 4.36 (d, 1H), 4.64 (bs, 1H), 4.96-4.99 (m, 1H), 5.26-5.32 (m, 2H), 5.68-5.71 (m, 1H), 7.12-7.39 (m, 5H), 7.67 (s, 2H, —NH$_2$), 8.11 (s, 3H). MS (ES+): m/z 602 [M+H]$^+$. HPLC (Analytical, Discovery C18 5 um 4.6×50 mm) A: 0.1% TFA/H$_2$O, B: 0.1% TFA/CH$_3$CN, gradient 5-90% B/5 min, 1.5 mL/min, 214 nm, rt 3.755.

Synthesis of Structure (14):

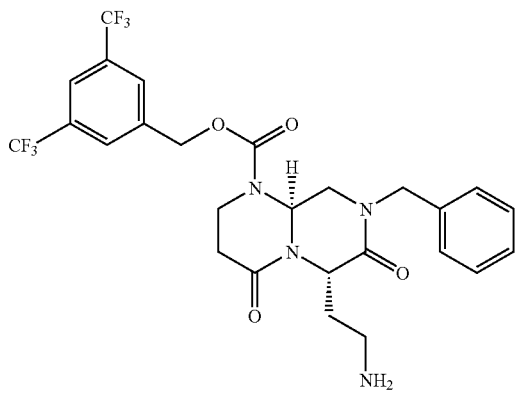

(14)

Compound (14) was synthesized following the general solid phase synthesis with the use of first amino acid having phthalimide protecting group at γ-amino group. After the cleavage of the product the protecting group is removed as given under Method C. $^1$H NMR was carried out on HPLC purified product. $^1$H NMR (500 MHz, DMSO-d$_6$, rt, ppm): δ 2.02-2.08 (m, 1H), 2.26-2.33 (m, 2H), 2.53-2.57 (m, 1H), 2.82-2.91 (m, 2H), 3.20-3.24 (m, 1H), 3.48 (bs, 1H), 3.74 (t, J=11 Hz, 1H), 4.00-4.04 (m, 1H), 4.42-4.62 (m, 2H), 5.01-5.03 (m, 1H), 5.30 (s, 2H), 5.66-5.68 (m, 1H), 7.22-7.34 (m, 5H), 7.71 (s, 2H, —NH$_2$), 8.11 (s, 3H). MS (ES+): m/z 573 [M+H]$^+$. HPLC (Analytical, Discovery C18 5 um 4.6×50 mm) A: 0.1% TFA/H$_2$O, B: 0.1% TFA/CH$_3$CN, gradient 5-90% B/5 min, 1.5 mL/min, 214 nm, rt 3.769.

Example 2

Solid Phase Synthesis of Representative Compounds

These examples illustrate the preparation of certain representative [4.4.0] bicyclic compounds carried out in solid phase. The solid phase syntheses of these compounds demonstrate that libraries containing such members may be readily prepared. Structures of representative compounds made by this procedure are set forth in Tables 3, 4 and 5. Reactions were generally carried out in plastic disposable syringes of the appropriate size, each fitted with a polypropylene frit to retain the resin, 1-10 ml reaction vessel compatible with Symphony Automated Peptide Synthesizer (Protein Technologies), ACT 90 Synthesizer (Advanced ChemTech), Robbins block, or IRORI system.

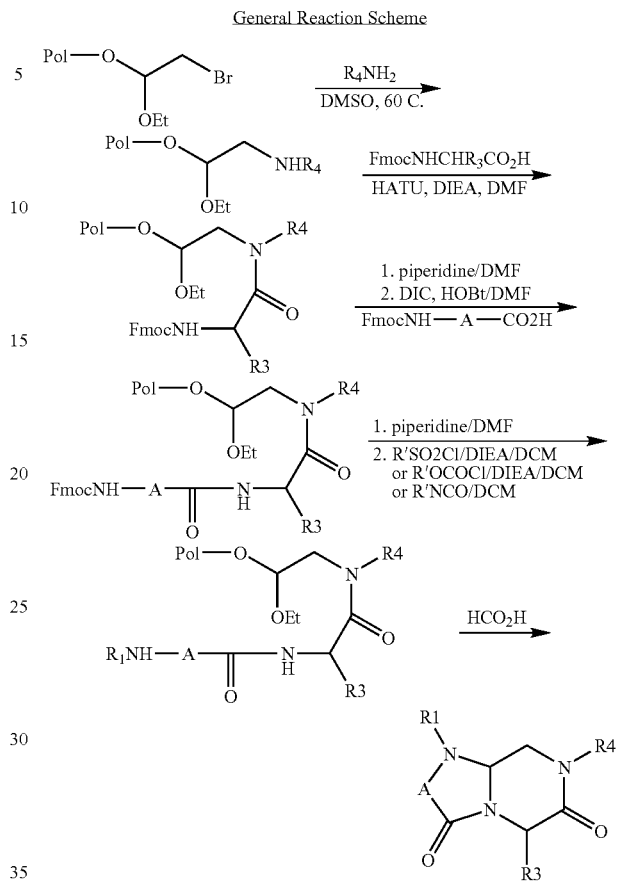

General Reaction Scheme

In the above General Reaction Scheme, "A" depicts the R$_2$-substituted ethylene (—CH$_2$CH$_2$—) portion of Structure (I). Commercially available 2-bromo-1-ethoxy-ethyl-1-oxy polystyrene resin purchased form Advanced Chemtech was treated with 2M DMSO solution of appropriate amine (R$_4$NH$_2$) at 60° C. for 24 hrs. Next, the resin was reacted with 3 eq of Fmoc amino acid (Fmoc-NHCHR$_3$—COOH) in the presence of HATU (3 eq) and DIEA (3 eq) in DMF for 16-18 hrs at which time chloranil test was negative. Then Fmoc protection was removed by treatment with 25% (v/v) piperidine/DMF solution over 10-20 minutes.

The resin after the Fmoc cleavage was then reacted with second Fmoc-β-amino acid (Fmoc-NH-A-CO$_2$H; wherein A is —CH$_2$CH$_2$—, —CH$_2$CHR$_2$— or —CHR$_2$CH$_2$—) in the presence of DIC (3 eq) and HOBt (3 eq) in DMF (1 mL) until the Kaiser test was negative (typically 1 hour). The resin was again treated with 25% (v/v) piperidine/DMF solution (2 mL) over 20-30 minutes.

The following methods B1-B4 were then used to generate the R$_1$ carbamate, urea, or sulphone.

Method B1

The free amine was protected as carbamate. For this, the corresponding alcohol R$_1$OH (5 eq) is activated by reaction with 4-nitrophenylchloroformate (4 eq) in the presence of pyridine (4 eq) in DCM for 1 hr at rt. The resulting mixture is added to the resin together with DIEA (6 eq) and shaken for 2 hrs at rt until Kaiser test turned negative.

Method B2

The free amine was reacted with R$_1$NCO in DCM for 8 hrs at rt.

Method B3

For this, the corresponding amine $R_1NH_2$ (5 eq) is activated by reaction with 4-nitrophenylchloroformate (4 eq) in presence of pyridine (4 eq) in DCM for 3 hrs at rt. The resulting mixture is added to the resin together with DIEA (6 eq) and shaken for 2 hrs at rt until Kaiser test turned negative.

Method B4

The resin-bound sequence was terminated by reaction with $R_1SO_2Cl$, in the presence of DIEA (3-4 eq) in DCM for 1 hr at rt until Kaiser test turned negative.

General Cleavage Condition for Methods B1-B4

The washed and dried resin was reswollen in DCM, drained and treated with HCOOH overnight (24 hrs) at rt. The supernatant was collected and combined with washes and evaporated in a speed vac. The residue obtained was redissolved in 50:50 mixture of acetonitrile-water, frozen and lyophilized.

Method C

General Procedure for sing Fmoc-diaminopropionic acid and Fmoc-diaminobutyric acid derivatives for $R_3$ The general synthetic procedure is same as given above with the use of the phthalamide protected β-amino or γ-amino group. However, after the cleavage of the product from the resin and evaporation of the solvent, the residue obtained was dissolved in EtOAc and washed with sat. $NaHCO_3$ solution followed by sat. brine, dried over anhydrous $Na_2SO_4$ and evaporated. The residue was then dissolved in EtOH and hydrazine monohydrate (3 eq) was added and refluxed for 1.5 hrs. Solvent was evaporated and the residue dissolved in EtOAc/water. The aqueous layer was removed and the organic layer was washed with sat. $NaHCO_3$, sat. brine, dried over anhydrous $Na_2SO_4$ and evaporated.

Method D

The general synthetic procedure is the same as given above except that the first Fmoc-amino acid (Fmoc-NH-CHR$_3$—COOH) is replaced by Fmoc-Asp(OAll)-OH. After finishing the above general procedure, the allyl protecting group was removed. For this, phenylsilane (8 eq) and tetrakis(triphenylphosphine) palladium(0) (0.4 eq) was dissolved in DCM and treated with the resin for 1.5 hrs. Subsequently the resin was reacted with amines, R'NH$_2$ (3 eq) in presence of PyBOP (3 eq), HOBt (3 eq) and DIEA (6 eq). Then the products were cleaved from the resin as described above.

Method E

The general synthetic procedure is the same as given above except that the first Fmoc aminoacid (Fmoc-NH-CHR$_3$—COOH) is replaced by Fmoc-Dpr(Alloc)OH. After finishing the above general procedure, the alloc group was removed. For this, phenylsilane (8 eq) and tetrakis(triphenylphosphine) palladium(0) (0.4 eq) were dissolved in DCM and added to the resin allowed to stand for 1.5 hrs (Kaiser test positive). Subsequently the resin was reacted with acids, R'COOH (3 eq) in presence of PyBOP (3 eq), HOBt (3 eq) and DIEA (6 eq) (Kaiser test negative). Then the products were cleaved from the resin as described above.

Method F1

Synthesis of 3,5-bistrifluoromethylbenzyl sulfonylamide analogs:

The bromoacetal resin was first coupled to Fmoc-amino acid with HATU (3 eq) and DIEA (3 eq) in DMF. After the Fmoc cleavage with 25% (v/v) piperidine/DMF over 20-30 minutes, the free amine with DIC (3 eq) and HOBt (3 eq) in DMF was reacted for 10-12 hrs at rt with the intermediate F1a. The F1a intermediate was prepared by addition of 3,5-bistrifluoromethylbenzyl sulphonyl chloride (commercially available) with DMAP as catalyst to an acetonitrile solution of β-amino acid t-butyl ester (HCl) and Et$_3$N with subsequent column chromatography and deprotection of t-Butyl with 50% TFA in DCM.

Method F2

Synthesis of 3,5-bistrifluoromethylbenzyl carbamate analogs:

The bromoacetal resin was first coupled to Fmoc-amino acid with HATU (3 eq) and DIEA (3 eq) in DMF. After the Fmoc cleavage with 25% (v/v) piperidine/DMF over 20-30 minutes, the free amine with DIC (3 eq) and HOBt (3 eq) in DMF was reacted for 10-12 hrs at rt with compound 2.

Method F3

Synthesis of 3,5-bistrifluoromethylbenzyl urea analogs:

The bromoacetal resin was first coupled to Fmoc-amino acid with HATU (3 eq) and DIEA (3 eq) in DMF. After the Fmoc cleavage with 25% (v/v) piperidine/DMF over 20-30 minutes, the free amine with DIC (3 eq) and HOBt (3 eq) in DMF was reacted for 10-12 hrs at rt with compound 2'.

General Cleavage Condition for Methods F1-F3:

To the resin resulting from Methods F1-F3 was washed, dried and reswollen in DCM, drained and treated with HCOOH overnight (24 hrs) at rt. The supernatant was collected and combined with washes and evaporated in a speed vac. The residue obtained was redissolved in 50:50 mixture of acetonitrile-water, frozen and lyophilized.

Method F4

Dimethylation of Free Amine;

To the cleaved free amine products in methanol was added aqueous formaldehyde (10 eq), followed by the slow addition of NaBH$_3$CN (20 eq). The reaction was stirred at rt overnight. The reaction was then terminated by the addition of water and the mixture was extracted with ethyl acetate (×3). The organic layer was then washed with aqueous NaHCO$_3$ (×3). The combined layer was dried over anhydrous Na$_2$SO$_4$ and evaporated.

Method G:

After coupling with the first Fmoc-amino acid (Fmoc-NHCHR$_3$—COOH), Fmoc protection was cleaved with piperidine/DMF. The resin was then reacted with commercially available Z-beta alanine in presence of DIC (3 eq) and HOBt (3 eq) in DMF until Kaiser test is negative. The products are then cleaved from the resin as given in the general procedure.

Method H:

After coupling with the first Fmoc-amino acid (Fmoc-CHR$_3$—COOH), Fmoc protection was cleaved with piperidine/DMF. The resin was then reacted with Fmoc-β-aminoacid, Fmoc-NHCH$_2$CH(NHAlloc)COOH in presence of DIC (3 eq) and HOBt (3 eq) in DMF until Kaiser test is negative. The resin was again treated with 25% piperidine/DMF solution for 20-30 minutes. The free amine was protected as carbamate as given in method B1. After finishing the above general procedure, the alloc group was removed. For this, phenylsilane (8 eq) and tetrakis(triphenylphosphine) palladium(0) (0.4 eq) was dissolved in DCM and treated with the resin for 1.5 hrs until Kaiser test is positive. Subsequently the resin was reacted with acids, R$_2$COOH (3 eq) in presence of PyBOP (3 eq), HOBt (3 eq) and DIEA (6 eq) until Kaiser test is negative. Then the products were cleaved from the resin as described above.

Method I:

After coupling with the first Fmoc-amino acid (Fmoc-CHR$_3$—COOH), Fmoc protection was cleaved with piperidine/DMF. The resin was then reacted with Fmoc-β-aminoacid, Fmoc-NHCH(R$_2$)CH$_2$COOH in presence of DIC (3 eq) and HOBt (3 eq) in DMF until Kaiser test is negative. The resin was again treated with 25% piperidine/DMF solution for 20-30 minutes. The free amine was protected as carbamate as given in method B1. Then the products were cleaved from the resin as described above.

Method J

General Reaction Scheme

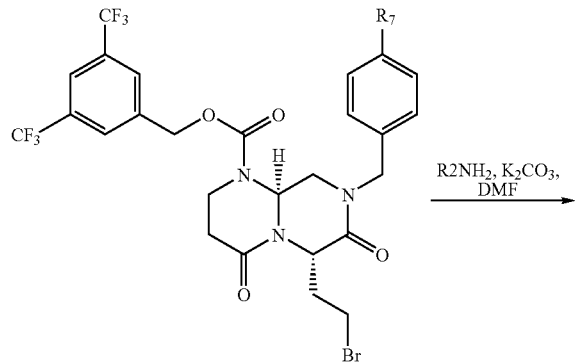

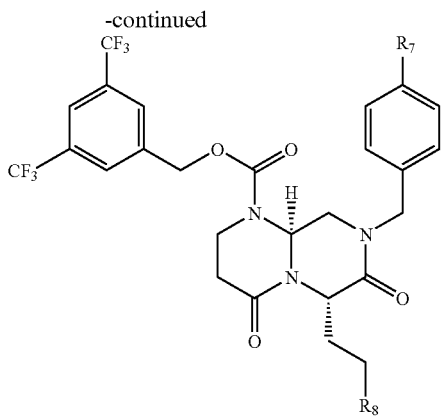

In the above General Reaction Scheme, an amine (R$_2$NH$_2$) is reacted with Compound (11) where R$_7$ is H or Compound (12) where R$_7$ is F and K$_2$CO$_3$ in DMF at rt for 16 hrs. Evaporation to dryness followed by column chromatography. (1-10% MeOH/CH$_2$Cl$_2$) gives the appropriate target compound.

Example 3

Representative Compounds of Structure (II) Made According to the Methods of Example 2

TABLE 3

| Cpd | R1 | R3 | R4 | Method * | LCRT (min) | (M + H)$^+$ |
|---|---|---|---|---|---|---|
| 1 | 3,5-bis(trifluoromethyl)benzyl carbamate (X$_1$) | isopropyl (X$_3$) | benzyl (X$_4$) | F2 | 1.89 | 572.5 |
| 2 | 3,5-bis(trifluoromethyl)benzyl carbamate (X$_1$) | X$_3$-(CH$_2$)$_4$-NH$_2$ | 3,5-bis(trifluoromethyl)benzyl (X$_4$) | F2 | 1.67 | 737.5 |

TABLE 3-continued
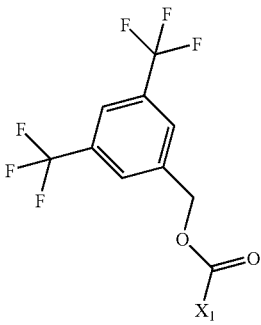
| Cpd | R1 | R3 | R4 | Method* | LCRT (min) | (M + H)+ |
|---|---|---|---|---|---|---|
| 3 |  | 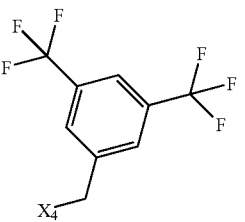 | 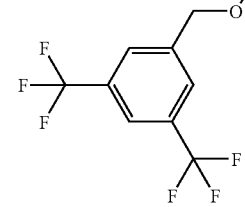 | F2 | 1.92 | 680.5 |
| 4 | 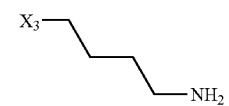 | 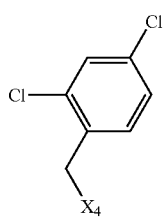 | 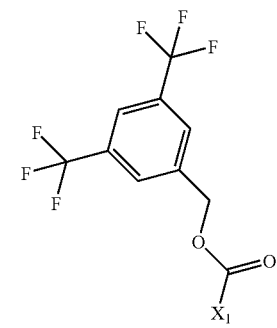 | F2 | 1.54 | 669.4 |
| 5 |  | 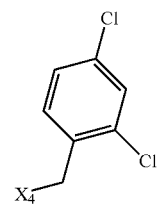 | 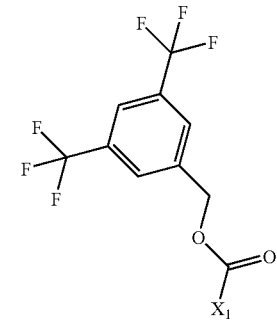 | F2 | 1.92 | 612.3 |
| 6 | 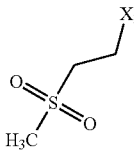 | 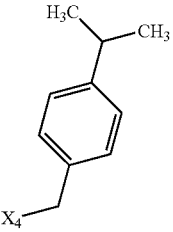 |  | F2 | 1.86 | 678.5 |

TABLE 3-continued
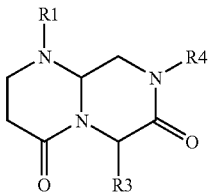
| Cpd | R1 | R3 | R4 | Method * | LCRT (min) | (M + H)+ |
|---|---|---|---|---|---|---|
| 7 | 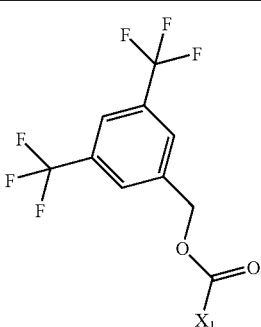 |  | 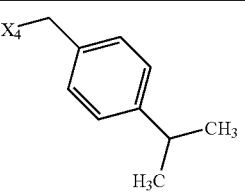 | F2 | 1.93 | 586.5 |
| 8 | 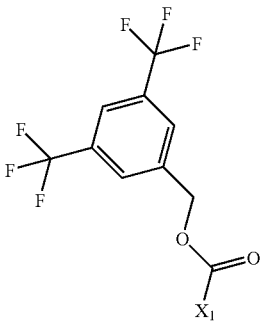 |  | 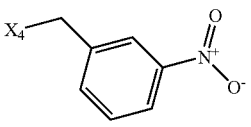 | F2 | 1.71 | 589.5 |
| 9 | 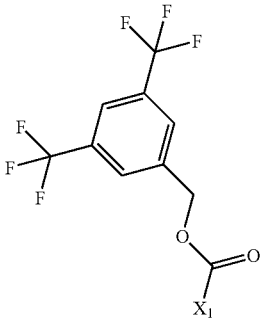 | 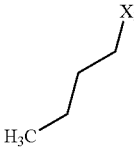 | 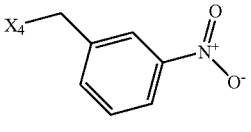 | F2 | 1.84 | 631.5 |
| 10 | 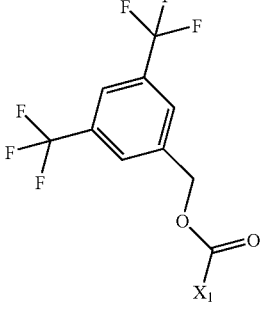 | 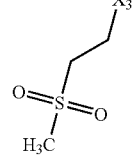 | 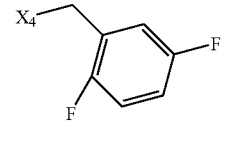 | F2 | 1.77 | 672.5 |

TABLE 3-continued
| Cpd | R1 | R3 | R4 | Method * | LCRT (min) | (M + H)+ |
|---|---|---|---|---|---|---|
| 11 | 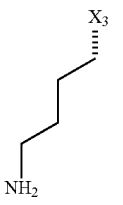 | 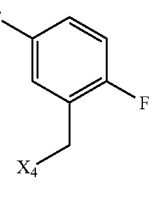 | 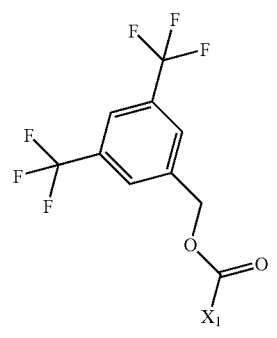 | F2 | 1.37 | 637.5 |
| 12 |  | 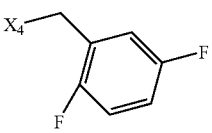 | 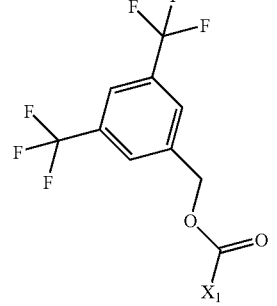 | F2 | 1.72 | 570.5 |
| 13 | 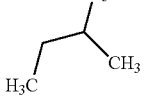 | 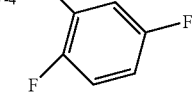 | 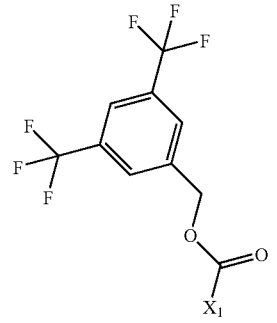 | F2 | 1.89 | 622.5 |
| 14 | 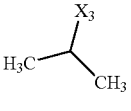 | 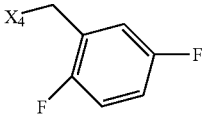 | | F2 | 1.88 | 608.5 |

TABLE 3-continued
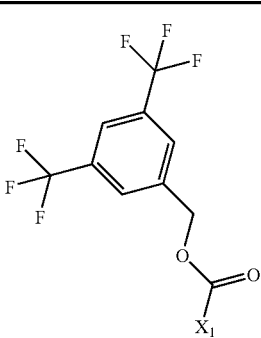
| Cpd | R1 | R3 | R4 | Method* | LCRT (min) | (M + H)+ |
|---|---|---|---|---|---|---|
| 15 |  | 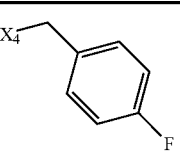 | 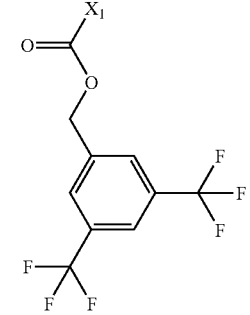 | F2 | 1.73 | 562.5 |
| 16 | 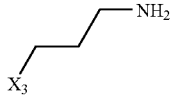 | 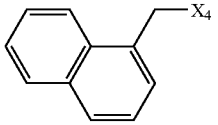 | 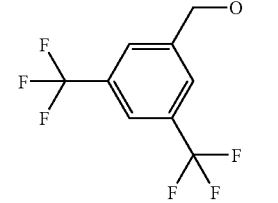 | F2 | 1.52 | 637.5 |
| 17 | 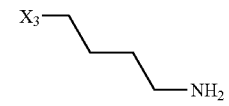 | 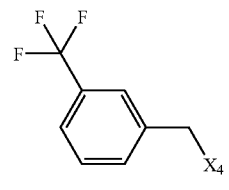 | 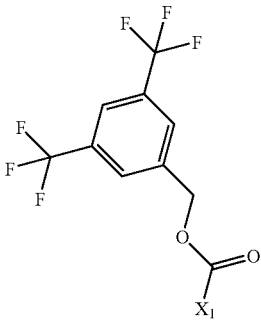 | F2 | 1.49 | 669.5 |
| 18 |  | 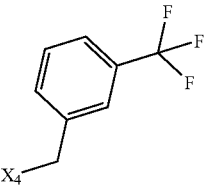 |  | F2 | 1.80 | 612.5 |

TABLE 3-continued

| Cpd | R1 | R3 | R4 | Method * | LCRT (min) | (M + H)+ |
|---|---|---|---|---|---|---|
| 19 | 3,5-bis(trifluoromethyl)benzyl carbonate | propylamine (X3-CH2CH2CH2-NH2) | 3-(trifluoromethyl)benzyl (X4) | F2 | 1.49 | 655.5 |
| 20 | 3,5-bis(trifluoromethyl)benzyl carbonate | butylamine (X3-(CH2)3-NH2) | 3-fluoro-5-(trifluoromethyl)benzyl (X4) | F2 | 1.54 | 687.5 |
| 21 | 3,5-bis(trifluoromethyl)benzyl carbonate | methyl (H3C-X3) | 3-fluoro-5-(trifluoromethyl)benzyl (X4) | F2 | 1.82 | 630.5 |
| 22 | 3,5-bis(trifluoromethyl)benzyl carbonate | propylamine (X3-CH2CH2CH2-NH2) | 3-fluoro-5-(trifluoromethyl)benzyl (X4) | F2 | 1.52 | 673.5 |

TABLE 3-continued

| Cpd | R1 | R3 | R4 | Method * | LCRT (min) | (M + H)+ |
|---|---|---|---|---|---|---|
| 23 | 3,5-bis(trifluoromethyl)benzyl carbonate (X1) | X3-(CH2)4-NH2 | 2-(thiophen-2-yl)ethyl (X4) | F2 | 1.40 | 621.5 |
| 24 | 3,5-bis(trifluoromethyl)benzyl carbonate (X1) | H3C-X3 | 2-(thiophen-2-yl)ethyl (X4) | F2 | 1.69 | 564.5 |
| 25 | 3,5-bis(trifluoromethyl)benzyl carbonate (X1) | H2N-(CH2)3-X3 | 2-(thiophen-2-yl)ethyl (X4) | F2 | 1.39 | 607.5 |
| 26 | 3,5-bis(trifluoromethyl)benzyl carbonate (X1) | H2N-(CH2)3-CH(X3)- | benzyl (X4) | F2 | 1.39 | 601.5 |

TABLE 3-continued

| Cpd | R1 | R3 | R4 | Method * | LCRT (min) | (M + H)+ |
|---|---|---|---|---|---|---|
| 27 | 3,5-bis(trifluoromethyl)benzyl carbonate (X1-O-C(=O)-O-CH2-Ar) | -(CH2)3-NH2 (X3) | 2,4-difluorobenzyl (X4) | F2 | 1.44 | 623.5 |
| 28 | 3,5-bis(trifluoromethyl)benzyl carbonate (X1-O-C(=O)-O-CH2-Ar) | -(CH2)3-NH2 (X3) | 2,4,6-trifluorobenzyl (X4) | F2 | 1.45 | 641.5 |
| 29 | 3,5-bis(trifluoromethyl)benzyl carbonate | -(CH2)4-NH2 (X3) | 2,4,6-trifluorobenzyl (X4) | F2 | 1.45 | 655.5 |
| 30 | 3,5-bis(trifluoromethyl)benzyl carbonate | -(CH2)2-NH2 (X3) | benzyl (X4) | F2 | 1.38 | 573.5 |

TABLE 3-continued

| Cpd | R1 | R3 | R4 | Method * | LCRT (min) | (M + H)+ |
|---|---|---|---|---|---|---|
| 31 | 3,5-bis(trifluoromethyl)benzyl carbonate (X1) | (R)-4-aminobutyl (X3) | 4-fluorobenzyl (X4) | F2 | 1.34 | 605.1 |
| 32 | 3,5-bis(trifluoromethyl)benzyl carbonate (X1) | (S)-CH(X3)-C(O)NH-N(4-methylpiperazine) | benzyl (X4) | F2,D | 1.35 | 685.3 |
| 33 | 3,5-bis(trifluoromethyl)benzyl carbonate (X1) | (R)-CH(X3)-CH2-C(O)NH-N(4-methylpiperazine) | benzyl (X4) | F2,D | 1.36 | 699.3 |
| 34 | 3-fluoro-5-(trifluoromethyl)benzyl carbonate (X1) | (R)-4-aminobutyl (X3) | benzyl (X4) | B1 | 1.24 | 551.1 |

TABLE 3-continued
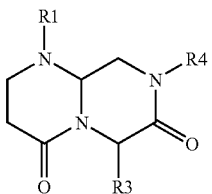
| Cpd | R1 | R3 | R4 | Method * | LCRT (min) | (M + H)+ |
|---|---|---|---|---|---|---|
| 35 | 3,5-bis(trifluoromethyl)benzyl carbonate (X1) | X3-CH2-NH-C(O)-CH(NH2)-CH3 | X4-benzyl | F2,E | 1.31 | 630.1 |
| 36 | 3,5-bis(trifluoromethyl)benzyl carbonate (X1) | X3-CH2-NH-C(O)-CH2-CH2-NH2 | X4-benzyl | F2,E | 1.3 | 630.1 |
| 37 | 3,5-bis(trifluoromethyl)benzyl carbonate (X1) | X3-CH2-NH-C(O)-pyrazinyl | X4-benzyl | F2,E | 1.63 | 665.1 |
| 38 | 3,5-bis(trifluoromethyl)benzyl carbonate (X1) | X3-CH2-NH-C(O)-CH2-(thyminyl) | X4-benzyl | F2,E | 1.51 | 725.1 |

TABLE 3-continued
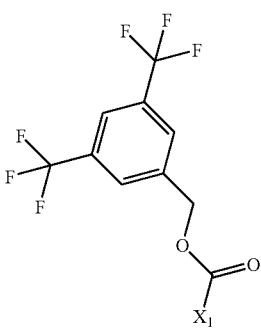
| Cpd | R1 | R3 | R4 | Method * | LCRT (min) | (M + H)+ |
|---|---|---|---|---|---|---|
| 39 | 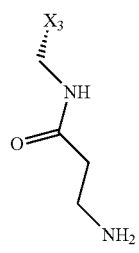 | 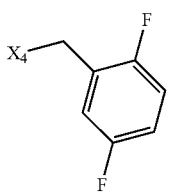 | 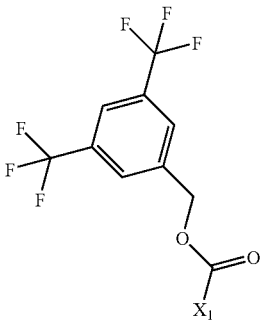 | F2,E | 1.27 | 666.1 |
| 40 | 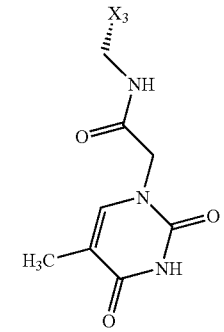 | 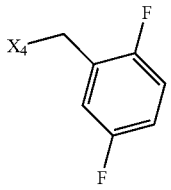 | 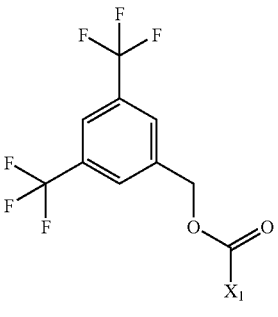 | F2,E | 1.53 | 761.1 |
| 41 | 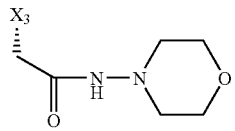 | 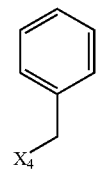 | 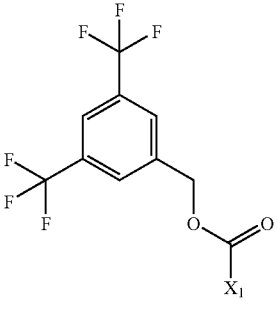 | F2,D | 1.58 | 672.1 |
| 42 | 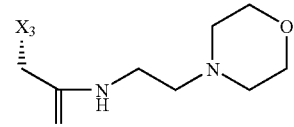 | 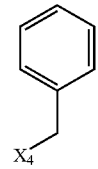 | | F2,D | 1.35 | 700.2 |

TABLE 3-continued
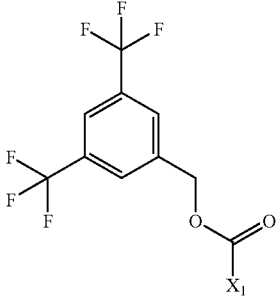
| Cpd | R1 | R3 | R4 | Method* | LCRT (min) | (M + H)+ |
|---|---|---|---|---|---|---|
| 43 | 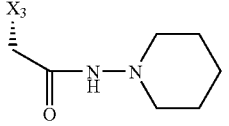 | 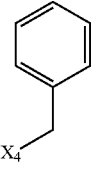 | 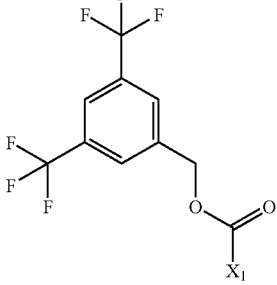 | F2,D | 1.54 | 672.1 |
| 44 | 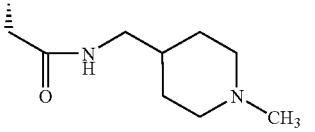 | 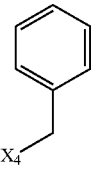 | 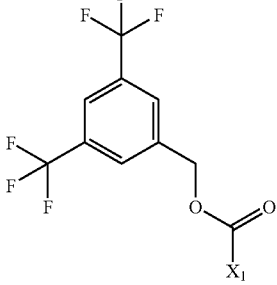 | F2,D | 1.32 | 698.2 |
| 45 | 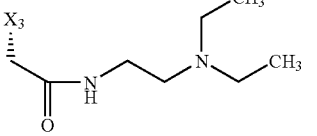 | 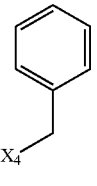 | 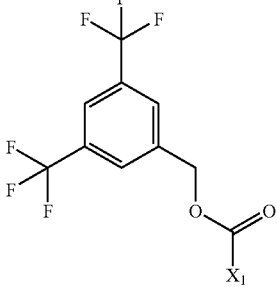 | F2,D | 1.36 | 686.5 |
| 46 | 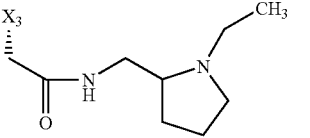 | 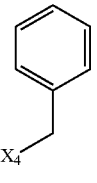 | | F2,D | 1.38 | 698.2 |

TABLE 3-continued

| Cpd | R1 | R3 | R4 | Method* | LCRT (min) | (M + H)+ |
|---|---|---|---|---|---|---|
| 47 | 3,5-bis(trifluoromethyl)benzyl carbonate | CH2-C(=O)-piperazinyl-NH | benzyl | F2,D | 1.30 | 656.6 |
| 48 | 3,5-bis(trifluoromethyl)benzyl carbonate | CH2-C(=O)-(4-methylpiperazinyl) | benzyl | F2,D | 1.31 | 670.2 |
| 49 | 3,5-bis(trifluoromethyl)benzyl carbonate | CH2-C(=O)-NH-CH2-CH(CH3)2 | benzyl | F2,D | 1.75 | 643.5 |
| 50 | 3,5-bis(trifluoromethyl)phenethyl ketone | CH2-C(=O)-N(CH3)2 | benzyl | F2,D | 1.64 | 615.2 |

TABLE 3-continued
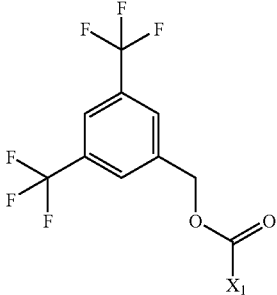
| Cpd | R1 | R3 | R4 | Method* | LCRT (min) | (M + H)+ |
|---|---|---|---|---|---|---|
| 51 | 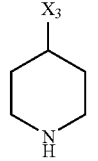 | 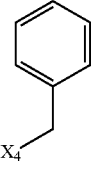 | 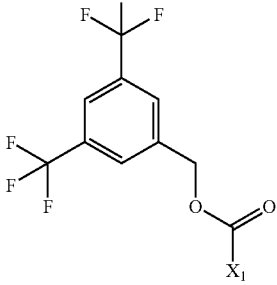 | F2 | 1.33 | 613.2 |
| 52 | 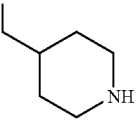 | 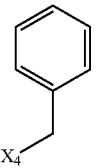 | 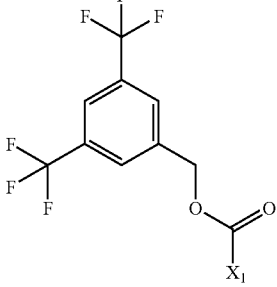 | F2 | 1.34 | 627.4 |
| 53 | 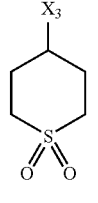 | 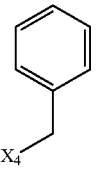 | 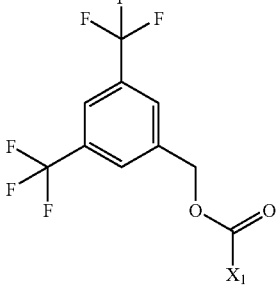 | F2 | 1.65 | 662.2 |
| 54 | 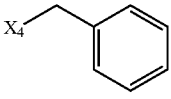 | 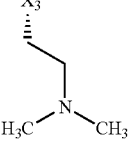 |  | C,F2,F4 | 1.37 | 601.5 |

TABLE 3-continued
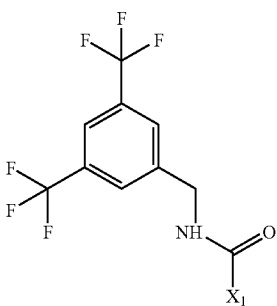
| Cpd | R1 | R3 | R4 | Method * | LCRT (min) | (M + H)+ |
|---|---|---|---|---|---|---|
| 55 | 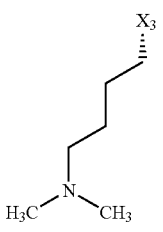 | 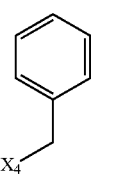 | 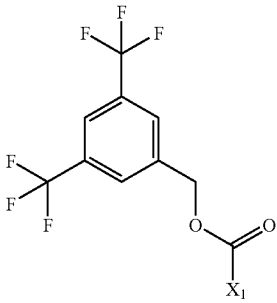 | F3,F4 | 1.31 | 628.1 |
| 56 | 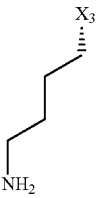 |  | 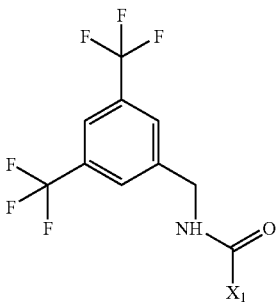 | F2 | 1.35 | 619.8 |
| 57 | 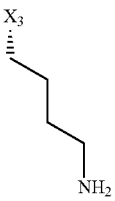 | 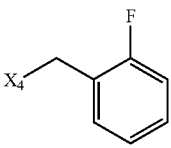 | 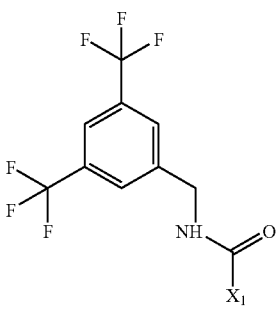 | F3 | 1.26 | 618.5 |
| 58 | 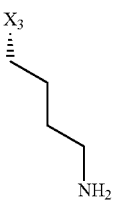 | 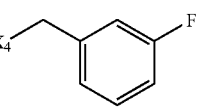 | | F3 | 1.29 | 618.6 |

TABLE 3-continued
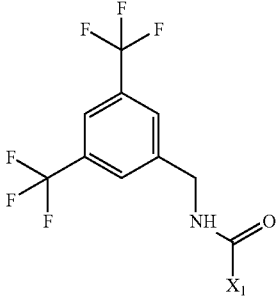
| Cpd | R1 | R3 | R4 | Method * | LCRT (min) | (M + H)+ |
|---|---|---|---|---|---|---|
| 59 | 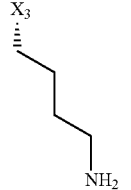 | 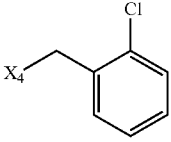 | 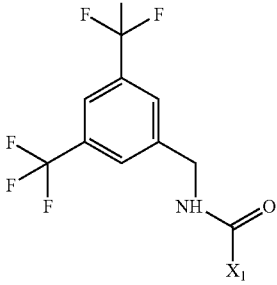 | F3 | 1.33 | 634.5 |
| 60 | 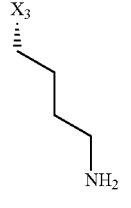 | 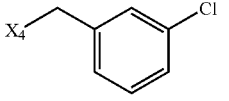 | 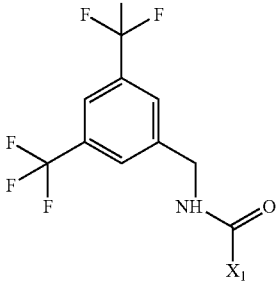 | F3 | 1.31 | 634.5 |
| 61 | 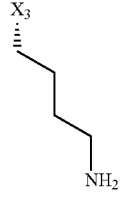 | 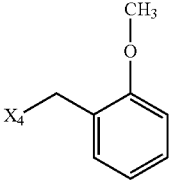 | 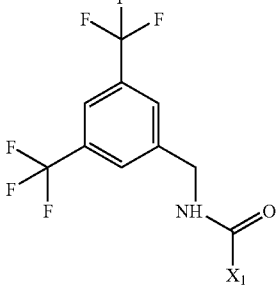 | F3 | 1.30 | 630.6 |
| 62 | 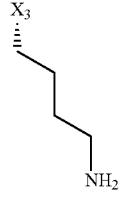 | 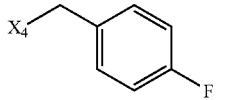 | | F3 | 1.32 | 618.6 |

TABLE 3-continued

| Cpd | R1 | R3 | R4 | Method* | LCRT (min) | (M + H)+ |
|---|---|---|---|---|---|---|
| 63 | 3,5-bis(trifluoromethyl)benzyl-NH-C(=O)-X₁ | X₃-CH₂CH₂-NH₂ | X₄-benzyl | C,F3 | 1.27 | 572.5 |
| 64 | 3,5-bis(trifluoromethyl)benzyl-NH-C(=O)-X₁ | X₃-CH₂CH₂-N(CH₃)₂ | X₄-benzyl | C,F3,F4 | 1.29 | 600.6 |
| 65 | 3,5-bis(trifluoromethyl)benzyl-O-C(=O)-X₁ | X₃-(CH₂)₃-NH₂ | X₄-(4-fluorobenzyl) | F2 | 1.35 | 619.5 |
| 66 | 3,5-bis(trifluoromethyl)benzyl-O-C(=O)-X₁ | X₃-(CH₂)₃-NH₂ | X₄-benzyl | F2 | 1.35 | 587.5 |

TABLE 3-continued
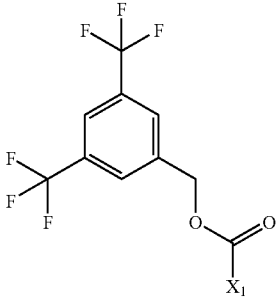
| Cpd | R1 | R3 | R4 | Method * | LCRT (min) | (M + H)+ |
|---|---|---|---|---|---|---|
| 67 | 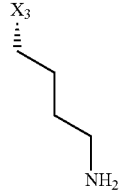 | 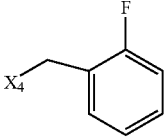 | 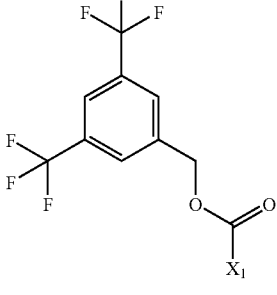 | C,F2 | 1.34 | 591.5 |
| 68 | 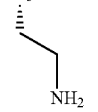 | 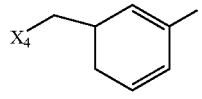 | 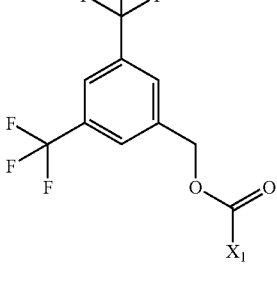 | C,F2 | 1.37 | 591.5 |
| 69 | 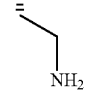 | 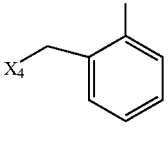 | 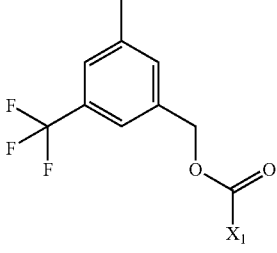 | C,F2 | 1.43 | 607.5 |
| 70 | 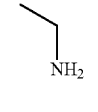 | 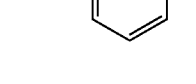 | | C,F2 | 1.43 | 607.5 |

TABLE 3-continued
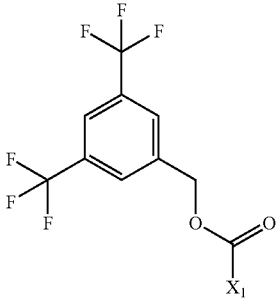
| Cpd | R1 | R3 | R4 | Method* | LCRT (min) | (M + H)+ |
|---|---|---|---|---|---|---|
| 71 | 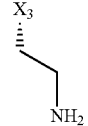 | 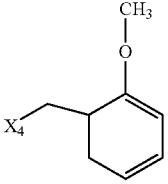 | 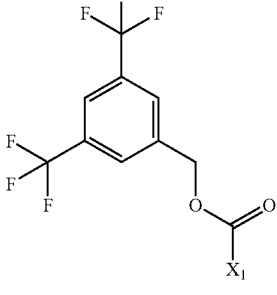 | C,F2 | 1.39 | 603.6 |
| 72 | 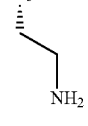 | 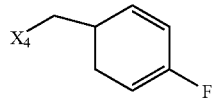 | 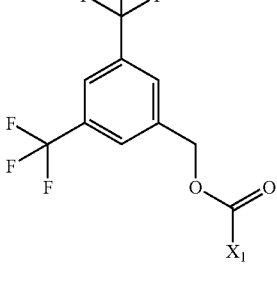 | C,F2 | 1.42 | 591.5 |
| 73 |  | 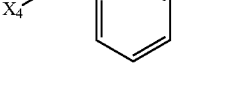 | 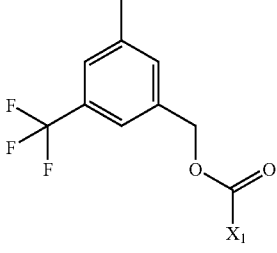 | C,F2 | 1.44 | 593.5 |
| 74 |  | 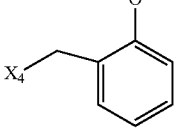 | | C,F2 | 1.40 | 589.5 |

TABLE 3-continued
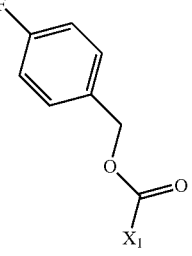
| Cpd | R1 | R3 | R4 | Method * | LCRT (min) | (M + H)+ |
|---|---|---|---|---|---|---|
| 75 | 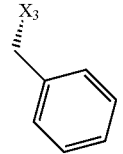 | 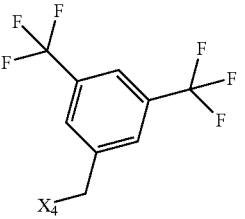 | 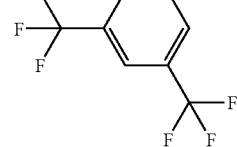 | B1 | 2.69 | 638.5 |
| 76 | 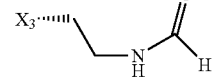 | 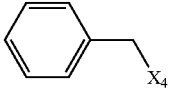 | 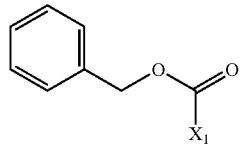 | F2 | 1.60 | 601.2 |
| 77 |  | 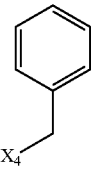 | 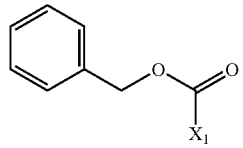 | G | 1.94 | 408.2 |
| 78 | 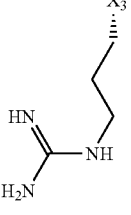 | 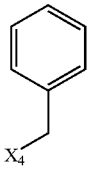 | 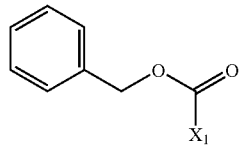 | G | 1.40 | 493.5 |
| 79 | 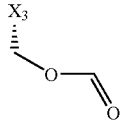 | 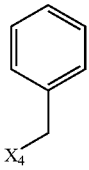 | 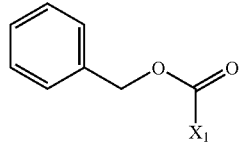 | G | 1.76 | 452.4 |
| 80 | 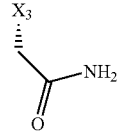 | 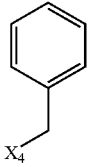 |  | G | 1.55 | 451.4 |

TABLE 3-continued
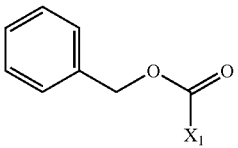
| Cpd | R1 | R3 | R4 | Method * | LCRT (min) | (M + H)+ |
|---|---|---|---|---|---|---|
| 81 | 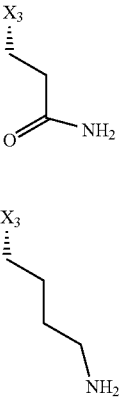 | 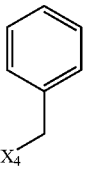 | 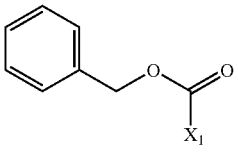 | G | 1.61 | 465.4 |
| 82 | 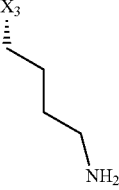 | 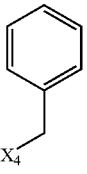 | 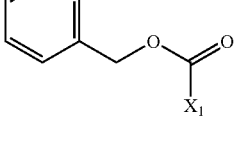 | G | 1.55 | 465.2 |
| 83 | 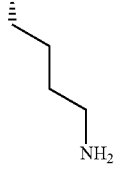 | 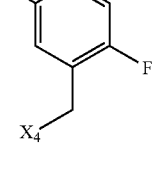 | 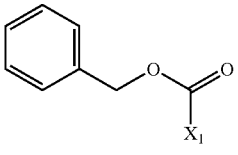 | G | 1.51 | 501.2 |
| 84 | 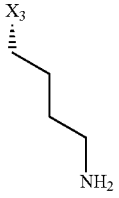 | 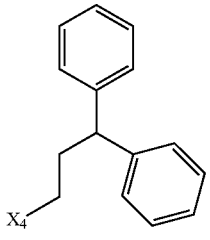 | 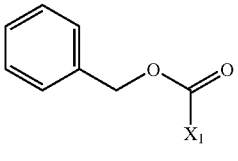 | G | 1.91 | 569.3 |
| 85 | 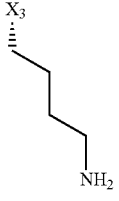 | 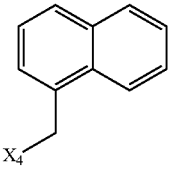 | 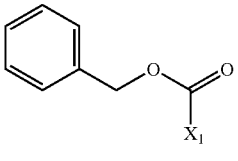 | G | 1.68 | 515.2 |
| 86 | 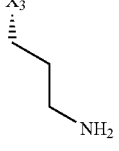 | 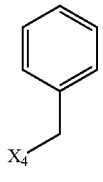 | 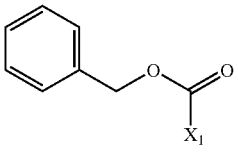 | G | 1.34 | 451.8 |

TABLE 3-continued

| Cpd | R1 | R3 | R4 | Method * | LCRT (min) | (M + H)+ |
|---|---|---|---|---|---|---|
| 87 | 3,5-bis(trifluoromethyl)benzyl carbonate | CH3 | benzyl | F2 | 2.21 | 544.2 |
| 88 | 3,5-bis(trifluoromethyl)benzyl carbonate | propyl urea CH2 | 4-(trifluoromethyl)benzyl | F2 | 1.74 | 712.5 |
| 89 | benzyl carbonate | CH3 | 3,5-bis(trifluoromethyl)benzamido ethyl | G | 1.62 | 601.5 |
| 90 | benzyl carbonate | ethyl urea CH2 | 3,5-bis(trifluoromethyl)benzamido ethyl | G | 1.51 | 687.6 |
| 91 | benzyl carbonate | 1-(benzyloxy)ethyl | 3,5-bis(trifluoromethyl)benzamido ethyl | G | 1.85 | 721.6 |

TABLE 3-continued

| Cpd | R1 | R3 | R4 | Method * | LCRT (min) | (M + H)+ |
|---|---|---|---|---|---|---|
| 92 | benzyl carbonate (X1) | 4-phenylbenzyl (X3) | 3,5-bis(trifluoromethyl)benzamidoethyl (X4) | G | 1.94 | 753.7 |
| 93 | benzyl carbonate (X1) | benzyl (X3) | 3,5-bis(trifluoromethyl)benzamidoethyl (X4) | G | 1.79 | 677.6 |
| 94 | 3,5-bis(trifluoromethyl)benzyl carbonate (X1) | benzyl (X3) | 3,5-bis(trifluoromethyl)benzamidoethyl (X4) | F2 | 1.95 | 813.7 |
| 95 | 3,5-bis(trifluoromethyl)benzyl carbonate (X1) | 4-aminobutyl (X3) | 2-chlorobenzyl (X4) | F2 | 1.76 | 635.1 |

TABLE 3-continued

| Cpd | R1 | R3 | R4 | Method * | LCRT (min) | (M + H)+ |
|---|---|---|---|---|---|---|
| 96 | 3,5-bis(trifluoromethyl)benzyl carbamate (X1-O-C(=O)-) | -(CH2)4-NH2 (X3) | 2-chlorobenzyl (X4) | F2 | 1.76 | 635.1 |
| 97 | 3,5-bis(trifluoromethyl)benzyl carbamate (X1-O-C(=O)-) | -(CH2)4-NH2 (X3) | 2-methoxybenzyl (X4) | F2 | 1.72 | 630.6 |
| 98 | 3,5-bis(trifluoromethyl)benzyl carbamate (X1-O-C(=O)-) | -(CH2)4-NH2 (X3) | 3-fluorobenzyl (X4) | F2 | 1.69 | 619.1 |
| 99 | 3,5-bis(trifluoromethyl)benzyl amide (X1-NH-C(=O)-) | CH3 (X3) | benzyl (X4) | F3 | 2.06 | 543.3 |

TABLE 3-continued

| Cpd | R1 | R3 | R4 | Method * | LCRT (min) | (M + H)+ |
|---|---|---|---|---|---|---|
| 100 | 3,5-bis(trifluoromethyl)benzyl-NHC(O)-X₁ | X₃-CH(propyl-NH₂) | X₄-benzyl | F3 | 1.63 | 586.5 |
| 101 | 3,5-bis(trifluoromethyl)benzyl-NHC(O)-X₁ | X₃-CH(butyl-NH₂) | X₄-benzyl | F3 | 1.64 | 600.5 |
| 102 | 3,5-bis(trifluoromethyl)benzyl-NHC(O)-X₁ | X₃-CH(propyl-NH-C(=NH)NH₂) | X₄-benzyl | F3 | 1.55 | 628.5 |
| 103 | H₂N-butyl-O-C(O)-X₁ | X₃-CH₂-(3,5-bis(trifluoromethyl)phenyl) | X₄-benzyl | B1 | 1.53 | 601.5 |

TABLE 3-continued
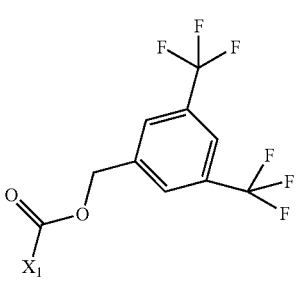
| Cpd | R1 | R3 | R4 | Method* | LCRT (min) | (M + H)+ |
|---|---|---|---|---|---|---|
| 104 |  | 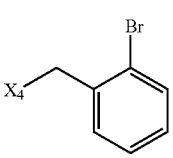 | 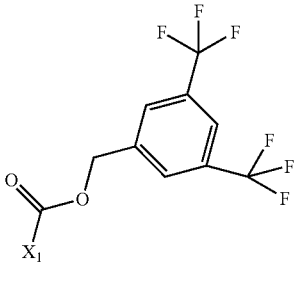 | F2 | 1.77 | 667.5 |
| 105 |  | 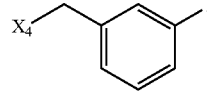 | 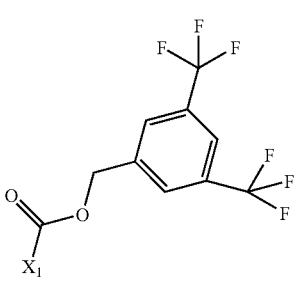 | F2 | 1.81 | 667.5 |
| 106 |  | 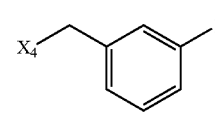 | 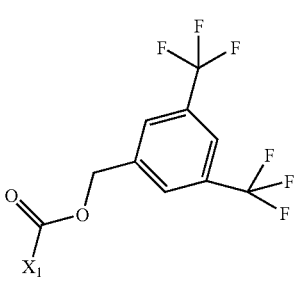 | F2 | 1.78 | 713.5 |
| 107 |  | 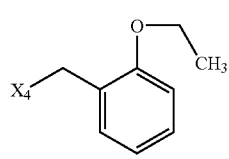 |  | F2 | 1.71 | 631.6 |

TABLE 3-continued

| Cpd | R1 | R3 | R4 | Method* | LCRT (min) | (M + H)+ |
|---|---|---|---|---|---|---|
| 108 | 3,5-bis(trifluoromethyl)benzyl carbonate (X1) | X3, NH2 (butyl) | 2-nitrobenzyl (X4) | F2 | 1.63 | 632.5 |
| 109 | 3,5-bis(trifluoromethyl)benzyl carbonate (X1) | X3, H2N (butyl) | 2-bromobenzyl (X4) | F2 | 1.68 | 680.5 |
| 110 | 3,5-bis(trifluoromethyl)benzyl carbonate (X1) | X3, H2N (butyl) | 3-bromobenzyl (X4) | F2 | 1.73 | 679.5 |
| 111 | 3,5-bis(trifluoromethyl)benzyl carbonate (X1) | X3, H2N (butyl) | 3-iodobenzyl (X4) | F2 | 1.73 | 727.5 |

TABLE 3-continued

| Cpd | R1 | R3 | R4 | Method* | LCRT (min) | (M + H)+ |
|---|---|---|---|---|---|---|
| 112 | 3,5-bis(trifluoromethyl)benzyl-NH-C(=O)-X1 | X3-CH(-)-CH2CH2-N(CH3)2 | X4-CH2-phenyl | F3,F4 | 1.24 | 614.4 |
| 113 | 3,5-bis(trifluoromethyl)benzyl-O-C(=O)-X1 | X3-CH(-)-CH2CH2-N(CH3)2 | X4-CH2-(2-fluorophenyl) | F2,F4 | 1.32 | 633.4 |
| 114 | 3,5-bis(trifluoromethyl)benzyl-O-C(=O)-X1 | X3-CH(-)-CH2CH2-N(CH3)2 | X4-CH2-(4-fluorophenyl) | F2,F4 | 1.29 | 633.4 |
| 115 | 3,5-bis(trifluoromethyl)benzyl-O-C(=O)-X1 | X3-CH(-)-CH2CH2-N(CH3)2 | X4-CH2-phenyl | F2,F4 | 1.27 | 615.4 |

TABLE 3-continued
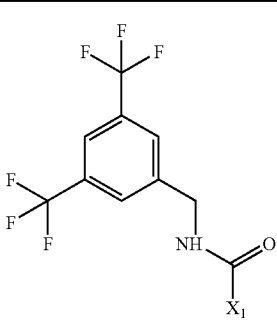
| Cpd | R1 | R3 | R4 | Method * | LCRT (min) | (M + H)+ |
|---|---|---|---|---|---|---|
| 116 | 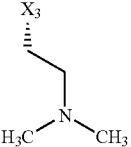 | 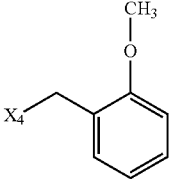 | 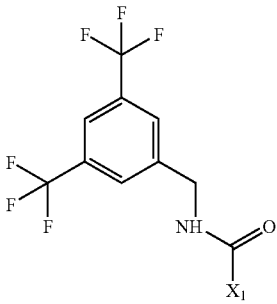 | F3,C,F4 | 1.31 | 630.5 |
| 117 | 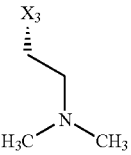 | 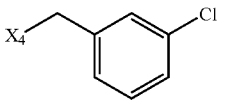 | 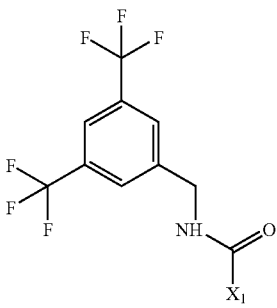 | F3,C,F4 | 1.32 | 634.4 |
| 118 | 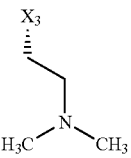 | 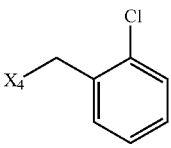 | 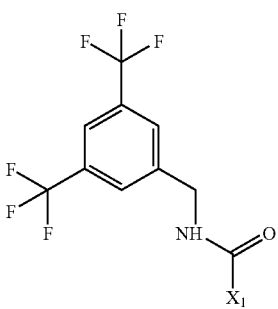 | F3,C,F4 | 1.33 | 634.4 |
| 119 | 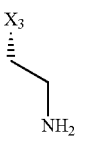 | 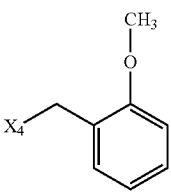 | 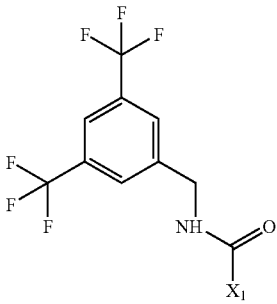 | F3,C | 1.34 | 602.5 |

TABLE 3-continued
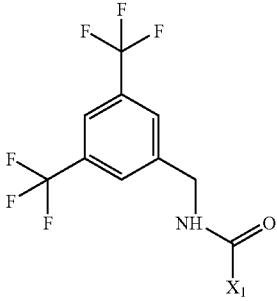
| Cpd | R1 | R3 | R4 | Method * | LCRT (min) | (M + H)+ |
|---|---|---|---|---|---|---|
| 120 | 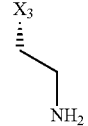 | 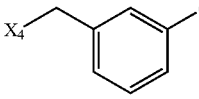 | 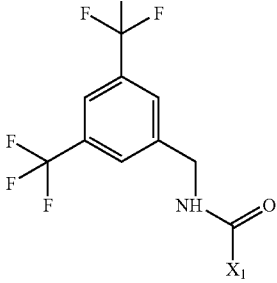 | F3,C | 1.32 | 606.4 |
| 121 | 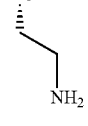 | 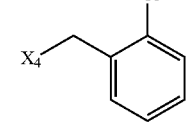 | 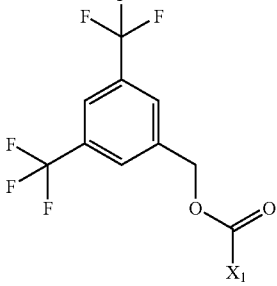 | F3,C | 1.31 | 606.4 |
| 122 | 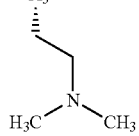 | 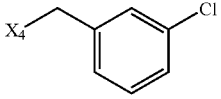 | 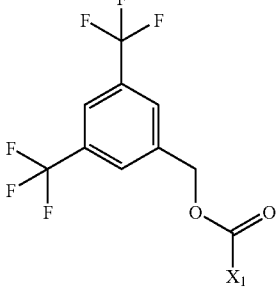 | F2,C,F4 | 1.33 | 635.3 |
| 123 | 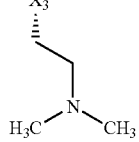 | 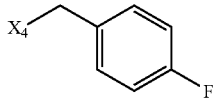 | | F2,C,F4 | 1.36 | 619.4 |

TABLE 3-continued
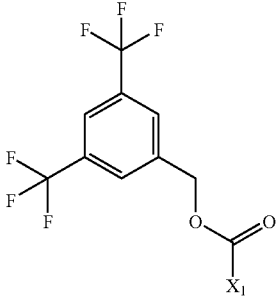
| Cpd | R1 | R3 | R4 | Method * | LCRT (min) | (M + H)+ |
|-----|----|----|----|----------|------------|----------|
| 124 | 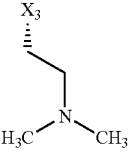 | 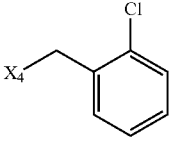 | 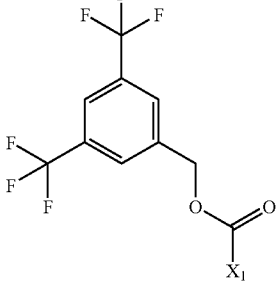 | F2,C,F4 | 1.44 | 635.5 |
| 125 | 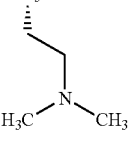 | 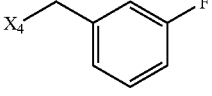 | 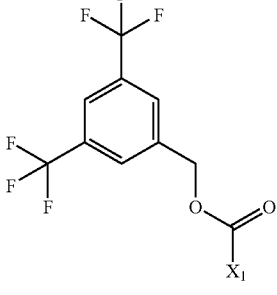 | F2,C,F4 | 1.39 | 619.5 |
| 126 | 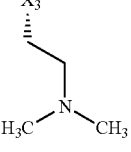 | 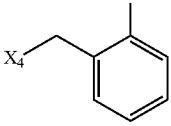 | 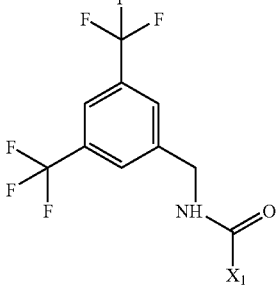 | F2,C,F4 | 1.39 | 646.5 |
| 127 | 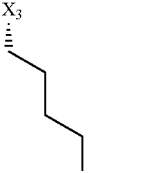 | 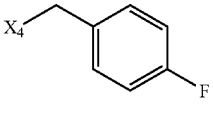 | | F3,F4 | 1.32 | 646.5 |

TABLE 3-continued
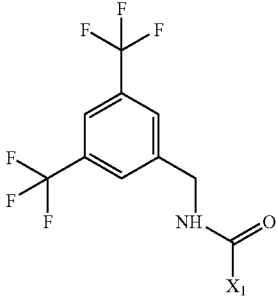
| Cpd | R1 | R3 | R4 | Method * | LCRT (min) | (M + H)+ |
|---|---|---|---|---|---|---|
| 128 | 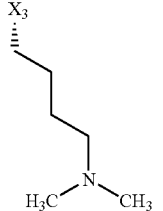 | 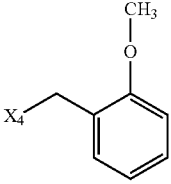 | 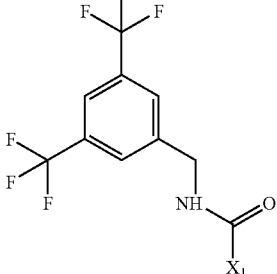 | F3,F4 | 1.34 | 658.5 |
| 129 | 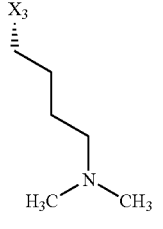 | 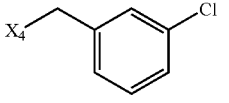 | 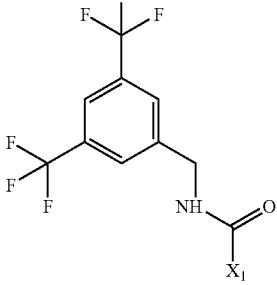 | F3,F4 | 1.37 | 662.5 |
| 130 | 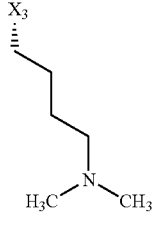 | 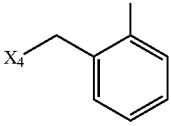 | 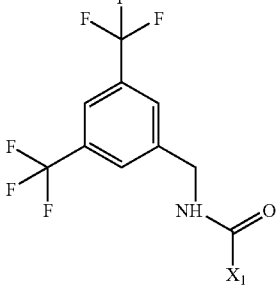 | F3,F4 | 1.33 | 662.4 |
| 131 | 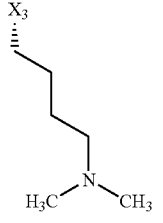 | 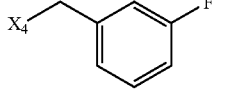 | | F3,F4 | 1.4 | 646.5 |

TABLE 3-continued
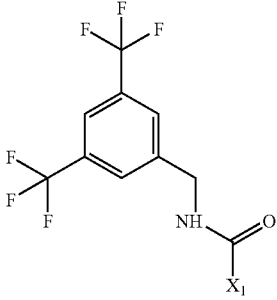
| Cpd | R1 | R3 | R4 | Method * | LCRT (min) | (M + H)+ |
|---|---|---|---|---|---|---|
| 132 | 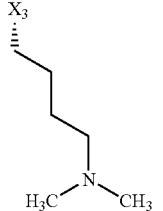 | 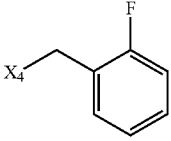 | 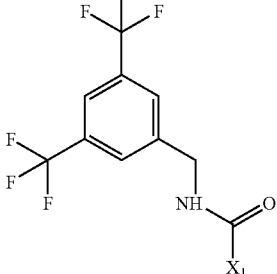 | F3,F4 | 1.45 | 646.6 |
| 133 | 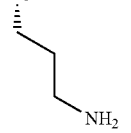 | 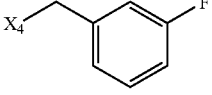 | 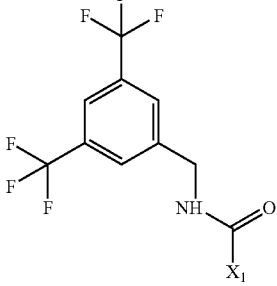 | F3 | 1.34 | 604.8 |
| 134 | 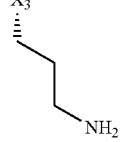 | 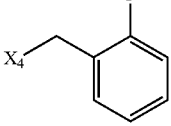 | 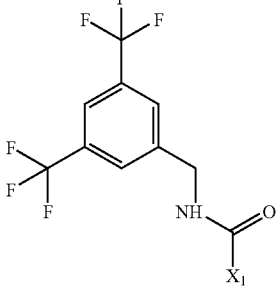 | F3 | 1.39 | 604.5 |
| 135 | 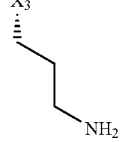 | 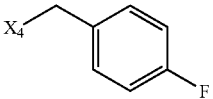 | | F3 | 1.82 | 604.5 |

TABLE 3-continued
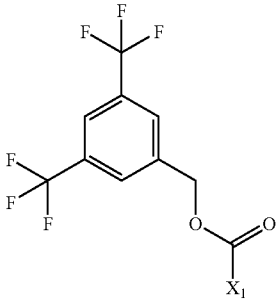
| Cpd | R1 | R3 | R4 | Method* | LCRT (min) | (M + H)+ |
|---|---|---|---|---|---|---|
| 136 | 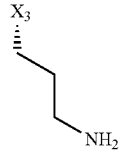 | 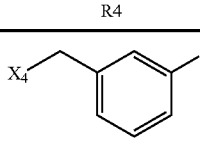 | 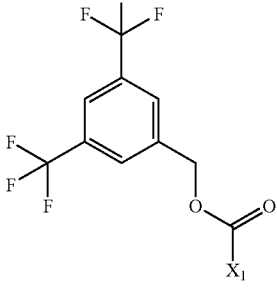 | F2 | 1.44 | 605.5 |
| 137 | 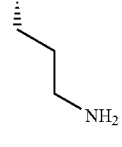 | 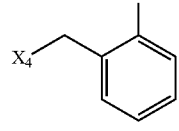 | 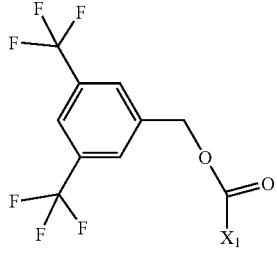 | F2 | 1.43 | 605.6 |
| 138 | 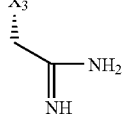 | 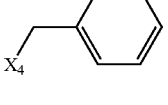 | 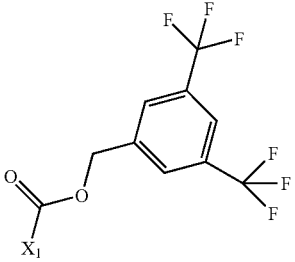 | A | 1.67 | 586.5 |
| 139 | 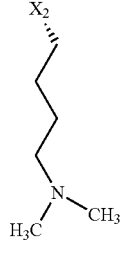 |  |  | F2,F4 | 1.78 | 649.5 |

TABLE 3-continued
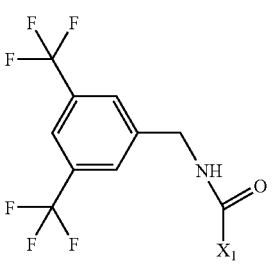
| Cpd | R1 | R3 | R4 | Method * | LCRT (min) | (M + H)+ |
|---|---|---|---|---|---|---|
| 140 | 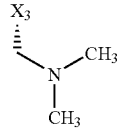 | 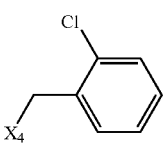 | 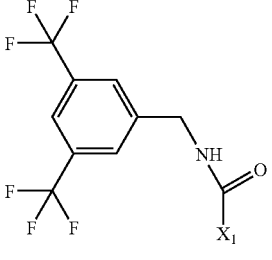 | C,F4 | 1.72 | 620.5 |
| 141 | 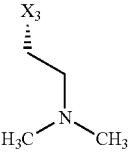 | 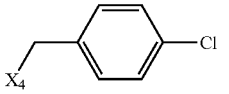 | 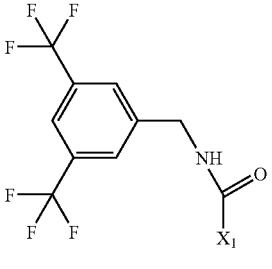 | C,F4 | 1.71 | 634.5 |
| 142 | 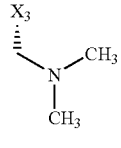 | 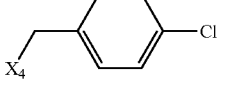 | 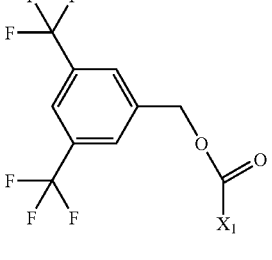 | C,F4 | 1.77 | 620.5 |
| 143 | 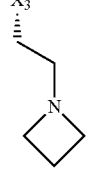 | 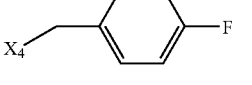 | 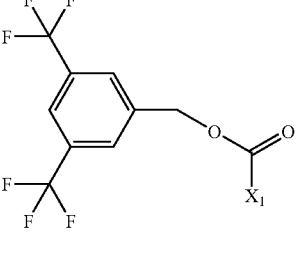 | J | 1.73 | 631.5 |
| 144 | 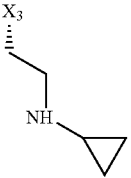 | 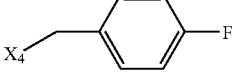 | | J | 1.73 | 631.4 |

TABLE 3-continued
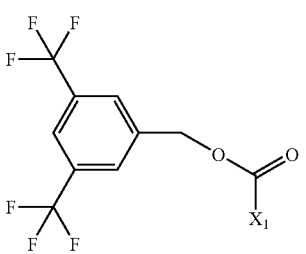
| Cpd | R1 | R3 | R4 | Method * | LCRT (min) | (M + H)+ |
|---|---|---|---|---|---|---|
| 145 | 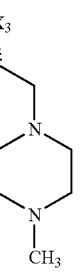 | 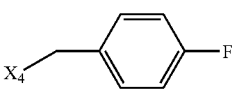 | 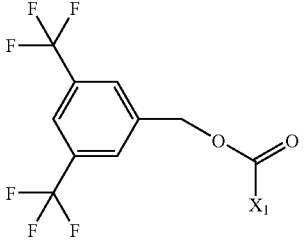 | J | 1.58 | 674.5 |
| 146 | 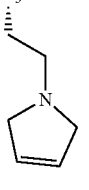 | 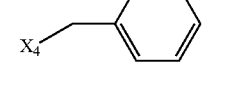 | 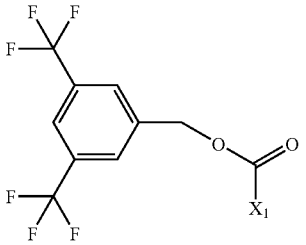 | J | 1.69 | 625.5 |
| 147 | 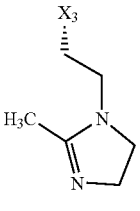 | 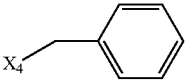 | 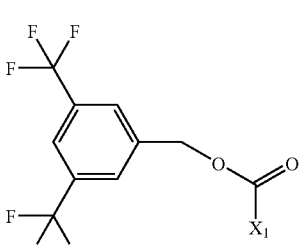 | J | 1.74 | 640.5 |
| 148 | 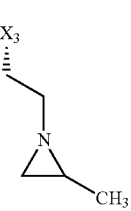 | 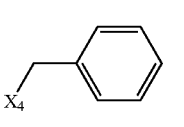 | 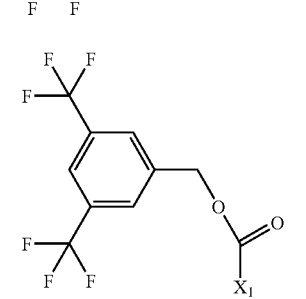 | J | 1.67 | 613.5 |
| 149 | 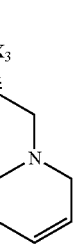 | 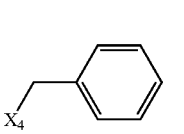 | 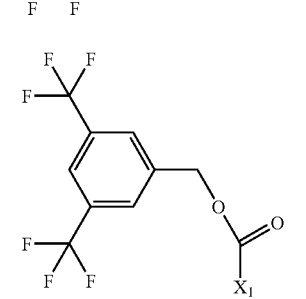 | J | 1.70 | 639.8 |

TABLE 3-continued

| Cpd | R1 | R3 | R4 | Method * | LCRT (min) | (M + H)+ |
|---|---|---|---|---|---|---|
| 150 | 3,5-bis(trifluoromethyl)benzyl -O-C(=O)-X1 | azepan-1-yl-CH2-CH(X3)- | benzyl-X4 | J | 1.81 | 655.5 |
| 151 | 3,5-bis(trifluoromethyl)benzyl -O-C(=O)-X1 | pyrrolidin-1-yl-CH2-CH(X3)- | benzyl-X4 | J | 1.72 | 627.4 |
| 152 | 3,5-bis(trifluoromethyl)benzyl -O-C(=O)-X1 | piperazin-1-yl-CH2-CH(X3)- | benzyl-X4 | J | 1.40 | 642.6 |
| 153 | 3,5-bis(trifluoromethyl)benzyl-NH-C(=O)-X1 | (CH3)2N-CH2CH2CH2-CH(X3)- | 4-chlorobenzyl-X4 | F3,F4 | 1.79 | 663.5 |
| 154 | 3,5-bis(trifluoromethyl)benzyl-NH-C(=O)-X1 | (CH3)2N-CH2CH2-CH(X3)- | 4-chlorobenzyl-X4 | F3,F4 | 1.63 | 648.5 |

TABLE 3-continued

| Cpd | R1 | R3 | R4 | Method* | LCRT (min) | (M + H)+ |
|---|---|---|---|---|---|---|
| 155 | 3,5-bis(trifluoromethyl)benzyl carbonate-X₁ | X₃-CH(-)-CH₂CH₂-N(CH₃)₂ | X₄-CH₂-(4-Cl-phenyl) | F2,F4 | 1.78 | 649.5 |
| 156 | 3,5-bis(trifluoromethyl)benzyl-NH-C(O)-X₁ | X₃-CH(-)-NH₂ | X₄-CH₂-(2-Cl-phenyl) | C | 1.64 | 592.4 |
| 157 | 3,5-bis(trifluoromethyl)benzyl carbonate-X₁ | X₃-CH(-)-NH₂ | X₄-CH₂-(2-Cl-phenyl) | C | 1.74 | 593.4 |
| 158 | 3,5-bis(trifluoromethyl)benzyl-NH-C(O)-X₁ | X₃-CH(-)-CH₂-NH₂ | X₄-CH₂-(4-Cl-phenyl) | C | 1.69 | 606.4 |
| 159 | 3,5-bis(trifluoromethyl)benzyl carbonate-X₁ | X₃-CH(-)-CH₂-NH₂ | X₄-CH₂-(4-Cl-phenyl) | C | 1.78 | 607.4 |

TABLE 3-continued

| Cpd | R1 | R3 | R4 | Method * | LCRT (min) | (M + H)+ |
|---|---|---|---|---|---|---|
| 160 | 3,5-bis(trifluoromethyl)benzyl-NH-C(=O)-X₁ | X₃-CH₂-NH₂ | X₄-CH₂-(4-chlorophenyl) | C | 1.67 | 592.4 |
| 161 | 3,5-bis(trifluoromethyl)benzyl-NH-C(=O)-X₁ | X₃-(CH₂)₃-NH₂ | X₄-CH₂-(4-chlorophenyl) | F3 | 1.64 | 634.4 |
| 162 | 3,5-bis(trifluoromethyl)benzyl-NH-C(=O)-X₁ | X₃-(CH₂)₂-NH₂ | X₄-CH₂-(4-chlorophenyl) | F3 | 1.67 | 620.4 |
| 163 | 3,5-bis(trifluoromethyl)benzyl-O-C(=O)-X₁ | X₃-(CH₂)₃-NH₂ | X₄-CH₂-(4-chlorophenyl) | F2 | 1.78 | 635.4 |
| 164 | 3,5-bis(trifluoromethyl)benzyl-O-C(=O)-X₁ | X₃-(CH₂)₂-NH₂ | X₄-CH₂-(4-chlorophenyl) | F2 | 1.76 | 621.3 |

TABLE 3-continued

| Cpd | R1 | R3 | R4 | Method* | LCRT (min) | (M + H)+ |
|---|---|---|---|---|---|---|
| 165 | 3,5-bis(trifluoromethyl)benzyl carbonate (X1) | X3-(CH2)3-N(CH3)2 | 3-fluorobenzyl (X4) | F2,F4 | 1.33 | 633.4 |
| 166 | 3,5-bis(trifluoromethyl)benzyl carbonate (X1) | X3-(CH2)4-N(CH3)2 | 3-fluorobenzyl (X4) | F2,F4 | 1.31 | 647.5 |
| 167 | 3,5-bis(trifluoromethyl)benzyl carbonate (X1) | X3-(CH2)4-N(CH3)2 | 2-fluorobenzyl (X4) | F2,F4 | 1.33 | 647.4 |
| 168 | 3,5-bis(trifluoromethyl)benzyl carbamate (X1) | X3-(CH2)3-N(CH3)2 | 2-fluorobenzyl (X4) | F3,F4 | 1.24 | 632.5 |

TABLE 3-continued

| Cpd | R1 | R3 | R4 | Method * | LCRT (min) | (M + H)+ |
|---|---|---|---|---|---|---|
| 169 | 3,5-bis(trifluoromethyl)benzyl-NH-C(=O)-X1 | X3-CH(-)-CH2CH2-N(CH3)2 | X4-CH2-(4-fluorophenyl) | F3,F4 | 1.27 | 632.4 |
| 170 | 3,5-bis(trifluoromethyl)benzyl-O-C(=O)-X1 | X3-CH(-)-CH2CH2CH2-NH2 | X4-CH2-(4-methylsulfonylphenyl) | F2 | 1.56 | 679.5 |
| 171 | 3,5-bis(trifluoromethyl)benzyl-O-C(=O)-X1 | X3-CH(-)-CH2CH2CH2-NH2 | X4-CH2-(4-nitrophenyl) | F2 | 1.68 | 646.5 |
| 172 | 3,5-bis(trifluoromethyl)benzyl-O-C(=O)-X1 | X3-CH(-)-CH2-NH2 | X4-CH2-(2-ethoxyphenyl) | C | 1.84 | 617.5 |

TABLE 3-continued
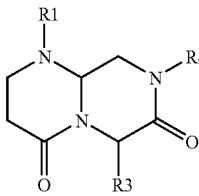
| Cpd | R1 | R3 | R4 | Method* | LCRT (min) | (M + H)+ |
|---|---|---|---|---|---|---|
| 173 | 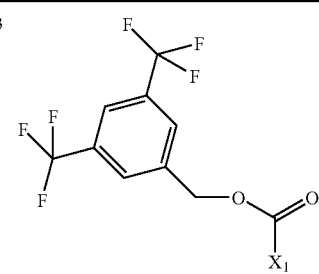 |  | 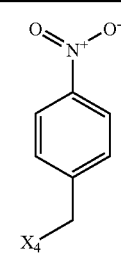 | C | 1.78 | 618.5 |
| 174 | 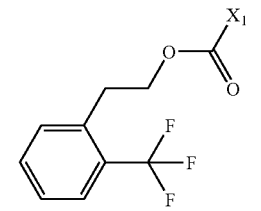 | 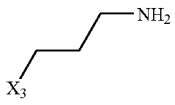 | 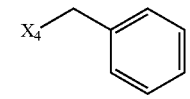 | B1 | 1.24 | 533.5 |
| 175 | 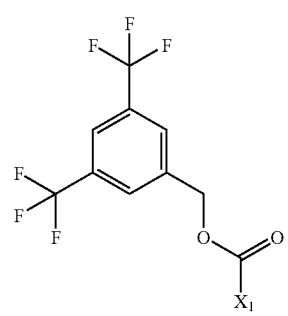 | 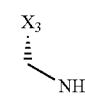 | 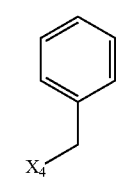 | C, F2 | 1.35 | 559.2 |
| 176 | 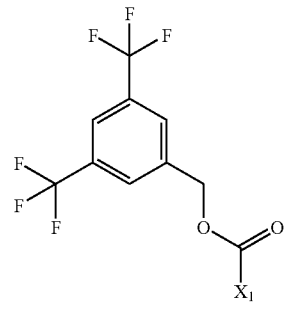 | 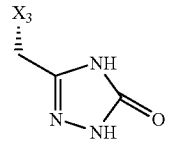 | 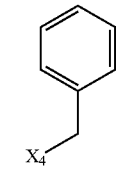 | A | 1.65 | 627.5 |

TABLE 3-continued
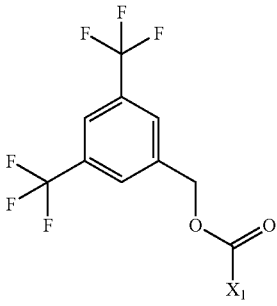
| Cpd | R1 | R3 | R4 | Method * | LCRT (min) | (M + H)+ |
|---|---|---|---|---|---|---|
| 177 |  | 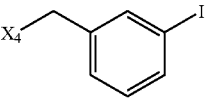 | 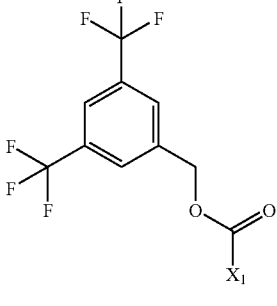 | C | 1.90 | 699.5 |
| 178 | 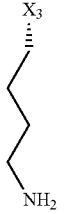 | 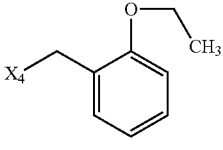 | 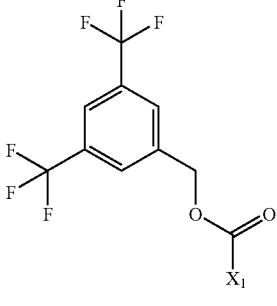 | F2 | 1.81 | 645.5 |
| 179 | 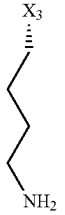 | 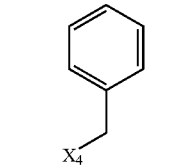 | 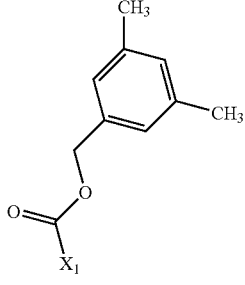 | F2 | 1.69 | 646.5 |
| 180 |  | 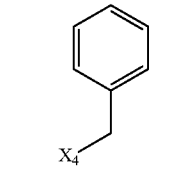 | 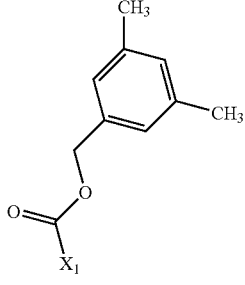 | F2 | 1.55 | 493.3 |

TABLE 3-continued

| Cpd | R1 | R3 | R4 | Method* | LCRT (min) | (M + H)+ |
|---|---|---|---|---|---|---|
| 181 | 4-isopropylbenzyl carbonate (X1) | X3-(CH2)4-NH2 | benzyl (X4) | B1 | 1.67 | 507.6 |
| 182 | 4-butylbenzyl carbonate (X1) | X3-(CH2)4-NH2 | benzyl (X4) | B1 | 1.75 | 521.6 |
| 183 | 4-tert-butylbenzyl carbonate (X1) | X3-(CH2)4-NH2 | benzyl (X4) | B1 | 1.7 | 521.6 |
| 184 | 2-methylbenzyl carbonate (X1) | X3-(CH2)4-NH2 | benzyl (X4) | B1 | 1.46 | 479.6 |

TABLE 3-continued
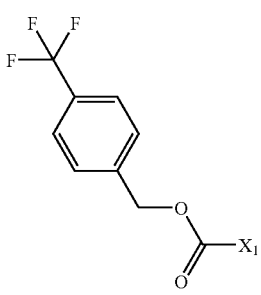
| Cpd | R1 | R3 | R4 | Method * | LCRT (min) | (M + H)+ |
|---|---|---|---|---|---|---|
| 185 | 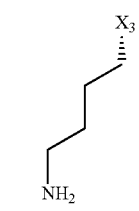 | 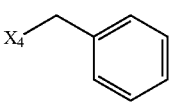 | 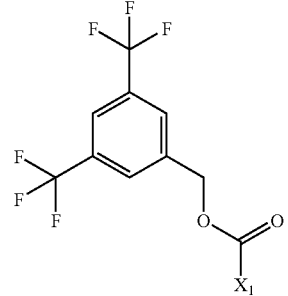 | B1 | 1.26 | 533.5 |
| 186 | 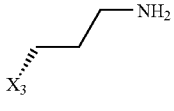 | 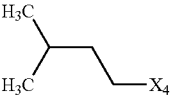 | 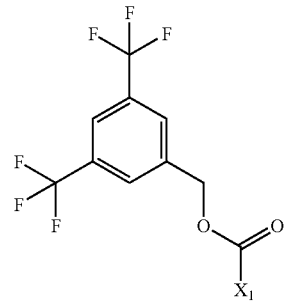 | F2 | 2.01 | 657.6 |
| 187 | 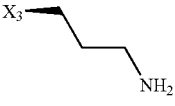 | 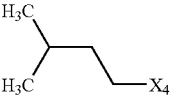 | 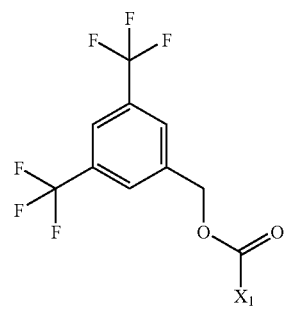 | F2 | 1.43 | 638.6 |
| 188 | 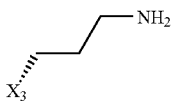 | 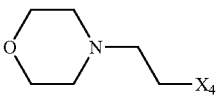 |  | F2 | 1.46 | 700.6 |

TABLE 3-continued
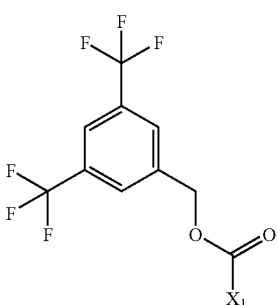
| Cpd | R1 | R3 | R4 | Method * | LCRT (min) | (M + H)+ |
|---|---|---|---|---|---|---|
| 189 | 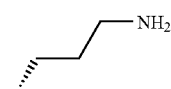 | 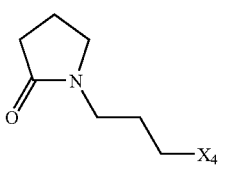 | 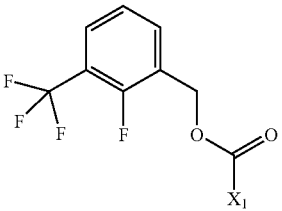 | F2 | 1.70 | 712.6 |
| 190 | 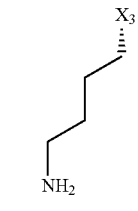 | 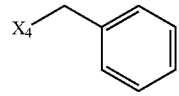 | 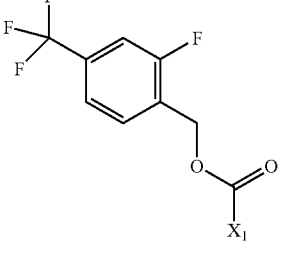 | B1 | 1.23 | 551.5 |
| 191 | 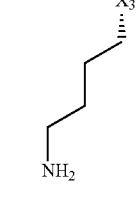 | 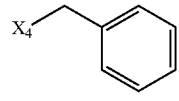 | 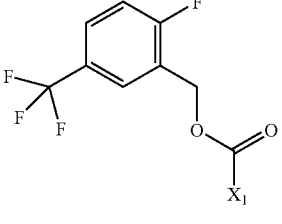 | B1 | 1.24 | 551.5 |
| 192 | 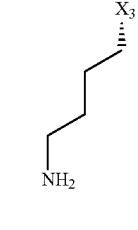 | 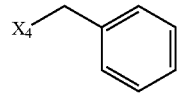 | 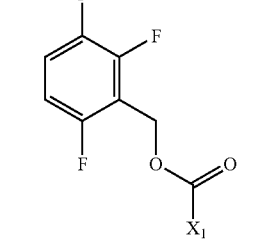 | B1 | 1.21 | 551.5 |
| 193 | 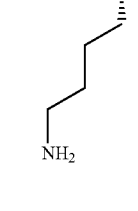 | 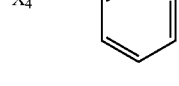 | | B1 | 1.21 | 519.5 |

TABLE 3-continued
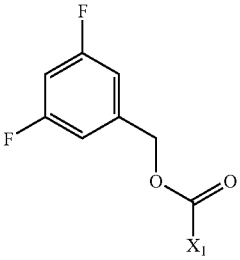
| Cpd | R1 | R3 | R4 | Method* | LCRT (min) | (M + H)+ |
|---|---|---|---|---|---|---|
| 194 | 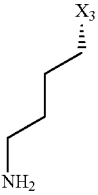 | 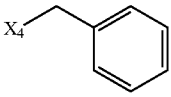 | 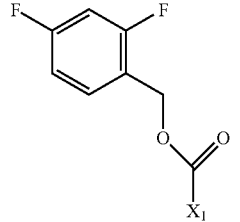 | B1 | 1.24 | 501.5 |
| 195 | 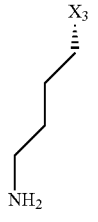 | 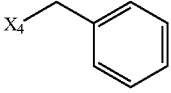 | 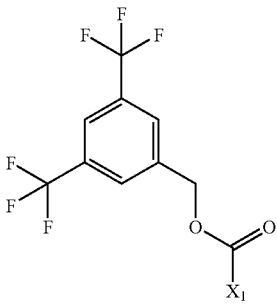 | B1 | 1.13 | 501.5 |
| 196 | 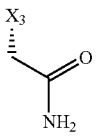 | 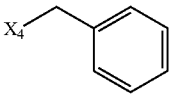 | 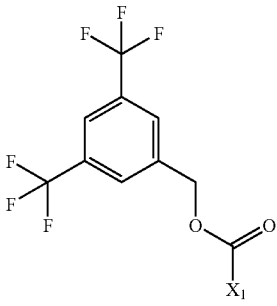 | F2 | 1.66 | 587.4 |
| 197 | 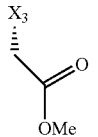 | 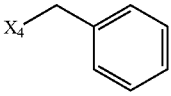 | | F2 | 2.40 | 602.5 |

TABLE 3-continued
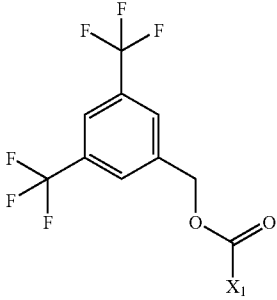
| Cpd | R1 | R3 | R4 | Method* | LCRT (min) | (M + H)+ |
|---|---|---|---|---|---|---|
| 198 | 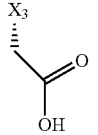 | 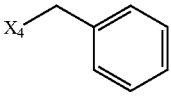 | 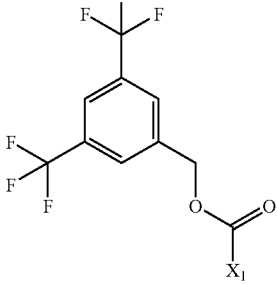 | F2 | 2.20 | 588.5 |
| 199 | 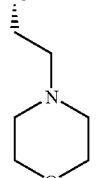 | 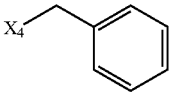 | 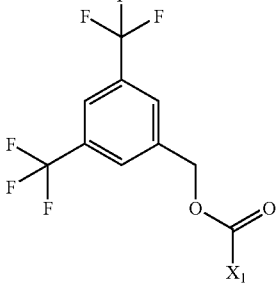 | J | 1.85 | 643.3 |
| 200 | 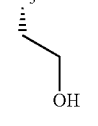 | 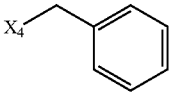 | 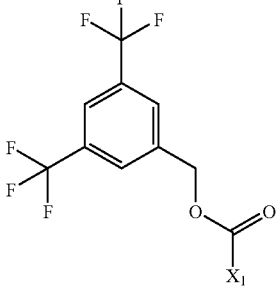 | ** | 2.02 | 574.5 |
| 201 | 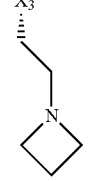 | 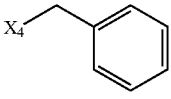 | 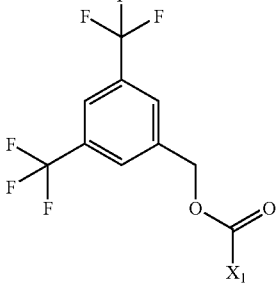 | J | 1.84 | 613.3 |

TABLE 3-continued

| Cpd | R1 | R3 | R4 | Method* | LCRT (min) | (M + H)+ |
|---|---|---|---|---|---|---|
| 202 | 3,5-bis(trifluoromethyl)benzyl carbamate | 2-bromoethyl (X3) | benzyl (X4) | *** | 1.82 | 637.4 |
| 203 | 3,5-bis(trifluoromethyl)benzyl carbamate | 2-((1-chloropropan-2-yl)amino)ethyl (X3) | benzyl (X4) | J | 1.93 | 649.0 |
| 204 | 3,5-bis(trifluoromethyl)benzyl carbamate | 2-(4-methylpiperazin-1-yl)ethyl (X3) | benzyl (X4) | J | 1.71 | 656.4 |
| 205 | 3,5-bis(trifluoromethyl)benzyl carbamate | 2-(cyclopropylamino)ethyl (X3) | benzyl (X4) | J | 1.92 | 613.3 |

TABLE 3-continued
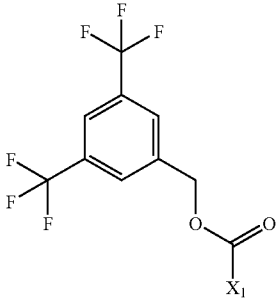
| Cpd | R1 | R3 | R4 | Method * | LCRT (min) | (M + H)+ |
|---|---|---|---|---|---|---|
| 206 | 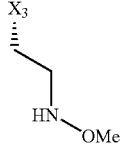 | 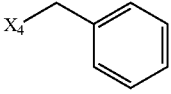 | 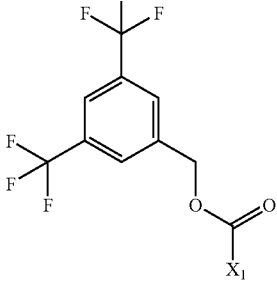 | J | 2.51 | 603.3 |
| 207 | 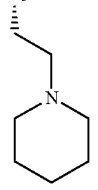 | 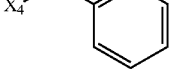 | 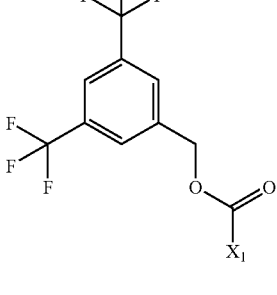 | J | 1.82 | 641.4 |
| 208 | 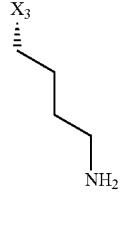 | 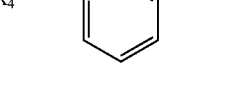 | 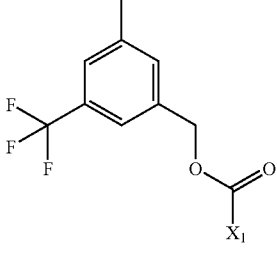 | F2 | 1.81 | 631.5 |
| 209 | 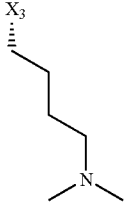 | 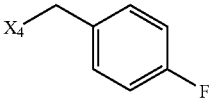 | | F2, F4 | 1.92 | 647.6 |

TABLE 3-continued
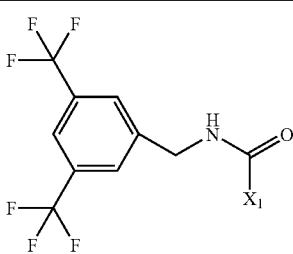
| Cpd | R1 | R3 | R4 | Method * | LCRT (min) | (M + H)+ |
|---|---|---|---|---|---|---|
| 210 | 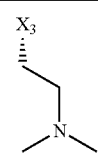 | 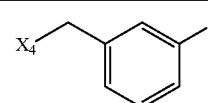 | 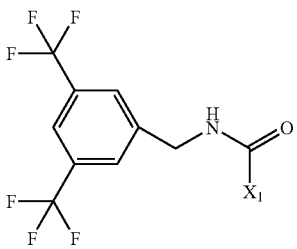 | F3,C,F4 | 1.40 | 618.5 |
| 211 | 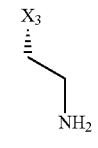 | 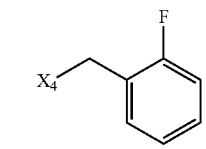 | 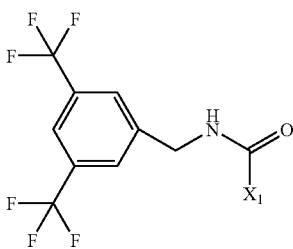 | F3,C | 1.38 | 590.5 |
| 212 | 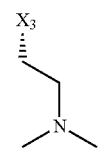 | 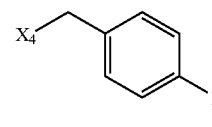 | 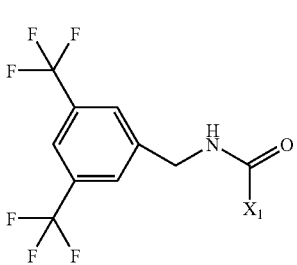 | F3,C,F4 | 1.39 | 618.5 |
| 213 | 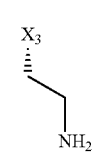 | 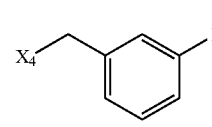 | | F3,C | 1.38 | 590.5 |

TABLE 3-continued

| Cpd | R1 | R3 | R4 | Method * | LCRT (min) | (M + H)+ |
|---|---|---|---|---|---|---|
| 214 | 3,5-bis(trifluoromethyl)benzyl-NH-C(O)-X1 | X3-CH2-NH2 | X4-CH2-phenyl | F3,C | 1.32 | 558.5 |
| 215 | 3,5-bis(trifluoromethyl)benzyl-NH-C(O)-X1 | X3-CH2CH2-NH2 | X4-CH2-(4-F-phenyl) | F3,C | 1.38 | 576.5 |
| 216 | 3,5-bis(trifluoromethyl)benzyl-NH-C(O)-X1 | X3-CH2CH2-N(CH3)2 | X4-CH2-(2-F-phenyl) | F3,C,F4 | 1.39 | 618.5 |
| 217 | 3,5-bis(trifluoromethyl)benzyl-O-C(O)-X1 | X3-CH2CH2-NH-CH2-cyclopropyl | X4-CH2-(4-F-phenyl) | J | 1.74 | 631.5 |
| 218 | 3,5-bis(trifluoromethyl)benzyl-O-C(O)-X1 | X3-CH2CH2CH2-NH2 | X4-CH2-(4-Cl-phenyl) | F2 | 1.76 | 663.5 |

* The methods of synthesis using the modular approach are as described in Example 1.
** Method described in Example 1, synthesis of compound 11.
*** Method described in Example 1, synthesis of compound 10.

Example 4

Representative Compounds of Structure (III) Made
According to the Methods of Example 2

TABLE 4

| Cpd | R1 | R2 | R3 | R4 |
|---|---|---|---|---|
| 219 | 3,5-bis(trifluoromethyl)benzyl-O-C(=O)-X₁ | X₂-(CH₂)₄-NH₂ | X₃—H | X₄-CH₂-phenyl |
| 220 | 3,5-bis(trifluoromethyl)benzyl-O-C(=O)-X₁ | X₂-CH₂-phenyl | X₃-(CH₂)₃-NH₂ | 1-(2-oxopyrrolidinyl)-(CH₂)₃-X₄ |
| 221 | 3,5-bis(trifluoromethyl)benzyl-O-C(=O)-X₁ | X₂-(CH₂)₄-NH₂ | X₃-(CH₂)₂-NH₂ | X₄-CH₂-phenyl |
| 222 | 3,5-bis(trifluoromethyl)benzyl-O-C(=O)-X₁ | X₂-(CH₂)₄-NH₂ | X₃-CH₃ | X₄-CH₂-phenyl |

TABLE 4-continued

TABLE 4-continued
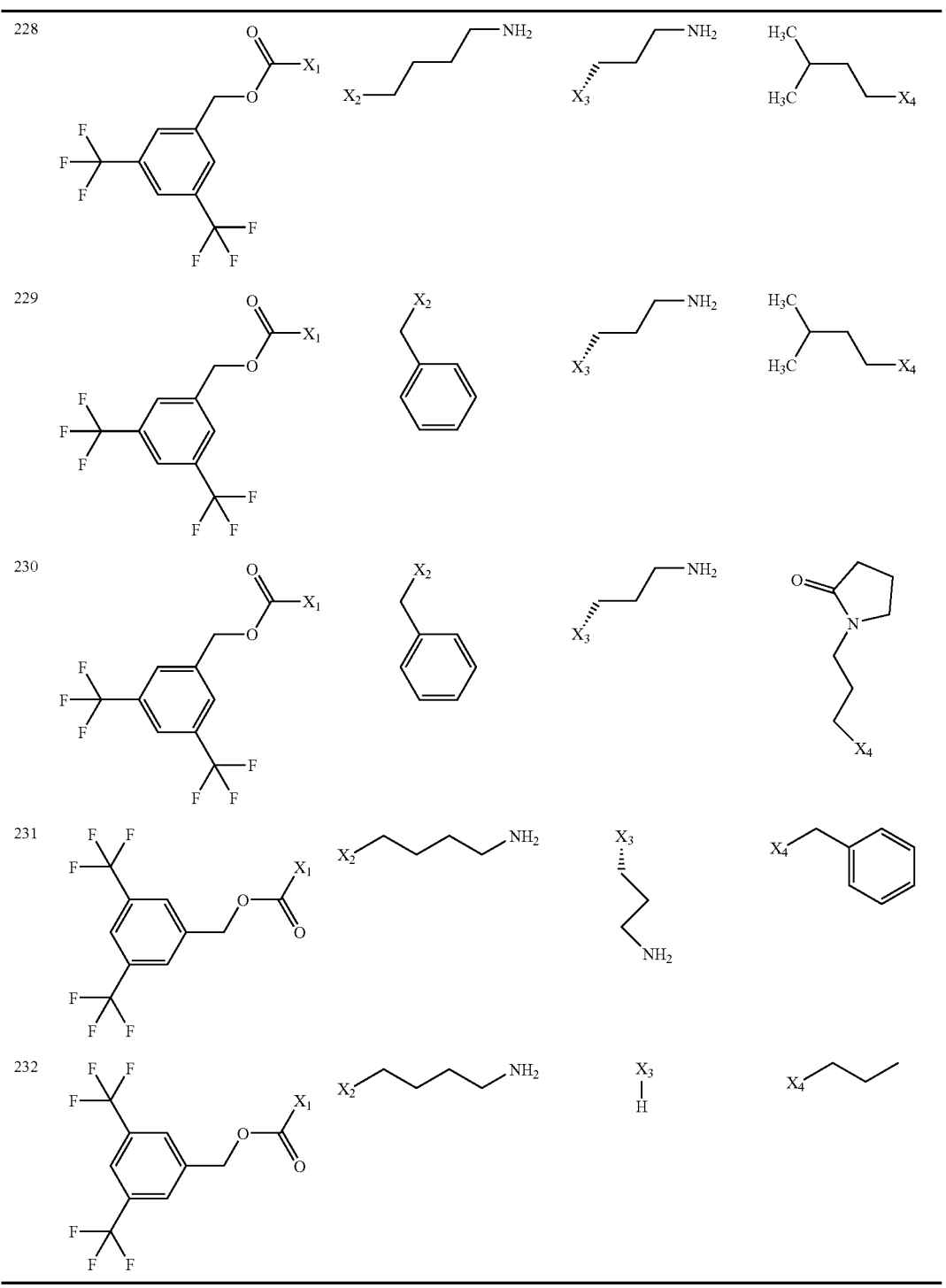
| Cpd | Method* | LCRT (mm) | (M + H)+ |
|---|---|---|---|
| 219 | F2 | 1.67 | 601.5 |
| 220 | F2 | 1.74 | 726.6 |
| 221 | F2 | 1.42 | 658.6 |
| 222 | F2 | 1.77 | 615.5 |
| 223 | F2 | 2.01 | 695.6 |
| 224 | F2 | 1.45 | 676.6 |
| 225 | F2 | 1.44 | 690.6 |
| 226 | F2 | 1.98 | 677.6 |
| 227 | F2 | 1.46 | 700.5 |

TABLE 4-continued

| | | | |
|---|---|---|---|
| 228 | F2 | 1.41 | 638.6 |
| 229 | F2 | 2.01 | 657.6 |
| 230 | F2 | 1.70 | 712.5 |
| 231 | F2 | 1.42 | 658.2 |
| 232 | F2 | 1.61 | 553.2 |

*The methods of synthesis using the modular approach are as described in Example 1.

Example 5

Representative Compounds of Structure (IV) Made According to the Methods of Example 2

TABLE 5

| Cpd | R1 | R2 | R3 | R4 |
|---|---|---|---|---|
| 233 | | | | |
| 234 | | | | |
| 235 | | | | |

TABLE 5-continued
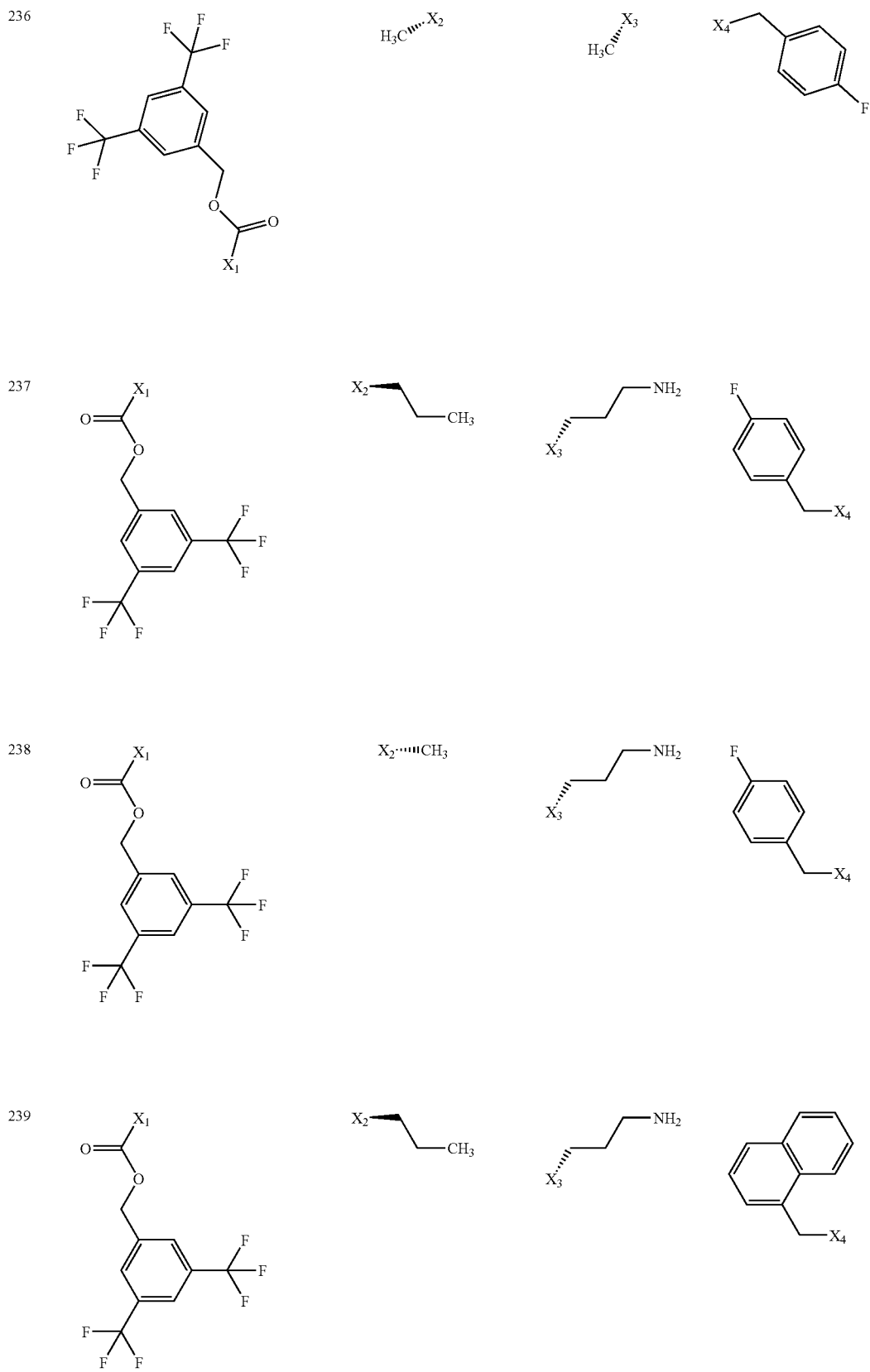

TABLE 5-continued

TABLE 5-continued
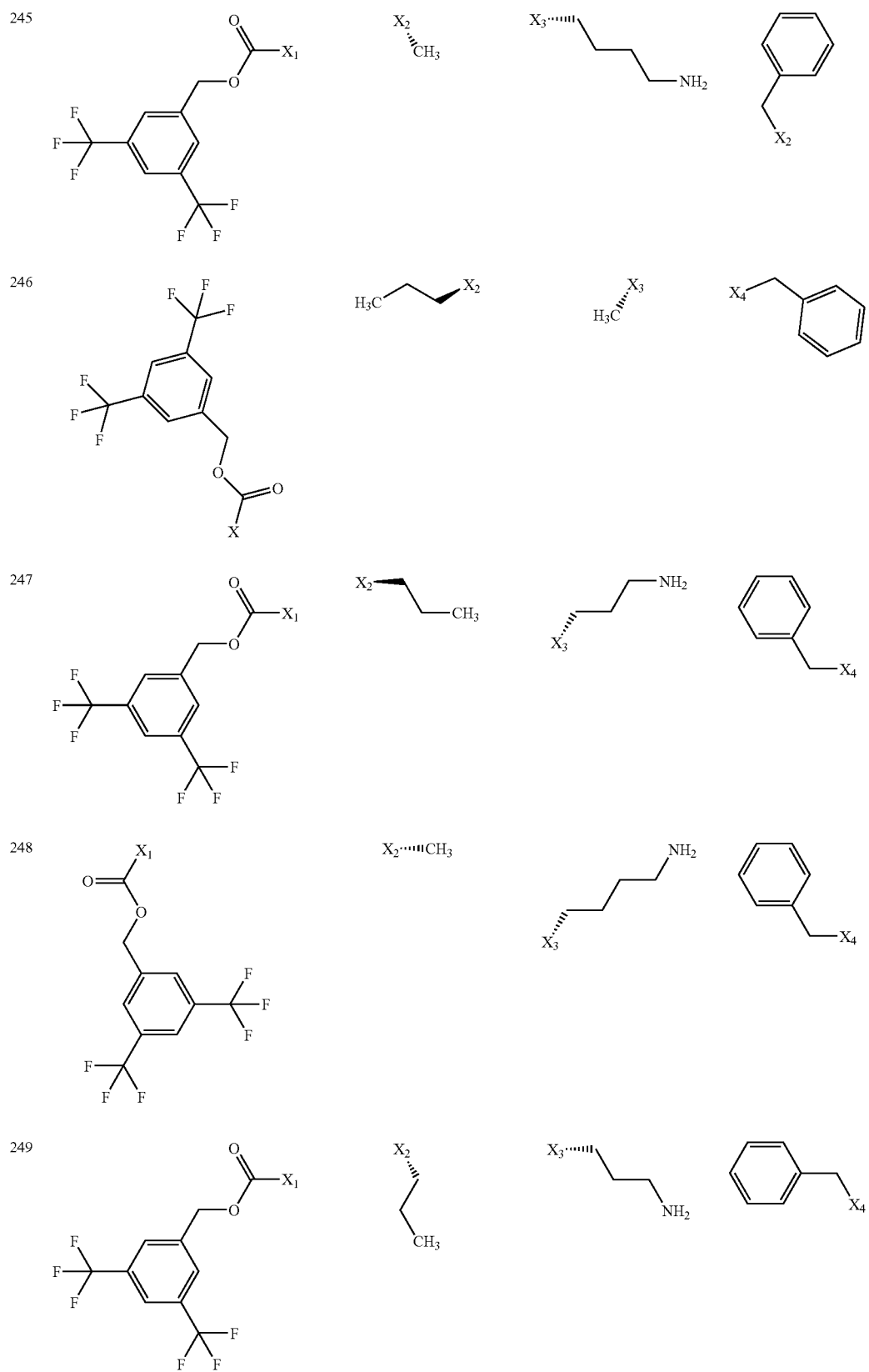

TABLE 5-continued
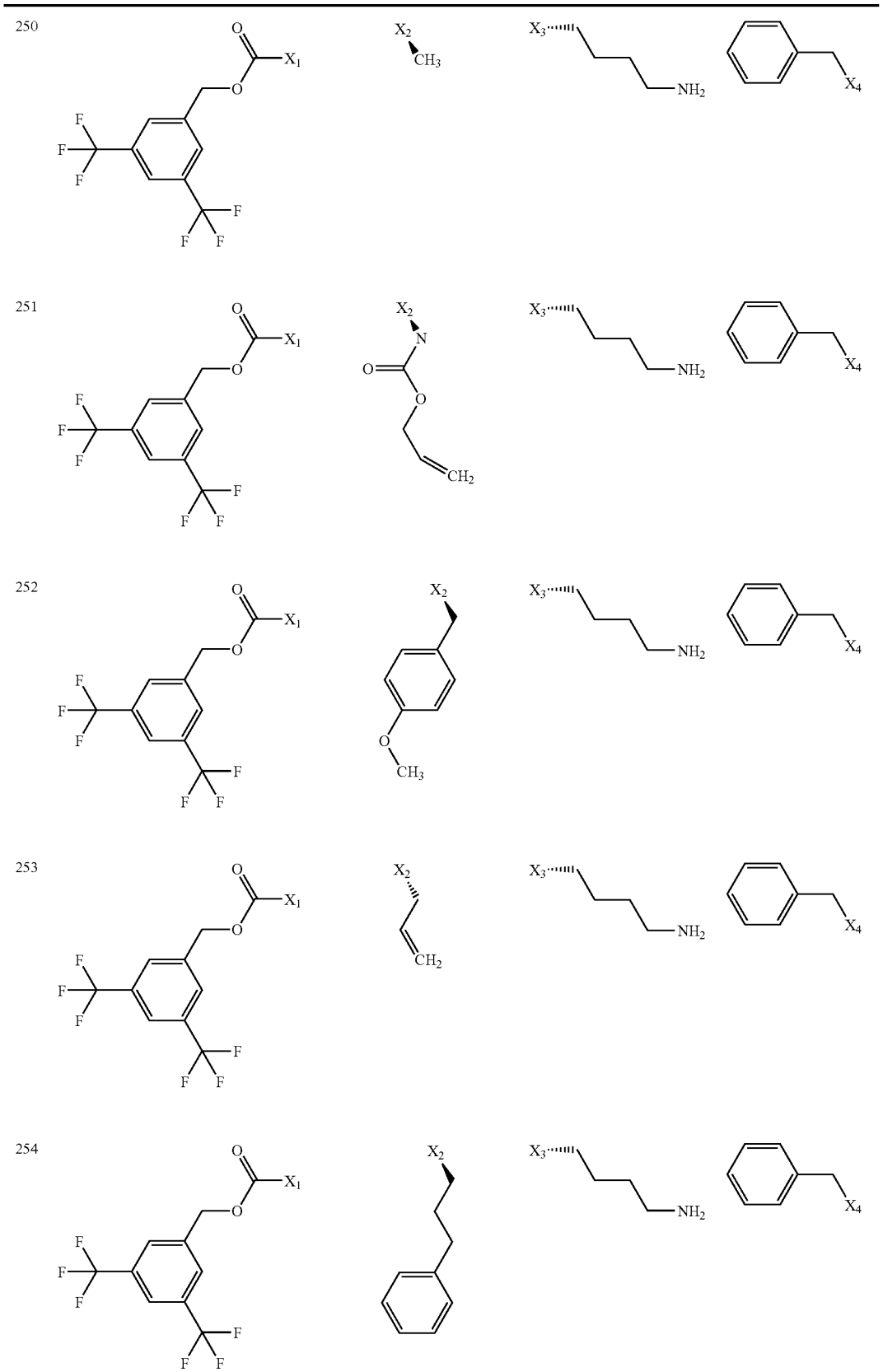

TABLE 5-continued
| | | | | |
|---|---|---|---|---|
| 255 | 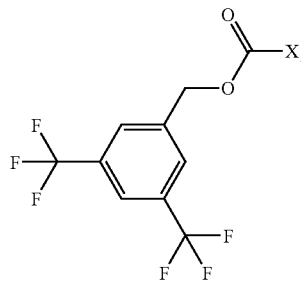 |  | 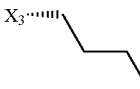 | 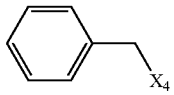 |
| 256 | 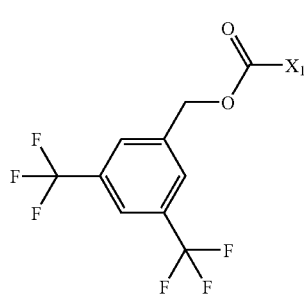 | 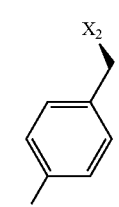 | 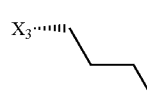 | 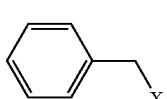 |
| 257 | 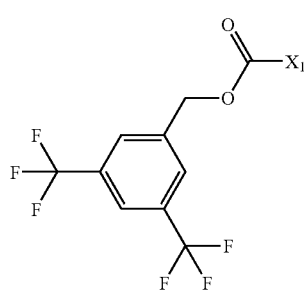 | 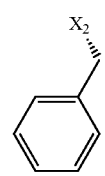 | 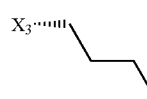 | 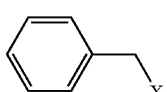 |
| 258 | 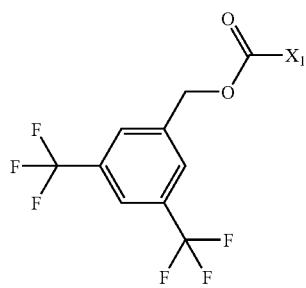 | 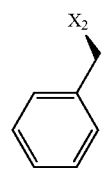 | 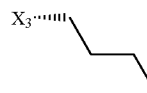 | 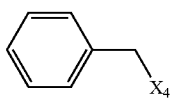 |
| 259 | 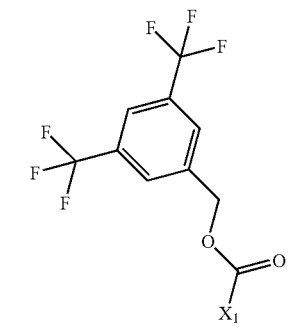 |  |  | 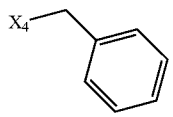 |

TABLE 5-continued
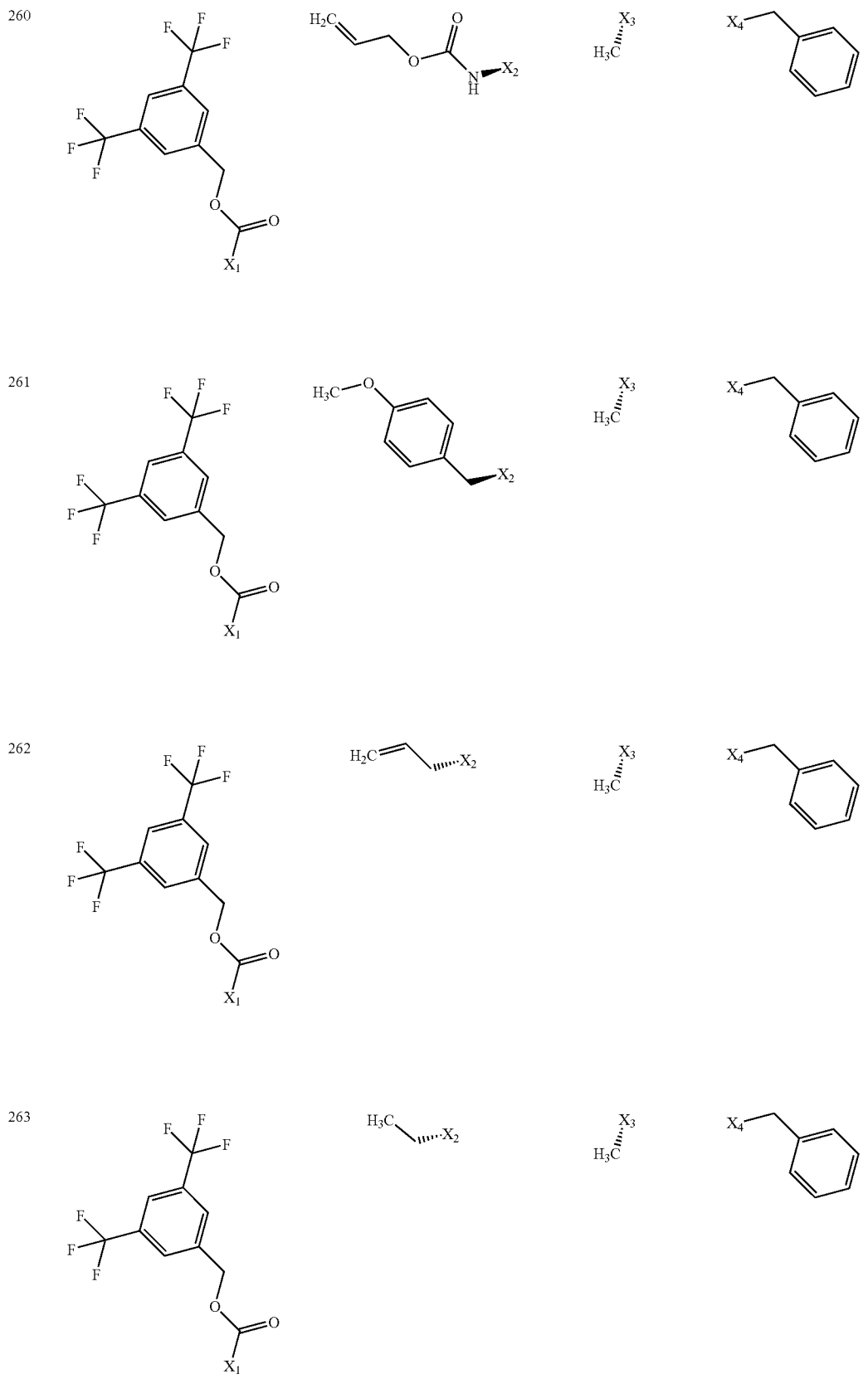

TABLE 5-continued
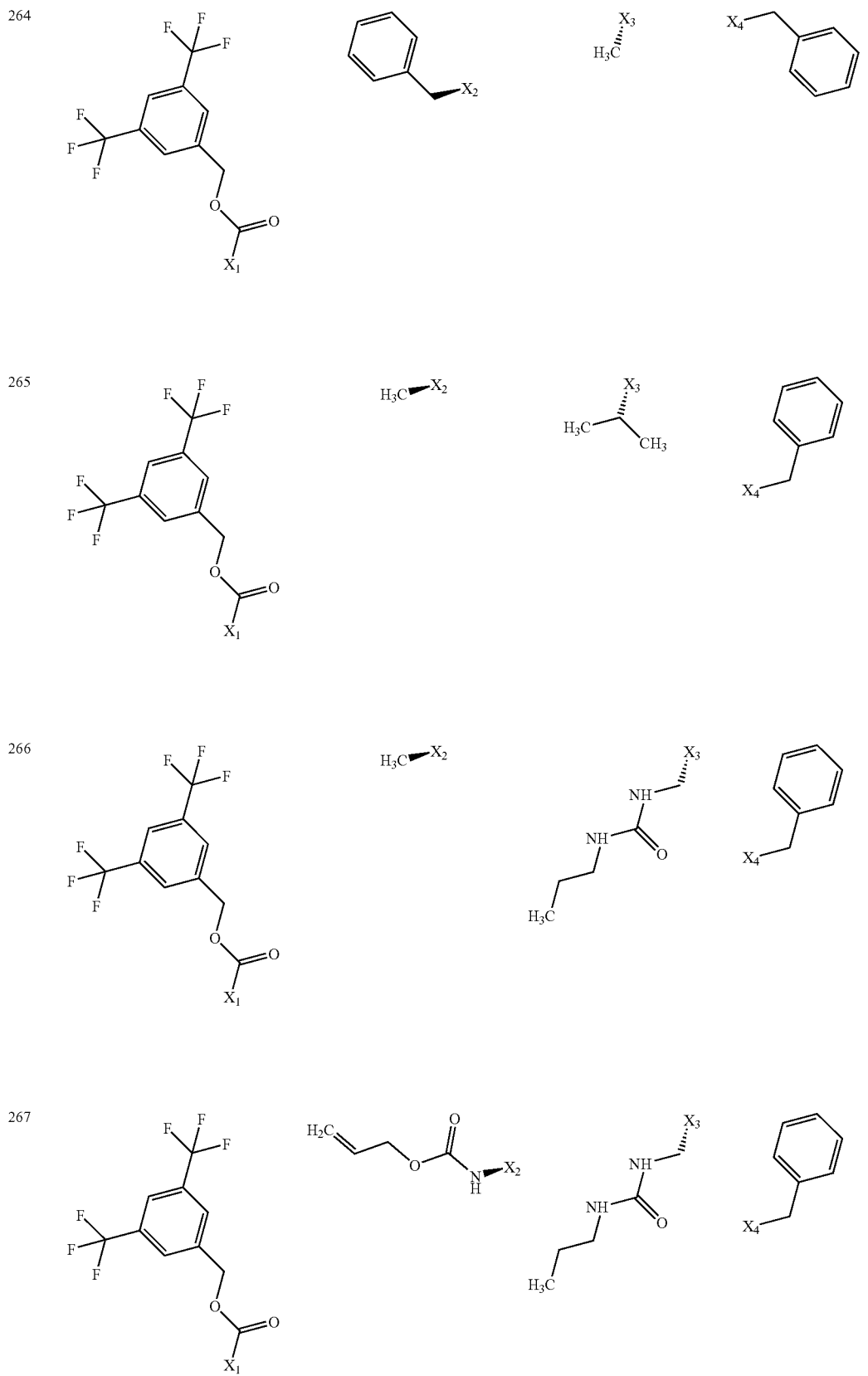

TABLE 5-continued
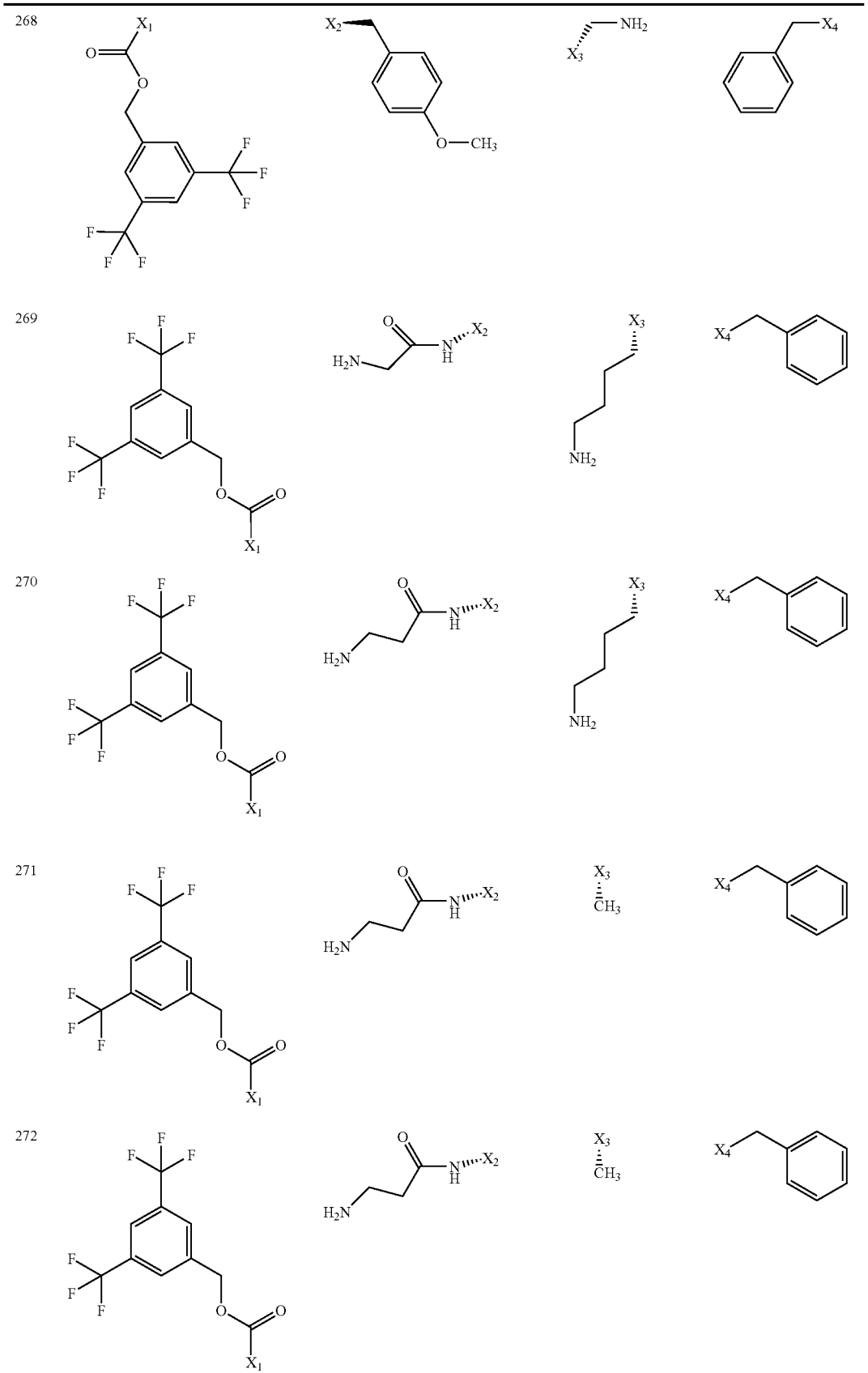

TABLE 5-continued

| | | | | |
|---|---|---|---|---|
| 273 | 3,5-bis(trifluoromethyl)benzyl-O-C(=O)-X₁ | X₂-CH₂-CH₃ (propyl) | X₃-CH₂-CH₂-NH₂ | 2,5-difluorobenzyl-X₄ |
| 274 | 3,5-bis(trifluoromethyl)benzyl-O-C(=O)-X₁ | X₂—CH₃ | X₃-CH₂-CH₂-NH₂ | 2,5-difluorobenzyl-X₄ |
| 275 | 3,5-bis(trifluoromethyl)benzyl-O-C(=O)-X₁ | X₂-CH₂-CH₂-phenyl | X₃-(CH₂)₃-NH₂ | H₃C-(CH₂)₃-X₄ |
| 276 | 3,5-bis(trifluoromethyl)benzyl-O-C(=O)-X₁ | X₂-CH₂-CH₂-phenyl | X₃-(CH₂)₃-NH₂ | cyclohexylmethyl-X₄ |
| 277 | 3,5-bis(trifluoromethyl)benzyl-O-C(=O)-X₁ | 4-methoxybenzyl-X₂ | X₃-CH₂-(1H-imidazol-5-yl) | benzyl-X₄ |
| 278 | 3,5-bis(trifluoromethyl)benzyl-O-C(=O)-X₁ | H₃C—X₂ | X₃-CH₂-(1H-imidazol-5-yl) | benzyl-X₄ |

TABLE 5-continued

TABLE 5-continued
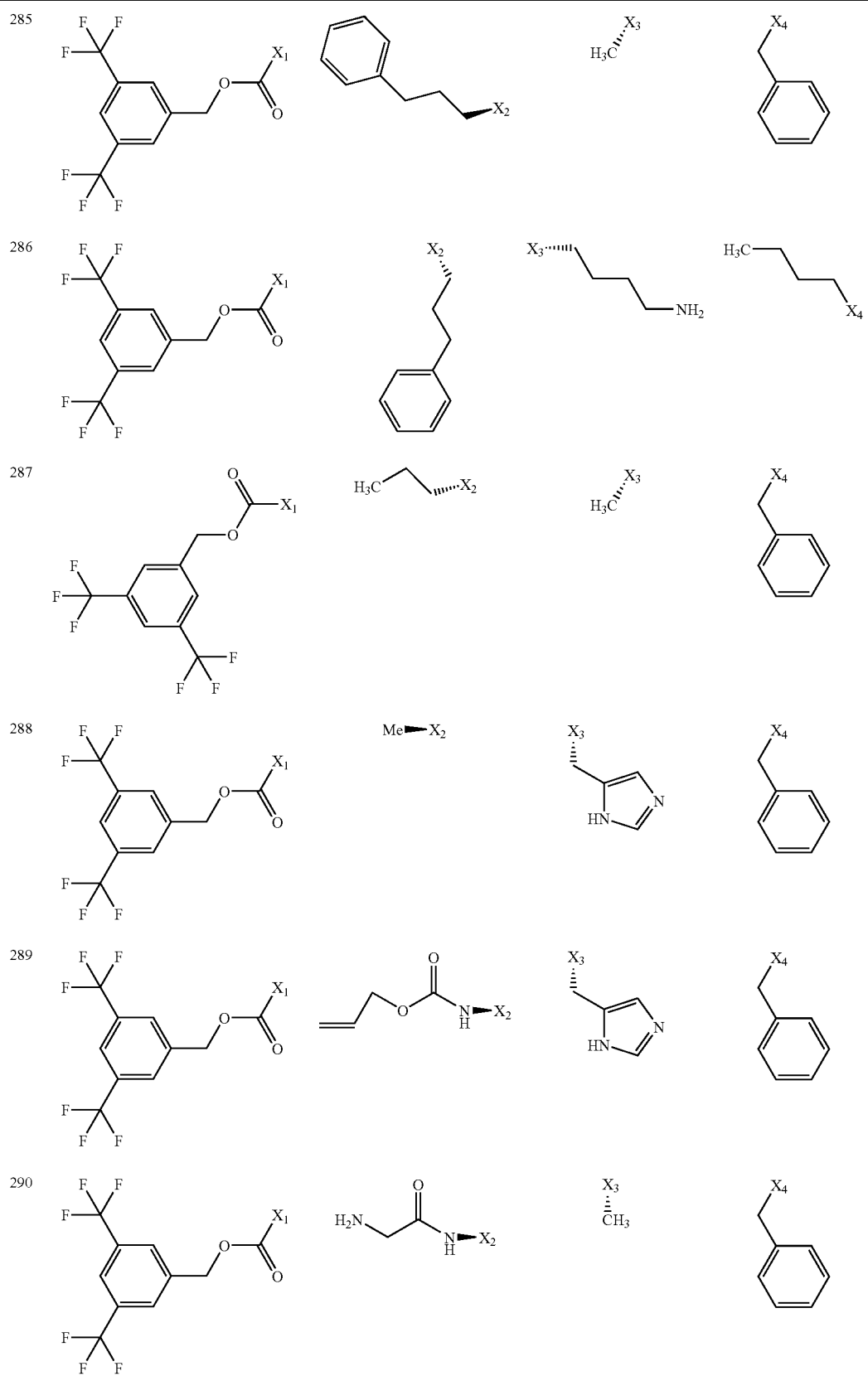

TABLE 5-continued
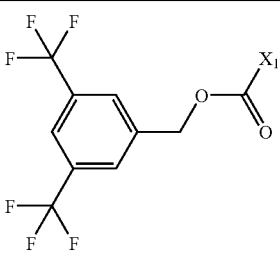
| Cpd | Method* | LCRT (min) | (M + H)+ |
| --- | --- | --- | --- |
| 233 | F2 | 1.84 | 704.6 |
| 234 | F2 | 1.57 | 661.6 |
| 235 | F2 | 1.46 | 633.5 |
| 236 | F2 | 1.82 | 576.5 |
| 237 | F2 | 1.57 | 647.6 |
| 238 | F2 | 1.47 | 619.5 |
| 239 | F2 | 1.67 | 679.6 |
| 240 | F2 | 1.57 | 651.6 |
| 241 | F2 | 1.60 | 577.5 |
| 242 | F2 | 1.59 | 713.6 |
| 243 | F2 | 1.63 | 697.6 |
| 244 | F2 | 1.57 | 643.6 |
| 245 | F2 | 1.46 | 615.5 |
| 246 | F2 | 1.93 | 586.2 |
| 247 | F2 | 1.57 | 629.5 |
| 248 | F2 | 1.45 | 601.5 |
| 249 | F2 | 1.58 | 643.5 |
| 250 | F2 | 1.47 | 615.5 |
| 251 | F2 | 1.51 | 700.6 |
| 252 | F2 | 1.61 | 721.6 |
| 253 | F2 | 1.55 | 641.5 |
| 254 | F2 | 1.73 | 719.7 |
| 255 | F2 | 1.52 | 629.5 |
| 256 | F2 | 1.07 | 705.6 |
| 257 | F2 | 1.63 | 691.6 |
| 258 | F2 | 1.63 | 691.6 |
| 259 | F2 | 1.80 | 558.5 |
| 260 | F2 | 1.80 | 643.5 |
| 261 | F2 | 1.95 | 664.5 |
| 262 | F2 | 1.92 | 584.5 |
| 263 | F2 | 1.85 | 572.5 |
| 264 | F2 | 1.98 | 634.5 |
| 265 | F2 | 1.91 | 586.5 |
| 266 | F2 | 1.76 | 658.6 |
| 267 | F2 | 1.75 | 743.7 |
| 268 | F2 | 1.65 | 679.6 |
| 269 | F2, H | 1.06 | 673.2 |
| 270 | F2, H | 1.04 | 687.2 |
| 271 | F2, H | 1.27 | 616.1 |
| 272 | F2, H | 1.27 | 630.1 |
| 273 | F2 | 1.60 | 665.6 |
| 274 | F2 | 1.47 | 637.5 |
| 275 | F2 | 1.72 | 685.7 |
| 276 | F2 | 1.84 | 725.7 |
| 277 | F2 | 1.55 | 730.4 |
| 278 | F2 | 1.42 | 624.4 |
| 279 | F2 | 1.95 | 652.5 |
| 280 | F2 | 1.78 | 677.5 |
| 281 | F2 | 1.77 | 699.5 |
| 282 | F2 | 1.49 | 573.5 |
| 283 | F2 | 1.99 | 634.5 |
| 284 | F2 | 2.04 | 648.5 |
| 285 | F2 | 2.07 | 662.5 |
| 286 | F2 | 1.70 | 685.7 |
| 287 | F2 | 1.96 | 586.5 |
| 288 | F2 | 1.48 | 624.5 |
| 289 | F2 | 1.52 | 709.5 |
| 290 | F2, H | 0.74 | 673.5 |
| 291 | F2, H | 0.74 | 687.5 |
*The methods of synthesis using the modular approach are as described in Example 1.

Example 6

Tachykinin Antagonism Assay

The compounds of this inventions are useful for antagonizing tachykinins, particularly substance P. Substance P is known to act upon cells via the mobilization of calcium (Bordey et al., *Glia* 11: 277-283, 1994). Test compounds were assessed for their ability to inhibit the action of substance P with the use of a Fluorescent Imaging Plate Reader (FLIPR) from Molecular Devices (Shroeder et al., *J. Biomol. Screening* 1: 75-80, 1996; U.S. Pat. No. 5,112,134; U.S. Pat. No. 4,968,148).

More specifically, U373 MG cells, which endogenously express the neurokinin-1 receptor for Substance P, were obtained from the American Type Culture Collection and grown to confluence in 96-well plates in modified Eagle's minimum essential medium (MEM) with 10% fetal bovine serum, 1 mM sodium pyruvate, 2 mM L-glutamine, and 1 mM non-essential amino acids in a humidified incubator at 37 C and 5% $CO_2$/95% filtered air. The cells were stained with Calcium Indicator dye from Molecular Devices for thirty minutes at room temperature; compounds were added to the cells, and the cells were further incubated for twenty minutes. This dye is similar to Fluo-3, Fluo-4, and Calcium Green dyes used by other researchers (Lin et al., *Biotechniques* 26: 318-326, 1999) in that it increases in fluorescence in the presence of calcium; the Molecular Devices version is preferable because the cells need not be washed following staining with the dye. Dye was made fresh on the day of the assay and included 2.5 mM probenecid, an anion exchange inhibitor which helps to keep the dye retained by the cells. Substance P was added in Hank's salt solution with 1% BSA to give a final concentration of 1 nM and the resultant change in fluorescence intensity was monitored for thirty seconds with an excitation wavelength of 480 nm and an emission of 515 nm. Some wells were maintained as controls which were not incubated with any compound, and the peak fluorescence readings resulting from the wells which received compounds were compared to these control wells in order to determine the degree of inhibition.

The compounds of this invention preferably have an inhibition value of better than 80% at 2 µM in this assay and/or $K_i$ of better than 200 nM. To this end, all the compounds listed in Tables 3, 4 and 5 satisfy this criteria.

Example 7

In Vivo Bioavailability in Monkeys

Bioavailability for representative compounds following intravenous and oral administration to Cynomolgus monkeys were obtained. The test compounds were typically dissolved in 10% propylene glycol:90% saline solution. Immediately after each formulation was completed, an aliquot (~0.15 mL) of the dosing solution for intravenous and oral administration was taken. Additional aliquots were taken after last animal was dosed on each dosing day. These aliquots were stored at −70° C.

Cynomolgus monkeys were selected for the study based on an acceptable health as determined by the attending veterinarian. The animals were given a complete physical examination by a staff veterinarian. This included abdominal palpation and observations of the condition of integument, respiratory and cardiovascular systems. The prestudy determination of health status include evaluation of a standard panel of serum chemistry and hematology parameters. The animals are purpose-bred and will be experimentally naïve at the outset of the study. Animals selected for use in this study will be as uniform in age and weight as possible. Prior to study, each animal had a central venous catheter (with a subcutaneous access port) surgically implanted in the femoral vein for blood sampling. All animals were fasted overnight prior to dosing. The animals received the test compounds by either the intravenous or oral (via nasogastric intubation) routs, with at least 21 days wash-out period between any two doses. Blood samples for pharmacokinetic analysis was collected prior to and at numerous timepoints following each dose.

IV Sample Preparation and Dosing

The animals were dosed via intravenous administration at a target dose level of 1.0 mg/kg at a concentration of 1.0 mg/mL, and at a volume of 1.0 mL/kg. Throughout dosing and sample collection, the animals were observed for any clinically relevant abnormalities. Blood samples of approximately 3 mL were collected in EDTA-containing tubes at the following timepoints: 5 min, 10 min, 20 min, 40 min, 1 h, 1.5 h, 2 h, 4 h and 8 h. All blood samples were collected from the access port attached to the implanted catheter. Whole blood was centrifuged to harvest plasma. Plasma samples were stored at −70° C.

PO Sample Preparation and Dosing

Oral dose was administered at a target dose level of 10 mg/kg at a concentration of 1 mg/mL and at a volume of 10 mL/kg. Throughout dosing and sample collection, the animals were observed for any clinically relevant abnormalities. Blood samples of approximately 3 mL were collected in EDTA-containing tubes at the following timepoints: 15 min, 30 min, 1 h, 1,5 h, 2 h, 3 h, 4 h, 6 h and 8 h. All blood samples were collected from the access port attached to the implanted catheter. Whole blood was centrifuged to harvest plasma. Plasma samples were stored at −70° C.

Plasma Analysis

Compound 26:

Off-line solid-phase extraction followed by evaporation and reconstitution of the sample in 20% aqueous acetonitrile was employed. Oasis HLB 96-well plate was used. They were pre-wetted with methanol followed by water, and then the sample was loaded after 1:1 dilution with water (1% phosphoric acid). This was washed 3 times with 2% ammonium hydroxide and 3 times with 2% formic acid both in 5% MeOH and the compounds were then eluted with acetonitrile. Eluent was dried and reconstituted in 20% acetonitrile with volume corresponding to the volume of plasma used. Samples were injected on LC-MS/MS system, Targa C18 reversed phase column, eluted with gradient initially held at 5% B for 0.5 minute, followed by linear segment from 5-95% B/2.5 minute (solvent A: water with 0.3% formic acid, B: acetonitrile with 0.3% formic acid). Detection was by electrospray with multiple reaction monitoring.

Quantitation was by external standard method with calibration curves constructed by spiking plasma with compound to give concentrations in the range 0.16-500 ng/ml.

Compound 26:

The calculation resulting from the plasma concentration of oral and intravenous administration to Cynomolgus monkeys showed bioavailability of 30%. As such, this compound shows oral bioavailability in Cynomolgus monkeys (FIG. 1).

Example 8

Pharmacokinetic Studies in Rats

Pharmacokinetics for several compounds of this invention following intravenous administration was obtained in male Sprague-Dawley rats using the method described below:

Sample Preparation and Dosing

The test compounds were dissolved in 10% propylene glycol:90% saline at a target concentration of 1.0 mg/mL or in 40:60 propylene glycol:water at a target concentration of 0.5 mg/mL for intravenous administration to the animals. A dose formulation aliquot (0.1 mL) was collected from each of the formulations prior to dosing. The aliquots were stored at −20±50° C.

Male Sprague-Dawley rats, were selected for the study based on acceptable health as determined by the attending veterinarian. All animals were fasted overnight prior to dosing. The animals were dosed via intravenous administration, through a percutaneous catheter placed in a tail vein, at a target dose level of 2 mg/kg or 1 mg/kg, and at a dose volume of 2 mL/kg. Immediately following the intravenous dose the catheters were flushed with 1 mL of vehicle prior to removal. Throughout dosing and sample collection, the animals were observed for any clinically relevant abnormalities.

Blood samples (maximum obtainable volume, whole blood, EDTA anticoagulant) were collected at the following timepoints: 0.5, 2 and 4 hours post-dose. All blood samples were collected via cardiac puncture. Whole blood was centrifuged to harvest plasma. Plasma samples were stored at −70±10° C. until assayed.

Plasma Analysis

On-line solid phase extraction (on-line SPE) followed by LC-MS/MS analysis was employed. An equivalent of sample was diluted 1:1 with 1% solution of ammonia, mixed, centrifuged at 10,000 g for 10 minutes, and 25 µL was injected on Oasis HLB SPE column. The column was washed for 20 sec with 2% solution of ammonium hydroxide in 5% methanol at flow rate of 4 ml/min followed by 30 sec wash with 2% formic acid in 5% methanol at the same flow rate from an auxiliary pump. After the wash period the column was switched in-line with gradient pump and compounds were eluted from the SPE column onto a regular analytical reverse-phase column (Zorbax Stable Bond C18, 2.1×50 mm, 3 µm particle size) connected to a triple quadrupole tandem mass spectrometer. Compounds were separated by linear gradient 5-95% B over 5 minutes (solvent A: water with 0.3% formic acid, B: acetonitrile with 0.3% formic acid) with detection by electrospray ionization with multiple reaction monitoring on the mass spectrometer.

Quantitation was determined by external standard method with calibration curves constructed by spiking plasma with compound to give concentrations in the range 0.16-500 ng/ml)

Compound 30:

Compound 30 was dissolved in 10% propylene glycol: 90% saline at a target concentration of 1.0 mg/mL for intravenous administration to the animals. The animals were dosed via intravenous administration, through a percutaneous catheter placed in a tail vein, at a target dose level of 2 mg/kg, and at a dose volume of 2 mL/kg. Blood samples (maximum obtainable volume, whole blood, EDTA anticoagulant) were collected from three animals per timepoint at the following timepoints: 0.5, 2 and 4 hours post-dose.

The results of the analysis indicated a decrease in the mean plasma level of the drug from ~43 ng/mL at 30 minutes to ~20 ng/nLl at 2 hours and ~13 ng/mL at 4 hours.

Compound 26:

Compound 26 was dissolved in 10% propylene glycol: 90% saline at a target concentration of 1.0 mg/mL for intravenous administration to the animals. The animals were dosed via intravenous administration, through a percutaneous catheter placed in a tall vein, at a target dose level of 2 mg/kg, and at a dose volume of 2 mL/kg. Blood samples (maximum obtainable volume, whole blood, EDTA anticoagulant) were collected from three animals per timepoint at the following timepoints: 0.5, 2 and 4 hours post-dose.

The results of the analysis indicated a decrease in the mean plasma level of the drug from ~125 ng/mL at 30 minutes to ~36 ng/mL at 2 hours and ~29 ng/mL at 4 hours.

Compound 87:

Compound 87 was dissolved in 40:60 propylene glycol: water at a target concentration of 0.5 mg/mL for intravenous administration to the animals. The animals were dosed via intravenous administration, through a percutaneous catheter placed in a tall vein, at a target dose level of 1 mg/kg, and at a dose volume of 2 mL/kg. Blood samples (maximum obtainable volume, whole blood, EDTA anticoagulant) were collected from three animals per timepoint at the following timepoints: 0.5, 2 and 4 hours post-dose.

The results of the analysis indicated a decrease in the mean plasma level of the drug from ~75 ng/mL at 30 minutes to ~20 ng/nLl at 2 hours and ~11 ng/mL at 4 hours.

Example 9

Drug-Brain Penetration Studies in Rats

Brain penetration following intravenous administration to male Sprague-Dawley rats for several representative compounds was determined using the method described below:

Sample Preparation and Dosing

The test compounds were dissolved in 10% propylene glycol:90% saline at a target concentration of 1.0 mg/mL or in 40:60 propylene glycol:water at a target concentration of 0.5 mg/mL for intravenous administration to the animals. A dose formulation aliquot (0.1 mL) was collected from each of the formulations prior to dosing. The aliquots were stored at −20±5° C.

Male Sprague-Dawley rats were selected for the study based on acceptable health as determined by the attending veterinarian. All animals were fasted overnight prior to dosing. The animals were dosed via intravenous administration, through a percutaneous catheter placed in a tall vein, at a target dose level of 2 mg/kg or 1 mg/kg, and at a dose volume of 2 mL/kg. Immediately following the intravenous dose the catheters were flushed with 1 mL of vehicle prior to removal. Throughout dosing and sample collection, the animals were observed for any clinically relevant abnormalities.

Brain samples were collected following euthanasia at the following timepoints: 0.5, 2, and 4 hours post dose. Brain samples were rinsed with saline, flash frozen and stored at −70±10° C. Brain weights were recorded at the time of collection.

Brain samples were homogenated using the following protocol: The whole dissected rat brain was placed in a Dounce Tissue Homogenator Tube and 4 mL of ice-cold acetonitrile was added. Fisher Sonic Dismembrator was used to homogenate the rat brain tissue (4×1 min). This was then allowed to settle in the homogenate tube in ice for 30 minutes. The homogenate was then using centrifuged at 25,000×g for 30 minutes. The resulting supernatant was transferred to a test tube for LC-MS analysis.

Brain Extract Analysis

Acetonitrile brain extracts were diluted 1:1 with water and 25 µL was injected on reverse-phase column. Compounds 26 and 30 were analyzed on Zorbax Stable Bond C18 column (2.1×50 mm, 3 µm particle size). Elution was effected by linear gradient 25-95% B over 5 minutes (solvent A: water with 0.3% formic acid, B: acetonitrile with 0.3% formic acid). Compound 87 was analyzed on Eclipse C8 column (2.1×150 mm, 5 µm particle size) with gradient 25-60% B/10'(solvent A: water with 0.3% formic acid, B: Acetonitrile with 0.3% formic acid). Compounds were detected by electrospray ionization with multiple reaction monitoring on the mass spectrometer.

Quantitation was by external standard method with calibration curves constructed by spiking acetonitrile extract of a blank brain with compound to give concentrations in the range of 0.25-200 ng/ml.

Compound 30:

Compound 30 was dissolved in 10% propylene glycol: 90% saline at a target concentration of 1.0 mg/mL for intravenous administration to the animals. The animals were dosed via intravenous administration, through a percutaneous catheter placed in a tall vein, at a target dose level of 2 mg/kg, and at a dose volume of 2 mL/kg. Brain samples were collected from three animals per timepoint following euthanasia at the following timepoints: 0.5, 2, and 4 hours post dose. Brain samples were rinsed with saline, flash frozen and stored at −70±10° C. Brain weights were recorded at the time of collection.

The results of the analysis indicated a level of the drug in the brain from ~45 ng/gm at 30 minutes to ~42 ng/gm at 2 hours and ~51 ng/gm at 4 hours. As such, this copound shows brain penetration in rats.

Compound 26:

Compound 26 was dissolved in 10% propylene glycol: 90% saline at a target concentration of 1.0 mg/mL for intravenous administration to the animals. The animals were dosed via intravenous administration, through a percutaneous catheter placed in a tall vein, at a target dose level of 2 mg/kg, and at a dose volume of 2 mL/kg. Brain samples were collected from three animals per timepoint following euthanasia at the following timepoints: 0.5, 2, and 4 hours post dose. Brain samples were rinsed with saline, flash frozen and stored at −70±10° C. Brain weights were recorded at the time of collection.

The results of the analysis indicated a level of the drug in the brain from ~34 ng/gm at 30 minutes to ~25 ng/gm at 2 hours and ~17 ng/gm at 4 hours. As such, this copound shows brain penetration in rats.

Compound 87:

Compound 87 was dissolved in 40:60 propylene glycol: water at a target concentration of 0.5 mg/mL for intravenous administration to the animals. The animals were dosed via intravenous administration, through a percutaneous catheter placed in a tall vein, at a target dose level of 1 mg/kg, and at a dose volume of 2 mL/kg. Brain samples were collected from three animals per timepoint following euthanasia at the following timepoints: 0.5, 2, and 4 hours post dose. Brain samples were rinsed with saline, flash frozen and stored at −70±10° C. Brain weights were recorded at the time of collection.

The results of the analysis indicated a level of the drug in the brain from ~105 ng/gm at 30 minutes to ~9 ng/gm at 2 hours and ~2 ng/gm at 4 hours. As such, this copound shows brain penetration in rats.

Example 10

Synthesis of (S)-6-(4-Hydroxy-benzyl)-8-naphthalen-1-ylmethyl-4,7-dioxo-hexahydro-pyrazino[1,2-a]pyrimidine-1-carboxylic acid benzylamide The scheme below depicts the synthesis of (S)-6-(4-Hydroxy-benzyl)-8-naphthalen-1-ylmethyl-4,7-dioxo-hexahydro-pyrazino [1,2-a]pyrimidine-1-carboxylic acid benzylamide, a compound of the present invention in which $R_1$ is —X—$R_5$, and X is —C(=O)NH—. As will be apparent to one of skill in the art, this scheme can be readily adapted to facilitate the synthesis of other compounds of the invention in which $R_1$ is —X—$R_5$, and X is —C(=O)NH—.

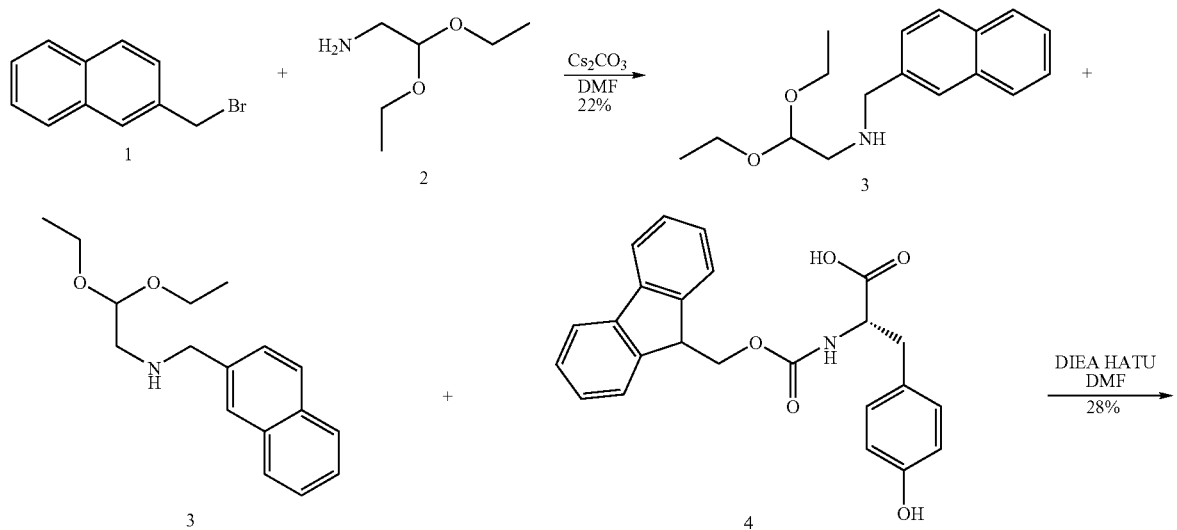

-continued
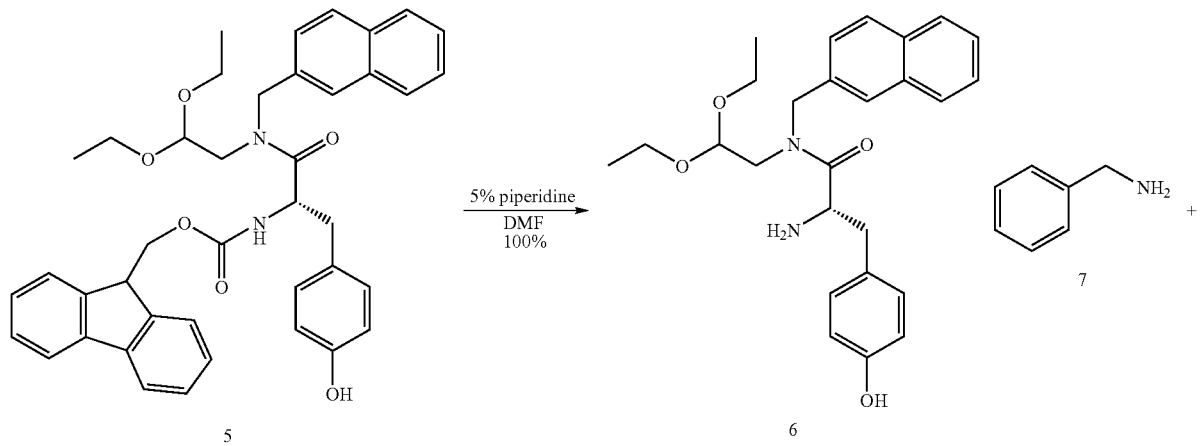
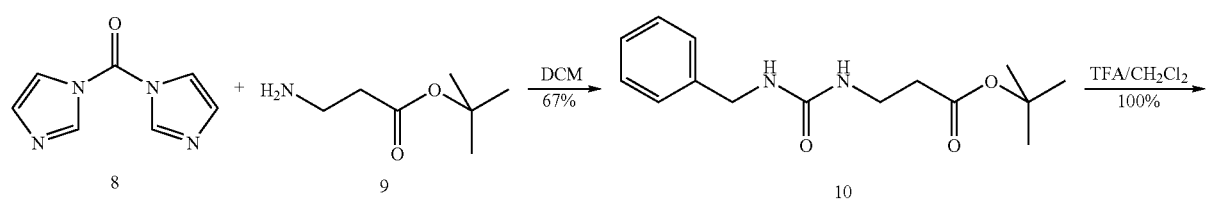
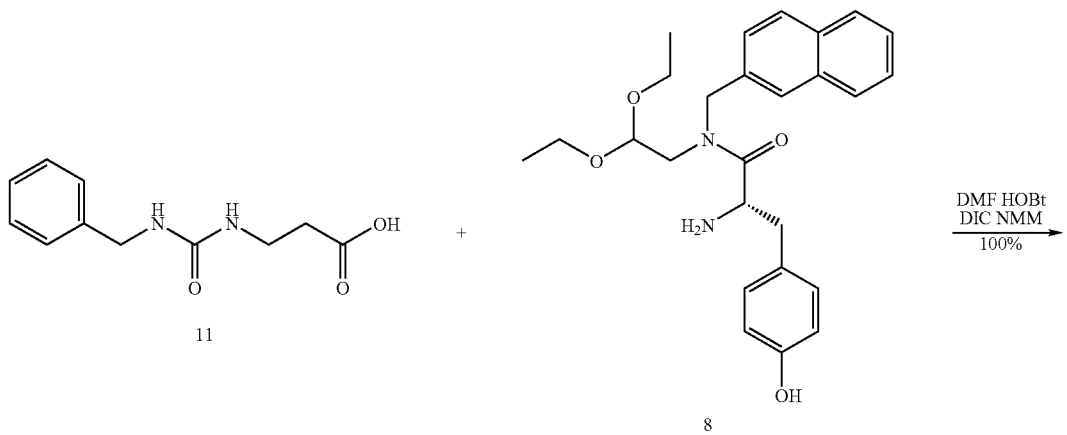
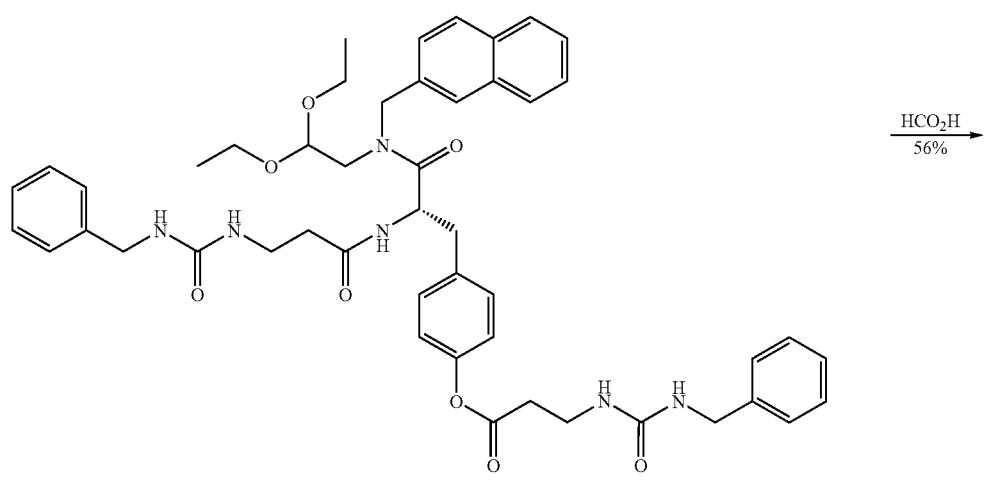

-continued
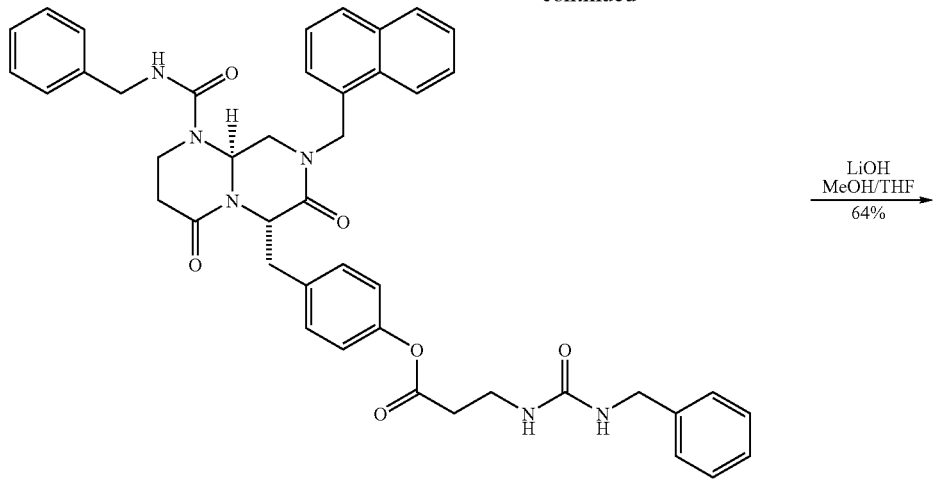
14
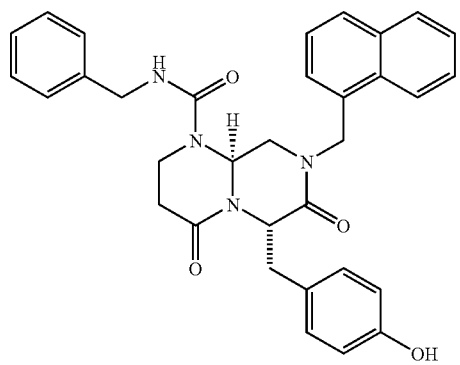
15
Example 11
Representative Compounds that can be Made by Methods Equivalent to Those of Example 10
TABLE 6
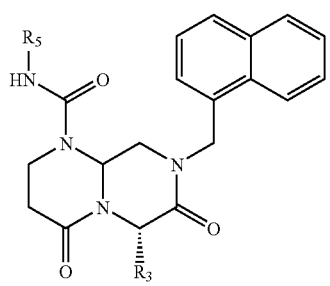
| Cpd | R₃ | R₅ | Formula | MW |
|---|---|---|---|---|
| 292 | isobutyl-X₃ | H₃C-O-C₆H₄-X₅ | $C_{30}H_{43}N_4O_4$ | 514.63 |

TABLE 6-continued

| Cpd | R₃ | R₅ | Formula | MW |
|---|---|---|---|---|
| 293 | isobutyl-X₃ | phenyl-X₅ | $C_{29}H_{32}N_4O_3$ | 484.60 |
| 294 | isobutyl-X₃ | 2-naphthyl-X₅ | $C_{33}H_{34}N_4O_3$ | 534.66 |
| 295 | isobutyl-X₃ | benzyl-X₅ | $C_{30}H_{34}N_4O_3$ | 498.63 |
| 296 | isobutyl-X₃ | 3-chlorophenyl-X₅ | $C_{29}H_{31}ClN_4O_3$ | 519.05 |
| 297 | isobutyl-X₃ | 4-methylphenyl-X₅ | $C_{30}H_{43}N_4O_3$ | 498.63 |
| 298 | isobutyl-X₃ | 4-acetylphenyl-X₅ | $C_{31}H_{34}N_4O_4$ | 526.64 |
| 299 | isobutyl-X₃ | (R)-1-phenylethyl-X₅ | $C_{31}H_{36}N_4O_3$ | 512.66 |
| 300 | 4-hydroxybenzyl-X₃ | 4-methoxyphenyl-X₅ | $C_{33}H_{32}N_4O_5$ | 564.65 |
| 301 | 4-hydroxybenzyl-X₃ | phenyl-X₅ | $C_{32}H_{30}N_4O_4$ | 534.62 |
| 302 | 4-hydroxybenzyl-X₃ | 2-naphthyl-X₅ | $C_{36}H_{32}N_4O_4$ | 584.68 |

TABLE 6-continued

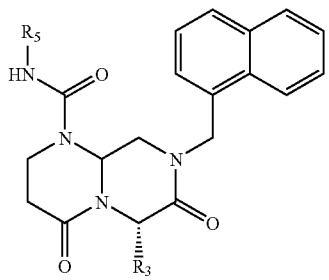

| Cpd | R$_3$ | R$_5$ | Formula | MW |
|---|---|---|---|---|
| 303 | HO—⟨⟩—X$_3$ | ⟨⟩—X$_5$ | C$_{33}$H$_{32}$N$_4$O$_4$ | 548.65 |
| 304 | HO—⟨⟩—X$_3$ | Cl-⟨⟩—X$_5$ | C$_{32}$H$_{29}$ClN$_4$O$_4$ | 569.07 |
| 305 | HO—⟨⟩—X$_3$ | H$_3$C—⟨⟩—X$_5$ | C$_{33}$H$_{32}$N$_4$O$_4$ | 548.65 |
| 306 | HO—⟨⟩—X$_3$ | H$_3$C—C(=O)—⟨⟩—X$_5$ | C$_{33}$H$_{32}$N$_4$O$_5$ | 576.66 |
| 307 | HO—⟨⟩—X$_3$ | (R)-CH(⟨⟩)—X$_5$ | C$_{34}$H$_{34}$N$_4$O$_4$ | 562.67 |

It will be appreciated that, although specific embodiments of the invention have been described herein for the purposes of illustration, various modifications may be made without departing from the spirit and scope of the invention. Accordingly, the invention is not limited except by the appended claims.

We claim:

1. A compound having the structure:

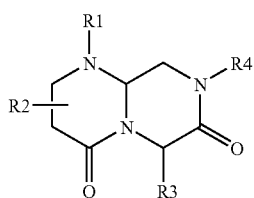

or a pharmaceutically acceptable salt or stereoisomer thereof, wherein

R$_1$ is —X—R$_5$, where X is —C(=O)NH—, and R$_5$ is an amino acid side chain moiety or an amino acid side chain derivative selected from the following list of amino acid side chain derivatives:

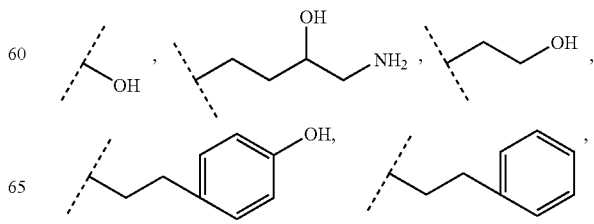

-continued
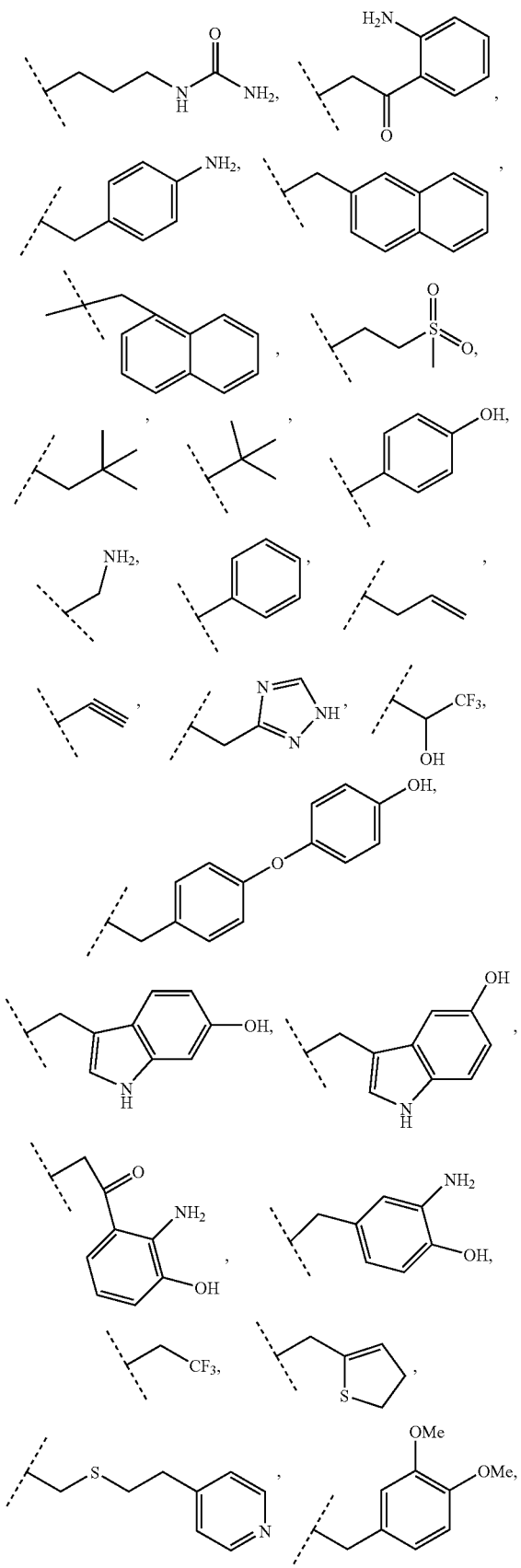
-continued
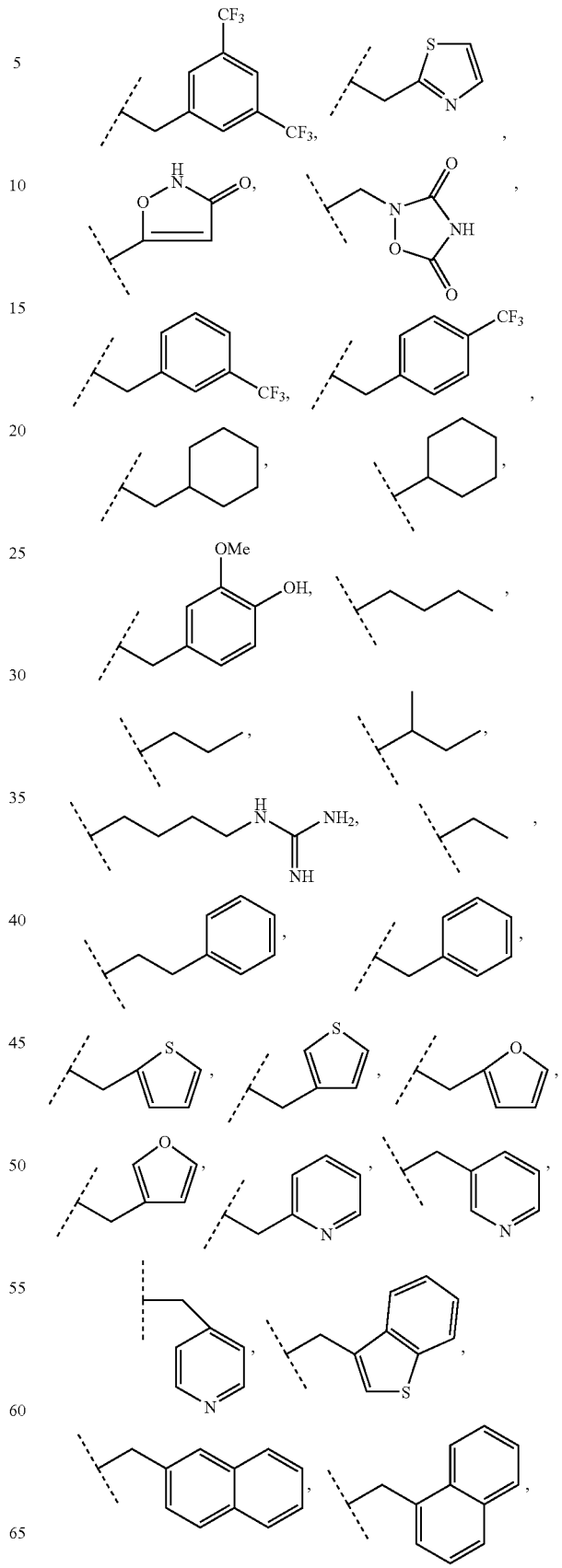

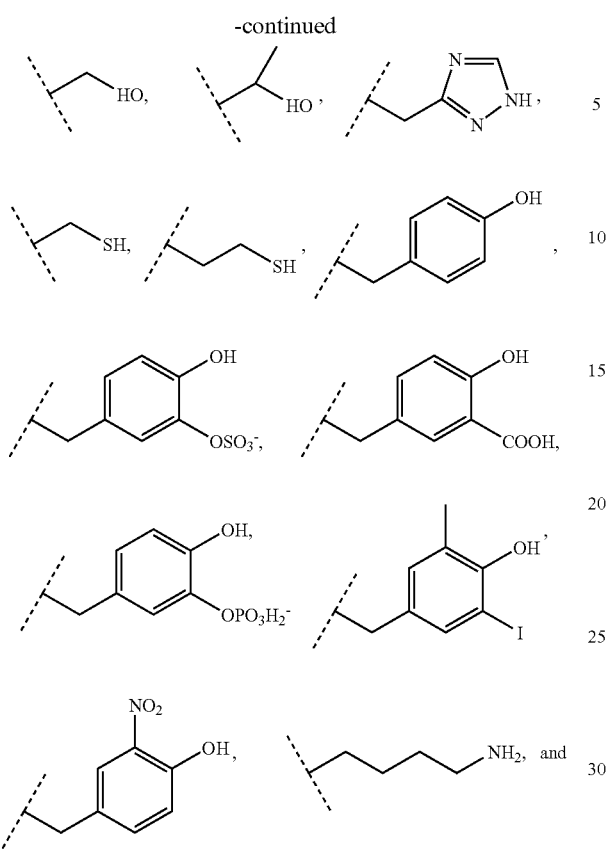

substituted or unsubstituted alkyl, aryl, arylalkyl, heteroaryl, heteroarylalkyl, heterocycle and heterocyclealkyl moieties;

R$_2$ is hydrogen or —Y—R$_6$, where Y is a direct bond, —NH—, —NHC(=O)—, —NHC(=O)O—, —NHC(=O)NH— or —NHSO$_2$—, and R$_6$ is an amino acid side chain moiety or an amino acid side chain derivative selected from the list of amino acid side chain derivatives above;

R$_3$ is —Z—R$_7$, where Z is a direct bond, —(CH$_2$)$_m$C(=O)NR$_8$—, —(CH$_2$)$_k$NHC(=O)— or —(CH$_2$)$_k$NHC(=O)NR$_8$—, R$_7$ and R$_8$ are independently amino acid side chain moieties or an amino acid side chain derivatives selected from the list of amino acid side chain derivatives above, m is an integer from 1 to 4 and k is 1 or 2; and R$_4$ is selected from a solid support, an amino acid side chain moiety, or the list of amino acid side chain derivatives above.

2. The compound of claim 1 having the structure:

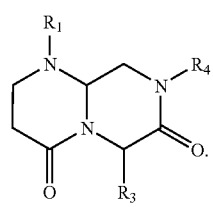

3. The compound of claim 1 having the structure:

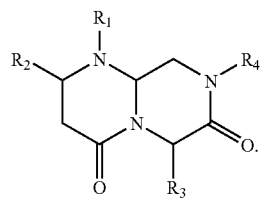

4. The compound of claim 1 having the structure:

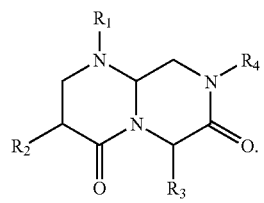

5. The compound of claim 1 wherein R$_5$ is an amino acid side chain moiety.

6. The compound of claim 1 wherein R$_5$ is an amino acid side chain derivative selected from the list of amino acid side chain derivatives in claim 1.

7. The compound of claim 6 wherein X is —C(=O)NH—.

8. The compound of claim 1 wherein R$_6$ is an amino acid side chain moiety.

9. The compound of claim 1 wherein R$_6$ is an amino acid side chain derivative selected from the list of amino acid side chain derivatives in claim 1.

10. The compound of claim 9 wherein Y is a direct bond.

11. The compound of claim 9 wherein Y is —NH—.

12. The compound of claim 9 wherein Y is —NHC(=O)—.

13. The compound of claim 9 wherein Y is —NHC(=O)O—.

14. The compound of claim 9 wherein Y is —NHC(=O)NH—.

15. The compound of claim 9 wherein Y is —NHSO$_2$—.

16. The compound of claim 1 wherein R$_7$ is an amino acid side chain moiety.

17. The compound of claim 1 wherein R$_7$ is an amino acid side chain derivative selected from the list of amino acid side chain derivatives in claim 1.

18. The compound of claim 17 wherein Z is a direct bond.

19. The compound of claim 17 wherein Z is —(CH$_2$)$_m$C(=O)NR$_8$— and m is 1 or 2.

20. The compound of claim 17 wherein Z is —(CH$_2$)$_k$—NHC(=O)—.

21. The compound of claim 17 wherein Z is —(CH$_2$)$_k$—NHC(=O)NR$_8$—.

22. The compound of claim 1 wherein R$_1$ is C(=O)NH—R$_5$, and
wherein
R$_5$ is R$_{1a}$, R$_{1b}$, R$_{1c}$, R$_{1d}$ or R$_{1e}$;
R$_{1a}$ is
(1) alkyl, or
(2) aminoalkyl,
wherein alkyl or aminoalkyl optionally and independently substituted with one or more substituents independently selected from R$_s$ and R$_t$;

$R_{1b}$ is —(CH$_2$)$_l$—NR$_d$R$_e$;

$R_{1c}$ is
- (1) aryl,
- (2) arylalkyl, or
- (3) Het wherein aryl, arylalkyl or Het are optionally and independently substituted with one or more substituents independently selected from R$_s$ and R$_t$;

$R_{1d}$ is
- (1) phenyl, or
- (2) benzyl, wherein phenyl and benzyl are optionally and independently substituted with one or more substituents independently selected from R$_s$ and R$_t$;

$R_{1e}$ is 3,5-bistrifluoromethylbenzyl;

$R_s$ is
- (1) halogen,
- (2) hydrogen,
- (3) haloalkyl,
- (4) —CN,
- (5) —CF$_3$,
- (6) —C(=O)OR$_d$,
- (7) —C(=O)R$_d$,
- (8) —C(=NR$_d$)(NR$_d$R$_e$),
- (9) —NR$_d$R$_e$,
- (10) —NR$_d$C(=O)R$_e$,
- (11) —NR$_d$C(=O)OR$_e$,
- (12) —NR$_d$C(=O)NR$_d$R$_e$,
- (13) —NO$_2$,
- (14) —OCF$_3$,
- (15) —OR$_d$,
- (16) —OC(=O)R$_d$,
- (17) —OC(=O)NR$_d$R$_e$,
- (18) —SR$_d$,
- (19) —S(O)$_k$R$_d$,
- (20) —S(O)$_2$OR$_d$,
- (21) —S(O)$_k$NR$_d$R$_e$, or
- (22) a group selected from R$_t$;

$R_t$ is
- (1) alkyl,
- (2) alkoxy,
- (3) aryloxy,
- (4) arylalkoxy, or
- (5) a group selected from R$_s$, wherein alkyl, alkoxy, aryloxy and arylalkoxy are optionally and independently substituted with one or more substituents independently selected from R$_s$;

$R_d$ and $R_e$ are independently selected from hydrogen, alkyl, aminoalkyl, aryl, arylalkyl and Het; or $R_d$ and $R_e$ taken together with the atoms to which they are attached form a mono- or bi-cyclic heterocyclic ring of 3 to 7 members each containing 0-3 additional heteroatoms independently selected from nitrogen, oxygen and sulfur;

k is an integer from 1 to 2;
l is an integer from 1 to 10;
m is an integer from 1 to 4; and
Het is heterocycle, heterocyclealkyl, heteroaryl or heteroarylalkyl.

23. The compound of claim 22 wherein R$_1$ is —C(=O)NH—R$_5$, and R$_5$ is an amino acid side chain derivative selected from the list of amino acid side chain derivatives in claim 1.

24. The compound of claim 23 wherein R$_5$ is 3,5-bistrifluoromethylbenzyl.

25. The compound of claim 22 wherein R$_{1a}$ is

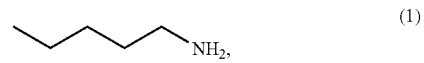 (1)

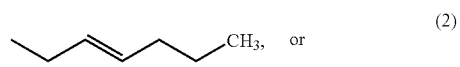 (2)

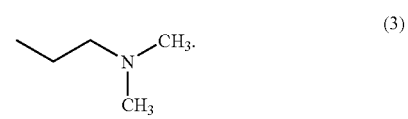 (3)

26. The compound of claim 22 wherein R$_{1c}$ is

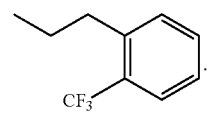

27. The compound of claim 22 wherein R$_{1d}$ is

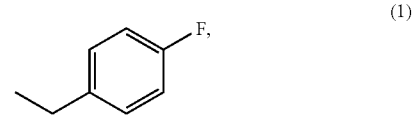 (1)

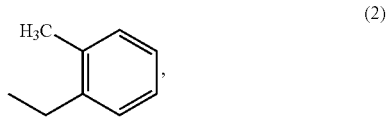 (2)

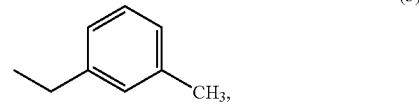 (3)

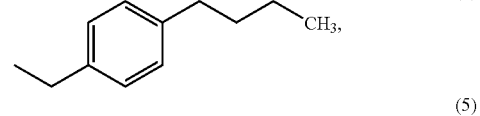 (4)

 (5)

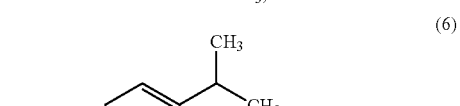 (6)

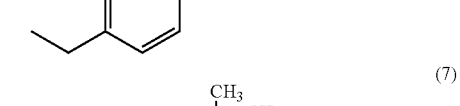 (7)

-continued

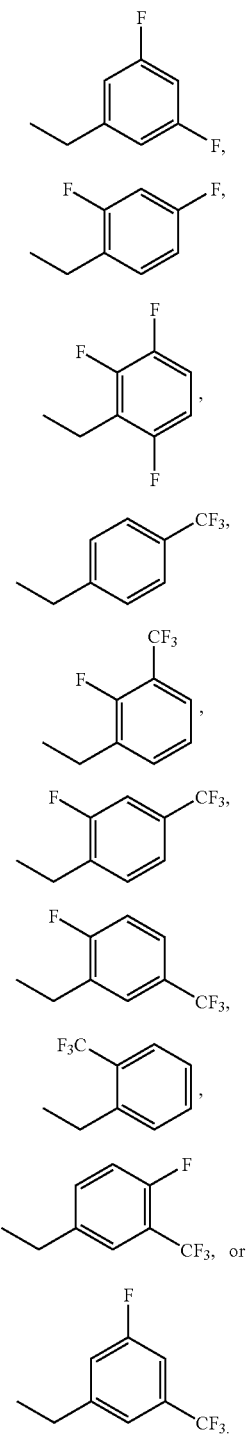

(8)

(9)

(10)

(11)

(12)

(13)

(14)

(15)

(16)

(17)

28. The compound of claim 1 wherein $R_2$ is:
(1) hydrogen,
(2) —$NHR_6$,
(3) —$NHC(=O)R_6$,
(4) —$NHC(=O)OR_6$,
(5) —$NHC(=O)NHR_6$,
(6) —$NHSO_2R_6$, or
(7) —$R_6$, wherein $R_6$ is $R_e$ and is optionally substituted with one or more substituents independently selected from $R_s$ and $R_t$;

$R_s$ is
(1) halogen,
(2) hydrogen,
(3) haloalkyl,
(4) —CN,
(5) —$CF_3$,
(6) —$C(=O)OR_d$,
(7) —$C(=O)R_d$,
(8) —$C(=NR_d)(NR_dR_e)$,
(9) —$NR_dR_e$,
(10) —$NR_dC(=O)R_e$,
(11) —$NR_dC(=O)OR_e$,
(12) —$NR_dC(=O)NR_dR_e$,
(13) —$NO_2$,
(14) —$OCF_3$,
(15) —$OR_d$,
(16) —$OC(=O)R_d$,
(17) —$OC(=O)NR_dR_e$,
(18) —$SR_d$,
(19) —$S(O)_kR_d$,
(20) —$S(O)_2OR_d$,
(21) —$S(O)_kNR_dR_e$, or
(22) a group selected from $R_t$;

$R_t$ is
(1) alkyl,
(2) alkoxy,
(3) aryloxy,
(4) arylalkoxy, or
(5) a group selected from $R_s$,
wherein alkyl, alkoxy, aryloxy and arylalkoxy are optionally and independently substituted with one or more substituents independently selected from $R_s$;

$R_d$ and $R_e$ are independently selected from hydrogen, alkyl, aminoalkyl, aryl, arylalkyl and Het; or $R_d$ and $R_e$ taken together with the atoms to which they are attached form a mono- or bi-cyclic heterocyclic ring of 3 to 7 members each containing 0-3 additional heteroatoms independently selected from nitrogen, oxygen and sulfur;

k is an integer from 1 to 2;
l is an integer from 1 to 10;
m is an integer from 1 to 4; and
Het is heterocycle, heterocyclealkyl, heteroaryl or heteroarylalkyl.

29. The compound of claim 28 wherein $R_2$ is hydrogen.
30. The compound of claim 28 wherein $R_2$ is
(1) methyl,
(2) ethyl,
(3) propyl, (4)

(5)

(6)

(7)

-continued

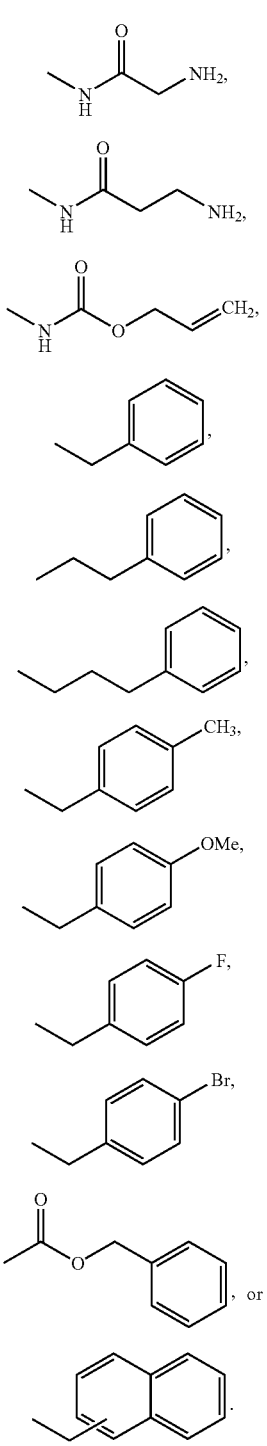

31. The compound of claim 1 wherein $R_3$ is:
(1) —$(CH_2)_mC(=O)N(R_7R_8)$,
(2) —$(CH_2)_kNHC(=O)R_7$,
(3) —$(CH_2)_kNHC(=O)N(R_7R_8)$, or
(4) —$R_7$,
wherein $R_7$ and $R_8$ are each independently selected from $R_e$ and are optionally and independently substituted with one or more substituents independently selected from $R_s$ and $R_t$;

$R_s$ is
(1) halogen,
(2) hydrogen,
(3) haloalkyl,
(4) —CN,
(5) —$CF_3$,
(6) —$C(=O)OR_d$,
(7) —$C(=O)R_d$,
(8) —$C(=NR_d)(NR_dR_e)$,
(9) —$NR_dR_e$,
(10) —$NR_dC(=O)R_e$,
(11) —$NR_dC(=O)OR_e$,
(12) —$NR_dC(=O)NR_dR_e$,
(13) —$NO_2$,
(14) —$OCF_3$,
(15) —$OR_d$,
(16) —$OC(=O)R_d$,
(17) —$OC(=O)NR_dR_e$,
(18) —$SR_d$,
(19) —$S(O)_kR_d$,
(20) —$S(O)_2OR_d$,
(21) —$S(O)_kNR_dR_e$, or
(22) a group selected from $R_t$;

$R_t$ is
(1) alkyl,
(2) alkoxy,
(3) aryloxy,
(4) arylalkoxy, or
(5) a group selected from $R_s$,
wherein alkyl, alkoxy, aryloxy and arylalkoxy are optionally and independently substituted with one or more substituents independently selected from $R_s$;

$R_d$ and $R_e$ are independently selected from hydrogen, alkyl, aminoalkyl, aryl, arylalkyl and Het; or $R_d$ and $R_e$ taken together with the atoms to which they are attached form a mono- or bi-cyclic heterocyclic ring of 3 to 7 members each containing 0-3 additional heteroatoms independently selected from nitrogen, oxygen and sulfur;

k is an integer from 1 to 2;
l. is an integer from 1 to 10;
m is an integer from 1 to 4; and
Het is heterocycle, heterocyclealkyl, heteroaryl or heteroarylalkyl.

32. The compound of claim 31 wherein $R_3$ is aminoalkyl.

33. The compound of claim 31 wherein $R_3$ is —$(CH_2)_mC(=O)N(R_7R_8)$.

34. The compound of claim 31 wherein $R_3$ is
(1) hydrogen,
(2) methyl,
(3) ethyl,
(4) 1-propyl,
(5) 2-propyl,
(6) n-butyl,
(7) 2-butyl,

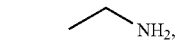  (8)

  (9)

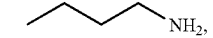  (10)

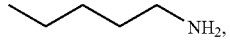  (11)

-continued
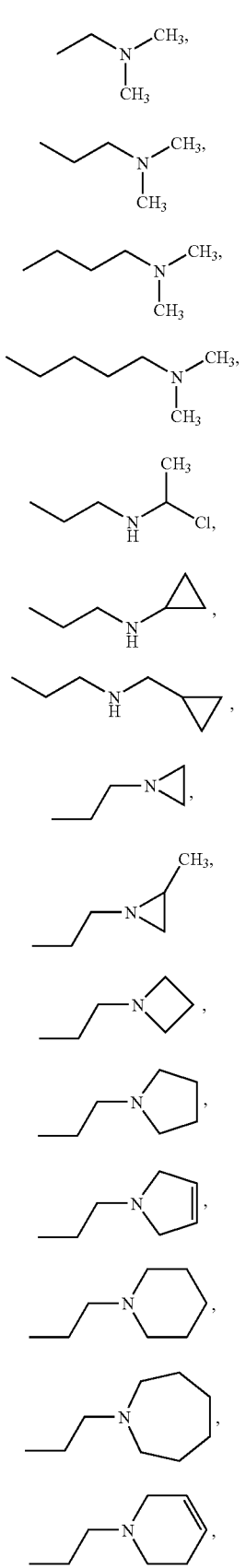
-continued
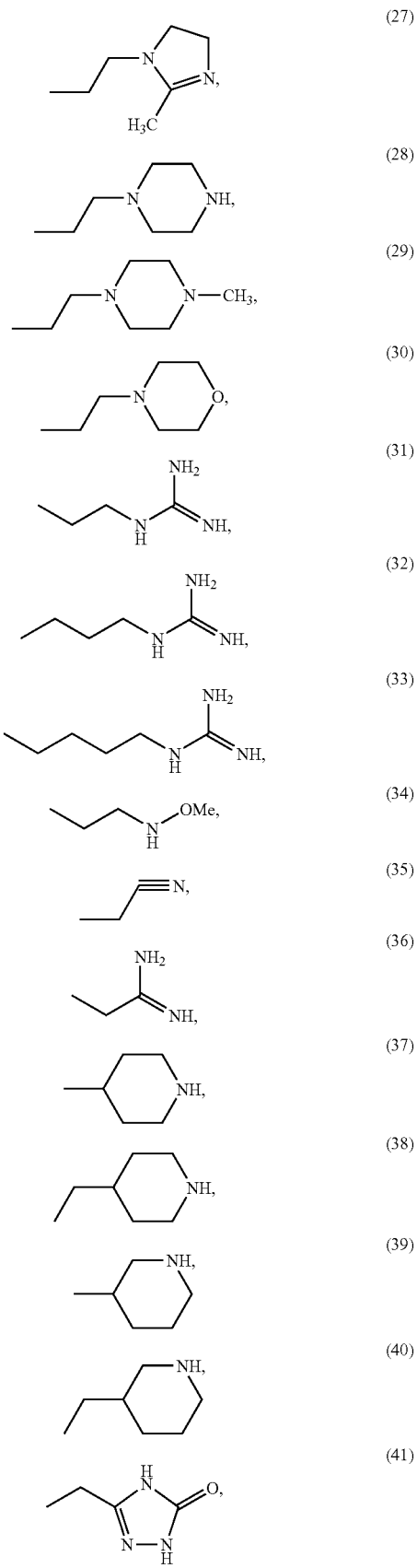

-continued
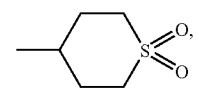 (42)
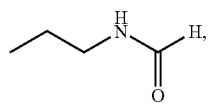 (43)
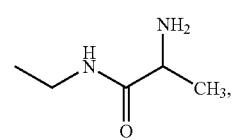 (44)
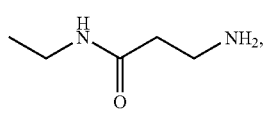 (45)
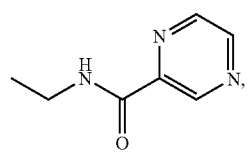 (46)
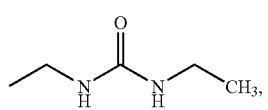 (47)
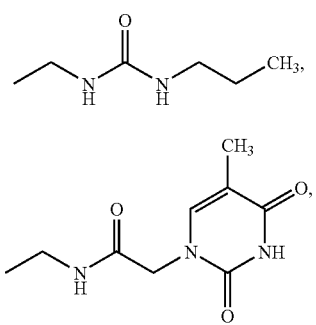 (48)
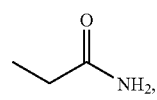 (49)
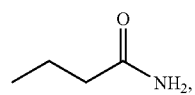 (50)
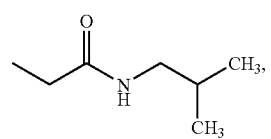 (51)
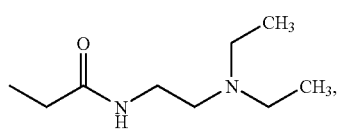 (52)
-continued
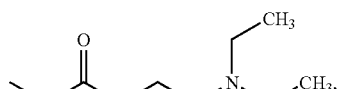 (53)
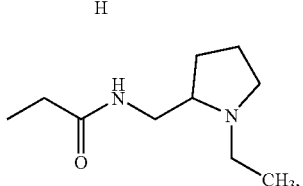 (54)
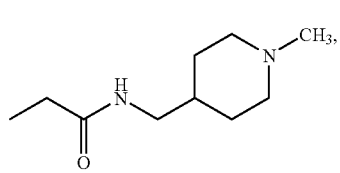 (55)
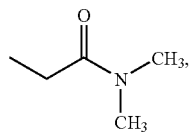 (56)
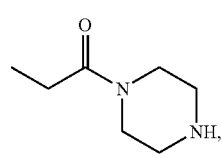 (57)
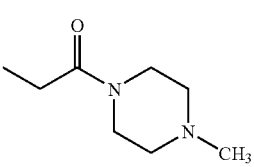 (58)
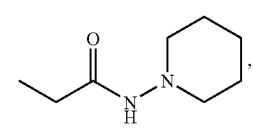 (59)
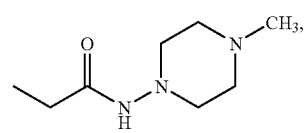 (60)
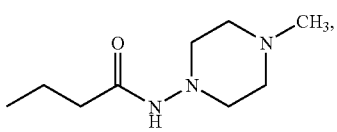 (61)
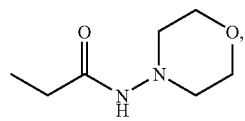 (62)
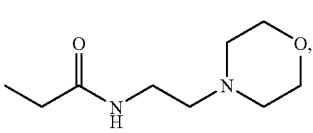 (63)
(64)

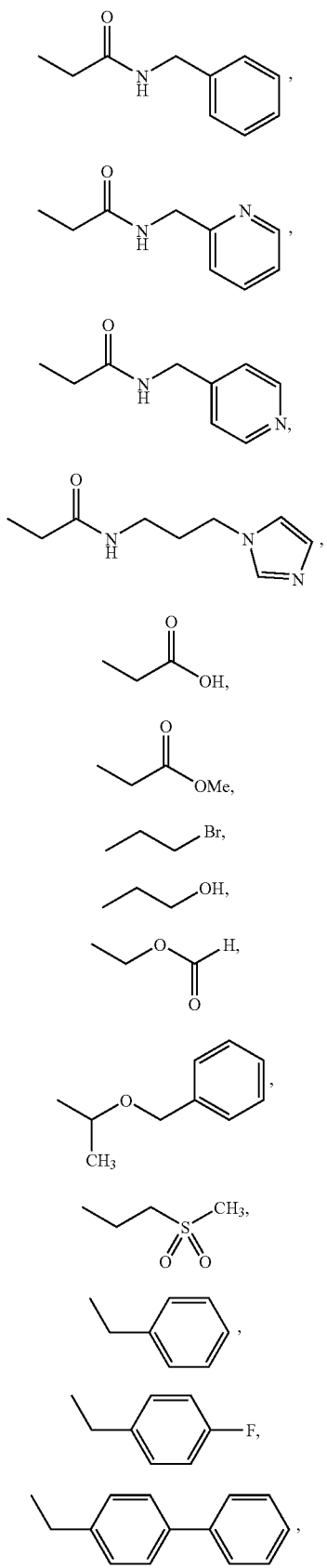

35. The compound of claim 1 wherein $R_4$ is:
(1) alkyl,
(2) aminoalkyl,
(3) aryl,
(4) arylalkyl,
(5) Het,
(6) —$(CH_2)_m NH(C=O)$-aryl, or
(7) —$(CH_2)_m NR_d R_e$,
wherein alkyl, aminoalkyl, aryl, arylalky and Het are optionally and independently substituted with one or more substituents independently selected from $R_s$ and $R_t$;
$R_s$ is
(1) halogen,
(2) hydrogen,
(3) haloalkyl,
(4) —CN,
(5) —$CF_3$,
(6) —$C(=O)OR_d$,
(7) —$C(=O)R_d$,
(8) —$C(=NR_d)(NR_d R_e)$,
(9) —$NR_d R_e$,
(10) —$NR_d C(=O)R_e$,
(11) —$NR_d C(=O)OR_e$,
(12) —$NR_d C(=O)NR_d R_e$,
(13) —$NO_2$,
(14) —$OCF_3$,
(15) —$OR_d$,
(16) —$OC(=O)R_d$,
(17) —$OC(=O)NR_d R_e$,
(18) —$SR_d$,
(19) —$S(O)_k R_d$,
(20) —$S(O)_2 OR_d$,
(21) —$S(O)_k NR_d R_e$, or
(22) a group selected from $R_t$;
$R_t$ is
(1) alkyl,
(2) alkoxy,
(3) aryloxy,
(4) arylalkoxy, or
(5) a group selected from $R_s$, wherein alkyl, alkoxy, aryloxy and arylalkoxy are optionally and independently substituted with one or more substituents independently selected from $R_s$;

$R_d$ and $R_e$ are independently selected from hydrogen, alkyl, aminoalkyl, aryl, arylalkyl and Het; or $R_d$ and $R_e$ taken together with the atoms to which they are attached form a mono- or bi-cyclic heterocyclic ring of 3 to 7 members each containing 0-3 additional heteroatoms independently selected from nitrogen, oxygen and sulfur;

k is an integer from 1 to 2;

l is an integer from 1 to 10;

m is an integer from 1 to 4; and

Het is heterocycle, heterocyclealkyl, heteroaryl or heteroarylalkyl.

36. The compound of claim 35 wherein $R_4$ is arylalkyl.

37. The compound of claim 35 wherein $R_4$ is (1) 1-propyl, (2) 1-butyl, (3) 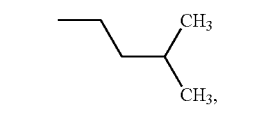

(4) 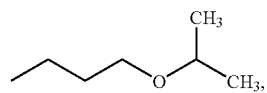

(5) 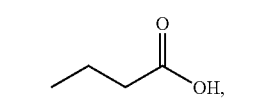

(6) 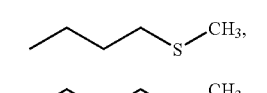

(7) 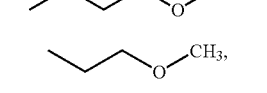

(8) 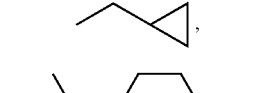

(9) 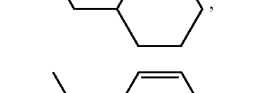

(10) 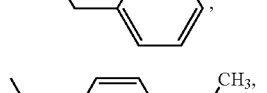

(11) 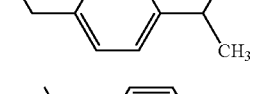

(12) 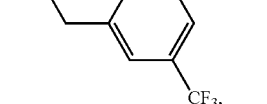

(13) 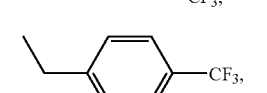

(14) 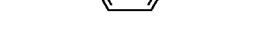

-continued

(15) 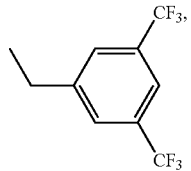

(16) 

(17) 

(18) 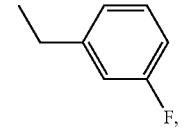

(19) 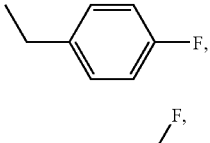

(20) 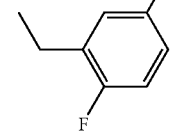

(21) 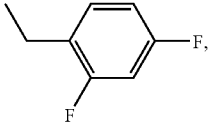

(22) 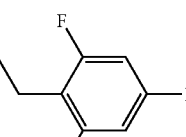

(23) 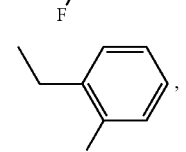

(24) 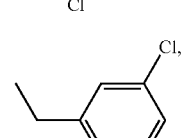

(25) 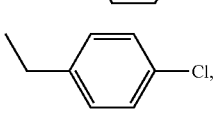

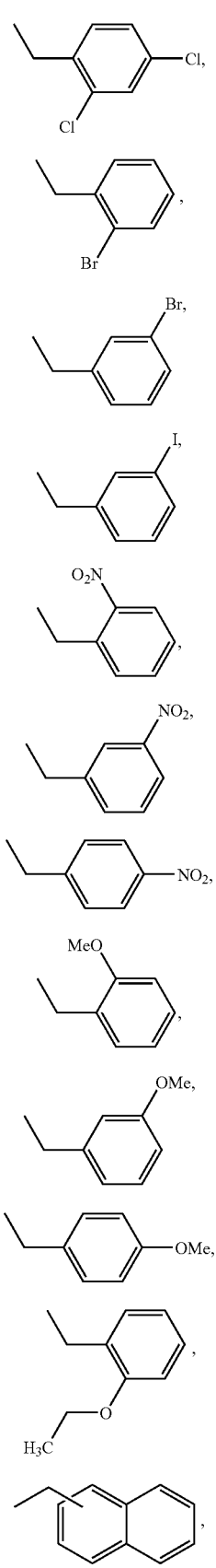
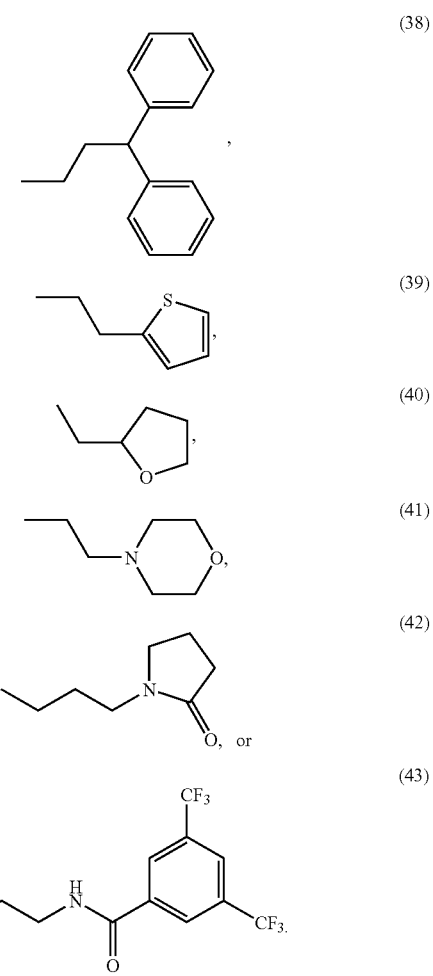
38. The compound of claim 1 having the following conformation:
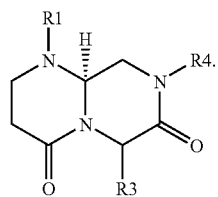
39. The compound of claim 1 having the following conformation:
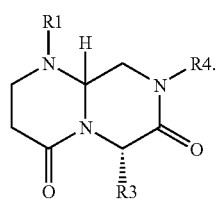

40. The compound of claim 1 having the following conformation:

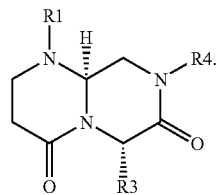

41. The compound of claim 1 having the following conformation:

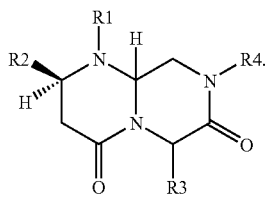

42. The compound of claim 1 having the following conformation:

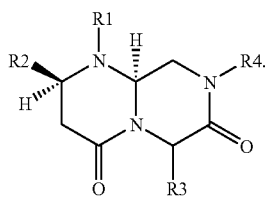

43. The compound of claim 1 having the following conformation:

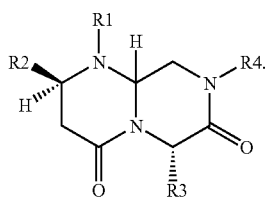

44. The compound of claim 1 having the following conformation:

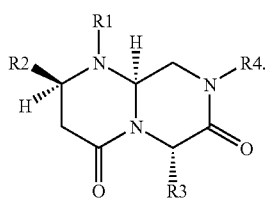

45. The compound of claim 1 having the following conformation:

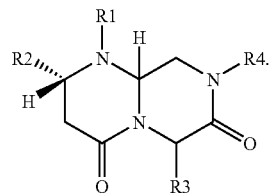

46. The compound of claim 1 having the following conformation:

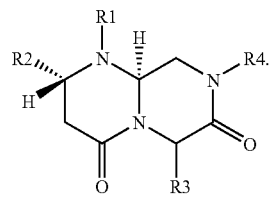

47. The compound of claim 1 having the following conformation:

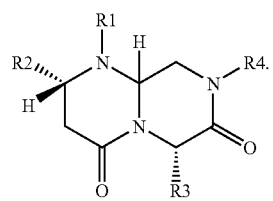

48. The compound of claim 1 having the following conformation:

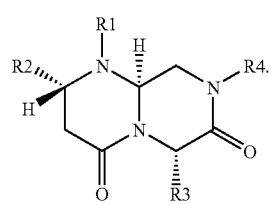

49. The compound of claim 1 having the following conformation:

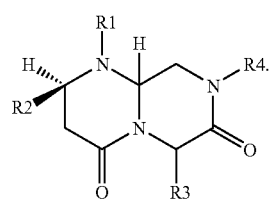

50. The compound of claim 1 having the following conformation:

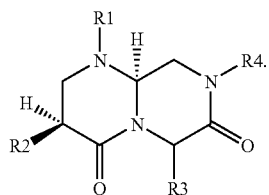

51. The compound of claim 1 having the following conformation:

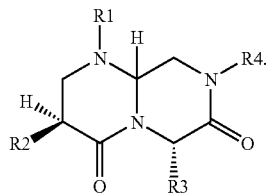

52. The compound of claim 1 having the following conformation:

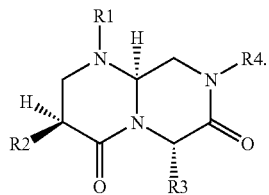

53. The compound of claim 1 having the following conformation:

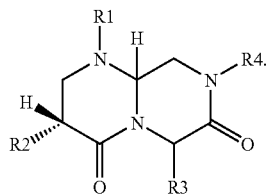

54. The compound of claim 1 having the following conformation:

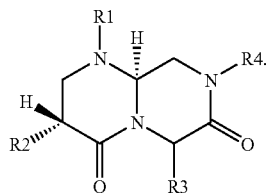

55. The compound of claim 1 having the following conformation:

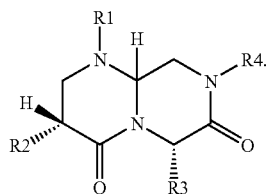

56. The compound of claim 1 having the following conformation:

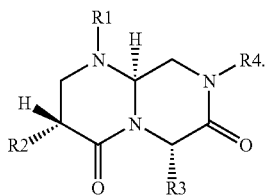

57. The compound of claim 1 wherein the compound has one of the following structures:

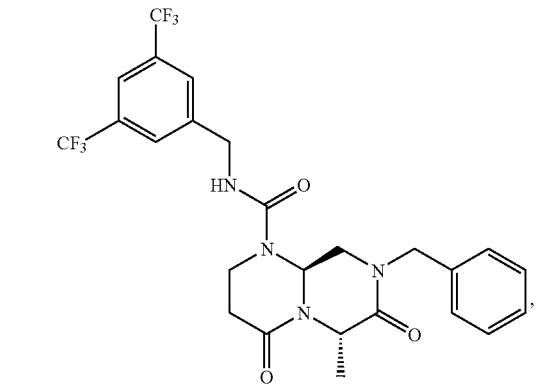

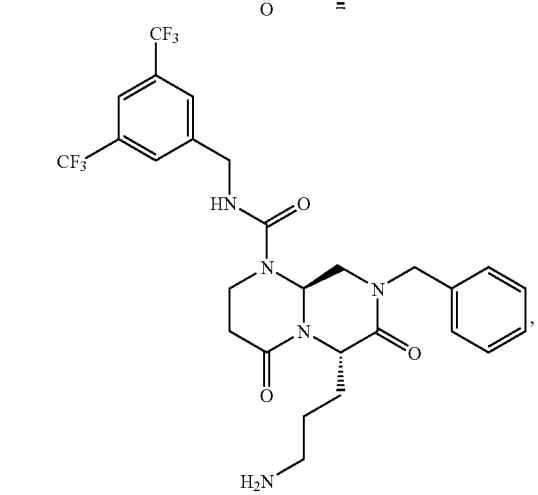

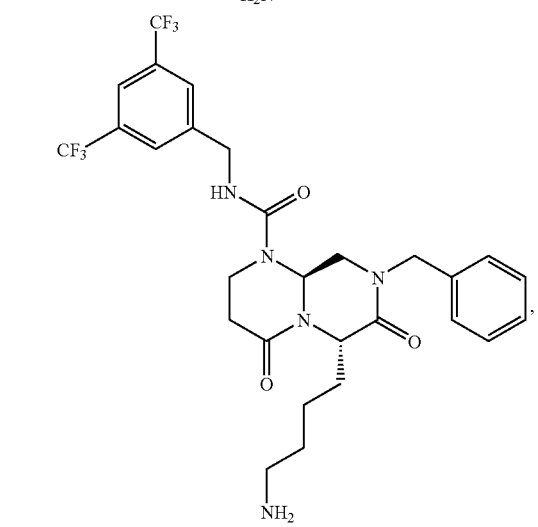

317
-continued
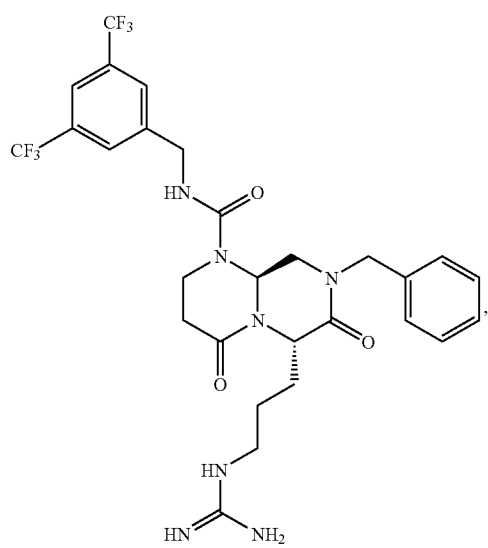
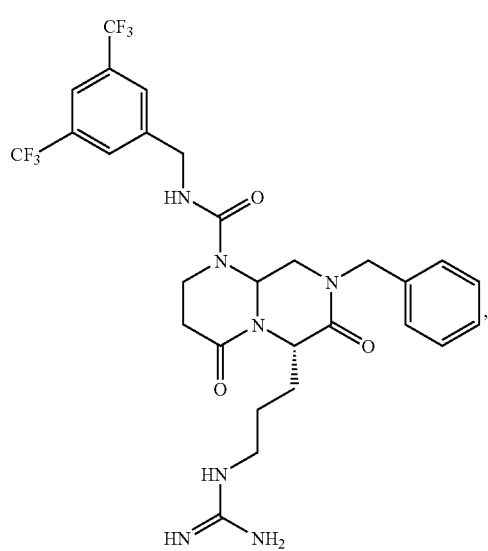
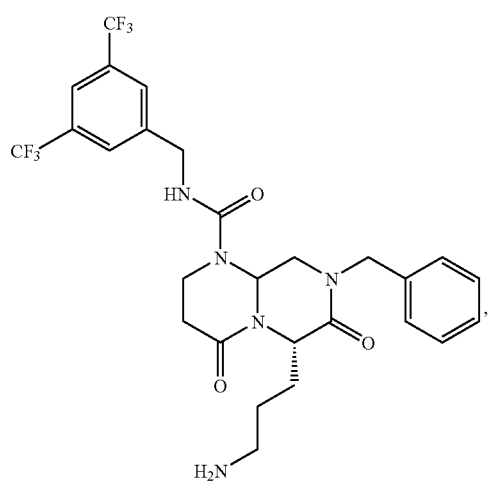
318
-continued
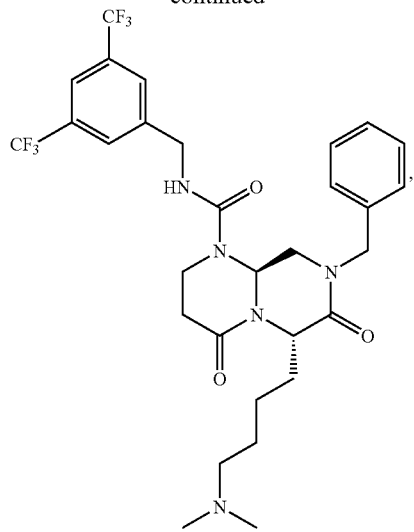
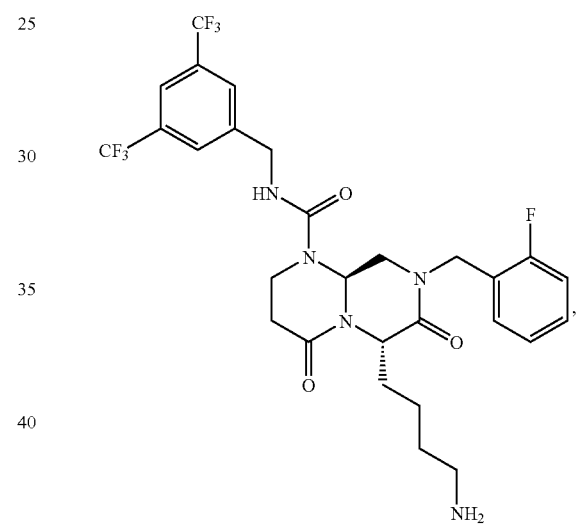
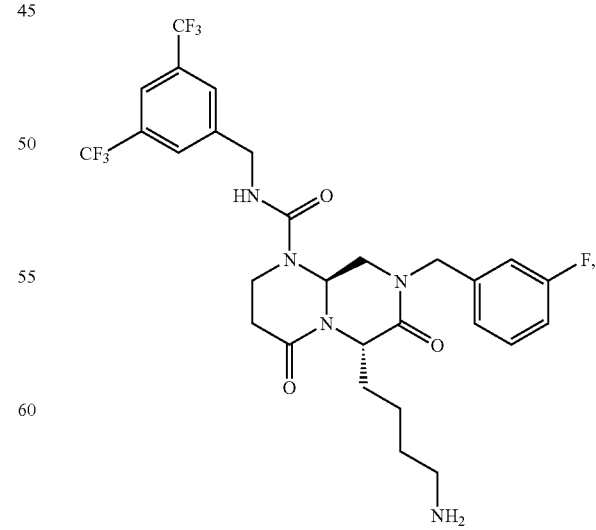

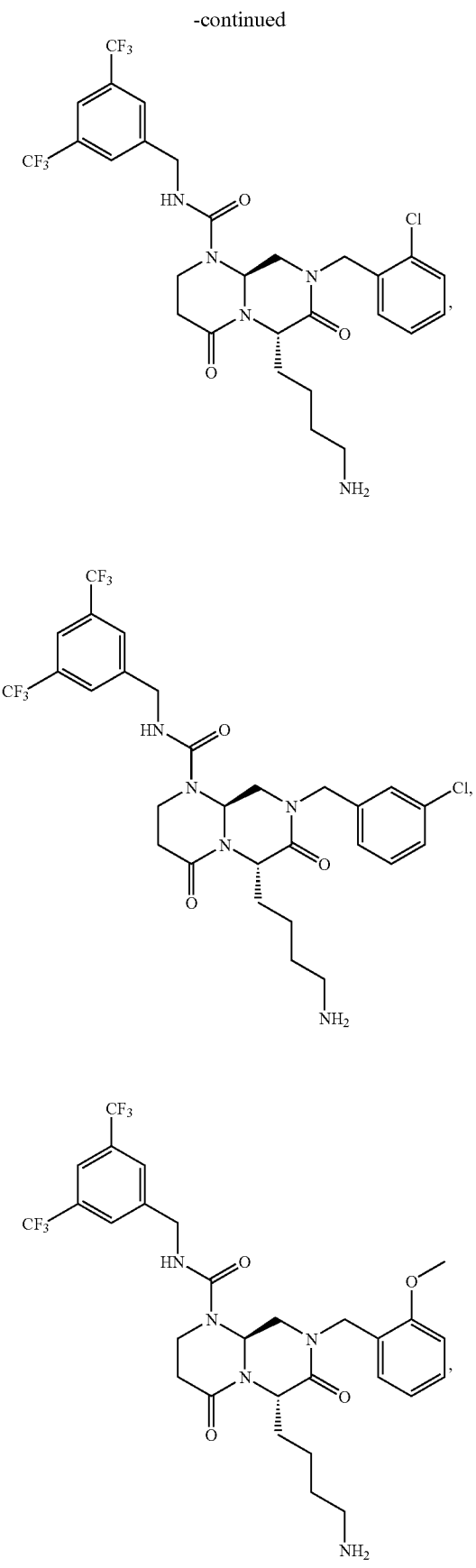

321
-continued
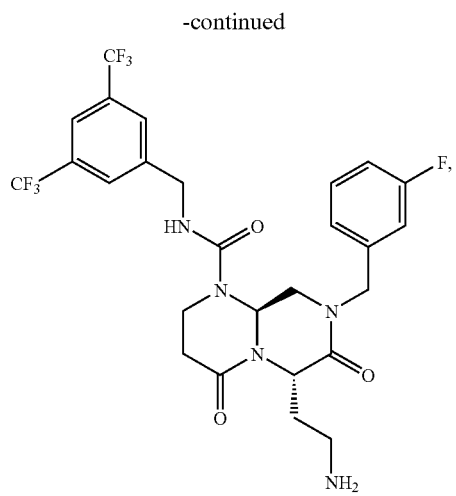
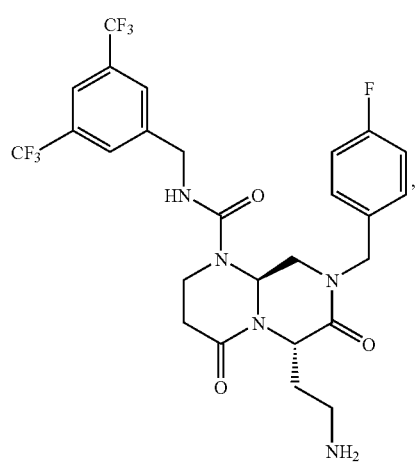
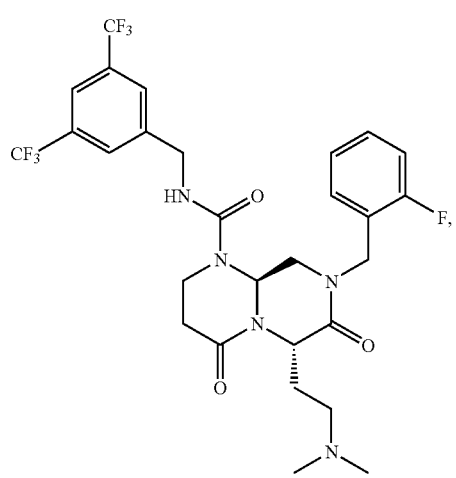
322
-continued
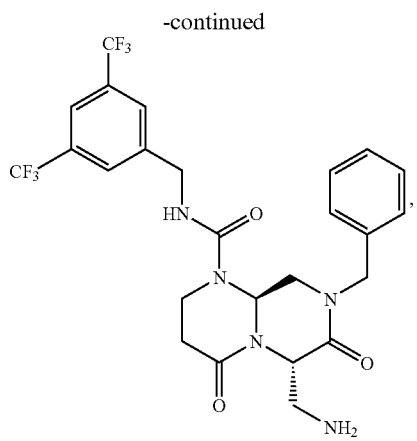
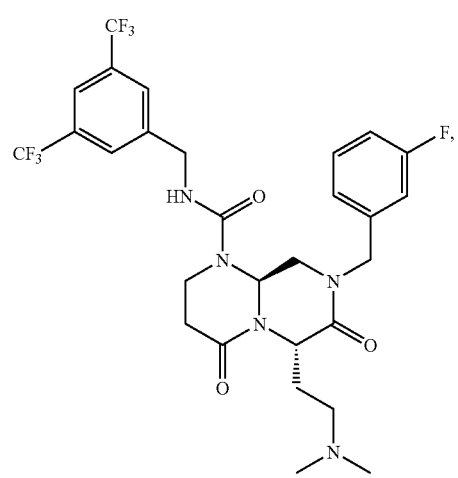
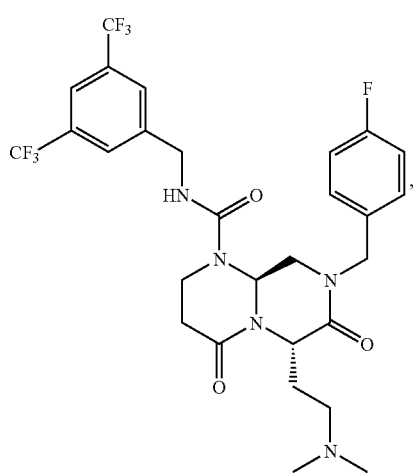

323
-continued
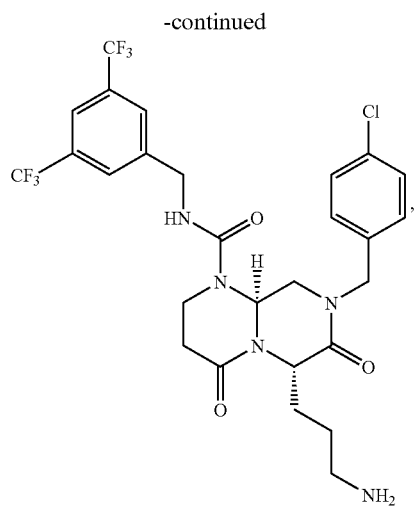
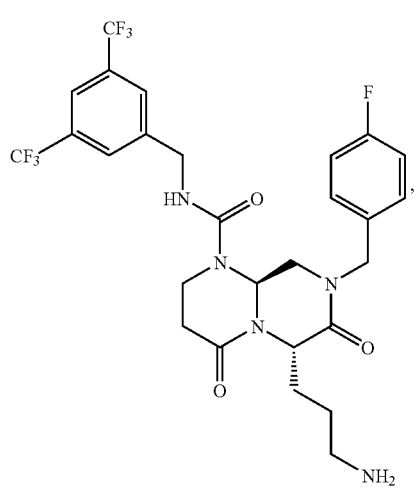
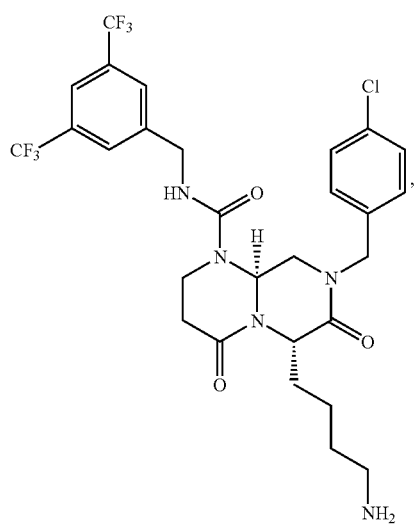
324
-continued
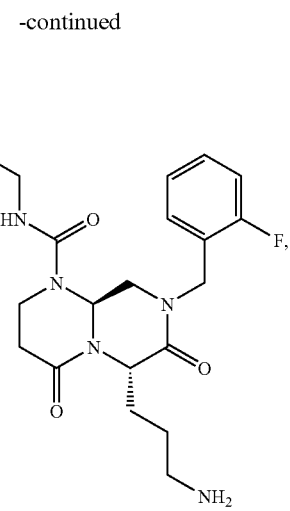
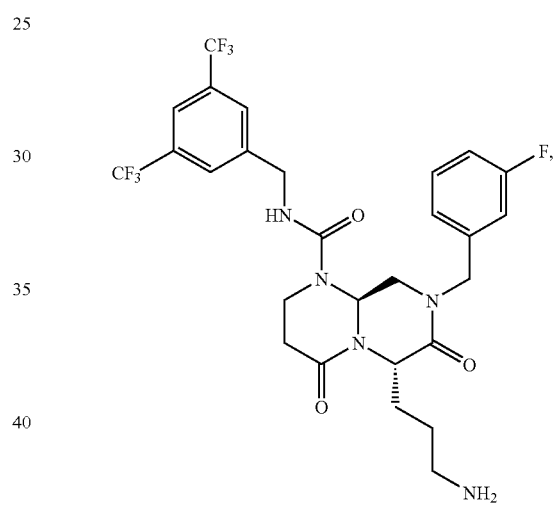
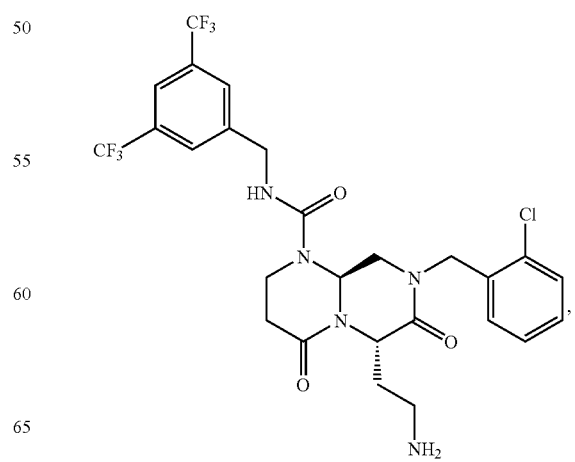

325
-continued
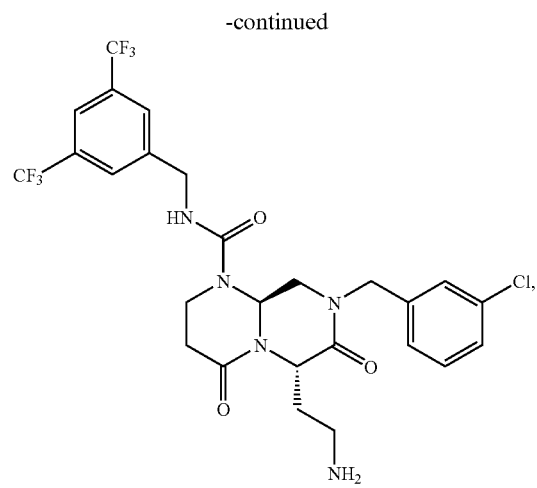
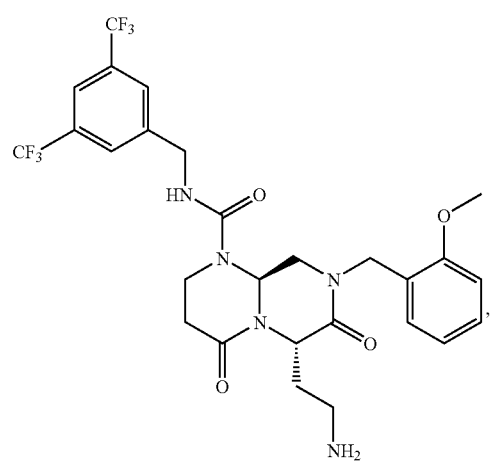
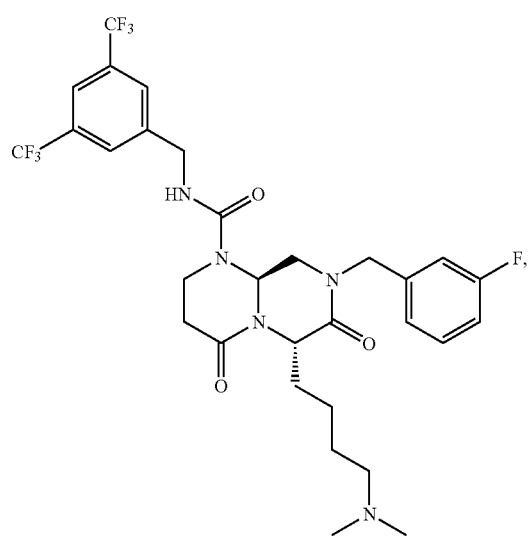
326
-continued
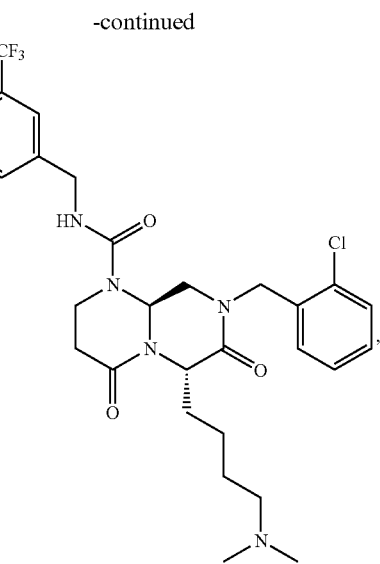
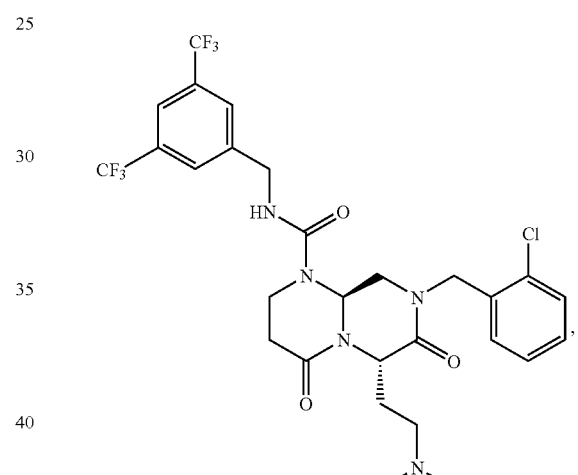
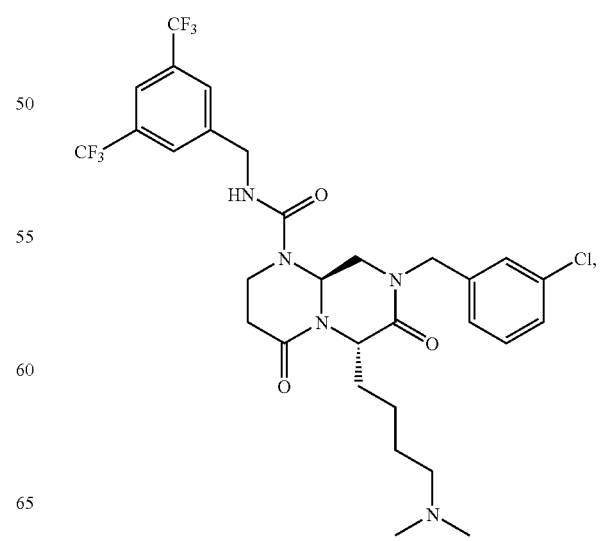

327
-continued
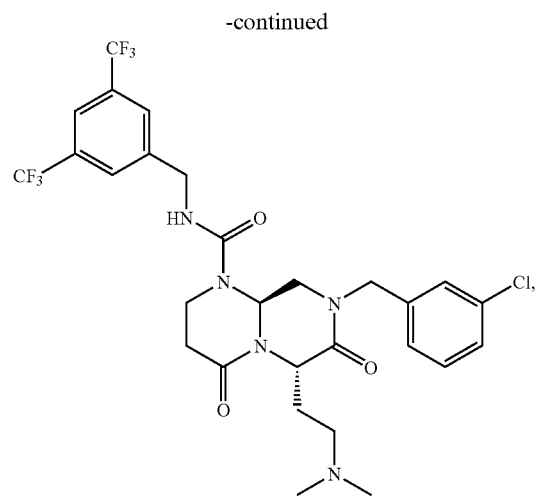
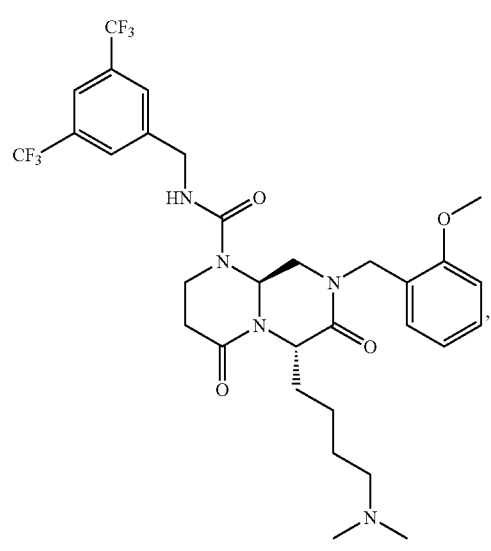
328
-continued
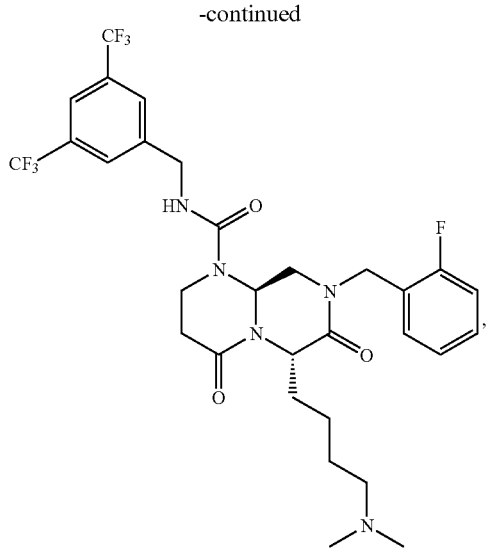
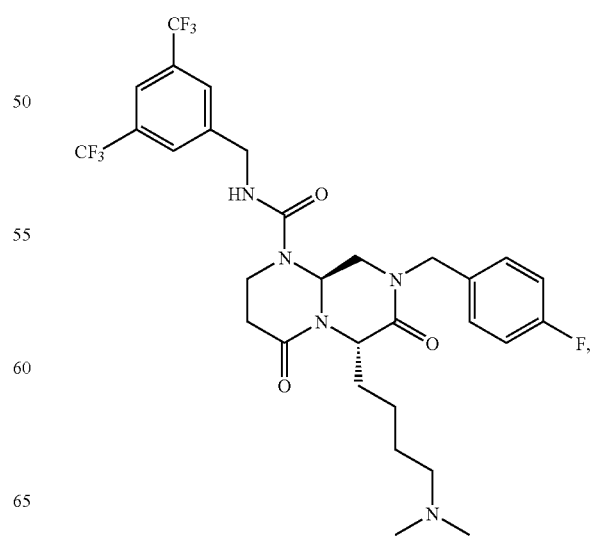

329
-continued
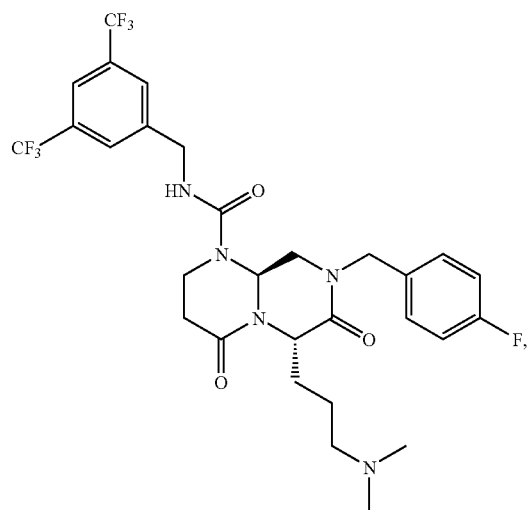
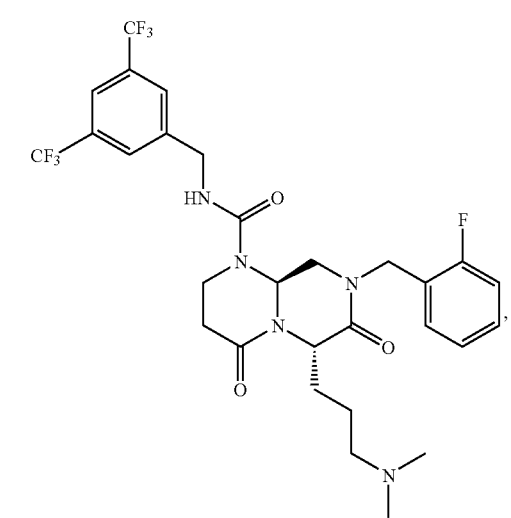
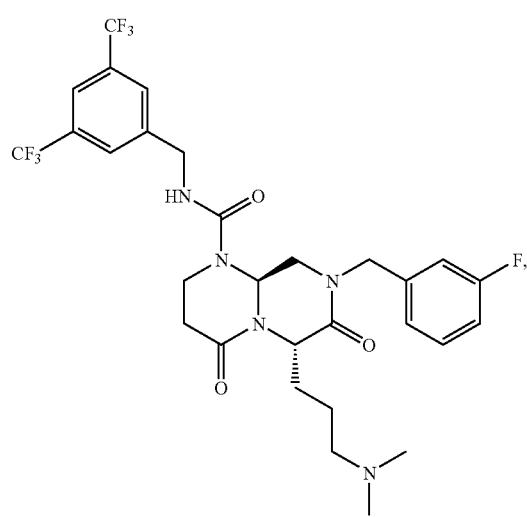
330
-continued
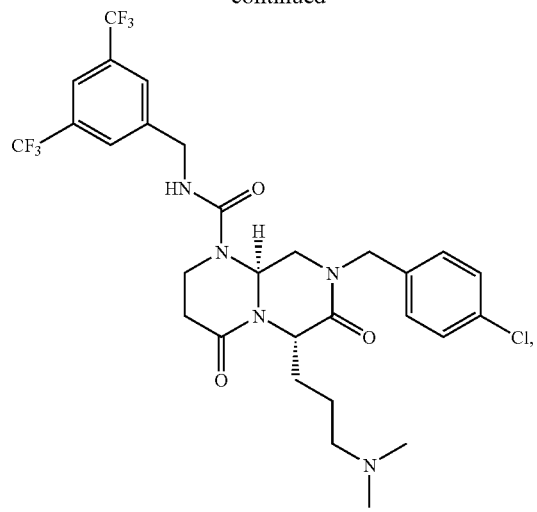
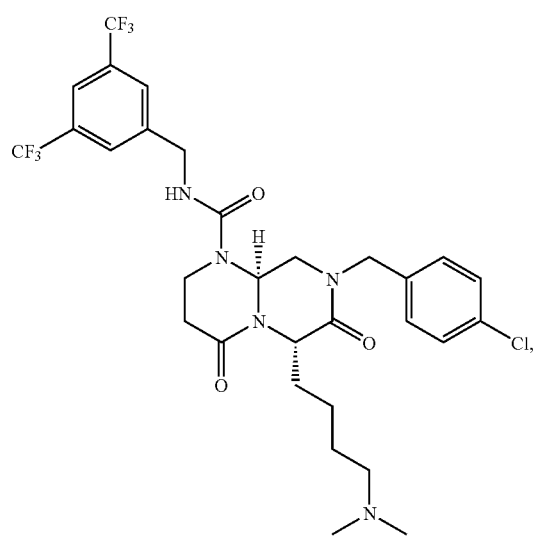
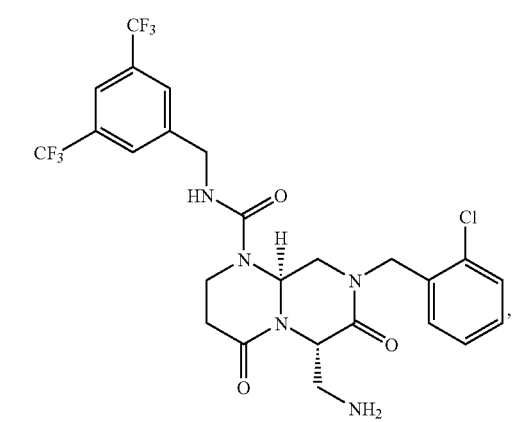

-continued

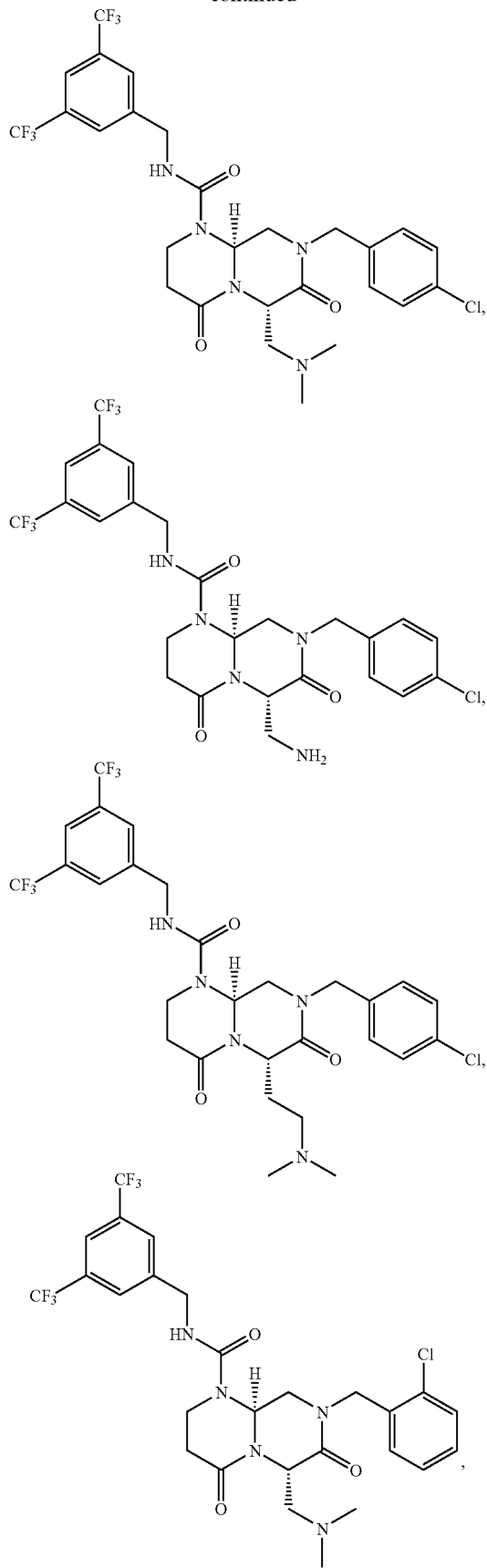

-continued

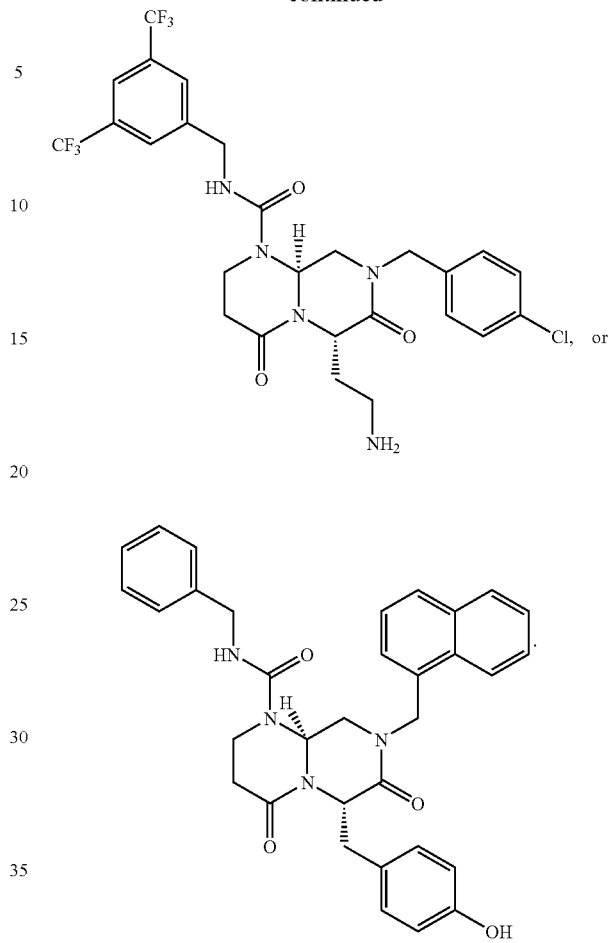

58. A composition comprising a compound of claim 1 and a pharmaceutically acceptable carrier.

59. A library of compounds comprising a plurality of library members, wherein at least one library member is a compound of claim 1.

60. The compound of claim 1 wherein X is —C(=O)NH—, $R_2$ is H, $C_1$-$C_6$ alkyl, or $C_7$-$C_{11}$ arylalkyl; $R_3$ is

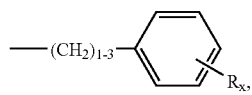

wherein $R_X$ is H, OH or halo; $R_4$ is $C_7$-$C_{11}$ arylalkyl; and $R_5$ is $C_7$-$C_{11}$ arylalkyl, and wherein $R_2$, $R_4$ and $R_5$ are optionally and independently substituted with 1-3 halogens, 1-3 $C_1$-$C_3$ haloalkyls, or 1-3 $C_1$-$C_3$ alkyl.

61. The compound of claim 1 wherein $R_1$ is —C(=O)(NH)—$R_5$ or —C(=O)O—$R_5$; $R_2$ is H, $C_1$-$C_6$ alkyl, or $C_7$-$C_{11}$ arylalkyl; $R_3$ is an amino acid side chain moiety; $R_4$ is $C_7$—$C_{11}$ arylalkyl; and $R_5$ is $C_6$-$C_{10}$ aryl or $C_7$-$C_{11}$ arylalkyl, and wherein $R_4$ and $R_5$ are optionally and independently substituted with 1-3 substituents selected from the group consisting of halogen, $C_1$-$C_3$ haloalkyl, $C_1$-$C_3$ alkyloxy, and $CH_3$(C=O)—.

62. The compound of claim 1 wherein the compound has the structure:
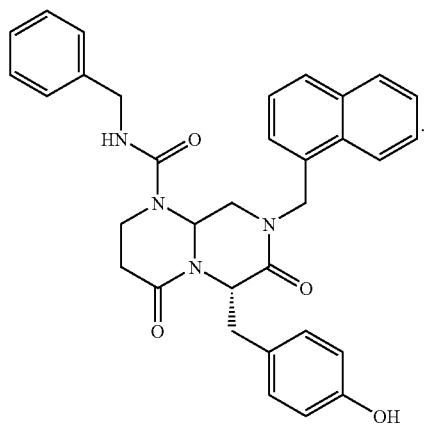
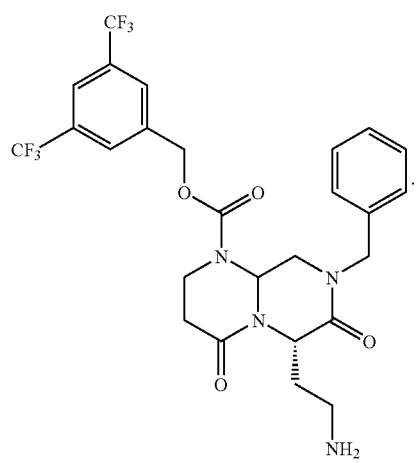
63. The compound of claim 1 wherein the compound has the structure:
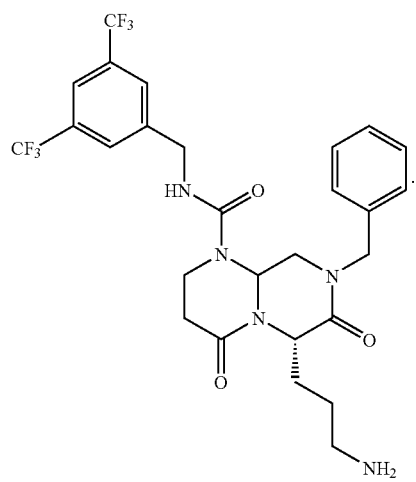
64. The compound of claim 1 wherein the compound has the structure:
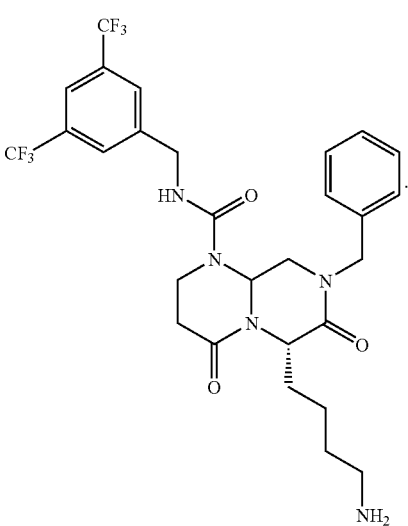
65. The compound of claim 1 wherein the compound has the structure:
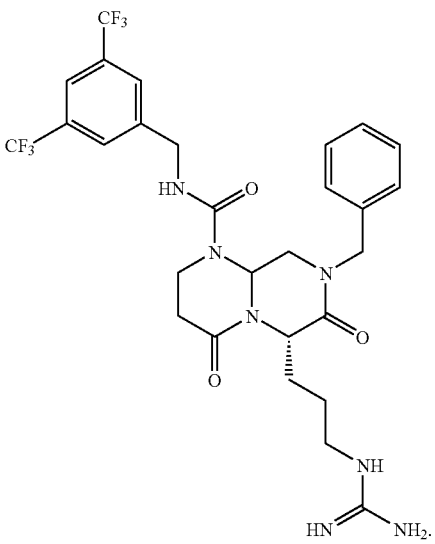
* * * * *